US009770280B2

(12) United States Patent
Diederich et al.

(10) Patent No.: US 9,770,280 B2
(45) Date of Patent: *Sep. 26, 2017

(54) IMPLANTABLE THERMAL TREATMENT METHOD AND APPARATUS

(71) Applicant: THE REGENTS OF THE UNIVERSITY OF CALIFORNIA, Oakland, CA (US)

(72) Inventors: Chris J. Diederich, Novato, CA (US); Jeffrey C. Lotz, San Mateo, CA (US); William H. Nau, Jr., Longmont, CO (US); David S. Bradford, Sausalito, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/197,107

(22) Filed: Mar. 4, 2014

(65) Prior Publication Data

US 2014/0288544 A1 Sep. 25, 2014

Related U.S. Application Data

(60) Continuation of application No. 13/792,001, filed on Mar. 9, 2013, now abandoned, which is a (Continued)

(51) Int. Cl.
*A61N 7/00* (2006.01)
*A61B 18/04* (2006.01)
(Continued)

(52) U.S. Cl.
CPC ................ *A61B 18/04* (2013.01); *A61N 7/02* (2013.01); *A61N 7/022* (2013.01); *A61B 8/56* (2013.01);
(Continued)

(58) Field of Classification Search
CPC .......... A61B 18/04; A61B 2017/00092; A61B 2017/00101; A61B 2017/00261;
(Continued)

(56) References Cited

U.S. PATENT DOCUMENTS 3,565,062 A 2/1971 Kuris
3,822,708 A 7/1974 Zilber
(Continued)

FOREIGN PATENT DOCUMENTS

EP 0643982 A1 3/1995
EP 03704007.8 A2 2/2005
(Continued)

OTHER PUBLICATIONS

Chen, S. S., Wright, N. T. and Humphrey, J. D., 1998, "Heat-induced changes in the mechanics of a collagenous tissue: isothermal, isotonic shrinkage." J Biomech Eng 3, 382-8.
(Continued)

*Primary Examiner* — Jonathan Cwern
(74) *Attorney, Agent, or Firm* — O'Banion & Ritchey LLP; John P. O'Banion

(57) ABSTRACT

A long-term implantable ultrasound therapy system and method is provided that provides directional, focused ultrasound to localized regions of tissue within body joints, such as spinal joints. An ultrasound emitter or transducer is delivered to a location within the body associated with the joint and heats the target region of tissue associated with the joint from the location. Such locations for ultrasound transducer placement may include for example in or around the intervertebral discs, or the bony structures such as vertebral bodies or posterior vertebral elements such as facet joints.

20 Claims, 66 Drawing Sheets

Related U.S. Application Data continuation of application No. 12/898,401, filed on Oct. 5, 2010, now Pat. No. 8,414,509, which is a division of application No. 10/351,450, filed on Jan. 23, 2003, now Pat. No. 7,819,826.

(60) Provisional application No. 60/351,875, filed on Jan. 23, 2002, provisional application No. 60/351,827, filed on Jan. 23, 2002, provisional application No. 60/410,603, filed on Sep. 12, 2002, provisional application No. 60/411,401, filed on Sep. 16, 2002.

(51) Int. Cl.
*A61N 7/02* (2006.01)
*A61B 17/00* (2006.01)
*A61B 18/00* (2006.01)
*A61B 8/00* (2006.01)
*A61B 90/00* (2016.01)

(52) U.S. Cl.
CPC ............... *A61B 2017/00092* (2013.01); *A61B 2017/00101* (2013.01); *A61B 2017/00261* (2013.01); *A61B 2018/00339* (2013.01); *A61B 2090/374* (2016.02); *A61N 7/00* (2013.01); *A61N 2007/0078* (2013.01)

(58) Field of Classification Search
CPC .. A61B 2018/00339; A61B 2019/5236; A61B 8/56; A61N 2007/0078; A61N 7/00; A61N 7/02; A61N 7/022
See application file for complete search history.

(56) References Cited

U.S. PATENT DOCUMENTS 3,938,502 A 2/1976 Bom
4,441,486 A * 4/1984 Pounds ............................ 601/3
4,449,528 A 5/1984 Auth et al.
4,528,979 A 7/1985 Marchenko et al.
4,530,360 A 7/1985 Duarte
4,569,351 A 2/1986 Tang
4,676,258 A 6/1987 Inokuchi et al.
4,750,499 A 6/1988 Hoffer
4,757,820 A 7/1988 Itoh
4,774,967 A 10/1988 Zanakis et al.
4,841,977 A 6/1989 Griffith et al.
4,907,589 A 3/1990 Cosman
4,924,863 A 5/1990 Sterzer
4,936,281 A 6/1990 Stasz
4,951,677 A 8/1990 Crowley et al.
4,959,063 A 9/1990 Kojima
4,976,711 A 12/1990 Parins et al.
5,000,185 A 3/1991 Yock
5,002,059 A 3/1991 Crowley et al.
5,031,618 A 7/1991 Mullett
5,078,736 A 1/1992 Behl
5,131,397 A 7/1992 Crowley
5,147,355 A 9/1992 Friedman et al.
5,156,157 A 10/1992 Valenta, Jr. et al.
5,186,177 A 2/1993 O'Donnell et al.
5,190,540 A 3/1993 Lee
5,226,430 A 7/1993 Spears et al.
5,242,439 A 9/1993 Larsen
5,255,679 A 10/1993 Imran
5,281,215 A 1/1994 Milder
5,282,468 A 2/1994 Klepinski
5,292,321 A 3/1994 Lee
5,295,484 A 3/1994 Marcus et al.
5,300,085 A 4/1994 Yock
5,304,214 A 4/1994 DeFord
5,305,756 A 4/1994 Entrekin et al.
5,324,255 A 6/1994 Passafaro et al.
5,325,860 A 7/1994 Seward et al.
5,342,292 A 8/1994 Nita et al.
5,342,357 A 8/1994 Nardella
5,342,409 A 8/1994 Mullett
5,344,435 A 9/1994 Turner et al.
5,345,940 A 9/1994 Seward et al.
5,348,554 A 9/1994 Imran et al.
5,366,490 A 11/1994 Edwards et al.
5,368,035 A 11/1994 Hamm et al.
5,368,557 A 11/1994 Nita et al.
5,368,558 A 11/1994 Nita
5,370,675 A 12/1994 Edwards et al.
5,370,678 A 12/1994 Edwards et al.
5,372,138 A 12/1994 Crowley et al.
5,383,876 A 1/1995 Nardella
5,385,148 A 1/1995 Lesh et al.
5,385,544 A 1/1995 Edwards et al.
5,391,197 A 2/1995 Burdette et al.
5,391,199 A 2/1995 Ben-Haim
5,411,527 A 5/1995 Alt
5,417,719 A 5/1995 Hull et al.
5,421,338 A 6/1995 Crowley
5,423,811 A 6/1995 Imran et al.
D361,555 S 8/1995 Erickson
5,441,527 A 8/1995 Erickson et al.
5,447,509 A 9/1995 Mills et al.
5,449,380 A 9/1995 Chin
5,454,373 A 10/1995 Koger et al.
5,471,988 A 12/1995 Fujio
5,474,530 A 12/1995 Passafaro et al.
5,501,703 A 3/1996 Holsheimer et al.
5,505,730 A 4/1996 Edwards
5,524,624 A * 6/1996 Tepper et al. ................. 600/439
5,529,580 A 6/1996 Kusunoki
5,540,679 A 7/1996 Fram et al.
5,545,161 A 8/1996 Imran
5,560,362 A 10/1996 Sliwa et al.
5,565,005 A 10/1996 Erickson et al.
5,571,088 A 11/1996 Lennox et al.
5,571,147 A * 11/1996 Sluijter et al. .................. 607/99
5,575,772 A 11/1996 Lennox
5,575,788 A 11/1996 Baker et al.
5,588,432 A 12/1996 Crowley
5,601,526 A 2/1997 Chapelon et al.
5,606,974 A 3/1997 Castellano et al.
5,620,479 A 4/1997 Diederich
5,628,317 A 5/1997 Starkebaum et al.
5,630,837 A 5/1997 Crowley
5,643,330 A 7/1997 Holsheimer et al.
5,658,278 A 8/1997 Imran et al.
5,685,839 A 11/1997 Edwards et al.
5,687,729 A 11/1997 Schaetzle
5,697,927 A 12/1997 Imran et al.
5,718,231 A 2/1998 Dewhurst et al.
5,720,286 A 2/1998 Chapelon et al.
5,722,403 A 3/1998 McGee et al.
5,725,494 A 3/1998 Brisken
5,728,062 A 3/1998 Brisken
5,730,706 A 3/1998 Garnies
5,733,315 A 3/1998 Burdette et al.
5,735,280 A 4/1998 Sherman et al.
5,735,811 A 4/1998 Brisken
5,735,846 A 4/1998 Panescu et al.
5,741,249 A 4/1998 Moss et al.
5,755,663 A 5/1998 Larsen et al.
5,762,616 A 6/1998 Talish
5,766,231 A 6/1998 Erickson et al.
5,800,429 A 9/1998 Edwards
5,800,432 A 9/1998 Swanson
5,807,391 A 9/1998 Wijkamp
5,824,021 A 10/1998 Rise
5,840,031 A 11/1998 Crowley
5,846,218 A 12/1998 Brisken et al.
5,931,805 A 8/1999 Brisken
5,976,105 A 11/1999 Marcove et al.
5,997,497 A 12/1999 Nita et al.
6,012,457 A 1/2000 Lesh
6,014,588 A 1/2000 Fitz
6,024,740 A 2/2000 Lesh et al.
6,030,374 A 2/2000 McDaniel
6,032,673 A 3/2000 Savage

(56) References Cited

U.S. PATENT DOCUMENTS

| | | | | |
|---|---|---|---|---|
| 6,038,480 | A | 3/2000 | Hrdlicka et al. | |
| 6,046,187 | A | 4/2000 | Berde et al. | |
| 6,047,214 | A | 4/2000 | Mueller et al. | |
| 6,071,279 | A | 6/2000 | Whayne et al. | |
| 6,074,352 | A | 6/2000 | Hynynen et al. | |
| 6,112,122 | A | 8/2000 | Schwardt et al. | |
| 6,117,101 | A | 9/2000 | Diederich et al. | |
| 6,120,502 | A | 9/2000 | Michelson | |
| 6,126,682 | A | 10/2000 | Sharkey | |
| 6,137,209 | A | 10/2000 | Nilsson | |
| 6,164,283 | A | 12/2000 | Lesh | |
| 6,169,924 | B1 | 1/2001 | Meloy et al. | |
| 6,171,239 | B1 | 1/2001 | Humphrey | |
| 6,206,842 | B1 | 3/2001 | Tu | |
| 6,210,393 | B1 | 4/2001 | Brisken | |
| 6,221,038 | B1 | 4/2001 | Brisken | |
| 6,228,046 | B1 | 5/2001 | Brisken | |
| 6,231,516 | B1 | 5/2001 | Keilman et al. | |
| 6,231,528 | B1 | 5/2001 | Kaufman et al. | |
| 6,233,488 | B1 | 5/2001 | Hess | |
| 6,245,064 | B1 | 6/2001 | Lesh et al. | |
| 6,248,345 | B1 | 6/2001 | Goldenheim et al. | |
| 6,254,553 | B1 | 7/2001 | Lidgren et al. | |
| 6,254,599 | B1 | 7/2001 | Lesh et al. | |
| 6,261,311 | B1 | 7/2001 | Sharkey | |
| 6,264,650 | B1 | 7/2001 | Hovda et al. | |
| 6,264,651 | B1 | 7/2001 | Underwood | |
| 6,264,659 | B1 | 7/2001 | Ross et al. | |
| 6,270,498 | B1 | 8/2001 | Michelson | |
| 6,287,272 | B1 | 9/2001 | Brisken et al. | |
| 6,292,699 | B1 | 9/2001 | Simon et al. | |
| 6,296,619 | B1 | 10/2001 | Brisken et al. | |
| 6,305,378 | B1 | 10/2001 | Lesh et al. | |
| 6,319,241 | B1 | 11/2001 | King et al. | |
| 6,361,531 | B1 | 3/2002 | Hissong | |
| 6,368,292 | B1 | 4/2002 | Ogden et al. | |
| 6,426,339 | B1 | 7/2002 | Berde et al. | |
| 6,428,491 | B1 | 8/2002 | Weiss | |
| 6,436,098 | B1 | 8/2002 | Michelson | |
| 6,447,448 | B1 | 9/2002 | Ishikawa et al. | |
| 6,464,695 | B2 | 10/2002 | Hovda et al. | |
| 6,485,271 | B1 | 11/2002 | Tack | |
| 6,493,592 | B1 | 12/2002 | Leonard et al. | |
| 6,524,261 | B2 | 2/2003 | Talish et al. | |
| 6,558,390 | B2 | 5/2003 | Cragg | |
| 6,562,033 | B2 | 5/2003 | Shah | |
| 6,575,969 | B1 | 6/2003 | Rittman, III et al. | |
| 6,575,979 | B1 | 6/2003 | Cragg | |
| 6,599,288 | B2 | 7/2003 | Maguire et al. | |
| 6,607,502 | B1 | 8/2003 | Maguire et al. | |
| 6,645,202 | B1 | 11/2003 | Pless et al. | |
| 6,673,063 | B2 | 1/2004 | Brett | |
| 6,689,086 | B1 | 2/2004 | Nita | |
| 6,689,125 | B1 | 2/2004 | Keith | |
| 6,736,835 | B2 | 5/2004 | Pellegrino | |
| 6,795,737 | B2 | 9/2004 | Gielen et al. | |
| 6,980,849 | B2 | 12/2005 | Sasso | |
| 7,065,408 | B2 | 6/2006 | Herman et al. | |
| 7,211,055 | B2 * | 5/2007 | Diederich et al. | 601/2 |
| 7,326,203 | B2 | 2/2008 | Papineau | |
| 7,819,826 | B2 | 10/2010 | Diederich et al. | |
| 7,883,481 | B2 * | 2/2011 | Lidgren | 601/2 |
| 8,414,509 | B2 * | 4/2013 | Diederich et al. | 601/3 |
| 8,915,949 | B2 * | 12/2014 | Diederich et al. | 607/96 |
| 2001/0029370 | A1 | 10/2001 | Hodva et al. | |
| 2001/0049527 | A1 | 12/2001 | Cragg | |
| 2001/0053885 | A1 | 12/2001 | Gielen et al. | |
| 2002/0035361 | A1 * | 3/2002 | Houser et al. | 606/15 |
| 2002/0111661 | A1 | 8/2002 | Cross et al. | |
| 2002/0115945 | A1 | 8/2002 | Herman et al. | |
| 2002/0193708 | A1 | 12/2002 | Thompson et al. | |
| 2003/0014088 | A1 | 1/2003 | Fang et al. | |
| 2003/0028147 | A1 | 2/2003 | Aves et al. | |
| 2003/0069569 | A1 | 4/2003 | Burdette et al. | |

FOREIGN PATENT DOCUMENTS

| | | | |
|---|---|---|---|
| WO | 95/03027 | | 2/1995 |
| WO | 95/19738 | | 7/1995 |
| WO | 97/32525 | | 9/1997 |
| WO | 97/33649 | | 9/1997 |
| WO | 97/37607 | | 10/1997 |
| WO | 97/45156 | | 12/1997 |
| WO | 9817184 | A1 | 4/1998 |
| WO | 9847569 | A1 | 10/1998 |
| WO | 99/00064 | A1 | 1/1999 |
| WO | 99/19025 | | 4/1999 |
| WO | 99/48621 | A1 | 9/1999 |
| WO | 9948621 | A2 | 9/1999 |
| WO | 99/44519 | | 10/1999 |
| WO | 99/56818 | A1 | 11/1999 |
| WO | 00/49978 | A1 | 8/2000 |
| WO | 00/56237 | A1 | 9/2000 |
| WO | 00/67648 | A1 | 11/2000 |
| WO | 00/67656 | | 11/2000 |
| WO | 00/71043 | A1 | 11/2000 |
| WO | 00/78389 | A1 | 12/2000 |
| WO | 01/26570 | A1 | 4/2001 |
| WO | 01/60234 | A3 | 8/2001 |
| WO | 02/09808 | A1 | 2/2002 |
| WO | 03/061756 | A1 | 7/2003 |
| WO | 03061756 | | 7/2003 |

OTHER PUBLICATIONS

Urban, J. P. and McMullin, J. F., 1985, "Swelling pressure of the intervertebral disc: influence of proteoglycan and collagen contents." Biorheology 2, 145-57.

Schwarzer, et al., The Prevalence and Clinical features of Internal Disc Disruption in Patients With Chronic Low Back Pain, Spine 1995; 20: 1878-1883.

Chen, S. S., Wright, N. T. and Humphrey, J. D., 1997, "Heat-induced changes in the mechanics of a collagenous tissue: isothermal free shrinkage." J Biomech Eng 4, 372-8.

Cox et al., The surgical treatment of atrial fibrillation, IV. Surgical technique, J. Thorac. Cardiovas. Surg. 1991;101:584-92.

Fram et al., Feasibility of Radiofrequency Powered, Thermal Balloon Ablation of Atrioventricular Byposs Tracts Via the Coronary Sinus: In Vivo Canine Studies, PACE 1995; 18:1518-1530.

Haissaguerre, et al., Right and left Atrial Radiofrequency Catheter Therapy of Paroxysmal Atrial Fibrillation, J Cardiovasc Electrophysiol, vol. 7, pp. 1132-1144, Dec. 1996.

Jais, et al., A Focal Source of Atrial Fibrillation Treated by Discrete Radiofrequency Ablation, Circulation, 1997;95:572-576.

Lesh, Interventional electrophysiology—State-of-the-art 1993, Am Heart J, 1993;126:686-698.

Jais, et al., Biatrial Dimensions Relevant to Catheter Ablation, Abstract, North American Society of Pacing and Electophysiology 17th Annual Scientific Sessions, Nov. 28, 1995.

McMath et al., Percutaneous laser balloon coagulation of accessory pathways, SPIE vol. 1425, Diagnostic and Therapeutic Cardiovascular Interventions, (1991) pp. 165-171.

Schuger et al., Long-term Effects of Percutaneous Laser Balloon Ablation From the Canine Coronary Sinus, Circulation, 1992;86:947-954.

Sueda et al, Simple left Atrial Procedure for Chronic Atrial Fibrillation Associated With Mitral Valve Disease, Ann Thorac Surg, 1996;62:1796-800.

Hendricks, et al., Catheter Ablation, Current Management of Arrhythmias; Ch IX Nonpharmocalogic management, 1991: 373-378.

Vujaskovic, et al., Effects of intraoperative hyperthermia on canine sciatic nerve: histopathologic and morphometric studies, Int. J. Hyperthermia, 1994, vol. 10, No. 6, 845-855.

Arnoczky, et al., Thermal Modification of Connective Tissues: Basic Science Considerations and Clinical Implications; AAOS Instructional Course Lectures, Ch. 1, vol. 50, 2001, pp. 3-11.

Amonoo-Kuofi, Morphometric changes in the heights and anteroposterior diameters of the lumbar intervertebral discs with age; J. Anat (1991), 175, pp. 159-168.

(56) References Cited

OTHER PUBLICATIONS

Hayashi, et al., Thermal Capsulorrhaphy Treatment of Shoulder Instability; Clinical Orthopaedics and Related Research; 2001, No. 390, pp. 59-72.
Saal, et al., Intradiscal Electrothermal Treatment for Chronic Discogenic Low Back Pain, Prospective Outcome Stud, Spine 2002;27:966-974.
Karasek et al., Twelve-Month Follow-Up of a Controlled Trial of Intradiscal Thermal Anuloplasty for Back Pain Due to Internal Disc Disruption, Spine 2000;25:2601-2607.
Miles et al., Polymer in-a-Box Mechanism for the Thermal Stabilization of Collagen Molecules in Fibers, Biophysical Journal, vol. 76, Jun. 1999, pp. 3243-3252.
Sminia et al., Effect of hyperthermia on the central nervous system: a review, Int. J. Hyperthermia, 1994, vol. 10, No. 1, pp. 1-30.
Schaefer, et al., Tissue Shrinkage With the Holmium: Yttrium Aluminum Garnet Laser, A Postoperative Assessment of Tissue Length, Stiffness, and Structure, Am. J. of Sports Medicine, 1997, vol. 25, No. 6, pp. 841-848.
Naseef III, et al., The Thermal Properties of Bovine Joint Capsule, The Basic Scienc of Laser-and Radiofrequency-Induced Capsular Shrinkage, Am. J. of Sports Medicine, 1997, vol. 25, No. 5, pp. 670-674.
Hayashi, et al., The Effect of Thermal Heating on the length and Histologic Properties of the Glenohumeral Joint Capsule, Am. J. of Sports Medicine, 1997, vol. 25, No. 1, pp. 107-112.
Diederich, et al., IDTT Therapy in Cadaveric Lumbar Spine: Temperature and Thermal Dose Distributions, Proceeding of SPIE, vol. 4247 (2001) pp. 104-108.
Dewey, Arrhenius relationships from the molecule and cell to the clinic, Int. J. Hyperthermia, 1994, vol. 10, No. 4, pp. 457-483.
Diederich et al., Induction of Hyperthermia Using an Intracavitary Multielement Ultrasonic Applicator, IEEE Trans. On Biomedical Engineering, vol. 36, No. 4 Apr. 1989, pp. 432-438.
Rubin, et al., Current Concepts Review, The Use of Low-Intensity Ultrasound to Accelerate the Healing of Fractures, The Jounral of Bone & Joint Surgery, Feb. 2001, vol. 83-A, No. 2, pp. 259-270.
Wallace, et al., Creep Behavior of a Rabbit Model of Ligament Laxity after Electrothermal Shrinkage In Vivo, Am. J. Sports Medicine, 2002, vol. 30, No. 1, pp. 98-102.
Nieminen, et al., Quantitative MR Microscopy of Enzymatically Degradded Articular Cartilage, Magn Reson Med 43:676-681 (2000).
Lopez, et al., Effects of Monopolar Radiofrequency Energy on Ovine Joint Capsular Mechanical Properties, Clinical Orthopaedics & Related Research, 2000;374:286-297.
Hecht, et al., Monopolar Radiofrequency Energy Effects on Joint Capsular Tissue: Potential Treatment for Joint Instability, Am J Sports Medicine, 1999, vol. 27, No. 6, pp. 761-771.
Heary, Intadiscal Electrothermal Annuloplasty: The IDET Procedure, Journal of Spinal Disorders, 2001, vol. 14, No. 4, pp. 353-360.
Gerber, et al., Thermal Capsulorrhaphy to Treat Shoulder Instabilitty, Cliical Orthopaedics and Related Research, 2002, No. 400, pp. 105-116.
Hall, The role of movement and tissue interactions in the development and growth of bone and secondary cartlage in the clavicle of the embryonic chick, J. Embryol. Exp. Morph. vol. 93, pp. 133-152 (1986).
Hayashi, et al., The Mechanism of Joint Capsule Thermal Modification in an In Vitro Sheep Model, Cliical Orthopaedics and Related Research, 2000, No. 370, pp. 236-249.
Masunaga, et al., Phase 1111 Trial of Preoperative Thermoradiotherapy in the Treatment of Urinary Bladder Cancer, Int. J. Hypothermia, 1994, vol. 10, No. 1, pp. 31-40. [2-page Abstract].
European Patent Office, Communication issued on Sep. 20, 2011 for related patent application No. EP 03 704 007.8 with claims examined, counterpart to International Patent Application No. PCT/US03/002211, pp. 1-10.
European Patent Office, related patent application EP 03 704 007.8, Communication issued on Jan. 5, 2009 with claims examined, counterpart to PCT/US03/002211, claiming priority to U.S. Appl. No. 60/351,875, pp. 1-8.
European Patent Office, related patent application EP 03 704 007.8, Supplementary European Search Report issued on Mar. 10, 200 (pp. 1-3), with claims examined (pp. 4-8), counterpart to PCTIUS03/002211, claiming priority to U.S. Appl. No. 60/351,875.
Flandin, F. et al. "A Differential Scanning Calorimetry Analysis of the Age-Related Changes in the Thermal Stability of Rat Skin Collagen" Biochimica et Biophysica Acta, 791 (1984) 205-211.
Kronick, P. et al.—"The Location of Collagens with Different Thermal Stabilities in Fibrils of Bovine Reticular Dermis"—Connect Tissue Res 2, 1988, pp. 123-134.
LeLous, M. et al.—"Influence of Collagen Denaturation on the Chemorheological Properties of Skin, Assessed by Differential Scanning Calorimetry and Hydrothermal Isometric Tension Measurement"—Biochimica et Biophysica Acta, D 717, 1982, pp. 295-300.
Saal, J.S. et al.—Management of Chronic Discogenic Low Back Pain With a ThermalIntradiscal Catheter—Spine, vol. 25, No. 3, undated, pp. 382-388.
Vangsness Jr., CT et al.—"Collagen Shortening: An Experimental Approach with Heat"—Clinical Orthopaedics and Related Research, No. 337, undated, pp. 267-271.
Wallace, A.L. et al.—"The scientific basis of thermal capsular shrinkage"—Journ. Shoulder Elbow Surg, vol. 9, 2000, pp. 354-360.
Schachar, "Radial Thermokeroplasty", International ophthalmology clinics, 1991, pp. 47-57.
USPTO, International Search Report issued on Jul. 17, 2003 for corresponding International Patent Application No. PCT/US03/02211 with claims searched.
Cox et al., The surgical treatment of atrial fibrillation, I. summary of the current concepts of the mechanisms of atrial flutter and atrial fibrillation, J. Thorac. Cardiovas. Surg. 1991;101:402-5.
Diederich et al., The development of intracavitary ultrasonic applicators for hyperthermia: A design and experimental study, Med. Phys 17(4) Jul./Aug. 1990, pp. 626-634.
Avitall, et al., Physics and Engineering of Transcatheter Cardiac Tissue Ablation, J Am Coll Cardiol 1993; vol. 22, pp. 921-932.
European Patent Office, related patent application EP 03 704 007.8, Communication issued on Sep. 20, 2011 with claims examined, counterpart to PCT/US03/002211, claiming priority to U.S. Appl. No. 60/351,875, pp. 1-10.
Jais et al.; Biatrial Dimensions Relevant to Catheter Ablation, North American Society of Pacing and Electrophysiology, 17th Annual Scientific Sessions Abstract Form, Dec. 1, 1995, Abstract Only.
European Patent Office, related Patent Application No. 03707439, Office Action dated Jul. 8, 2011 (pp. 1-4), with claims (pp. 5-13), counterpart to PCT/US03/01568, claiming priority to U.S. Appl. No. 60/349,207.
WIPO, related PCT Application No. PCT/US2003/01568, International Publication No. WO 2003/059437 dated Jul. 24, 2003, including international search report issued on Oct. 8, 2003, pp. 1-168.

* cited by examiner 3.5mm curvilinear ExDUSTT ex vivo (0°C cooling)

3.5mm curvilinear ExDUSTT ex vivo (RT cooling)

3.5mm curvilinear ExDUSTT ex vivo (0°C cooling)

2.5mm curvilinear ExDUSTT ex vivo (0°C cooling)

2.5mm curvilinear ExDUSTT ex vivo (RT cooling)

Table 3. Thermal Dosimetry Data (Hedgehog Sheep Spine Study)

| Case | Applicator | | T (°C) | $T_{Ave}$ (°C) | $StDev_{Tave}$ (°C) | Dose ($EM_{43°C}$) |
|---|---|---|---|---|---|---|
| C23 | None | Max | | | | |
| Sham | | Min | | | | |
| C34 | HSA#7 | Max | 75.0 | 74.2 | 1.1 | $2.99 \times 10^{10}$ |
| High | | Min | 58.4 | 57.8 | 0.7 | $3.34 \times 10^{5}$ |
| C45 | HSA#6 | Max | 55.4 | 52.8 | 1.0 | $1.07 \times 10^{4}$ |
| Low | | Min | 50.7 | 43.9 | 3.1 | $7.35 \times 10^{1}$ |
| C56 | HSA#5 | Max | | | | |
| Sham | | Min | | | | |

FIG. 57

Table: Hedgehog Sheep Spine Study -- Thermal Dosimetry Data
| Case | Applicator | | T (˚C) | $T_{Ave}$ (˚C) | $StDev_{Tave}$ (˚C) | Dose ($EM_{43˚C}$) |
|---|---|---|---|---|---|---|
| C23 | ISA#D | Max | 71.3 | 70.2 | 0.6 | $1.7 \times 10^9$ |
| High | ISA#11 | Min | 56.3 | 55.7 | 0.6 | 72786 |
| C34 | ISA#D | Max | 49.2 | 48.0 | 0.3 | 347 |
| Low | | Min | 43.0 | 42.3 | 0.7 | 6 |
| C45 | ISA#D | | | | | |
| Sham | | | | | | |
FIG. 60
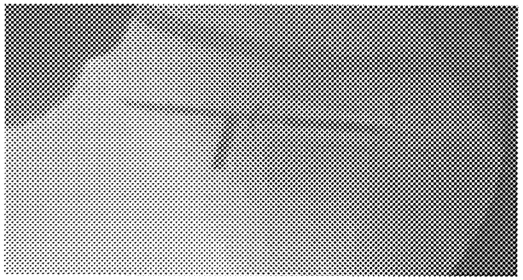
C2/3
High Temp Trial
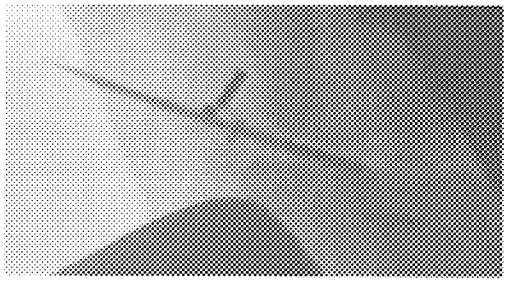
C3/4
Low Temp Trial
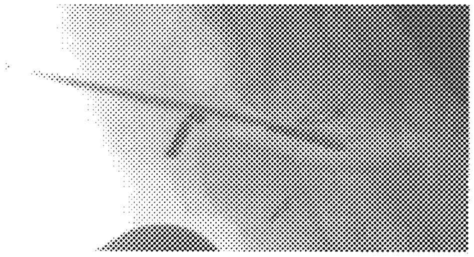
C4/5
Sham
FIG. 61

Table: Hedgehog Sheep Spine Study -- Thermal Dosimetry Data

| Case | Applicator | | T (°C) | $T_{Ave}$ (°C) | $StDev_{Tave}$ (°C) | Dose ($EM_{43°C}$) |
| --- | --- | --- | --- | --- | --- | --- |
| C23 | HSA#6 | Max | 80.0 | 77.4 | 0.9 | $2.54 \times 10^{11}$ |
| High | | Min | 63.6 | 61.6 | 0.9 | $5.05 \times 10^{6}$ |
| C34 | HSA#6 | Max | 53.7 | 53.0 | 0.4 | $1.12 \times 10^{4}$ |
| Low | | Min | 48.2 | 47.8 | 0.1 | $3.12 \times 10^{2}$ |
| C45 | | Max | | | | |
| Sham | | Min | | | | |
| C56 | HSA#6 | Max | 80.2 | 77.5 | 1.2 | $2.91 \times 10^{11}$ |
| High | | Min | 63.6 | 69.3 | 1.1 | $2.72 \times 10^{6}$ |

$T_{ave}$ Average temperature during the 10 minute steady - state treatment period
$StDev_{Tave}$ Standard deviation of temperature during 10 minute steady - state treatment period
Dose Accumulated thermal dose expressed in equivalent minutes at 43°C ($EM_{43°C}$)

FIG. 63

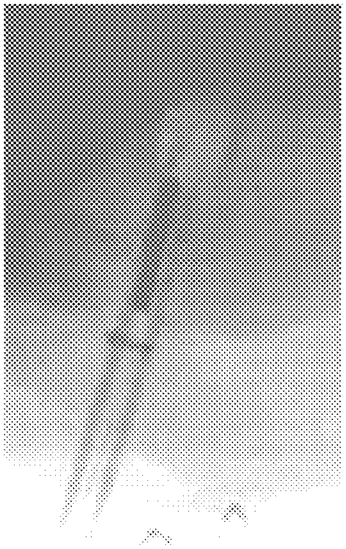
C23High Temp Trial
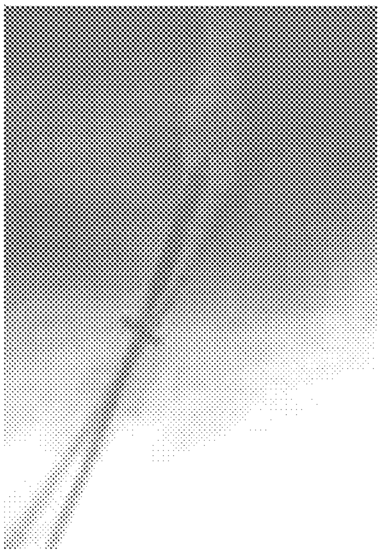
C34 Low Temp Trial
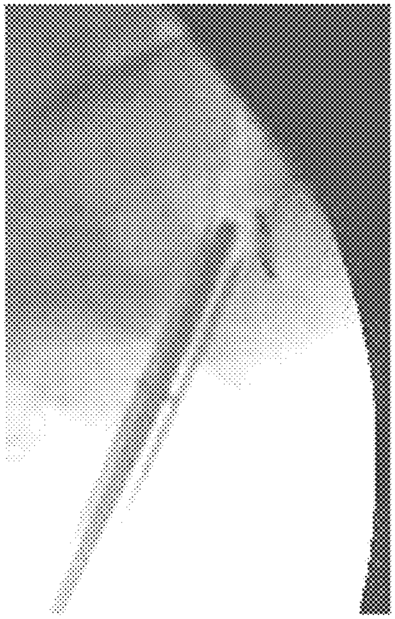
C45 Sham
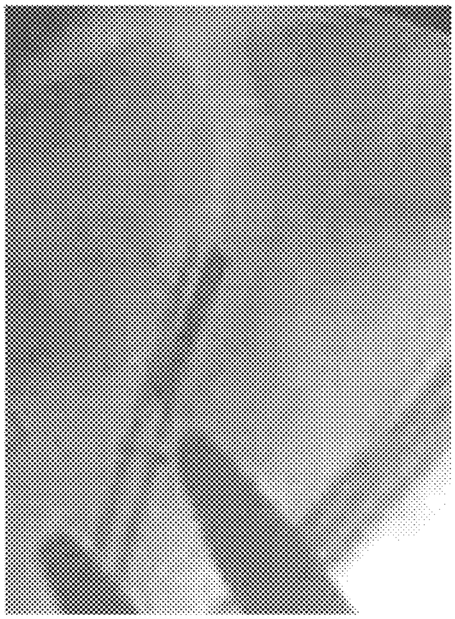
C56 High Temp Trial
FIG. 64

IMPLANTABLE THERMAL TREATMENT METHOD AND APPARATUS

CROSS-REFERENCE TO RELATED APPLICATIONS

This application is a continuation of U.S. patent application Ser. No. 13/792,001 filed on Mar. 9, 2013, incorporated herein by reference in its entirety, now abandoned, which is a continuation of U.S. patent application Ser. No. 12/898,401 filed on Oct. 5, 2010, now U.S. Pat. No. 8,414,509, incorporated herein by reference in its entirety, which is a division of U.S. patent application Ser. No. 10/351,450, filed on Jan. 23, 2003, now U.S. Pat. No. 7,819,826, incorporated herein by reference in its entirety, which claims the benefit of U.S. provisional patent application Ser. No. 60/351,875 filed on Jan. 23, 2002, incorporated herein by reference in its entirety, which claims the benefit of U.S. provisional patent application Ser. No. 60/351,827 filed on Jan. 23, 2002, incorporated herein by reference in its entirety, which claims the benefit of U.S. provisional patent application Ser. No. 60/410,603 filed on Sep. 12, 2002, incorporated herein by reference in its entirety, and which claims the benefit of U.S. provisional patent application Ser. No. 60/411,401 filed on Sep. 16, 2002, incorporated herein by reference in its entirety. Priority is claimed to each of the foregoing applications.

This application is related to PCT International Application No. PCT/US2003/002211, filed on Jan. 23, 2003 and published as WO 03/061256 A2 on Jul. 31, 2003, which publication is incorporated herein by reference in its entirety.

This application is also related to European Patent Application No. European Patent Office No. 03704007.8, which entered the national stage on Nov. 29, 2004 and was granted on Oct. 31, 2012 as EP Patent No. 1503685, incorporated herein by reference in its entirety.

STATEMENT REGARDING FEDERALLY SPONSORED RESEARCH OR DEVELOPMENT

Not Applicable

REFERENCE TO A COMPUTER PROGRAM APPENDIX

Not Applicable

BACKGROUND OF THE INVENTION

1. Field of the Invention

The present invention is an implantable surgical device system and method for delivering therapeutic levels of energy to tissue in a living body. More specifically, it is a long-term implantable system and method for delivering therapeutic levels of ultrasound energy invasively within the body in order to treat chronic disorders associated with skeletal joints. Still more specifically, it is a long-term implant system and method for delivering therapeutic ultrasound energy to spinal joints, such as in particular intervertebral discs or associated bony vertebral structures.

2. Description of the Background Art

For many years, much research and commercial development has been directed toward delivering energy to tissue in order to achieve various desired therapeutic results. Examples of energy modalities previously described for tissue treatment include: electrical current (both DC and AC, e.g. radiofrequency or "RF" current), plasma ion energy, sonic energy (in particular ultrasound), light energy (e.g. laser, infrared or "IR", or ultraviolet or "UV"), microwave induction, and thermal energy (e.g. convection or conduction). Other modalities for treating tissue include without limitation: cryotherapy (cooling tissue to desired levels to affect structure of function), and chemical therapy (delivering chemicals to the tissue to affect the tissue structure of function). Each of these energy delivery and other treatment modalities has been extensively studied and characterized as providing unique benefits, as well as unique issues and concerns, with respect to tissue therapy. Accordingly, many specific energy delivery methods and systems have been disclosed to provide unique benefits for particular intended therapeutic applications.

Various specific tissue responses to energy delivery have also been observed and reported during the course of significant study and characterization. In one regard, tissues or their function may be damaged by energy delivery such as thermal therapy. Examples of previously disclosed, differentiated effects of thermal tissue therapy generally characterized to damage tissue include, without limitation: ablation (which has been defined as either molecular dissociation or by achieving cellular necrosis), coagulation, degranulation, and desiccation. Alternatively, energy delivery in certain particular forms has also been characterized as promoting reproductive stimulation in certain tissues. Certain desired results have been disclosed with respect to intending controlled tissue damage with tissue thermal therapy; other desired results have been disclosed with respect to promoting tissue reproduction with tissue thermal therapy. In any event, because of the pronounced effects observed from tissue energy delivery, it is often desired to control and accurately select the localization of tissue/energy interaction in order to treat only the intended tissue, else normal surrounding tissue is effected with harmful results.

Accordingly, the different energy delivery modalities have been specifically characterized as providing particular benefits and problems versus other modalities with respect to various specific tissues and related medical conditions. Examples of specific medical conditions and related tissue that have been studied and characterized for tissue energy delivery include: tumors such as cancer (e.g. liver, prostate, etc.); vascular aneurysms, malformations, occlusions, and shunts; cardiac arrhythmias; eye disorders; epidermal scarring; wrinkling; and musculo-skeletal injury repair. The nature of the condition to be treated, as well as the anatomy of the area, can have significant impact on the desired result of energy delivery, which directly differentiates between the appropriateness or inappropriateness of each of the different energy delivery modalities for such application (as well as the corresponding particular operating parameters, systems, and methods for delivering such energy).

Depending upon the particular energy modality, various different parameters may be altered to affect the thermal effect in particular tissues, including which type of effect is achieved (e.g. ablation, coagulation, desiccation, etc.), as well as depth or degree of the effect in surrounding tissues. For the purpose of a general understanding, however, known tissue responses to thermal therapies, e.g. effect of changing temperatures to particular levels, have been previously characterized for certain tissues in prior disclosures which are summarized as follows.

As described above, temperature elevation of biological tissues is currently used for outright tissue destruction or to modify tissues to enhance other therapies. Low temperature elevations (41-45° C.) of relatively short duration (<30-60 min) have been disclosed as being associated with cell damage, but generally only to such extent to be repairable and considered non-lethal. In this range, it is believed that heat mediated physiological effects include heat induced acceleration of metabolism or cellular activity, thermal inactivation of enzymes, rupture of cell membranes, and delayed onset of increasing blood flow and vessel permeability. Prior disclosures addressing temperature exposures in excess of 45° C. and/or longer durations have stated that cellular repair mechanisms no longer function due to denaturation of key proteins or can't keep up with the accumulating damage. According to thermal therapy at such temperatures, complete cell death and necrosis have been observed in certain particular tissues to be fully expressed in approximately 3-5 days. Temperature exposures in the 42-45° C. regimen are commonly used for example as an adjuvant to radiation cancer therapy and chemotherapy, and have been considered for enhancing gene therapy and immunotherapy as well. Higher temperature elevations (50+° C.) have been investigated for inducing desirable physical changes in tissue, ranging from applications such as controlled thermal coagulation for "tightening" ligaments and joint capsules, tissue reshaping, and selective tissue thermal coagulation for destroying cancerous and benign tumors. High temperature exposures (50+° C.) are generally believed to produce rather lethal and immediate irreversible denaturation and conformational changes in cellular and structural proteins in various tissues, thereby thermally coagulating such tissues.

In general, heat-induced cell damage or tissue structural changes described above are believed to be attributed to thermal denaturation and aggregation of key protein structures. The accumulation of this thermal damage can be modeled using the Arrhenius rate process equation, which establishes a relationship between rate of thermal damage and the duration and temperature of exposure:

$$\frac{1}{\tau} = A \cdot e^{-\Delta E/RT}, \tag{1}$$

where ΔE is activation energy (J $mol^{-1}$), R is the universal gas constant (8.32 J $mol^{-1}K^{-1}$), A is the rate constant ($s^{-1}$), T is temperature in Kelvin, and 1/τ is rate of thermal damage ($s^{-1}$). Using this expression (Eqn. 1), a relationship can be derived to determine an exposure time ($\tau_2$) and/or temperature elevation ($T_2$) required to produce an equivalent observed biological effect associated with a specified temperature ($T_1$) and time exposure ($\tau_1$). This is the basis of the thermal iso-effect equation as shown below, which is non-linear with respect to temperature exposure and linear with respect to exposure time:

$$\tau_2=\tau_1 e^{(\Delta E/RT_1T_2)(T_1-T_2)}=\tau_1 K^{(T_1-T_2)}, \tag{2}$$

where the parameter K is approximated as constant for typical therapeutic temperature elevations (10-30° C.). Furthermore, extensive in vitro and in vivo studies have demonstrated that ΔE for thermal damage is approximately constant at 140 J $mol^{-1}$ for temperatures greater than 43° C. Thus, the relationship between time and temperature for a given biological effect depends upon activation energy only. Thus, as determined from the hyperthermia biology literature, $K\cong 2$ for $T\geq 43°$ C. and $K\cong 4$-6 for $T<43°$ C. The different values split at approximately 43° C. in order to model the biphasic behavior in the rate response, with faster damage accumulation after a break around 43° C. These values hold for lethal cellular damage, but not coagulation of structural proteins (collagen). Traditionally this iso-effect dose has been used to characterize hyperthermia cancer treatments with a target temperature elevation of 42.5-45° C., and has led to 43° C. becoming the historical reference dose temperature. This forms the basis of the thermal iso-effect dose (TID) equation, which as shown below can be used to calculate thermal dose of a varying temperature exposure over time as an equivalent exposure duration at 43° C. (or other reference temperature). Temperature time history is equated to a thermal dose at a known temperature reference.

$$EM_{43} = \int_0^{t_f} K^{(T-43)}dt = \sum_{t=0}^{t_{final}} \Delta t K^{(T-43)}, \tag{3}$$

where dt is a time step (min) and $EM_{43}$ is thermal dose expressed in equivalent minutes at 43° C.

Various previously published disclosures have verified the Arrhenius model and the iso-effect relationship of different temperature-time exposures for generating trans-epidermal thermal necrosis in skin. Applying the TID analysis, a threshold of approximately 320 $EM_{43}$ (wherein "EM" represents "equivalent minutes" at the given temperature shown in subscript) as found for temperatures between 44-60° C. Thermal dosages between 10-100 $EM_{43}$ have been shown to correlate with improved response to hyperthermia and radiation therapy. For a conservative approach 250 $EM_{43°\ C.}$ is a threshold dose for complete thermal necrosis, where reported values range from 25-240 EM43° C. for brain and muscle tissue, respectively.

In addition, thermal coagulation or coagulation necrosis have been disclosed to occur in tissues exposed to temperatures greater than approximately 55° C. for a duration of minutes, in particular respect to collagen in certain structures studied. Thermal coagulation of soft tissues generally takes place only for temperatures in excess of 50° C. Numerous investigators have validated the "TID" (or "temperature iso-dose") concept for predicting lesions using 240-340 EM 43° C. as a threshold dose and critical temperatures of 53-54° C. for coagulating muscle.

Therapeutic Energy Delivery for Spinal Disorders

Spinal disorders have been the topic of significant study and commercial development for therapeutic energy delivery. In particular, various specific conditions that have been studied with respect to particular modes of therapeutic energy delivery.

Of particular interest has been chronic lower back pain. Chronic low back pain is a significant health and economic problem in the United States, being the most costly form of disability in the industrial setting. For a substantial number of these patients the intervertebral disc is considered the principal pain generator. Traditionally, patients who fail conservative therapy have few treatment options beside discectomy or fusion, either of which can result in significant morbidity and variable outcomes. Recent efforts have been directed toward investigating thermal therapy for providing a healing effect on collagenous tissues, and therefore this modality has been incorporated into several minimally invasive back pain treatments.

Early orthopedic use of high temperature heat therapy was to manage shoulder instability. In this application, the shoulder capsule is treated with laser or radio-frequency (RF) thermal energy to temperatures typically in the range of 70 to 80° C. This treatment has been disclosed to stabilize the joint by inducing tissue contraction. Such treatment also has been disclosed to result in an acute decrease in stiffness (e.g. as much as 50%) that may be recovered due to biologic remodeling. However, the long-term benefits of this treatment have been questioned since the collagenous tissue may re-lengthen over time.

The contraction associated with thermal therapy, which can reach as high as 50% along the fiber direction in the shoulder capsule, has been correlated with thermal denaturation. Thermal denaturation is an endothermic process in which the collagen triple helix unwinds after a critical activation energy is reached. Differential scanning calorimetry (DSC) is a technique to measure both the denaturation temperature ($T_m$—the peak temperature corresponding to this critical activation energy) and the total enthalpy of denaturation (ΔH—the total energy required to fully denature the collagen). This technique can be used to correlate thermal exposure with the resulting degree of denaturation for a specific collagenous tissue, and thus to guide the development of an optimal thermal dose.

Intradiscal electrothermal therapy (IDET) has been recently introduced as a minimally invasive, non-operative therapy in which a temperature elevation is applied in order to treat discogenic low back pain. In this procedure, a temporary catheter containing a 5 cm long resistive-wire heating coil is introduced percutaneously into the disc under fluoroscopic guidance. The internal temperature of the device is then raised from 65° C. to 90° C. over a course of 16 minutes. This procedure is intended to produce temperatures sufficient to contract annular collagen and ablate annular nociceptors. A controlled, 12 month trial of IDET on a relatively small patient population (36 individuals) demonstrated some relief of back pain in 60% of patients and total relief in 23%. A two-year follow-up study of 58 patients was disclosed to result in clinically significant improvement in pain, physical function, and quality of life. While these results have been considered by some to be promising, prospective placebo-controlled trials are lacking, and the therapeutic mechanisms of thermal therapy are unknown. Proposed therapeutic mechanisms of such technique have included: 1) collagen denaturation, causing annular stiffening, and tissue remodeling; 2) annular de-innervation; and 3) ablation of cytokine-producing cells. Due to mechanistic uncertainty, treatment optimization and patient selection are generally empirically based.

The effect of heat on collagen denaturation and biomechanical properties has been investigated in various tissues: knee and shoulder capsule, tendon, and chordae tendineae. In general, at least one prior disclosure reports that significant denaturation and shrinkage occurred in tissue treated at 65° C. and above for 1-5 minutes. However, given that the annular architecture of intervertebral discs is quite different from these other tissues it is has not been previously made clear that prior results can be directly extrapolated to the intervertebral disc.

Further more detailed background information related to various aspects of thermal tissue therapy and/or chronic back pain is variously disclosed in the following publications: Amonoo-Kuofi, H. S., 1991, "Morphometric changes in the heights and anteroposterior diameters of the lumbar intervertebral discs with age." J Anat 159-68;

Arnoczky, S. P. and Aksan, A., 2001, "Thermal modification of connective tissues: basic science considerations and clinical implications." Instr Course Lect 3-11; Chen, S. S., Wright, N. T. and Humphrey, J. D., 1997, "Heat-induced changes in the mechanics of a collagenous tissue: isothermal free shrinkage." J Biomech Eng 4, 372-8; Chen, S. S., Wright, N. T. and Humphrey, J. D., 1998, "Heat-induced changes in the mechanics of a collagenous tissue: isothermal, isotonic shrinkage." J Biomech Eng 3, 382-8; Dewey, W. C., 1994, "Arrhenius relationships from the molecule and cell to the clinic." Int J Hyperthermia 4, 457-83; Flandin, F., Buffevant, C. and Herbage, D., 1984, "A differential scanning calorimetry analysis of the age-related changes in the thermal stability of rat skin collagen." Biochim Biophys Acta 2, 205-11; Gerber, A. and Warner, J. J., 2002, "Thermal capsulorrhaphy to treat shoulder instability." Clin Orthop 400, 105-16; Hall, B. K., 1986, "The role of movement and tissue interactions in the development and growth of bone and secondary cartilage in the clavicle of the embryonic chick." J Embryol Exp Morphol 133-52; Hayashi, K. and Markel, M. D., 2001, "Thermal capsulorrhaphy treatment of shoulder instability: basic science." Clin Orthop 390, 59-72; Hayashi, K., et al., 2000, "The mechanism of joint capsule thermal modification in an in-vitro sheep model." Clin Orthop 370, 236-49; Hayashi, K., et al., 1997, "The effect of thermal heating on the length and histologic properties of the glenohumeral joint capsule." Am J Sports Med 1, 107-12; Heary, R. F., 2001, "Intradiscal electrothermal annuloplasty: the IDET procedure." J Spinal Disord 4, 353-60; Hecht, P., et al., 1999, "Monopolar radiofrequency energy effects on joint capsular tissue: potential treatment for joint instability. An in vivo mechanical, morphological, and biochemical study using an ovine model." Am J Sports Med 6, 761-71; Karasek, M. and Bogduk, N., 2000, "Twelve-month follow-up of a controlled trial of intradiscal thermal anuloplasty for back pain due to internal disc disruption." Spine 20, 2601-7; Kronick, P., et al., 1988, "The locations of collagens with different thermal stabilities in fibrils of bovine reticular dermis." Connect Tissue Res 2, 123-34; Le Lous, M., et al. 1982. "Influence of collagen denaturation on the chemorheological properties of skin, assessed by differential scanning calorimetry and hydrothermal isometric tension measurement." Biochim Biophys Acta 2, 295-300; Lopez, M. J., et al., 2000, "Effects of monopolar radiofrequency energy on ovine joint capsular mechanical properties." Clin Orthop 374, 286-97; Miles, C. A. and Ghelashvili, M. 1999, "Polymer-in-a-box mechanism for the thermal stabilization of collagen molecules in fibers." Biophys J 6, 3243-52; Naseef, G. S., et al., 1997, "The thermal properties of bovine joint capsule. The basic science of laser- and radiofrequency-induced capsular shrinkage." Am J Sports Med 5, 670-4; Nieminen, M. T., et al., 2000, "Quantitative MR microscopy of enzymatically degraded articular cartilage." Magn Reson Med 5, 676-81; (Nrc/Im), N. R. C. A. I. O. M. (2001). "*Musculoskeletal Disorders and the workplace: low back and upper extremities.*" Washington D.C., National Academy Press; Saal, J. A. and Saal, J. S., 2002, "Intradiscal electrothermal treatment for chronic discogenic low back pain: prospective outcome study with a minimum 2-year follow-up." Spine 9, 966-73; discussion 973-4; Saal, J. S. and Saal, J. A., 2000, "Management of chronic discogenic low back pain with a thermal intradiscal catheter. A preliminary report." Spine 3, 382-8; Schachar, R. A., 1991, "Radial thermokeratoplasty. Int Ophthalmol" Clin 1, 47-57; Schaefer, S. L., et al., 1997, "Tissue shrinkage with the holmium:yttrium aluminum garnet laser. A postoperative assessment of tissue length, stiffness, and structure." Am J Sports Med 6, 841-8; Schwarzer, A. C., et al., 1995, "The prevalence and clinical features of internal disc disruption in patients with chronic low back pain." Spine 17, 1878-83; Urban, J. P. and Mcmullin, J. F., 1985, "Swelling pressure of the intervertebral disc: influence of proteoglycan and collagen contents." Biorheology 2, 145-57; Vangsness, C. T., Jr., et al., 1997, "Collagen shortening. An experimental approach with heat." Clin Orthop 337, 267-71; Vujaskovic, Z., et al., 1994, "Effects of intraoperative hyperthermia on peripheral nerves: neurological and electrophysiological studies." Int J Hyperthermia 1, 41-9; Wallace, A. L., et al., 2000, "The scientific basis of thermal capsular shrinkage." J Shoulder Elbow Surg 4, 354-60; and Wallace, A. L., et al., 2002, "Creep behavior of a rabbit model of ligament laxity after electrothermal shrinkage in vivo." Am J Sports Med 1, 98-102. The disclosures of these references are herein incorporated in their entirety by reference thereto.

Chronic lower back pain (e.g. discogenic lumbar pain) and related motor nerve deficit is typically due to damaged or herniated vertebral discs which either directly impinge on surrounding nerves or cause irritating inflammation. Traditional treatment options include surgery, anti-inflammatory drugs, physical therapy, etc., with surgery typically the last option. Due to difficulty of surgical procedure, complications and time of recovery, alternative procedures have been investigated. Recently, intradiscal thermal therapy has been introduced as a minimally-invasive alternative in the treatment of various spinal disorders such as chronic low back pain and otherwise disorders related to intervertebral disc abnormalities.

In particular, several different systems and methods have been disclosed for treating various abnormal conditions associated with intervertebral discs specifically by delivering electrical current in the RF range during invasive treatment procedures in and around the disc within the body. Other previously disclosed examples intended to invasively deliver therapeutic levels of energy in order to treat various spinal disorders include delivery of plasma ion energy (e.g. CoblationR from Arthrocare, Inc.), laser light energy, or thermal energy from conductive heating elements (e.g. the SpineCATH DEC procedure, commercially available from Oratec Interventions, introduced above). At least one other prior disclosure is intended to deliver heated thermoplastic material to allow it to flow into and then set upon cooling within the nucleus of an intervertebral disc in order to replace the nucleus pulposus.

Further more detailed examples of energy delivery systems and methods such as of the types just described, that are intended to provide invasive therapy to treat various conditions associated with intervertebral disc disorders are variously disclosed in the following issued U.S. Patents: U.S. Pat. No. 4,959,063 to Kojima; U.S. Pat. No. 6,264,650 to Hovda et al.; U.S. Pat. No. 6,264,659 to Ross et al. Examples are also disclosed in the following published U.S. patent application: US 2001/0029370 to Hodva et al., now U.S. Pat. No. 6,464,695. Other examples are disclosed in the following published international patent applications: WO 00/49978 to Guagliano et al.; WO 00/71043 to Hovda et al.; WO 01/26570 to Alleyne et al. Additional disclosure is provided in the following published reference: Diederich C J, Nau W H, Kleinstueck F, Lotz J, Bradford D (2001) "IDTT Therapy in Cadaveric Lumbar Spine: Temperature and thermal dose distributions, Thermal Treatment of Tissue: Energy Delivery and Assessment," Thomas P. Ryan, Editor, Proceedings of SPIE Vol. 4247:104-108. The disclosures of all these references provided in this paragraph are herein incorporated in their entirety by reference thereto.

Ultrasound energy delivery and the effects of such energy on various different tissue structures has been the topic of significant recent study. The particular benefits of ultrasound delivery have been substantially well characterized, in particular with respect to different types of tissues as well as different ultrasound energy deposition modes. Many different medical device systems and methods have been disclosed for delivering therapeutic levels of ultrasound to tissues to treat wide varieties of disorders, including for example arterial blockages, cardiac arrhythmias, and cancerous tumors. Such disclosures generally intend to "ablate" targeted tissues in order to achieve a desired result associated with such particular conditions, wherein the desired response in the particular tissues, and the ultrasound delivery systems and methods of operation necessary for the corresponding energy deposition modalities, may vary substantially between specific such "ultrasound ablation" systems and methods.

Further more detailed examples of ultrasound delivery systems and methods such as of the type just described are disclosed in the following issued U.S. patents which are incorporated herein by reference: U.S. Pat. No. 5,295,484 to Marcus et al.; U.S. Pat. No. 5,620,479 to Diederich; U.S. Pat. No. 5,630,837 to Crowley; U.S. Pat. No. 5,733,280 to Sherman et al.; U.S. Pat. No. 6,012,457 to Lesh; U.S. Pat. No. 6,024,740 to Lesh et al.; U.S. Pat. No. 6,117,101 to Diederich et al.; U.S. Pat. No. 6,164,283 to Lesh; U.S. Pat. No. 6,245,064 to Lesh et al.; U.S. Pat. No. 6,254,599 to Lesh et al.; and U.S. Pat. No. 6,305,378 to Lesh et al. Other examples are disclosed in the following published foreign patent applications which are incorporated herein by reference: WO 00/56237 to Maguire et al.; WO 00/67648 to Maguire et al.; WO 00/67656 to Maguire et al.; WO 99/44519 to Langberg et al.

In addition, ultrasound enhanced drug delivery into tissues, e.g. to increase dispersion, permeability, or cellular uptake of therapeutic compounds such as drugs, has been well characterized and disclosed in many different specific forms.

Further more detailed examples of ultrasound energy delivery systems and methods such as those just described are disclosed in the following U.S. Patent References: U.S. Pat. No. 5,725,494 to Brisken; U.S. Pat. No. 5,728,062 to Brisken; U.S. Pat. No. 5,735,811 to Brisken; U.S. Pat. No. 5,846,218 to Brisken et al.; U.S. Pat. No. 5,931,805 to Brisken; U.S. Pat. No. 5,997,497 to Nita et al.; U.S. Pat. No. 6,210,393 to Brisken; U.S. Pat. No. 6,221,038 to Brisken; U.S. Pat. No. 6,228,046 to Brisken; U.S. Pat. No. 6,287,272 to Brisken et al.; and U.S. Pat. No. 6,296,619 to Brisken et al. The disclosures of these references are herein incorporated in their entirety by reference thereto.

Additional previously disclosed examples for ultrasound energy delivery systems and methods are intended to treat disorders associated with the spine in general, and in some regards of the intervertebral disc in particular. However, these disclosed systems are generally adapted to treat such disorders chronically from outside of the body, such as for example via transducers coupled to a brace worn externally by a patient. Therefore locally densified US energy is not achieved selectively within the tissues associated with such disorders invasively within the body. At least one further disclosure, however, proposes delivering focused ultrasound energy from outside the body for the intended purpose of treating intervertebral disc disorders, in particular with respect to degenerating the nucleus pulposus to reduce the pressure within the disc and thus onto the adjacent spinal cord. However, the ability to actually achieve such targeted energy delivery at highly localized tissue regions associated with such discs, and to accurately control tissue temperature to achieve desired results, without substantially affecting surrounding tissues has not been yet confirmed or taught.

Further more detailed examples of such systems and methods intended to treat spinal disorders with ultrasound energy from outside of the body are variously disclosed in the following issued U.S. Patents: U.S. Pat. No. 5,762,616 to Talish; U.S. Pat. No. 6,254,553 to Lidgren et al. Other examples are disclosed in the following published international patent applications: WO 97/33649 to Talish; WO 99/19025 to Urgovich et al.; and WO 99/48621 to Cornejo et al. The disclosures of these references are herein incorporated in their entirety by reference thereto.

Exposure of soft and hard tissue, including the spine and joints, to varied degrees of heat or other energy delivery can provide varied therapeutic effects. For example, heat at high temperatures and thermal doses can shrink tissues, change the structural matrix, and generate physiological changes and/or kill cells. Heat at low temperatures and can generate permeability changes or changes in the cellular transport/metabolism that increase effectiveness or deposition of certain pharmaceutical agents.

Heat can be provided using ultrasound (US), radio frequency (RF), laser, and the like, using invasive or non-invasive application techniques. For example, in order to treat internally embedded sensitized nerves or cells making inflammatory factors, invasive techniques are preferred so that the heat source can be placed in close proximity to the target tissue. This can be accomplished using conventional surgical techniques, where the patient is opened, and a heat source is inserted directly (e.g., using a directly implantable device such as described in U.S. Pat. No. 5,620,497, incorporated herein by reference), or indirectly through a catheter or other delivery device. When the procedure is complete, the heat source is removed and the patient is closed.

However, despite the many benefits of temporary devices and their acutely delivered treatments, a single treatment or a contemporaneous series of discrete treatments in those previous examples may not provide adequate results in many cases. In one regard, the ability to treat many chronic ailments is limited in the setting of an acute invasion into the body required by temporary devices. Therefore, it may be necessary to repeat the treatment at a later date if a single application is not sufficient for the ailment. Accordingly, longer term implantable devices and treatments are preferred for many medical therapies.

In this regard, the term "temporary" as herein used to describe certain medical devices, systems, or methods, including with respect to implants, is intended to mean adapted for acute use, such as in a hospital or outpatient surgical room or suite, over a relatively short period of time. In general, patients do not carry temporary devices implanted within them away from a healthcare facility—they are used in an acute setting typically accompanied by observation by healthcare personnel (e.g. such observation by a healthcare provided may be either continuous, or for longer temporary treatments may be sporadic, or may simply initiate a procedure via an implant and return to remove it after a time specified or an endpoint parameter is met). The time period by which temporary medical devices are typically left indwelling within the body is usually on the order of minutes, or possibly hours, though in some extreme cases some temporary medical devices can be left indwelling for as much as 1-5 days (though again typically under professional care, such as during a hospital stay). Temporary medical devices also often include portions of the device extending externally of the patient's body, such as for example catheters or leads that interface with other cooperating hardware such as actuators or diagnostic systems.

In contrast, the terms "permanent implant" are herein intended to mean a medical device implant that is intended for long-term implantation for chronic therapy or use. In such cases, patient's carry such implant indwelling within their bodies during their daily lives. Typically, these permanent implants are intended for indefinite periods and associated with chronic conditions ameliorated or diminished by the permanent implant, but typically not cured upon removal of the permanent implant. As such, they are not generally intended to be removed, though often may require removal, such as for replacement due to limitation of the lifespan of the implant itself, or for example changing condition of the patient. Such changing conditions may include, for example and without limitation: growth with respect to pediatric patients, other changes in physique, changes in condition being treated or otherwise with respect to the environment and/or needs underlying the implant's presence.)

The terms "semi-permanent implant" are herein intended to mean implants that are intended for implantation over a period that lasts longer than considered under an "acute" setting, e.g. longer than typically provided for under the care of a healthcare provider and longer than most "temporary" medical devices such as temporary implants, though usually over a shorter period than most "permanent implants". Semi-permanent implants are typically carried indwelling within the patient away from the healthcare facility and out from under the direct observation of a professional caregiver. They most usually remain indwelling during the patient's daily living for a period of days, possibly weeks, and possibly in some cases even years. These implants are generally intended to be carried within the patient for a limited period of time, however, and then to be removed.

Moreover, the terms "long-term" where herein used to describe an implantable device, or related system or procedure, include both permanent and semi-permanent implants unless otherwise specifically indicated or would be otherwise readily apparent to one of ordinary skill. Moreover, the use of the terms "permanent implant" generally contemplate similar application with respect to "semi-permanent implants" unless otherwise specifically indicated or readily apparent to be exclusive to one of ordinary skill.

Various medical device systems and methods have been disclosed related to chronic treatment of various medical disorders by delivering energy to tissue from permanent or semi-permanent implants. Many such prior disclosures relate specifically to providing implantable electrical energy delivery devices, and in particular relation to spinal cord stimulation. Many of such devices are intended to be long-term implants.

One example of a disclosed method of using a spinal cord stimulation lead involves implanting the lead in the epidural space and includes an elongate lead paddle located at the distal end of the lead. An array of electrodes is located on the lead paddle. The array has at least three columns of electrodes and includes a column having at least one electrode positioned substantially over the midline of the lead paddle, a column of at least one electrode positioned laterally of the midline on one side thereof, and a column of at least one electrode positioned laterally of the midline on the other side thereof. At least one of the columns within the array has more than one electrode. Each of the electrodes is interconnected by a conductor to a respective terminal at the proximal end of the lead. The lead is implanted such that the midline of the lead paddle is positioned over the midline of the spinal cord. Each electrode is independently selectable such that the spinal cord may be stimulated unilaterally or bilaterally.

Another example of an apparatus for multi-channel transverse epidural spinal cord stimulation uses a multi-channel pulse generator driving a plurality of electrodes mounted near the distal end of a lead. These electrodes are mounted in one or more lines, generally perpendicular to a lead axis, and having a planar surface along one surface of the lead.

The lead is implanted adjacent to the spinal cord dura mater with the electrodes transverse and facing the spinal cord. Pulses generated by the pulse generator for each channel are normally simultaneous, of equal amplitude and of equal duration, however the pulse generator is arranged such that pulses for each channel can selectably alternate in time, can selectably be of unequal amplitude, or both. The changes in pulse timing and magnitude permit shifting the electrical stimulation field and the resulting paresthesia pattern after installation to accommodate improper lead placement or postoperative dislocation and to minimize unwanted motor responses.

A wide variety of spinal stimulation energy delivery systems and methods have been disclosed, generally with respect to providing electrical current to cause a nervous stimulation to produces a change in some innervated bodily function. For example, at least one disclosure involves an apparatus providing timed electrical stimulus pulses in the fluid of the sacral canal to conduct electrical stimulus to the spinal cord to stimulate miturition and certain muscles in paraplegic mammals, e.g. to evacuate the bladder.

In another example, a method for electrical spinal cord stimulation was disclosed for treating orgasmic dysfunction. Stimulating electrodes are placed in the spinal canal via a needle inserted between the appropriate vertebrae in parallel with the spinal cord. The electrodes are connected to a power source. Through variable transmission of electrical signals a patient suffering from orgasmic dysfunction may once again achieve orgasm.

Long-term, electrical spinal cord stimulation has been widely investigated for treating various types of pain, such as back pain in particular, as well as other types of pain such as angina.

According to at least one example, a facet joint pain relief method and apparatus is disclosed that depolarizes the medial branch of the spinal nerve associated with a painful facet joint so as to block pain impulses from reaching the spinal cord. The preferred apparatus includes a neurostimulator and two or more electrodes which carry electrical pulses to the target nerve or nerves. The impulses are intense enough to cause depolarization of a given medial branch and its articular branches, but not so large as to cause depolarization of the spinal cord itself. The stimulator in one regard is physically small and battery operated, facilitating implantation underneath the skin. The stimulator includes a controller and appropriate electronics operative to generate electrical impulses tailored to an individual's need for appropriate pain relief in terms of pulse frequency, pulse width, and pulse amplitude. In an alternative embodiment, the stimulator further includes electrodes and electrical circuitry operative to monitor myoelectrical activity generated by the surrounding muscles and modulate the impulses generated by the stimulator to meet the demands of the individual's activity and/or prolong battery life.

Another example provides a method and apparatus for providing feedback to spinal cord stimulation for angina treatment. Techniques for cardiac monitoring and angina pectoris treatment using a cardiac condition detector and stimulating electrode are disclosed. The detector and electrode are implanted, and angina is relieved by transmitting electrical pulses to the stimulating electrode while the patient is giving an indication of an ischemic event that otherwise would be indicated by the angina.

A variety of mechanisms have been previously disclosed that are intended to provide paths to and into bony structures of the spine for delivering a spinal implant there. Many disclosures have intended to address maintaining position of electrodes during electrical coupling to tissue. Several disclosures provide techniques intended for implanting a lead with therapy delivery elements, such as electrodes or drug delivery ports, within vertebral or cranial bone so as to maintain those elements in a fixed position relative to a desired treatment site. Additional techniques have been intended for non-invasively positioning and re-positioning the therapy delivery elements after implantation into such bone cavities. Further technique is disclosed using a position control mechanism and/or a position controller for adjusting in situ the position of the therapy delivery elements relative to the targeted tissue. The therapy delivery elements may be positioned laterally in any direction relative to the target, or toward or away from the treatment site. These techniques have been particularly intended for use with electrical stimulation or drug infusion to the targeted tissue.

Another disclosure provides an apparatus for providing a therapy in or through one or more trans-sacral axial instrumentation/fusion (TASIF) bore through vertebral bodies in general alignment with visualized, anterior or posterior axial instrumentation/fusion line (AAIFL or PAIFL) in a minimally invasive, low trauma manner and providing a therapy to the spine employing the trans-sacral axial bore. Anterior or posterior starting positions aligned with the AAIFL or PAIFL are accessed through respective anterior and posterior tracts. Curved or relatively straight anterior and curved posterior TASIF bores are formed from the anterior and posterior starting positions. The therapies performed through the TASIF bores include ductoscopy, full and partial discectomy, vertebroplasty, balloon-assisted vertebroplasty, drug delivery, electrical stimulation and various forms of spinal disc cavity augmentation, spinal disc replacement, fusion of spinal motion segments, and radioactive seeds implantation. Axial spinal implants and bone growth materials can also be placed in the TASIF bores.

Various disclosures have also been intended to provide feedback control for either adjusting the positioning of therapy delivery elements or other aspects of therapy, and in particular relation to spine therapy delivery elements.

In one group of examples, an apparatus and technique for electrical stimulation of the central or peripheral nervous system based upon changes in the position of a patient is disclosed. A position sensor is chronically implanted in the patient, such as in one specific example a mercury switch position sensor which indicates whether a patient is erect or supine. This position information is used by a chronically implanted pulse generator to vary the stimulation intensity. The intensity may be controlled by changes in pulse amplitude, pulse width, number of pulses per second, burst frequency, number of pulses per burst, electrode polarity, or other convenient parameter which accomplishes the particular medical purpose within an application. The output of the chronically implanted pulse generator is applied to the spinal cord, peripheral nerves, and/or targets in the brain with leads and electrodes in a manner consistent with the given medical need. Such stimulation is useful in the treatment of chronic intractable pain, hemodynamic insufficiency resulting in angina, peripheral vascular disease, cerebral vascular disease, various movement disorders, and bowel and bladder control.

Another example is directed toward living tissue stimulation and recording techniques with local control of active sites. Implantable electrodes are adapted to interact with electrically excitable tissue by an implantable, programmable controller that receives power from a main cable and data from a data conductor that identifies the stimulation and recording electrodes to be activated. The implantable controller enables electrical signals to be transmitted between a distal site of power generation and a selected subset of multiple electrodes with a minimum number of conductor wires.

Long-term electrical stimulus, such as via long-term implants, has also been investigated for promoting bone growth, in particular relation to the spine, as follows.

According to one general example, two electrodes are implanted into the tissue near the base site for bone growth. The electrodes are coupled to a bone growth stimulator which generates an alternating current that stimulates bone growth. Other examples using electrical stimulus to promote bone growth abound, in particular with respect to bony structures and implants related to the spine.

In one additional example, an implantable growth tissue stimulator and method is disclosed with a hand-held programmer/monitor for programming and monitoring an implantable tissue growth stimulator. The stimulator includes circuitry for implementing selected operations in response to a down-link signal transmitted by the programmer/monitor, various circuits such as control circuit and transmit/receive circuit is used for transmitting up-link and down-link signals to and from the implantable bone growth stimulator.

According to another example a preformed extendable mesh cathode for an implantable bone growth stimulator has been disclosed. An electrical signal generator is provided connected with an anode and a prefabricated wire mesh cathode that is extendable to at least twice its preformed initial length. The cathode in a preferred embodiment includes a single chain of conductive wire links formed as alternating loops and twists of two strands of monofilament titanium wire.

Still another example apparatus has been disclosed for the delivery of electric current for interbody spinal arthrodesis. Electrical current is delivered to an implant surgically implanted within the intervertebral space between two adjacent vertebrae of the spine to promote bone growth and the fusion process to areas adjacent to the implant. The implant is self-contained with a surgically implantable, renewable power supply and related control circuitry for delivering electrical current directly to the implant and thus directly to the area in which the promotion of bone growth is desired. The desired areas of bone growth promotion are intended to be controlled by conducting negative charge only to the desired location of promotion.

A further disclosed example provides direct current stimulation of spinal interbody fixation device has also been disclosed. A spinal fusion stimulator has an interbody fustion cage or other interbody fixation device adapted to be implanted in the intervertebral disc space of a patient's spine, the interbody fusion cage having a hollow body with internal and external conductive surfaces. The stimulator includes a constant current generator connected to the interbody fusion cage and set to provide a DC current effective to produce a surface current density of at least 1 uA/cm$^2$ in the interbody fusion cage when implanted.

Additional long-term electrical delivery implant devices and related methods have been disclosed for other intended uses related for example to neural stimulation, nerve regeneration, and muscle stimulation.

At least one published example provides for nerve regeneration by way of electrical stimulus as follows. In vivo mammalian nerve regeneration of a damaged nerve is attempted by using an electric current through the damaged nerve while the nerve ends are abutted against one another, sutured together or spaced apart from each other. The apparatus is intended to be implantable in a human body so that the electric current can be maintained for an extended period of time to produce regeneration of the damaged nerve.

Various disclosures have also intended to provide percutaneous intramuscular stimulation electrodes, such as for treating shoulder dysfunction in patients who have suffered disruption of the central nervous system such as a stroke, traumatic brain injury, spinal cord injury, or cerebral palsey. An external microprocessor based multi-channel stimulation pulse train generator is used for generating select electrical stimulation pulse train signals. In another example, a closed-loop, implanted-sensor (e.g. force sensor), functional electrical stimulation system for partial restoration of motor functions is provided.

Further more detailed examples of devices, systems, and methods similar to those described above, such as with respect to long-term energy delivery implants, spinal therapy implants, or related devices and methods providing additionally helpful understanding, are variously disclosed in one or more of the following issued U.S. Patents: U.S. Pat. No. 4,569,351 to Tang; U.S. Pat. No. 4,750,499 to Hoffer; U.S. Pat. No. 4,774,967 to Zanakis et al.; U.S. Pat. No. 5,031,618 to Mullett; U.S. Pat. No. 5,282,468 to Klepinski; U.S. Pat. No. 5,342,409 to Mullett; U.S. Pat. No. 5,417,719 to Hull et al.; U.S. Pat. No. 5,441,527 to Erickson et al.; U.S. Pat. No. 5,501,703 to Holsheimer et al.; U.S. Pat. No. 5,565,005 to Erickson et al.; U.S. Pat. No. 5,643,330 to Holsheimer et al.; U.S. Pat. No. 5,766,231 to Erickson et al.; U.S. Pat. No. 5,824,021 to Rise; U.S. Pat. No. 6,014,588 to Fitz; U.S. Pat. No. 6,038,480 to Hrdlicka et al.; U.S. Pat. No. 6,112,122 to Schwardt et al.; U.S. Pat. No. 6,120,502 to Michelson; U.S. Pat. No. 6,169,924 to Meloy et al.; U.S. Pat. No. 6,171,239 to Humphrey; U.S. Pat. No. 6,270,498 to Michelson; U.S. Pat. No. 6,292,699 to Simon et al.; U.S. Pat. No. 6,319,241 to King et al.; and U.S. Pat. No. 6,436,098 to Michelson. Additional devices, systems, and methods are disclosed in the following U.S. Patent Application Publications: US 2001/0053885 to Gielen et al., now U.S. Pat. No. 6,795,737; 2002/0111661; 2003/0014088 to Fang et al. now U.S. Pat. No. 6,485,271. Additional examples are also disclosed in the following PCT Patent Application Publications: WO 99/56818 to Racz; and WO 00/78389 to Fitz. Another device is shown in the following U.S. Design Patent: Des. 361,555 to Erickson et al. The disclosures of these references listed variously throughout this paragraph are herein incorporated in their entirety by reference thereto.

Notwithstanding substantial benefits gained by many of the long-term implantable devices and chronic therapy methods previously described, each generally has respective limitations and shortcomings concomitant with their specified indications for use and with respect to certain therapies to which they are not generally applicable.

For example, the various disclosed not generally adapted to provide thermal therapy the many electrical therapy devices described are specially adapted to provide electrical nervous stimulus, and. Even to the extent thermal therapy may or would be delivered, however, such electrical devices and methods have shortcomings in their ability to deliver adequate thermal therapy to tissue as required, in particular in and around the spine, and in particular in a manner that penetrates structures sufficient to provide relatively deep heating from the energy delivery element, and/or that is controlled, directed, or focused for highly localized thermal treatment. Moreover, the various previously disclosed references do not adequately accommodate the need to control and isolate temperatures if thermal therapy were to be delivered, which is highly advantageous in particular during thermal treatment of structures in and around the spinal cord.

Still further, none of the previous disclosures noted above provide adequate devices and/or methods for controlling long-term thermal therapy of various tissues associated with skeletal joints, again in particular the spine, in order to achieve isolated, desired results such as thermal remodeling of tissue support structures (in particular stressed structures such as collagenous tissues of intervertebral discs), controlled cellular necrosis (including either in combination with or exclusive of tissue remodeling), or cellular regeneration or stimulation, or enhanced drug delivery.

At least two ultrasound systems and methods have been disclosed that are intended to provide ultrasound energy delivery to tissue via long-term implantable devices in order to treat chronic medical conditions such as of the types generally introduced above with primary respect to electrical energy delivery.

For example, ultrasonic techniques have been disclosed for using ultrasonic imaging to assist in neurostimulator control wherein the primary therapeutic energy delivery is electrical. A lead adapted to be implanted adjacent to a spinal cord located within a spinal column of a vertebrate in order to facilitate stimulation of the spinal cord or adjacent tissue. An ultrasonic transmitter/receiver produces an ultrasonic sound wave that creates ultrasonic echo waves reflected from a predetermined portion of the spinal cord and generates a distance signal related to the distance between the transducer/receiver and the predetermined portion of the spinal cord. The distance signal is used to adjust the amplitude of an electrical stimulation signal that stimulates the spinal cord or adjacent tissue so that the value of the stimulation signal tends to remain uniform in spite of changes in the relative distance between the transducer/receiver and the predetermined portion of the spinal cord. Accordingly, such use of ultrasound is as a diagnostic tool, and generally not therapeutic US energy delivery.

In another example, an apparatus and method that stimulates with ultrasound the growth of a tissue or produces an image at a site within a patient is disclosed. A housing may be subcutaneously implanted within the patient such that the ultrasound is directed toward the site. A generator disposed within the housing produces a signal, which a transducer converts into ultrasound. The transducer is partially disposed within the housing. The device may include an imaging circuit for processing ultrasound echoes received by the transducer to generate images of the tissue at the site. A remote control may be used to control the device while it is implanted within the patient.

Further more detailed examples of ultrasound devices and methods related to neurostimulator control and/or stimulating tissue growth are disclosed in the following issued U.S. Patents: U.S. Pat. No. 5,524,624 to Tepper et al.; and U.S. Pat. No. 5,628,317 to Starkebaum et al. The disclosures of these references are herein incorporated in their entirety by reference thereto.

Despite the benefits that such implantable ultrasound devices provide, they are still limited as to the ability to provide a wide variety of important long-term ultrasound therapies via permanent or semi-permanent implantable transducers. Moreover, other desirable features that are not provided by various of the prior electrical stimulation systems and methods are also not provided by these ultrasound devices and methods.

There is still a need for a long-term thermal or ultrasound therapy implant system that is adapted to provide one or more of the following beneficial features affecting the desired therapy: active and localized cooling of targeted and/or non-targeted tissues, use of ultrasonically transmissive coupling members to enhance energy delivery at the tissue interface, directionality, focusing and/or collimation of the US energy delivery, substantial depth of heating, and temperature and dosing controls around values adapted to provide various intended tissue responses (in particular within stressed tissues such as in spinal joints).

Moreover, the devices and related noted above lack the ability to provide additional benefits that may be harnessed from controlled, long-term ultrasound energy delivery into certain tissues in order to achieve a variety of desired tissue responses.

There is still a need for an improved, long-term implantable thermal therapy system that can be activated when necessary over prolonged periods of time in order to provide long term therapy to patients' joints, such as in particular spinal joints, in addition to other tissues in the body.

There is in particular still a need for a long-term, implantable ultrasound therapy system adapted to provide long-term ultrasound delivery to treat chronic ailments not adequately treated or cured by acute thermal therapy treatments.

There is also still a need for providing long-term thermal therapy to tissue, and in particular stressed tissue such as found in spinal joints, that allows for sufficient thermal doses to be delivered to achieve certain intended results according to lower elevated temperatures and over longer periods of time than otherwise currently available.

There is also still a need for a long-term implantable thermal therapy system and method that is adapted to provide long term, directional energy delivery into tissue within the body, in particular tissue associated with joints, and further more particularly spinal joints.

There is still a need for a system and method for locally delivering therapeutic amounts of ultrasound energy from long term implants within the body in order to treat disorders associated with the spine and other joints or tissues.

There is also still a need for a system and method adapted to locally deliver ultrasound energy to a highly localized region of tissue, such as only a portion of a disc associated with a spinal joint, when needed over long periods of time and without requiring multiple, repeat surgeries.

BRIEF SUMMARY OF THE INVENTION

An object of the invention is to deliver long-term, therapeutic levels of ultrasound energy to intervertebral discs in order to treat disorders associated therewith.

Another object of the invention is to provide a kit of long-term, implantable energy delivery devices with varied shapes along the energy delivery portion thereof in order to specifically treat different regions of intervertebral discs having varied geometries from within the nucleus.

Another object of the invention is to deliver therapeutic levels of energy over long-term duration and sufficient to cause necrosis of particular cellular structures associated with an intervertebral disc without substantially remodeling or affecting the structure integrity of the annulus fibrosus of the disc.

Another object of the invention is to provide long-term, thermal therapy to a region of tissue associated with a joint in the body without substantially remodeling structural support tissues associated with the joint.

Another object of the invention is to treat chronic inflammation and pain associated with disorders of the spine in general and intervertebral discs in particular.

Another object of the invention is to denervate or necrose nociceptive fibers or cells in certain regions of tissue associated with an intervertebral disc.

Another object of the invention is to reduce chronic inflammation associated with damaged intervertebral discs.

Another object of the invention is to provide long-term implantable devices for repairing damaged regions of intervertebral discs.

Another object of the invention is to achieve cellular necrosis of certain particular tissues associated with an intervertebral disc disorder without substantially altering the structure of the annulus fibrosus of the respective disc.

Another object of the invention is to remodel cartilaginous tissue associated with spinal joints, and in particular intervertebral discs.

Another object of the invention is to provide sufficient thermal therapy to a region of stressed tissue to cause a remodeling of the tissue over prolonged treatment periods.

Another object of the invention is to provide sufficient thermal therapy to a region of an intact mammalian intervertebral disc to cause a remodeling of at least one support structure.

Another object of the invention is to provide a thermal therapy device that can substantially heat deep regions of tissue from the site of therapy, such as with respect to spinal joints at least about 4 mm, 7 mm, or even 10 mm from the site of therapy.

Another object of the invention is to provide therapeutic levels of thermal therapy to tissue within relatively short durations of energy delivery, though over relative long-term duration of overall therapy.

Another object of the invention is to direct therapeutic energy into targeted tissues from remote locations within the body, such as in or around joints, without substantially harming closely adjacent tissues, such as nerves, vessels, or other tissues not intended to be treated.

Another object of the invention is to focus energy into targeted regions of tissue within the body.

Another object of the invention is to enhance cellular functions in certain tissue structures so as to provide a therapeutic effect.

Another object of the invention is to enhance drug delivery into remotely located body tissues, such as within or around joints such as spinal joints.

Another object of the invention is to treat chronic back pain.

Another object of the invention is to treat chronic arthritis.

Another object of the invention is to locally enhance the delivery, permeability, or cellular uptake related to certain therapeutic compounds delivered within the spine and other joints.

Accordingly, one aspect of the invention is an ultrasound energy delivery system for providing long term treatment to a region of tissue associated with a skeletal joint. The system includes a long-term implantable ultrasound treatment assembly with an ultrasound transducer, and a skeletal joint delivery assembly that is adapted to deliver the ultrasound treatment assembly into the body with the ultrasound transducer positioned at a location within the body associated with the skeletal joint. The ultrasound treatment assembly is adapted to provide long-term delivery of a therapeutic level of ultrasound energy from the location and into the region of tissue.

According to one mode of this aspect, a controller is provided that is adapted to couple with and control the ultrasound transducer, and that also a long-term implant that is adapted to be implanted within the body of the patient. In one embodiment, the controller includes a power source, which may in a further regard be rechargeable such as a rechargeable battery. In a further variation, the power source is adapted to be recharged by exposure to a magnetic field across a skin barrier of the patient.

According to further modes, the controller includes one or more of a microprocessor, a monitoring assembly, and/or a data storage system.

In another mode, the controller is adapted to communicate across the patient's skin barrier via wireless communications system so as to provide telemetry with respect to the ultrasound therapy.

In another mode, the system further comprises an external assembly that is adapted to communicate with the controller via wireless signals so as to receive telemetry with respect to the ultrasound therapy.

According to another aspect of the invention, a long-term implantable ultrasound controller is provided that is adapted to control ultrasound energy delivery from a long-term implantable ultrasound treatment assembly. In one mode, the controller is adapted to operate the ultrasound treatment assembly according to a set of operating parameters adapted to stimulate bone growth. In a further embodiment of this mode, the set of operating parameters comprises: a transmission power level between about 0.1 to about 1 W/cm2, and about 1.5 MHz, and at about 1 kHz repetition, and with burst intervals between about 100 to about 200 microseconds. In another embodiment, the set of parameters further includes: total aggregate time of ultrasound delivery is between about 10 to 30 minutes per day for at least one day of long-term ultrasound treatment.

According to another mode, the controller is adapted to operate the ultrasound treatment assembly according to a set of operating parameters adapted to enhance drug delivery therapy to the tissue at the location. In one embodiment of this mode, the set of operating parameters includes: transmission power between about 0.5 to about 2 W/cm2, operating frequency between about 5 to about 12 MHz, and continuous wave delivery. In a further embodiment, the set of parameters further comprises: aggregate time of ultrasound delivery between about 5 to about 60 minutes per day over at least one day of long-term ultrasound treatment.

In another mode, the controller is adapted to operate the ultrasound transducer according to the following set of ultrasound operating parameters: transmission power between about 1 to about 30 W/cm2, transmission bursts lasting between 50 to 200 microseconds, repetition between bursts between about 1 Hz to about 5 kHz, and at ultrasound operating frequencies between about 0.5 to about 15 MHz.

In another mode, the controller is adapted to operate the ultrasound transducer at operating frequencies between about 12 to about 15 MHz.

In another mode, the controller is adapted to operate the ultrasound transducer so as to provide thermal therapy in addition to acoustic nervous stimulation.

In another mode, the controller is adapted to operate the ultrasound treatment assembly according to a set of ultrasound operating parameters adapted to stimulate nervous impulses at the location.

According to one embodiment of this mode, the set of operating parameters includes: pulsed ultrasound delivery over periods of less than or equal to about 70 microseconds, and operating frequency of about 5 MHz.

In another mode, the controller is adapted to operate the ultrasound treatment assembly according to a set of ultrasound operating parameters adapted to accomplish at least one of: regenerate peripheral nerves, repair pseudarthrosis and bone fractures, stimulate bone growth, and stimulate osteogenesis with respect to repairing fractures.

In one embodiment of this mode, the set of ultrasound operating parameters includes: transmission power of about 0.5 W/cm2, operating frequency of about 1.5 MHz, treatment interval durations of between about 5 to about 25 minutes per day for at least one day over a long-term treatment regimen. In a further variation, the set of operating parameters further includes a total period of therapy of about four weeks.

In another mode, the set of ultrasound operating parameters includes: ultrasound transmission at about 0.5 W/$cm^2$ aggregate daily treatment of about 15 minutes per day for at least one day over a long-term treatment regime.

Another aspect of the invention is a skeletal joint therapy device and includes a long-term implantable thermal treatment assembly with an energy emitter. The thermal treatment assembly is adapted to be implanted at a location within a body of a patient. The energy emitter is adapted to follow a long-term protocol for energy delivery into a region of tissue associated with a skeletal joint, such that the thermal treatment assembly is adapted to heat tissue up to a distance of at least 4 mm from the energy emitter to a temperature of at least 75 degrees C., and is adapted to heat tissue up to a distance of at least about 7 mm from the energy emitter to a temperature of at least about 55 degrees C., and is adapted to heat tissue up to a distance of at least about 10 mm from the energy emitter to a temperature of at least about 45 degrees C.

In a highly beneficial mode of this aspect, the thermal treatment assembly includes an ultrasound transducer.

In another mode, the device further comprises a long-term implantable controller that is adapted to be coupled to and control operation of the thermal treatment assembly according to the long-term protocol and according to a set of operating parameters.

Another aspect of the invention is a long-term implantable ultrasound thermal treatment system, and includes a long-term implantable ultrasound treatment assembly with an ultrasound transducer, and a long-term implantable coupling probe having a elongate body with a proximal end portion and a distal end portion. The distal end portion has a proximal section with a longitudinal axis, a distal section with a distal tip, and a bend between the proximal and distal sections. The ultrasound treatment assembly is located along the distal section of the distal end portion and extending at an angle from the proximal section. The distal end portion is adapted to be implanted within the body of a mammal by manipulating the proximal end portion such that the ultrasound treatment assembly is positioned at a location associated with a region of tissue to be treated. The proximal end portion is also adapted to be implanted within the body with the distal end portion implanted with the ultrasound treatment assembly at the location. The ultrasound treatment assembly is adapted to follow a long-term therapeutic protocol of ultrasound energy delivery into the region of tissue from the location within the body.

Another aspect of the invention is a long-term implantable ultrasound thermal therapy system with a long-term implantable ultrasound heating assembly with an ultrasound transducer and that is adapted to be implanted within a body of a mammal with the ultrasound transducer positioned at a location such that the ultrasound transducer is adapted to deliver a ultrasound energy into a targeted region of tissue in the body from the location. Also includes is a long-term ultrasound therapy control system that is adapted to be coupled to the ultrasound heating assembly. The long-term implantable ultrasound therapy control system is adapted to be coupled to and control operation of the ultrasound heating assembly while it is implanted at the location according to a long-term ultrasound thermal therapy protocol.

Another aspect of the invention is a long-term directional ultrasound spinal thermal therapy system that includes a long-term implantable ultrasound delivery assembly with a directional ultrasound transducer that is adapted to be positioned at a location associated with a spinal joint and to deliver a directed, therapeutic amount of ultrasound energy from the location and to a region of tissue associated with the spinal joint.

Another aspect of the invention is a long-term implantable skeletal joint ultrasound delivery system with a long-term implantable ultrasound treatment assembly with an ultrasound transducer and a coupling member. The ultrasound delivery assembly is adapted to be implanted within a body of a mammal with the ultrasound transducer positioned at a location within the body associated with a skeletal joint. The ultrasound transducer is adapted to deliver a therapeutic amount of ultrasound energy to a region of tissue associated with the skeletal joint via the coupling member and according to a long-term ultrasound treatment protocol.

Another aspect of the invention is a long-term implantable ultrasound thermal therapy system that includes a long-term implantable ultrasound heating assembly that is adapted to be implanted at a location within a body of a mammal so as to deliver ultrasound energy into a region of tissue in the body from the location. This system also includes a control system that is adapted to be coupled to the ultrasound heating assembly and to control operation of the ultrasound heating assembly according to a long-term ultrasound thermal therapy protocol and such that a region of tissue being heated by the ultrasound heating assembly exceeds a temperature of at least about 70 degrees C.

Another aspect of the invention is an ultrasound thermal therapy system with a long-term implantable ultrasound heating assembly that is adapted to be implanted within a body of a patient and to couple with an ultrasound controller from the location, and also with a curvilinear ultrasound transducer having a concave surface with a radius of curvature around a reference axis such that ultrasound energy transmitted therefrom converges into a region of tissue at a target location.

Another aspect of the invention is a method for providing long-term, invasive treatment for a medical condition associated with a skeletal joint within a body of a patient. This method aspect includes delivering a therapeutic level of ultrasound energy to a region of tissue associated with the joint from a location within the body of the patient and according to a long-term ultrasound therapy protocol.

Another aspect of the invention is a method for providing long-term, invasive treatment for a medical condition associated with a skeletal joint within a body of a patient. This method aspect includes delivering sufficient energy to a region of tissue associated with the skeletal joint that is sufficient to necrose nociceptive nerve fibers or inflammatory cells in such tissue region without substantially affecting collagenous structures associated with the skeletal joint and according to us of a long-term energy delivery implant and according to a long-term energy delivery therapeutic protocol.

Another aspect of the invention is a method for providing long-term, invasive treatment to a region of tissue associated with an intervertebral disc in a body of a patient. this method aspect includes implanting a long-term ultrasound transducer implant at a location within the body such that a therapeutic level of ultrasound may be coupled from the transducer to the tissue and according to a long-term ultrasound therapy protocol.

Other method aspects of the present invention with respect to providing long term tissue therapy via long-term implants include various long-term implantable adaptations of other aspects elsewhere herein described.

Another aspect of the invention is an implantable spinal thermal therapy system with a spinal delivery system and a spinal thermal therapy device. The spinal delivery system is adapted to deliver a thermal therapy assembly of the spinal thermal therapy device to a location within the body such that the energy may be coupled to a region of tissue associated with a vertebral joint.

Another aspect of the invention is an ultrasound energy delivery system for treating a region of tissue associated with a skeletal joint, and includes an ultrasound treatment assembly with an ultrasound transducer; and a skeletal joint delivery assembly. The skeletal joint delivery assembly is adapted to deliver the ultrasound treatment assembly into the body with the ultrasound transducer positioned at a location within the body associated with the skeletal joint. The ultrasound treatment assembly is adapted to deliver a therapeutic level of ultrasound energy from the location and into the region of tissue.

Another aspect of the invention is a skeletal joint thermal therapy device with a thermal treatment assembly on the distal end of a delivery member. The thermal treatment assembly includes an energy emitter. The distal end portion is adapted at least in part to deliver the thermal treatment assembly into a body of an animal with the energy emitter positioned at a location such that the energy emitter is adapted to deliver energy into a region of tissue associated with a skeletal joint. The thermal treatment assembly is adapted to heat tissue up to a distance of at least 4 mm from the energy emitter to a temperature of at least 75 degrees C., and is adapted to heat tissue up to a distance of at least about 7 mm from the energy emitter to a temperature of at least about 55 degrees C., and is adapted to heat tissue up to a distance of at least about 10 mm from the energy emitter to a temperature of at least about 45 degrees C.

Another aspect of the invention is an ultrasound thermal treatment system with an ultrasound treatment assembly with an ultrasound transducer on a distal end portion of a rigid delivery probe. The probe's distal end portion has a proximal section with a longitudinal axis, a distal section with a distal tip, and a bend between the proximal and distal section. The ultrasound treatment assembly is located along the distal section of the distal end portion and extending at an angle from the proximal section. The distal end portion is adapted to be delivered into the body of an animal by manipulating the proximal end portion externally of the body and such that the ultrasound treatment assembly is positioned at a location associated with a region of tissue to be treated. Moreover, the ultrasound treatment assembly is adapted to deliver a therapeutic level of ultrasound energy into the region of tissue from the location within the body.

Another aspect of the invention is an ultrasound thermal therapy system with an ultrasound heating assembly with an ultrasound transducer and a therapy control system coupled to the ultrasound heating assembly. The ultrasound heating assembly is adapted to be delivered into a body of an animal with the ultrasound transducer positioned at a location such that the ultrasound transducer is adapted to deliver a therapeutic amount of ultrasound energy into a targeted region of tissue in the body from the location. The therapy control system is adapted to control operation of the ultrasound heating assembly such that a substantial portion of the region of tissue being heated by the ultrasound heating assembly does not exceed a maximum temperature of at least about 70 degrees C.

Another aspect of the invention is a directional ultrasound spinal thermal therapy system with an ultrasound delivery assembly. The ultrasound delivery assembly has a directional ultrasound transducer that is adapted to be positioned at a location associated with a spinal joint and to deliver a directed, therapeutic amount of ultrasound energy from the location and to a region of tissue associated with the spinal joint.

Another aspect of the invention is a skeletal joint ultrasound delivery system with an ultrasound treatment assembly with an ultrasound transducer and a coupling member. The ultrasound delivery assembly is adapted to be delivered into a body of a mammal with the ultrasound transducer positioned at a location within the body associated with a skeletal joint. The ultrasound transducer is adapted to deliver a therapeutic amount of ultrasound energy to a region of tissue associated with the Another aspect of the invention is an ultrasound thermal therapy system with an ultrasound heating assembly and a control system. The ultrasound heating assembly is adapted to be positioned at a location within a body of a mammal so as to deliver ultrasound energy into a region of tissue in the body from the location. The control system is adapted to couple to the ultrasound heating assembly and to control operation of the ultrasound heating assembly such that a region of tissue being heated by the ultrasound heating assembly exceeds a temperature of at least about 70 degrees C.

Another aspect of the invention is an ultrasound thermal therapy system with a an ultrasound heating assembly located along the distal end portion of a delivery member. The ultrasound heating assembly has a curvilinear ultrasound transducer having a concave surface with a radius of curvature around a reference axis that is transverse to the longitudinal axis of the distal end portion.

Another aspect of the invention is a method for treating a medical condition associated with a skeletal joint within a body by delivering sufficient energy to a region of tissue associated with the skeletal joint that is sufficient to necrose nociceptive nerve fibers or inflammatory cells in such tissue region without substantially affecting collagenous structures associated with the skeletal joint.

Another aspect of the invention is a method for treating a region of tissue associated with an intervertebral disc in a body of an animal by delivering an ultrasound transducer to a location within the body such that a therapeutic level of ultrasound may be coupled from the transducer to the tissue.

Another aspect of the invention is a method for treating an animal by delivering energy to a region of tissue associated with the spine, wherein such energy delivery is between about 10 and about 300 equivalent minutes at 43 degrees C.

Another aspect is a method for invasively treating a medical condition associated with an intervertebral disc within a body of animal by delivering a therapeutic level of ultrasound energy to a region of tissue associated with an intervertebral disc from a location within the body of the patient.

Another aspect of the invention is a method for treating medical condition associated with a joint between two bony structures in a body of an animal by delivering an ultrasound transducer to a location within the patient's body associated with the joint; and emitting ultrasound energy from the transducer at the location so as to provide a therapeutic effect to at least a portion of the joint.

Another aspect of the invention is a method for treating an animal by introducing an ultrasound transducer into a body of the animal; positioning the ultrasound transducer at a location within the animal that is adjacent to at least one of an annulus fibrosus of an intervertebral disc, a nucleus pulposus of the intervertebral disc, or a vertebral body associated with a spinal joint in the body; and emitting ultrasound energy from the ultrasound transducer at the location.

Another aspect of the invention is a method for providing ultrasound energy delivery within a body of an animal by introducing an ultrasound transducer into a body of a patient; positioning the ultrasound transducer at a location within the patient that is within at least one of an annulus fibrosus of an intervertebral disc, a nucleus pulposus of the intervertebral disc, or a vertebral body associated with a spinal joint in the body; and emitting ultrasound energy from the ultrasound transducer at the location.

Another aspect of the invention is a method for treating a patient by ultrasonically heating a region of tissue associated a spinal joint to a temperature between about 45 to about 90 degrees Fahrenheit for sufficient time to cause a therapeutic result in the tissue.

Further objects and advantages of the invention will be brought out in the following portions of the specification, wherein the detailed description is for the purpose of fully disclosing preferred embodiments of the invention without placing limitations thereon.

BRIEF DESCRIPTION OF THE DRAWINGS

The invention will be more fully understood by reference to the following drawings which are for illustrative purposes only:

FIGS. 11-13 show alternative modes of operating an ultrasound treatment device for treating different respective regions of an annulus fibrosus of a disc from externally of the annulus fibrosus and without entering the nucleus, wherein FIGS. 11 and 13 show a posterior-lateral approach to right lateral and posterior wall regions of the annulus, respectively, and FIG. 12 shows an anterior approach to a left lateral wall region of the annulus.

FIGS. 14A-B show plan perspective views of the distal end portion of another ultrasound treatment device of the invention during various modes of operation, wherein FIG. 14A shows a straight configuration for the device, and FIG. 14B shows two modes of angular deflection for the distal end portion of the device.

FIG. 57 shows a table providing thermal dosimetry data collected during certain modes of in-vivo operation for various working embodiments of an InDUSTT system similar to that shown in FIGS. 54-55B and providing therapeutic ultrasonic heating at various temperature modes of powered operation corresponding to C2/3, C3/4, C4/5, and C5/6 intervertebral sheep discs, respectively.

FIG. 60 shows another table providing thermal dosimetry data collected during modes of in-vivo operation for various working embodiments of a directly coupled InDUSTT system providing therapeutic ultrasonic heating from within C2/3, C3/4, and C4/5 intervertebral discs of a sheep. Rise time is the period of time to reach target treatment temperature. $T_{ave}$ is the average temperature during the 10 minute steady-state treatment period. $StDev_{T_{ave}}$ is the standard deviation of temperature during 10 minute steady-state treatment period. Dose is the accumulated dose expressed in equivalent minutes at 43° C. ($EM_{43C}$).

FIG. 61 shows various respective X-ray pictures of certain transducer placements for the directly coupled InDUSTT during in-vivo spinal disc thermal therapy at the C2/3, C3/4, and C4/5 intervertebral sheep discs corresponding to the similarly designated rows of data illustrated in the table of FIG. 60.

FIG. 63 shows another table providing thermal dosimetry data collected during modes of in-vivo operation for various working embodiments of a catheter cooled InDUSTT system providing ultrasonic heating from within C2-3, C3-4, C4-5, and C5-6 intervertebral discs of a sheep.

FIG. 64 shows various respective X-ray pictures of certain transducer placements for the catheter cooled InDUSTT during in-vivo thermal spinal disc therapy at the C2-3, C3-4, C4-5 and C5-6 intervertebral discs corresponding to the similarly designated rows of data illustrated in the table of FIG. 63.

DETAILED DESCRIPTION OF THE INVENTION

Figure 1A:
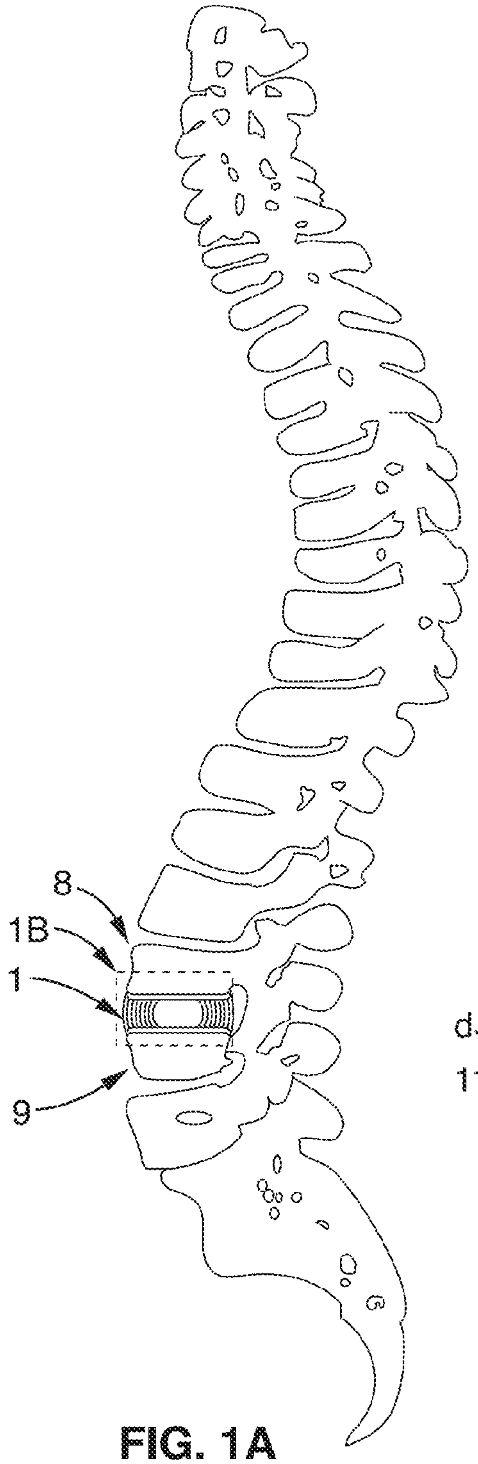
FIG. 1A shows a side perspective view of an illustration of a typical human spine for treatment according to the systems and methods of the invention.
Figure 1B:
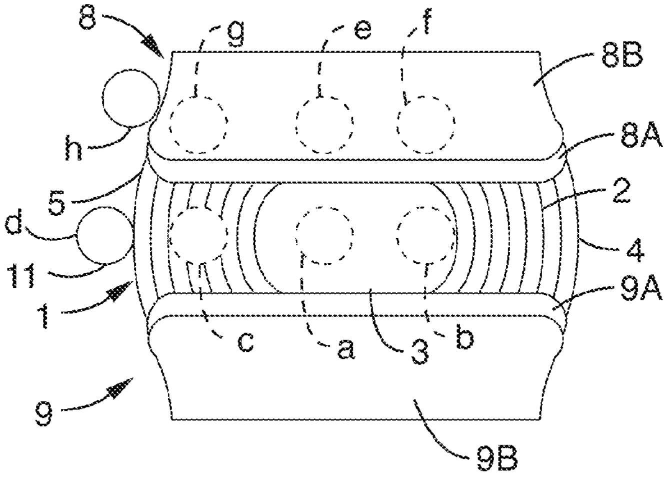
FIG. 1B shows an exploded, cross-sectioned side view of the region depicted as 1B in FIG. 1A, and shows an intervertebral disc between two adjacent vertebral bodies.
Figure 2:
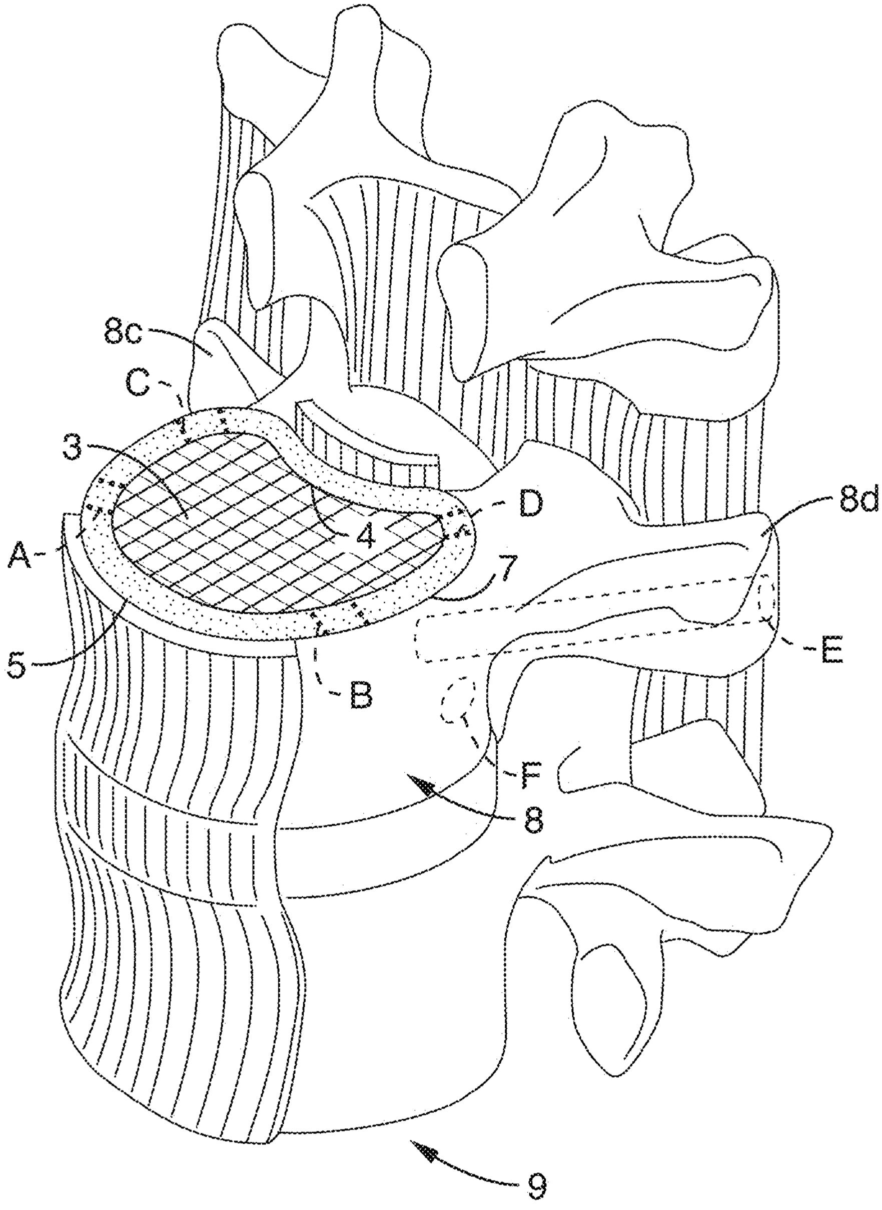
FIG. 2 shows an angular perspective view of a transversely cross-sectioned intervertebral disc in relation to adjacent spinal structures.
Figure 65A:
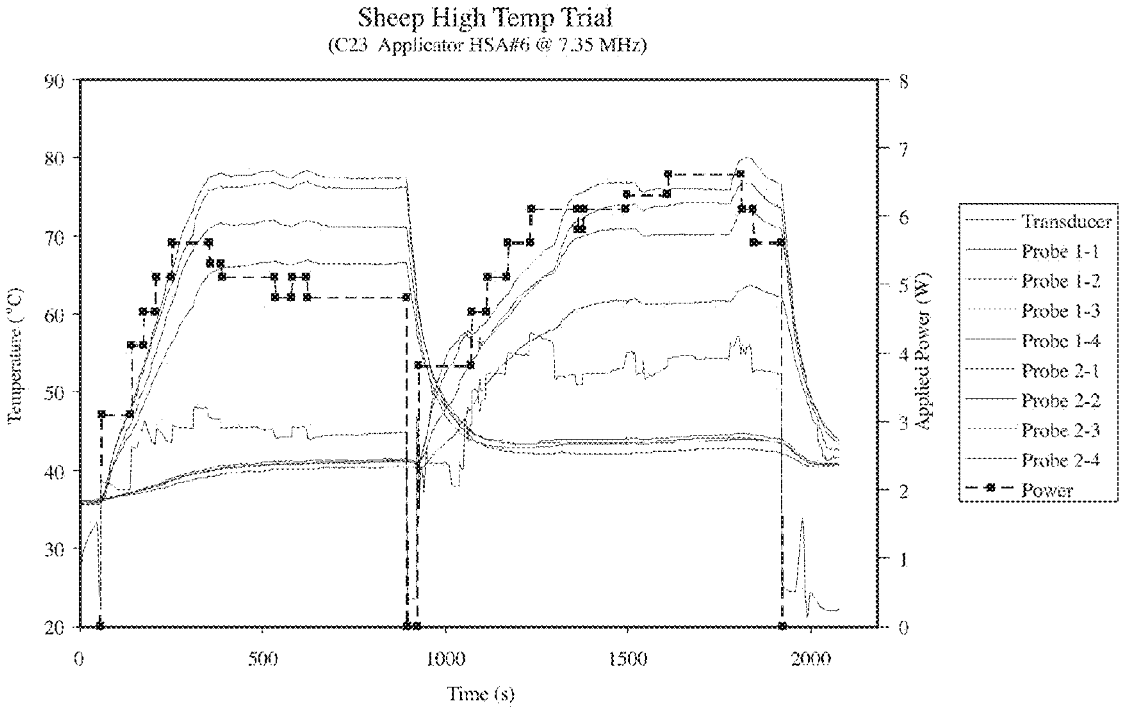
FIG. 65A shows a graph of the relatively high temperature, catheter cooled InDUSTT therapy of the C2/3 disc as monitored over multiple temperature sensors along first and second temperature probes positioned within the disc.
Figure 65B:
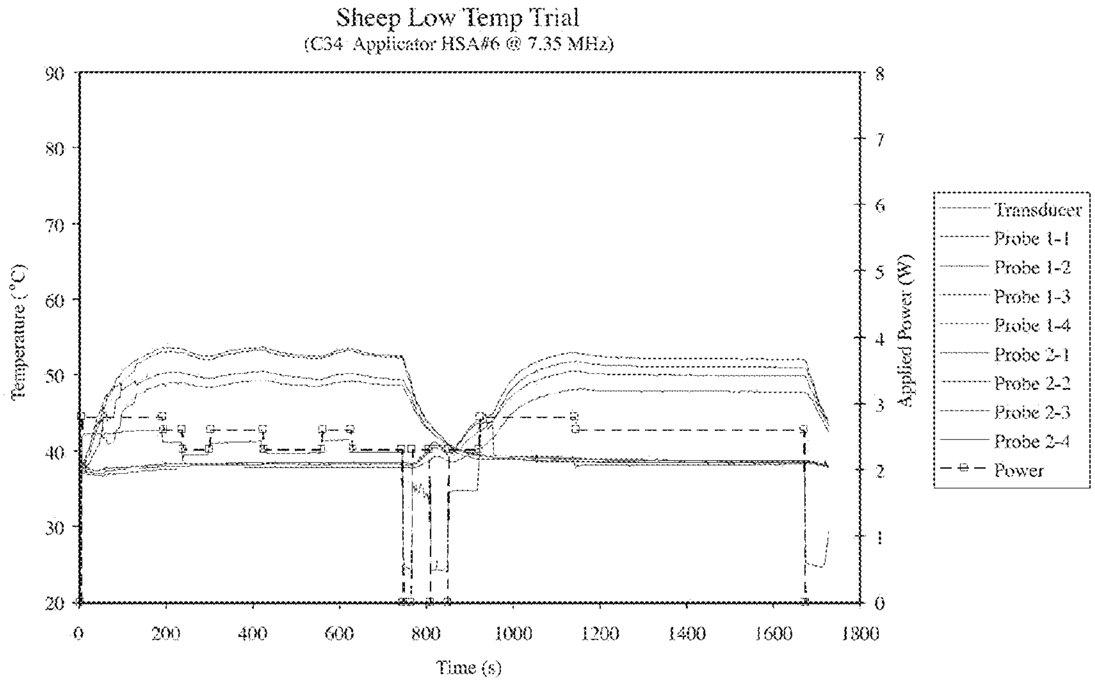
FIG. 65B shows a temperature vs. time graph of the relatively low temperature mode of operation for the catheter cooled InDUSTT therapy in the C3/4 disc and as monitored over multiple temperature sensors along first and second temperature monitoring probes positioned within the disc.
Figure 65C:
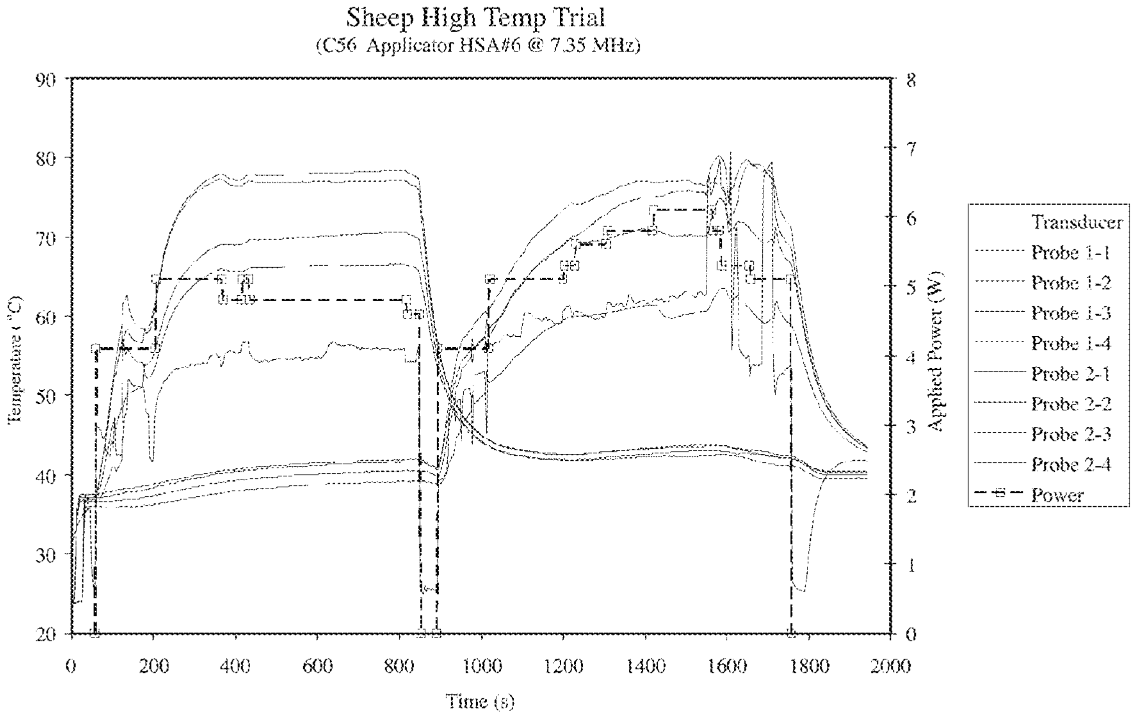
FIG. 65C shows a temperature vs. time graph of the relatively high temperature, catheter cooled InDUSTT therapy of the C5/6 disc as monitored over the multiple temperature sensors along first and second temperature monitoring probes positioned within the disc.
Figure 65D:
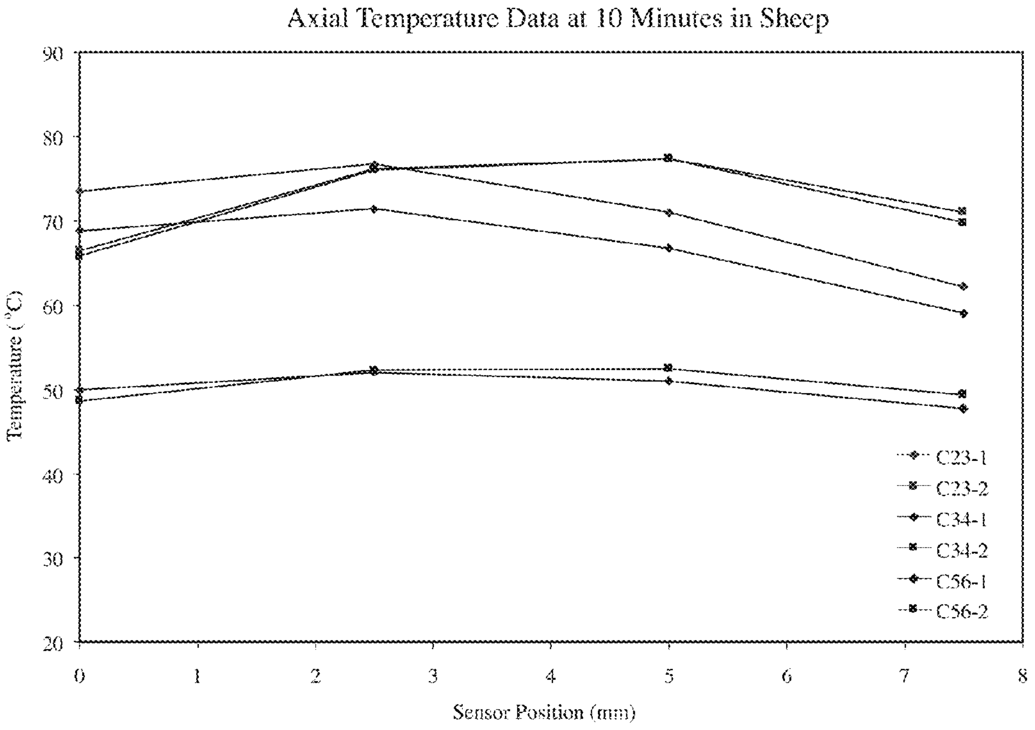
FIG. 65D shows a graph of temperature monitored at various axial positions relative to the transducer during 10 minute catheter cooled InDUSTT heating, and shows curves for thermal treatment results at various locations in the C2/3 disc at relatively high temperature power level, in the C3/4 disc at relatively low temperature power level, and C5/6 disc at relatively high temperature power levels.

Referring more specifically to the drawings, for illustrative purposes the present invention is intended to provide thermal treatment to spinal joints, and in particular intervertebral discs as illustrated in FIGS. 1A-2, as embodied in the apparatus shown and characterized by way of the various modes of operation with respect to certain intended anatomical environments of use variously throughout FIGS. 3-65D. It will be appreciated that the apparatus may vary as to configuration and as to details of the parts, and that the method may vary as to the specific steps and sequence, without departing from the basic concepts as disclosed herein.

As an initial introduction, various respective aspects, modes, embodiments, variations, and features of the invention are herein shown and described, both broadly and in variously increasing levels of detail. Each provides individual benefit, either in its own regard, or in the ability to provide enhanced modes of operation and therapy by way of combinations with other aspects or features. Moreover, their various combinations, either as specifically shown or apparent to one of ordinary skill, provide further benefits in providing useful healthcare to patients.

In one regard, two illustrative ultrasound spinal thermal therapy probe configurations are described for applying thermal (heat) therapy or ultrasound (US) exposure to tissues within the spine or other joints. Heat at high temperatures and thermal doses can shrink tissues, change the structural matrix, generate physiological changes and/or kill cells. Heat at relatively lower temperatures and US exposure can generate permeability changes or changes in the cellular transport/metabolism that increase effectiveness or deposition of certain pharmaceutical agents. The heat or US can be delivered with the present invention in a highly controlled fashion to selected tissue regions in order to exploit these physiological effects for therapeutic purposes. Ultrasound applicators may achieve more precise targeting or heating control not possible with current RF and Hot Source techniques. For soft tissue or bone surfaces within the spine or other joints, the high temperature exposure can be used to shrink tissue impinging on nerves, re-structure and possibly strengthen mechanical properties of the disc or joint material, destroy abnormal or undesirable cells or tissue, destroy nerves responsible for pain, seal leaks from the disc annulus/nucleus, joint capsules, etc. Novel ultrasound applicators and treatment methodologies are thus herein shown and described which allow for the interstitial insertion or laparoscopic or arthroscopic placement of these applicators within or upon targeted tissue to receive such treatments or prophylaxis.

As will be further developed by reference to the Figures below, one exemplary type of such an applicator and treatment methodology provides a segmented array of tubular, sectored tubular, plate, hemispherical, or portions of cylinders (e.g. convex) with linear control of US exposure or heating via power level adjustments and angular control of US exposure or heating via directional characteristics of the applicators. (e.g. angularly directive with an inactive zone). These transducers are mounted over a guidewire lumen or tube or structure to facilitate placement, wires, and/or cooling structures. Thermometry sensors can be placed directly on the transducer/tissue or applicator/tissue interface. Internal cooling via gas or liquid or external cooling via an outer plastic sheath or catheter can be accomplished, though may not be necessary in many instances. These can be inserted within the disc or laparoscopically placed against the target tissue or directed toward the target tissue. Acoustic gain and temperature regulation of applicator surface(s) can help control distance of heated regions and effects from the applicator surface. Frequency and depth of focus can be selected to control heating pattern, and time can be varied to control heating effects and distribution. Some of the device and method embodiments provided herein may incorporate various features similar to those previously disclosed such as in U.S. Pat. No. 5,620,479 to Diederich, though in many instances will be modified specifically for heating within the special environment of use within or around intervertebral discs or other joints.

Another illustrative type of applicator according to the present invention incorporates a segmented array similar to that described above, but using concave sections of cylindrical or tubular transducers or spherical or semi-spherically focused transducers. The outer diameter (OD) of the tubes used to form such transducers are much larger than the applicator diameter for the tubes—the sectors activated are a small arc of the tube they otherwise would be a part of. Thus, a line of convergence, e.g. focus, is produced at depth over a small arc angle, producing an intense US exposure or heating pattern which is approximately the same length as the tubular segment transducer emitting the US, though very narrow (e.g. 1-5 degrees) in the angular dimension. The length and number of segments can be varied in either applicator type described here for introduction purposes (or elsewhere herein), and may be a single transducer versus an array. These applicators can also have internal cooling or external cooling as described above and further detail with respect to the particular embodiments below. The applicators can be inserted within the disc or laparoscopically placed against the target tissue or directed toward the target tissue. Acoustic gain and temperature regulation of applicator surface can help control distance of the heated region and effects from the applicator surface. Further applicable features may by incorporated from other prior disclosures, such as U.S. Pat. No. 5,391,197 to Burdette et al. disclosing prostate therapy devices and methods, and may be modified to suit the particular needs for the present invention. Frequency and depth of focus can be selected to control heating pattern, and time can be varied to control heating effects and distribution.

The various embodiments herein described have applications in other soft and/or hard tissue sites and body parts where ultrasound exposure, high temperature, low temperature, or combination effects are desired.

Each type of applicator can be designed with or without cooling balloons, distendable (e.g. compliant and/or elastomeric) or pre-shaped (e.g. substantially non-compliant with relatively fixed inflation size and shape), and symmetric or asymmetric shapes are considered. The devices' respective chasses may be substantially stiff, e.g. rigid probes, or flexible. They may further be either implantable within the target tissue, or be used on surface contact. They may be delivered on a guidewire rail platform, through pre-shaped insertion or placement guides, or have their own steerability or deflectability. For spinal treatments, they may be placed surgically following for example a posterior approach, or laparoscopic/arthroscopic lateral/anterior directed to the spinal joint for treatment.

Treatment methodologies contemplated include implanting the devices within or positioning them next to the target tissue for heating, such as for example inserted into a disc or joint capsule, or placed outside of the disc or joint.

Directivity and cooling aspects, when incorporated, protect sensitive non-targeted tissue, which is highly beneficial for example in spinal applications protecting spinal nerves. Applicators herein described are repositionable according to various modes to control angular thermal profile according to their directed energy delivery. In one example for further illustration, a specially adapted spinal disc insertion apparatus is adapted to deflect an applicator being delivered therethrough into the spinal disc from an angle. Other special procedures and tools are also herein described to align the applicators with target areas of tissue such as with respect to spinal joints and intervertebral discs in particular.

Though many different configurations, sizes, shapes, and dimensions are contemplated consistent with the overall intent to meet the various objects of the invention, exemplary devices may be provided with outer diameters between about 1.2 to about 3 mm, though may be up to 5 mm in some instances, deliverable as desired to spinal joint areas from 18 gauge.

Insertion techniques into tissue to be treated may progress according to several examples. In one mode, a relatively stiff (e.g. sufficient to support the intended use), pre-shaped guidewire is used which may be with or without memory metal alloy such as nickel titanium for example. The guidewire is inserted under fluoroscopy and positioned in an annulus fibrosus or posterior annulus, avoiding the nucleus of the disc. An applicator of the relatively more flexible variety is then inserted over the guidewire and into position. In another regard, a relatively stiff (e.g. sufficient support) pre-shaped insertion tool guides the applicator with a sharp tip into the annulus from outside without requiring the guidewire (though they may be used in conjunction). Similar insertion techniques may be used for thermometry placement, if desired. Such delivery tool may thus be multi-lumened to integrate both placements (e.g. applicator and temperature probes) simultaneously for better positioning, etc.

Contact therapy techniques of operation may also proceed according to a variety of modes. An arthroscopic approach is suitable for many applications, such as for example as follows. Internal tip deflection may be used to align (e.g. steer) the applicator with or along the outside of an annulus—e.g. similar to certain intracardiac catheters (such as mapping or ablation devices). Such may be integrated to a steerable catheter. The device according to these modes may be placed lateral or posterior behind the disc and nerves, or ventral. The device is aligned with the disc, the region is targeted and then treated with directional thermal therapy.

Various of the components herein described for the various embodiments may be provided together, or may be provided separately. For example, implements for providing streaming liquid or balloon to protect tissue from transducer conductive heating may be an integral part of the respective applicator, or may be separate as an accessory.

The applicators and respective insertion and/or guidance tools herein described may be further adapted to be compatible with magnetic resonance imaging for real time monitoring of the procedure. Other imaging modalities may also be used for positioning, monitoring, thermal monitoring, lesion assessment, real-time monitoring of coagulation, etc. This includes ultrasound monitoring.

Further to the ultrasound aspects of the various embodiments, use of such energy modality provides temperature elevation as one mode of creating an intended effect, but also provides other non-thermal effects on tissues, such as for example drug activation, etc., such as for example to treat arthritis at joints where the applicator is being used.

It is to be appreciated that the invention is in particular well adapted for use in treating intervertebral disc disorders of the spine, such as at spinal joints, and in particular at an intervertebral disc 1 shown in various relation to surrounding spinal structures of a spinal joint in FIGS. 1A-2. In particular, as will be further developed below, disc disorders associated with chronic lower lumbar back pain are to be beneficially treated according to the invention. However, it is to be appreciated that other disorders of the discs in particular, and of other joints (e.g. hips, knees, shoulders, etc.) may also be treated according to the device systems and methods herein shown and described. For example, other regions of the vertebrae will be beneficially treated with invasive ultrasound delivery according to the invention in order to promote bone growth, such as for example to assist in the healing of injuries or bone-grafts. Areas between the vertebral bodies, or the spinal processes, for example, may be treated with US application from the present devices and according to the methods as herein shown and described. In particular, regions such as graft between inner bodies through nucleus; anterior inner body fusion; posterior lateral fusion are contemplated. Ultrasound energy may be delivered with collagen matrixes or autograft/allograft materials to bone.

A typical intervertebral disc 1 such as shown in FIGS. 1A-2 generally includes an annulus fibrosus 2 that surrounds a nucleus pulposus 3 along a plane that lies between two adjacent vertebrae 8,9, respectively, that are located above and below, also respectively, disc 1 along the spine. More specifically, disc 1 lies between two the two cartilaginous endplates 8*a*,9*a* that border two adjacent vertebral bodies 8*b*,9*b* of vertebrae 8,9, respectively.

As will be further developed below, an ultrasound treatment device according to the invention may be located in various places in and around a disc 1. A variety of such locations is shown for the purpose of illustration at locations a-d in FIG. 1B, wherein device 11 is shown: within the middle of the nucleus at location a; along the border between the nucleus 3 and the annulus 2 such as shown at proximal wall at location b; in the wall of the annulus itself, as shown for example at location c; or outside of the disc 1 around the outer periphery of annulus 3, as shown at location d. Moreover, the device may also be delivered into and around bony structures associated with the spinal joint, such as for example shown at locations e, f, g, or h in FIG. 1B. Such positioning may be accomplished for example by drilling a bore into the vertebral body from a posterolateral approach through an associated pedicle, as shown in shadow at location E in FIG. 2, or via a more lateral approach as shown directly into the body at location F in FIG. 2. Such positioning and heating within bone structures associated with the joint may be in particular useful in one regard for treating bone cancer, destroying nociceptive nerves, stimulating growth or drug uptake (e.g. low thermal dose applications). Either the vertebral body itself may the target for heating, or the end plate, or the disc from such location. A further particular useful application of this is treatment of osteoporotic back pain.

As shown in particular in FIG. 2, disc 1 also has a shape similar to a “kidney”-shape with a concave curvature along a proximal wall 4 that borders the spinal cord (not shown), as well as along opposite anterior wall 5. Right and left anterior walls 6,7 are generally characterized by a more acute radius of curvature than posterior and anterior walls 4,5. As will be further developed below, each of these uniquely located and anatomical wall regions may be selectively treated with localized therapeutic ultrasound energy according to the system and method of the present invention. In general, intervertebral discs (with respect to the lumbar region associated with lower back pain) are typically 30 mm wide (e.g. laterally from right wall 6 to left lateral wall 7, about 20 mm front-back, e.g. anterior wall 5 to posterior wall 4); and approximately 10 mm tall, e.g. from end plate 8*a* to endplate 9*a*. Accordingly, the devices herein shown and described are to be particularly adapted to operate within this general description of the intended environment of use within intervertebral discs.

As will be appreciated by the description below of the various modes of operating the ultrasound treatment system of the invention, treatment of the annulus fibrosus 2 from within the nucleus may be achieved via various approaches. In particular, regions A and B shown in FIG. 2 correspond to right and left anterior approaches, whereas regions C and D correspond to right and left posterior-lateral approaches around right and left vertebral prostheses 8*c*,8*d*, respectively Multiple ultrasound probe configurations are herein described for applying thermal (heat) therapy or ultrasound (US) exposure to tissues within the spine in particular, though other joints such as knee, hip, etc. are contemplated. It is to be appreciated that the two specific probe configurations shown and described provide highly beneficial embodiments, though they are exemplary and other configurations, improvements, or modifications according to one of ordinary skill based upon this disclosure in view of the known art are contemplated.

In any event, heat produced according to the present invention at high temperatures and thermal doses can shrink tissues, change the structural matrix, generate physiological changes, and/or kill cells within the targeted region of tissue associated with a disc. Heat at low temperatures and US exposure can generate permeability changes or changes in the cellular transport/metabolism that increase effectiveness or deposition of certain pharmaceutical agents. The heat or US can be delivered with this technology in a highly controlled fashion to selected tissue regions in order to exploit these physiological effects for therapeutic purposes.

Ultrasound applicators may achieve a degree of precise targeting or heating control generally not possible with previously disclosed RF, plasma ion, or heat source techniques. In addition, ultrasound energy actually penetrates surrounding tissues, rather than according to other modes (e.g. RF and laser) that heat the closest tissues the hottest and allowing conduction therefrom in a diminishing temperature profile curve with distance away. For soft tissue or bone surfaces within the spine or other joints, high temperature exposure by use of the invention is used to shrink tissue impinging on nerves, re-structure and possibly strengthen mechanical properties of the disc or joint material, destroy abnormal or undesirable cells or tissue, destroy nerves responsible for pain, and seal leaks from the disc annulus/nucleus, joint capsules, etc.

In particular to disc applications, three general goals are intended to be achieved according to use of the present invention: (1) collagen associated with the annulus fibrosus may be reorganized to reshape the annulus; (2) nerve ingrowth in and around the annulus or nucleus may be killed; or (3) inflammatory cells around areas of injury or otherwise penetrating areas in or around a disc may be killed or ablated. In particular with respect to causing nerve damage, this may include regions of the annulus itself, at the endplates, usually is located posteriorly, and rarely but at times may be within the region of the nucleus itself. In any event, such nervous ingrowth is typically related to structural disc damage that is identified e.g. in a discogram and therefore predicted to be where pain/nerve treatment should be directed.

In one particular non-limiting application, either or both of nerve and inflammatory cells are necrosed by US delivery without achieving sufficient heating to denature or weaken, or to denature but not weaken, or to reshape the disc annulus. This is possible using the devices and methods of the invention herein described at levels of energy delivery between about 10 to about 300 EM43 deg C. (e.g. may be from 1 to 60 min at between about 42 deg C. and about 45 deg C.). Where collagen denaturation, modification, or reshaping is desired, energy delivery from the ultrasound devices herein described may be from between about 55 deg C. to about 85 deg C. for between about 10 sec to about 30 min.

The novel ultrasound applicators and treatment methodologies herein disclosed allow for the interstitial insertion or laparoscopic or arthroscopic placement of these applicators within or upon targeted tissue, in particular with respect to intervertebral discs.

Figure 3A:
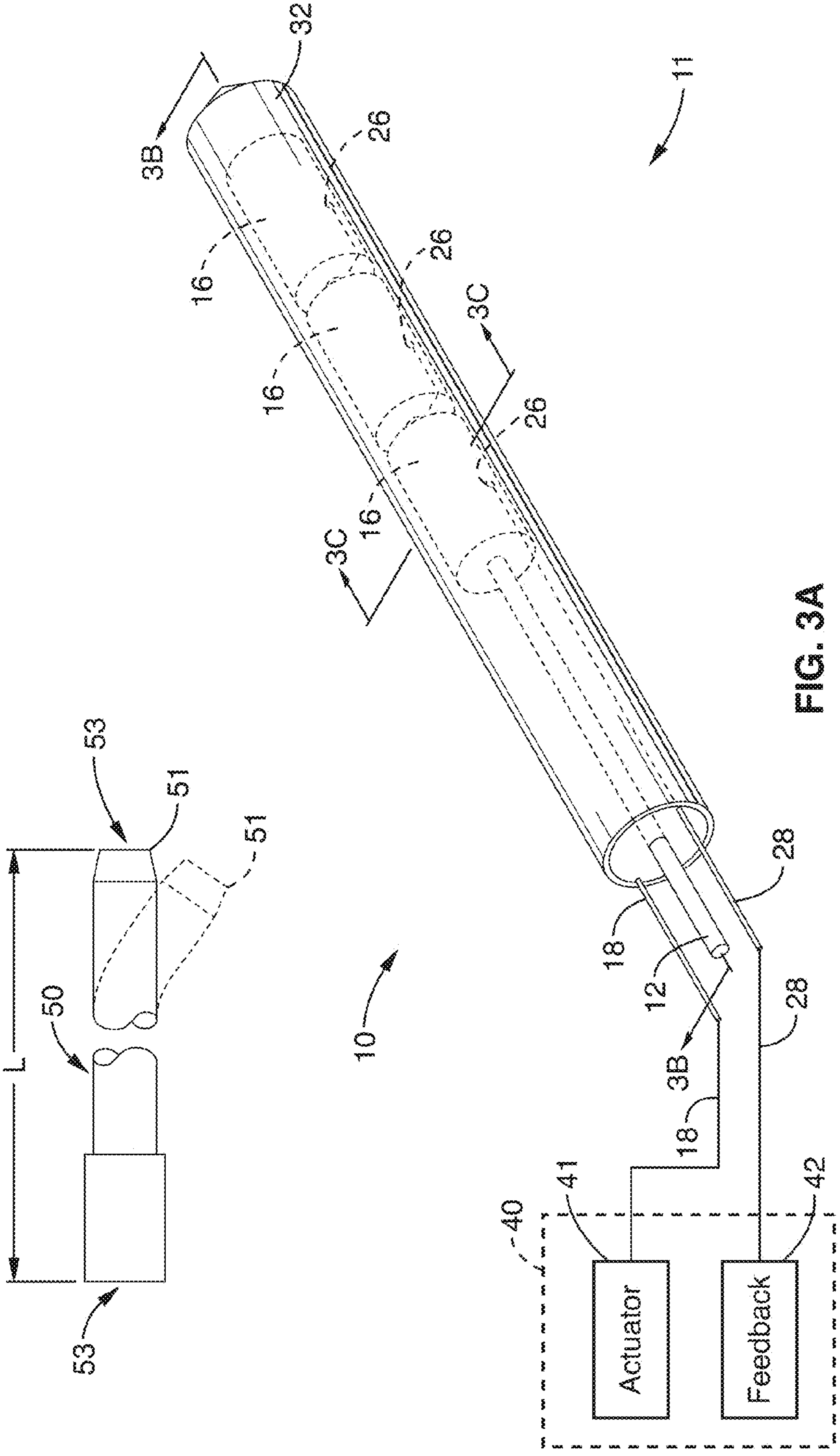
FIG. 3A shows an angular perspective view of an ultrasonic intervertebral disc therapy system according to the invention, and includes a partially segmented view of an ultrasound treatment device, a schematic view of an ultrasound drive system, and an angular perspective view of an introduction device, respectively, of the system.
Figure 3B:
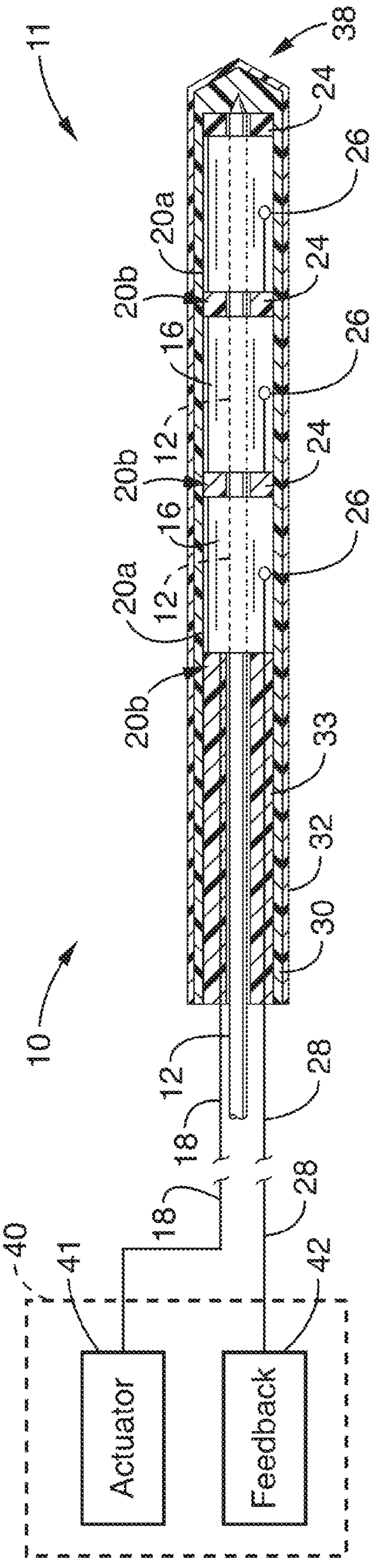
FIG. 3B shows a longitudinal side view taken along lines 3B-3B in FIG. 3A.
Figure 3C:
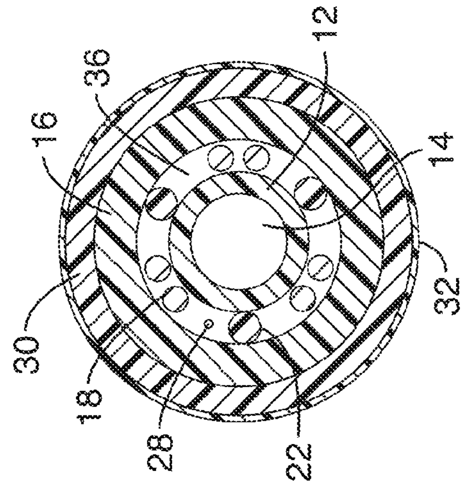
FIG. 3C shows a transverse cross-sectioned view taken along lines 3C-3C in FIG. 3A.

One particularly beneficial embodiment of the invention is shown at ultrasound treatment system 10 in FIGS. 3A-C. This system 10 includes an ultrasound device 11, ultrasound drive system 40, and intervertebral disc delivery assembly 50.

Device 11 is shown to couple proximally to an a proximal end portion (not shown) that generally includes a handle (not shown) that is adapted to couple to ultrasound drive system 40, which includes an ultrasound actuator 41. Drive system 40 may be operated empirically, such that a predetermined delivery of energy is achieved at a desired level known to produce a desired result. Or, external therapy monitoring may be employed during treatment, e.g. MRI, CT, fluoroscopy, X-ray, discogram, or PET in order to control energy delivery and determine appropriate levels and time duration for a particular case. These monitoring modalities may be effective prior to treatment in order to identify the area of concern to be treated, which may impact the choice of particular device to be used as provided according to the embodiments herein. Still in a further alternative embodiment, a treatment feedback device 42, such as a temperature monitoring system, may be incorporated in a feedback control system, as shown in FIG. 3A.

Device 11 is also adapted to be delivered to the desired location for treatment through delivery assembly 50 and therefore has a length corresponding to length L of delivery assembly 50 that is adapted for use in standard access procedures for intervertebral disc repair. For posterior-lateral approaches, such as for example in order to invade the nucleus 3 through posterior-lateral sites B or C shown in FIG. 2, delivery assembly 50 is typically a spinal needle of about 18 Gauge having a needle bore 53 and sharp pointed tip 51. Accordingly, the length for device 11 may be about 30 cm long, with a corresponding outer diameter for device 11 adapted to fit within such a needle, generally less than about 3 mm, generally between about 1 and about 3 mm, typically between about 1.2 and 3 mm. However, other sizes may be realized for applications not requiring delivery through size-limiting delivery assemblies such as spinal needles, and up to or greater than 5 mm OD is realizable (e.g. in particular for applications outside of the disc nucleus or within the annulus). For anterior delivery such as at sites A or B shown in FIG. 2, delivery assembly 50 may be minimally invasive delivery device such as an arthroscope or laparoscopic assembly.

Device 11 is of a type that contains a linear array of segmented transducers 16 that are adapted to provide selective, localized ultrasonic heating via radial, collimated energy delivery in tissue adjacent to the array. The particular device 11 of the present invention, including corresponding elements such as transducers 16 located thereon, are generally smaller and more flexible than elsewhere previously described for other linear array transducer devices. In addition, fewer transducers 16 are typically required for treating the generally smaller regions of the intervertebral discs as contemplated herein. These substantial modifications are believed to significantly enhance the controllability and performance of ultrasound therapy within the unique (and often dangerous) anatomy of an intervertebral disc. Otherwise, the basic components for segmented, linear array transducer device 11 may be similar to those previously described in U.S. Pat. No. 5,620,479, which has been previously incorporated by reference above.

Figure 4:
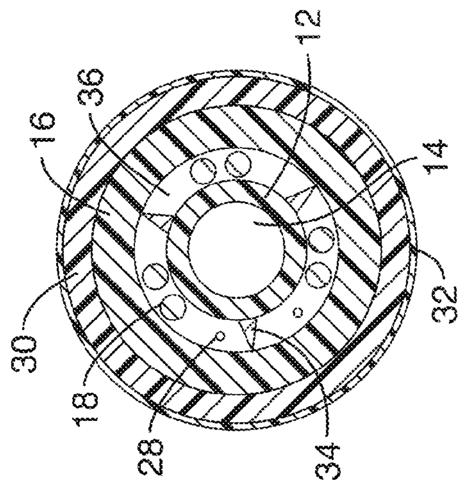
FIG. 4 shows a transverse cross-sectioned view of the distal end portion of another ultrasound treatment device of the invention with a different support structure under the ultrasound transducer of the device than the support structure shown in FIG. 3C.

Referring more specifically to FIGS. 3A through 4, an ultrasound applicator 11 of the invention preferably includes a cylindrical support member such as a tube, conduit or catheter 12 which may be compatible for adjunctive radiation therapy of the spine such as according to remote afterloaders and standard brachytherapy technology. Since catheter 12 includes a coaxial longitudinal inner lumen 14, a source of radiation, a drug or a coolant can be inserted therein, as well as guidewires, deflection members, stylets, etc., according to modified embodiments elsewhere herein described. One highly beneficial embodiment for example uses a polyurethane or other similar polymer that is of a soft, low modulus type according to uses as contemplated herein within the sensitive intervertebral discs and elsewhere along the spine and related, highly sensitive nervous tissues. Where direct access to the desired treatment location is possible without risk of damaging soft, sensitive tissues around the spine, a more rigid support may be used, and may even include a thin-walled stainless steel hypodermic tubing or stiff conduits (though shapes may be important as further developed below).

Catheter 12 is coaxially disposed through a plurality of tubular piezoceramic transducers 16 which are spaced apart and electrically isolated as shown, thus forming a segmented array of tubular ultrasound transducers which radiate acoustical energy in the radial dimension. Transducers 16 may be formed from a variety of materials as has been previously disclosed. Transducers 16 may have an outer diameter between about 0.5 to about 6 mm, though with respect to energy therapy from within the nucleus 3, is more typically between about 0.5 mm and about 1.5 mm.

It is preferred that the wall thickness for transducers 16 be substantially uniform in order to generate uniform acoustic patterns where such energy delivery is desired. Further to conjunctive radiation therapy (e.g. spinal tumor therapy), the transducer material is preferably stable when exposed to typical radiation sources.

The frequency range of the transducers will vary between approximately 5-12 MHz depending upon the specific clinical needs, such as tolerable outer diameter, depth of heating, and inner catheter outer diameter. Inter-transducer spacing is preferably approximately 1 mm or less. Those skilled in the art will appreciate that, while three transducers 16 are shown in FIG. 3A-B, the number and length of transducers can be varied according to the overall desired heating length and spatial resolution of the applicator and depth of penetration desired. This may vary for example for devices 11 intended to treat along the entire length of posterior wall 4 of disc annulus 2, versus a lateral wall 6,7 thereof, versus the anterior wall 5. Even the desired length along a given one of these regions may vary depending upon the particular patient, or even within a given patient depending upon a particular region of the spine being treated (e.g. lower discs along the spine increase in size). Therefore, a kit of devices 11 having varied lengths and sizes for the array of treatment transducers 16 is contemplated according to such variances. Transducers 16 are also shown to be substantially cylindrical for the purpose of illustration, and which design may be desired where uniform heating around the circumference of the device 11 is desired. However, as developed below, the highly selective tissue therapy typically desired within and around intervertebral discs may require in many cases more radial selectivity around the device 11, as further developed below.

Each transducer 16 is electrically connected to actuator 41 of drive assembly 40, which is typically an RF current supply. This electrically coupling is achieved via separate pairs of signal carrying wires 18, such as 4-8 mil silver wire or the like, soldered directly to the edges of the transducer surface to form connections 20*a*,20*b*. One wire in the pair is connected to the edge of transducer 16 at its outer surface, while the other is connected to the edge of transducer 16 at its inner surface, although other connection points and modalities are also contemplated. Each wire 18 is routed through the center of the transducers between the outer wall of catheter 12 and the inner wall of the transducer 16, as can be seen in FIG. 3B, and from there to the connection point through the spaces between the individual transducer elements.

In order to ensure that each transducer 16 in the array is kept centered over catheter 12 while still maintaining flexibility and not impending transducer vibration, a plurality of spacers 22 are disposed between the transducers and catheter 12. These spacers 22 may take various forms as previously described. For the particularly smaller designs herein contemplated for spinal applications, a "spring-ground lead" comprising 3-4 mil stainless steel wire or the like wound to form a coaxial spring may be placed between a transducer 16 and an electroded outer surface of inner catheter 12 where such coil is soldered directly thereto. Such electroded outer surface may be a common ground for all transducers 16.

As previously disclosed, transducers 16 are preferably "air-backed" to thereby produce more energy and more even energy distribution radially outwardly from device 11. To ensure such air-backing and that the transducers 16 are electrically and mechanically isolated, a conventional sealant 24 as previously described is injected around exposed portions of catheter 12, wires 18, and spacers 22 between transducers 16. Sealant 24 serves multiple functions in this application, as has been previously described.

As a means for monitoring temperature of tissue surrounding the transducers 16, and to provide for temperature control and feedback where desired, a plurality of small (e.g. 25.4 um) thermocouple sensors 26, such as copper-constantan or constantan-maganin fine wire junctions, are placed along the outer surface of each transducer at points which are approximately one-half of the length of the transducer, and connected to individual temperature sensing wires 28 which run along one-half of the length of the transducer 16 and then through the annular space 36 between catheter 12 and the transducers 16. A conventional acoustically compatible flexible epoxy 30 such as has been described is then spread over the transducers, thereby embedding the temperature sensors. The epoxy coated transducers are then sealed with an ultra thin walled (e.g. about 0.5 to about 3 mil) tubing 32 that may for example be a heat shrink tubing such as polyester or the like. Or, the epoxy coated transducers may otherwise covered, as is known. Heat shrink tubing 32 extends beyond the area over transducers 16 and covers substantially the length of device 11 to distal end 38. To support tubing 32 in such extended area, a filler 33 of chosen composition (preferably flexible) is placed around catheter 12 and between it and tubing 32.

According to the present embodiments and those elsewhere herein shown and described, a cooling system may be included, which has been characterized to increase heating efficiency by about 20-30% versus non-cooled embodiments. In addition, as shown in FIG. 4, standoffs 34 may be used to support transducers 16, which are preferably flexible and may be an integral part of catheter 12.

For spinal disc therapies herein contemplated, device 11 is generally designed to be sufficiently flexible to be delivered in a substantially straight configuration through delivery device 50, and thereafter be adapted to assume a configuration appropriate for delivering energy along a length corresponding to an interface between the linear array of transducers 16 and the desired region of tissue to treat. This flexibility may be modified according to various different modes elsewhere herein described in order to achieve appropriate positioning and shape conformability used in a particular case.

Figure 5A:
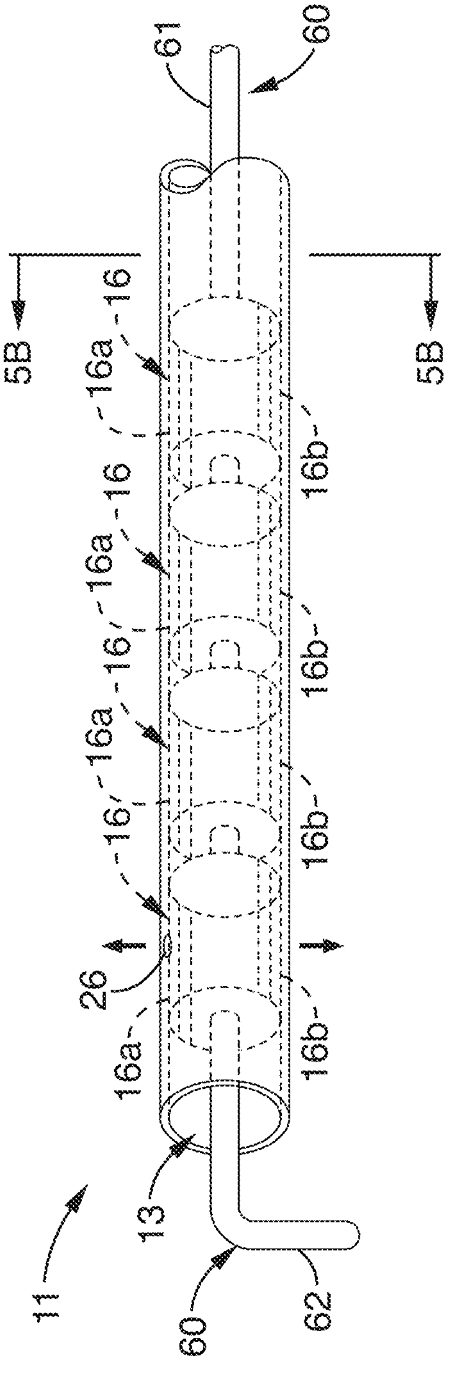
FIG. 5A shows a slightly angled side view of the distal end portion of another ultrasound treatment device according to the invention, and also shows a schematic view of a guide wire included in the system.
Figure 5B:
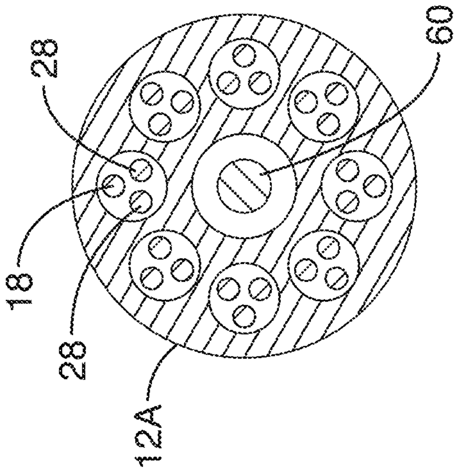
FIG. 5B shows a cross-sectioned side view of the device taken along lines 5B-5B in FIG. 5A.

In one particularly beneficial further embodiment shown variously in FIGS. 5A-B, device 11 is modified from the previous embodiment of FIGS. 3A-4 such that inner support catheter, similar to catheter 12 in FIGS. 3A-4, provides a through lumen 13 that is adapted to slideably receive a guidewire 60 therethrough. Guidewire 60 includes a stiff proximal end portion and either a shaped or shapeable, more flexible distal end portion 62. According to this guide wire-based embodiment for system 10, guidewire 60 is adapted to be placed within the desired region of treatment by steering and advancing the shaped distal end portion 62 with manipulation of proximal end portion 61 externally of a patient's body. Device 11 along the array of treatment transducers 16 is sufficiently flexible to track over guidewire 60 in order to be positioned for treatment along the desired treatment region. Guidewire 60 may be of a shape memory type, or may be designed according to many other previous guidewire disclosures. Moreover, device 11 may be adapted to receive and track over guidewire 60 over substantially the length of device 11, also known as "over-the-wire", or may be of a "rapid exchange" or "monorail"-type wherein guidewire 60 exits proximally from device 11 at a port along device 11 that is distal to the most proximal end of device 11.

FIG. 5A also shows the linear array of transducers 16 to be of the segmented type, wherein each linear location for a transducer 16 corresponds to two opposite transducer regions 16*a*,16*b* that may be independently or alternatively actuated for energy delivery. This allows localization of US energy along only one radial aspect surrounding device 11. Particular designs and methods incorporating linear array of segmented or partially activated US transducer regions is disclosed in U.S. Pat. No. 5,733,315 to Burdette et al., which has been previously incorporated herein above. It is to be appreciated herein that each transducer segment 16*a* or 16*b* is in effect an independently actuatable transducer, though shown and described as sub-parts of an overall transducer 16 for illustrative simplicity. Corresponding transducer regions 16*a* may be all actuated simultaneously along the array, without actuating the opposite regions 16*b*, in order to ablate along a length only along one radial aspect of device 11 corresponding to actuated regions 16*a*. Or, the other regions 16*b* may be actuated without regions 16*a* emitting US energy. The device of FIG. 5A provides this selectivity, which may be useful for treating different regions of a disc annulus as further discussed below.

Various different shaft structures may be appropriate for housing the corresponding functional components of a device 11 according to the embodiment of FIG. 5A, though one particular cross-section is shown in FIG. 5B for illustration. Due to the radially segmented aspect of the transducer array of this embodiment, the number of actuatable transducer elements corresponding to a given length of the array is doubled compared to the earlier embodiment (e.g., each linear region is split into two radial regions). Therefore, twice the number of electrode leads 18 and thermocouple leads 28 must be housed. The cross-sectioned, multi-lumen tubing 12A shown in FIG. 5B therefore has a plurality of surrounding lumens 14 surrounding a central guidewire lumen 13. This is adapted to give an organized shaft structure for adapting a proximal pin connector to interface with drive and control system 40, as well as uniform flexibility in multiple planes to enhance delivery and position control in use.

Device 11 as illustrated by the FIG. 5A embodiment may include transducers 16 having many different geometries that may be customized for a particular energy delivery profile along the transducer array. Examples include tubular (e.g. FIGS. 3A-4), sectored tubular (e.g. FIG. 5A), and also as further examples planar or plate, hemispherical, or portions of cylinders (convex), depending upon the desired energy delivery for a particular application. Further to the FIG. 5A embodiment, a distinct radial region of a transducer location along the array may be rendered completely inoperative for US delivery, such as for example in order to protect against delivery into sensitive tissues such as the spinal cord. In any event, according to the various embodiments, device 11 may be adapted for linear control of US exposure or heating via power level adjustments and angular control of US exposure or heating via directional characteristics of transducer emitters 16 (e.g., angularly directive with an inactive zone).

Figure 6A:
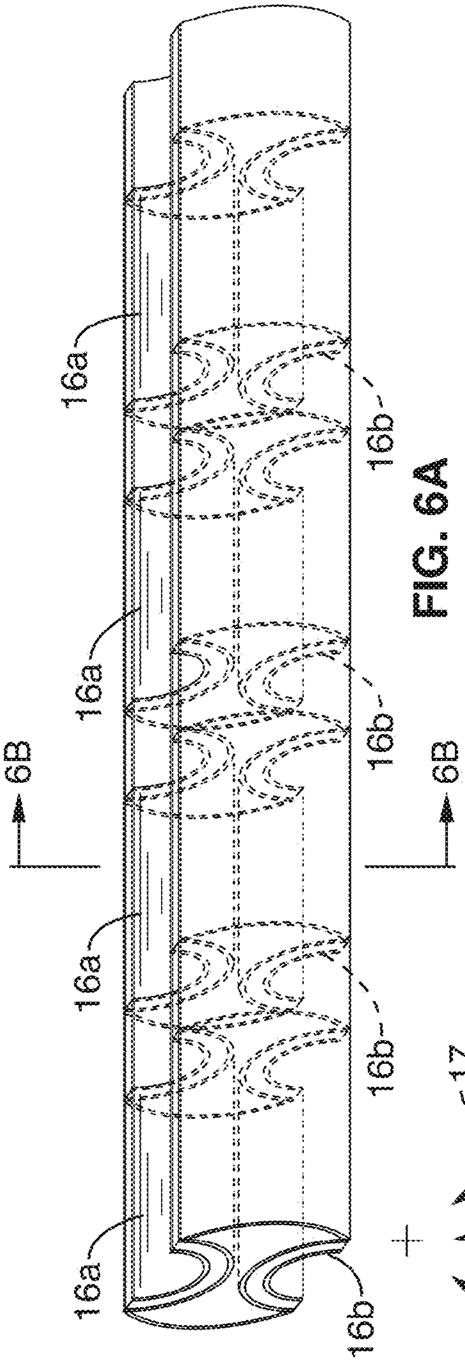
FIG. 6A shows a slightly angled side view of an ultrasound transducer component assembly for use in the distal end portion of another ultrasound treatment device according to the invention.
Figure 6B:
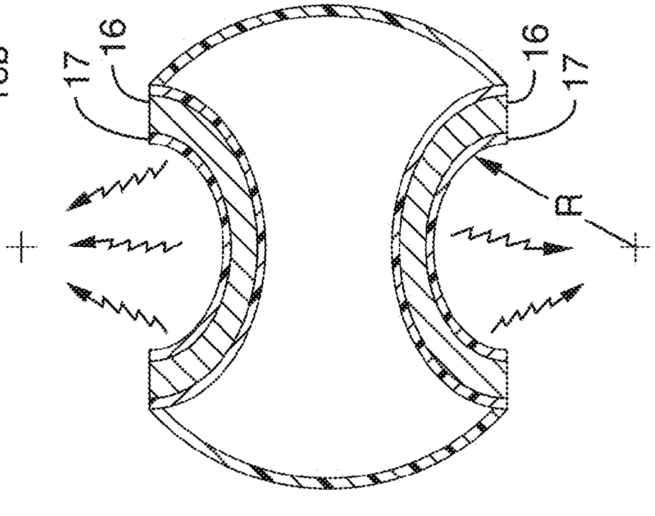
FIG. 6B shows a cross-sectioned transverse view taken along lines 6B-6B in FIG. 6A.
Figure 6C:
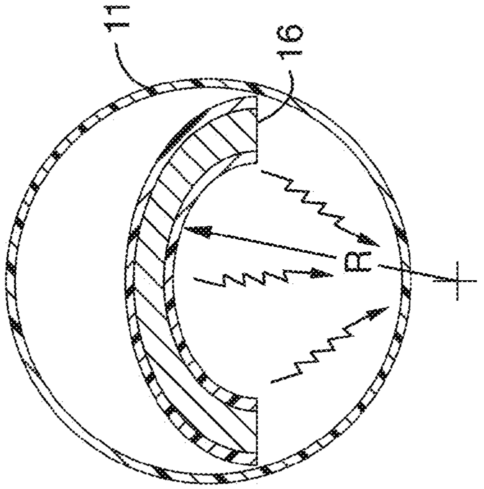
FIG. 6C shows a schematic cross-sectioned side view of an alternative ultrasound transducer component assembly within an ultrasound treatment device according to the invention versus that shown in FIG. 6B.

A further embodiment shown in FIGS. 6A-C further provides semi-hemispherically shaped transducers 16 that are essentially flipped to have an opposite radial orientation relative to the radius of device 11 as compared to otherwise similar transducer sectors 16*a,b* in FIG. 5A. More specifically, transducer segments 16*a,b* each have their concave surfaces 17 facing outwardly from device 11. This is believed to allow for a focused US signal to be emitted therefrom to a focal point or depth in relation to device 11 that is controlled by the radius of curvature R for the corresponding transducer. Such an arrangement may include two radial sides of linearly spaced transducers, e.g. 16*a,b* as shown in FIGS. 6A-B. Or, device 11 may be adapted to house a single such transducer segment 16, as shown in FIG. 6C, which limits the radial emission choices to one region around the device periphery, but increases the design real estate and options for device 11 to house this unique transducer configuration. In any event, the applicator device 11 may be repositioned to control angular thermal profile. Where angular control is of important necessity (such as treatment immediately adjacent spinal column), device 11 may be designed to be in particular torqueable from outside the body in order to rotate the radially focused transmission with the shaft, such as via use of metal reinforcements or tubular members, or in general composite shaft designs such as wire or braid reinforcements.

As elsewhere herein shown and described, device 11 along the US path from transducer 16 generally includes an ultrasonically translucent medium, such as a fluid. Acoustic gain and temperature regulation of applicator surface can help control distance of heated region and effects from applicator surface. Frequency and depth of focus can be selected to control heating pattern, and time can be varied to control heating effects and distribution.

The segmented array of FIG. 6C can use many different types of transducers 16, such as for example concave sections of cylindrical or tubular transducers or spherical or semi-spherically focused transducers. The outer diameter of the tubes used to form the transducer shown in FIG. 6C is much larger than the diameter for device 11 that supports the transducer 16. The transducer sectors are a small arc; thus, a line focus is produced at depth over a small arc angle, producing an intense US exposure or heating pattern which is approximately the same length as the tubular segment, but very narrow in the angular dimension, which can beneficially be as narrow as from about 1 to about 10 deg., preferably as narrow as from about 1 deg. to about 5 deg. The length and number of segments can be varied.

Figure 6D:
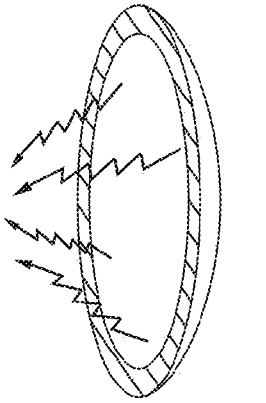
FIG. 6D shows an angular perspective view of a semi-spherical disc-shaped transducer for use according to a further embodiment of the invention.

Referring to the particular embodiment shown in FIG. 6D, a conical or semi-spherical disc-shaped transducer 16 is shown which focuses energy not only radially along a length of the corresponding transducer, but instead focuses along the entire surface of the disc-shape. Therefore such shaped transducer more precisely and densely focuses and localizes the energy being delivered into a very small region of tissue. While an array of such shaped disc transducers 16 is contemplated, the focused pattern may create energy gaps between adjacent elements—therefore this design may be more applicable to precise treatment in one area by one transducer, which may be followed by moving the transducer, either together with or along the supporting device 11 to another location to be treated.

As previously mentioned above, the embodiments of FIG. 6A-D, in addition to the other embodiments contemplated herein, can cooled either externally or internally, an can be inserted within the disc or laparoscopically placed against the target tissue or directed toward the target tissue. Acoustic gain and temperature regulation of applicator surface can help control distance of heated region and effects from applicator surface. Frequency and depth of focus can be selected to control heating pattern, and time can be varied to control heating effects and distribution. Other examples of ultrasound array techniques for adjusting the selectivity of ultrasound transmission from a device are disclosed in U.S. Pat. No. 5,391,197, which has been previously incorporated by reference above; the various embodiments of that disclosure are contemplated in combination with this disclosure with respect to segmented array of US transducers, where appropriate and as modified according to this disclosure according to one of ordinary skill.

As elsewhere provided herein, the illustrative embodiments and procedures have applications in many different soft/hard tissue sites and body parts where ultrasound exposure, high temperature, low temperature or combination of effects are desired. Joints in particular are locations where the present invention is well suited for providing therapy. However, as stated above of particular benefit is use of the present invention for treating intervertebral discs.

Therefore, one example of a method for treating an intervertebral disc according to the present invention is provided according to various sequential modes of use shown in FIGS. 7A-F. This procedure for the purpose of illustration more specifically shows posterior-lateral approach to treating a posterior wall of an intervertebral disc from a location within the nucleus. However, because selectivity in disc treatment is so very important, clearly other procedures are contemplated as will be further developed through other examples below.

Figure 7A:
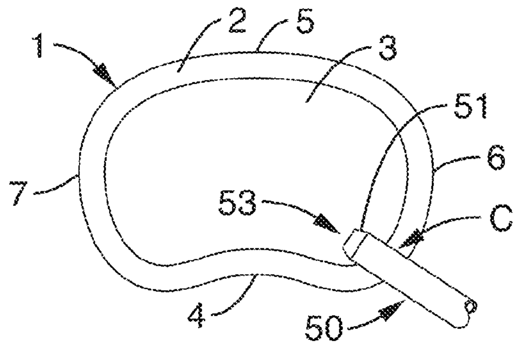
FIGS. 7A-F show a top perspective view of a laterally cross-sectioned intervertebral disc during respectively sequential modes of operating the ultrasound treatment system for intervertebral disc therapy according to the invention.

More specifically, according to FIG. 7A a posterior wall 4 of annulus 2 is observed to require thermal treatment, either due to physical damage to the annulus 2 structure (e.g. herniation), or otherwise, such as for example innervation with unwanted nervous tissue causing pain or other inflammatory cells (which may be directly or indirectly related to disc damage such as herniation). As shown in FIG. 7A, a sharp, pointed tip 51 of a spinal needle 50 is used in a posterior-lateral approach to puncture through the posterior-lateral region of the wall of annulus 2. This gives lumenal access through needle bore 53 into the nucleus 3 for ultrasound probe delivery.

Figure 7B:
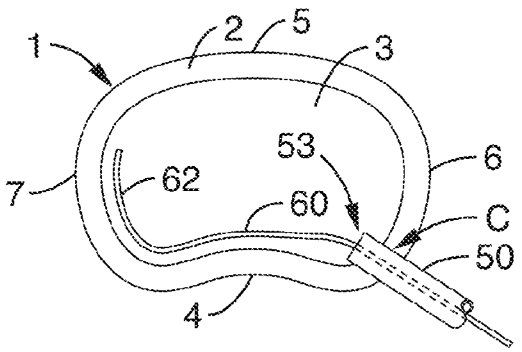
Figure 7C:
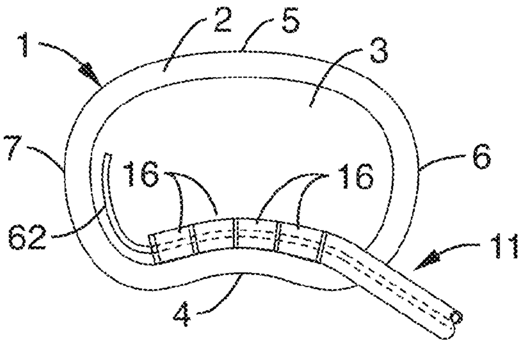
Figure 7D:
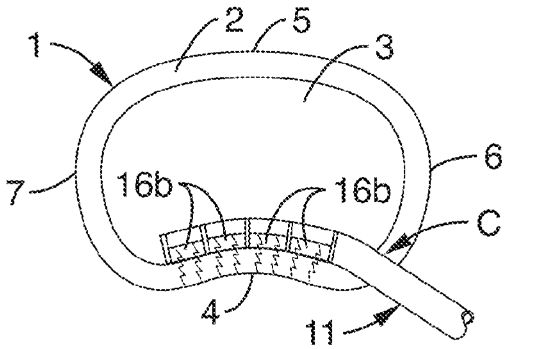
Figure 7E:
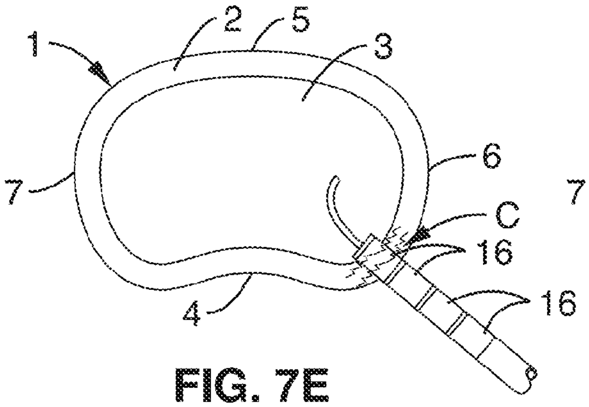

As shown in FIG. 7B, a guidewire 60 having a steerable distal tip 62 is then advanced through needle bore 53 and into nucleus 3. It is contemplated that guidewire 60 may be used for many purposes within the nucleus 3, or otherwise in or around disc 1. However, one particularly beneficial use is shown, wherein guidewire is tracked along proximal wall 4, and then further around the more severe radius along lateral wall 7. This gives a rail along proximal wall 4 along which a highly flexible device 11 may track for ablation there. This is shown in FIG. 7C, wherein ultrasound transducers 16 are of length, size, and location along device 11 such that they are positioned over guidewire 60 to coincide with the area along posterior wall 4 to be treated. According to the embodiment shown in FIG. 7D, only one radial aspect of device 11 is actuated for US emission and treatment, which is shown to be transducer segments 16*b* in an array on one radial aspect of device 11 interfaced with or facing proximal wall 4. Thus US energy is transmitted into wall 4 to treat that region without substantial treatment elsewhere.

Figure 7F:
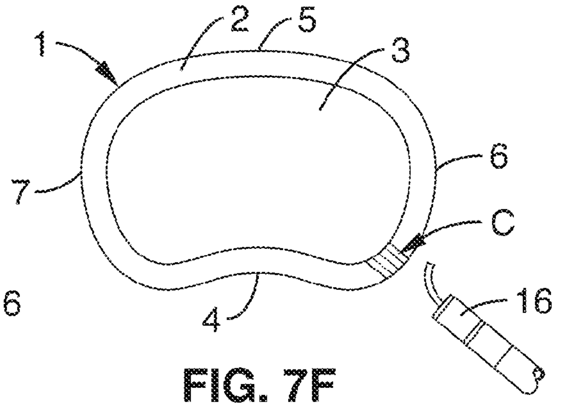

After treatment, other regions may be treated by further manipulating guidewire 60 and/or device 11 within the nucleus 3 (or outside of annulus if desired). Once treatment within the annulus is completed, device 11 may be withdrawn. In the embodiments shown in FIGS. 7E-F, the ultrasound transducers 16 may be used to assist in closing the wound formed at entry site C through annulus, such as by elevating the temperature in that area sufficient to cause collagen shrinkage to aid in closing that aperture, as shown in FIG. 7F for example. In this application, the entire circumference of device 11 may be activated for US emission, or if only a radial region is adapted for such emission, it may be rotated to heat all aspects of the wound aperture to seal it. In addition, a sealant may be administered through the distal end of device 11 to close the wound, such as at introduction region C, either instead of or in conjunction with ultrasonic emission from device 11.

Figure 8:
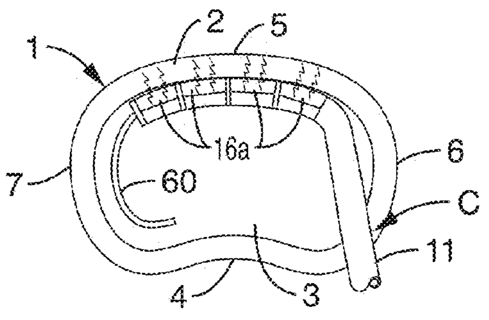
FIGS. 8-9 show alternative modes of operating an ultrasound treatment device according to the invention for treating different respective regions of an annulus fibrosus of a disc from within the nucleus and according to a posterior-lateral approach into the disc.
Figure 9:
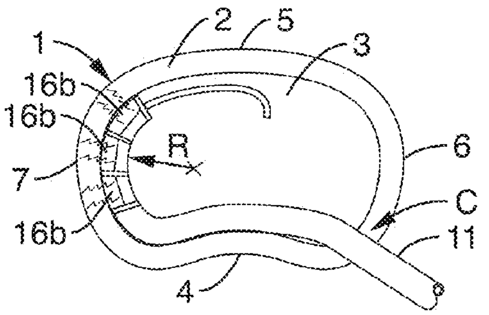

Other regions of disc 1 may also require localized, selective therapy with US, and the present invention allows for highly specialized treatments in the various regions. FIGS. 8 and 9 for example show use of device 11 from the right posterior-lateral approach through site C shown in FIGS. 7A-F, but for treating anterior wall 5 and left lateral wall 7 regions, respectively. For the embodiments shown wherein device 11 is highly flexible for sufficient trackability over guidewire 60, the same device may be used for treating the very different areas shown in FIGS. 7A-F, FIG. 8 (anterior wall), and FIG. 9 (left lateral wall). However, as shown in comparing FIGS. 7A-F, 8, and 9, different radial regions of device 11 may be activated to treat the respective interfacing wall (where angular specificity is provided, which may not be required though often preferred). In particular, the guidewire trackability of the present embodiments provides for highly beneficial flexibility between the ability to treat these very different segments, in particular in view of the generally more significant curvature associated with the anatomy around the lateral wall regions as shown at radius R for lateral wall region 7 shown in FIG. 9.

Figure 10:
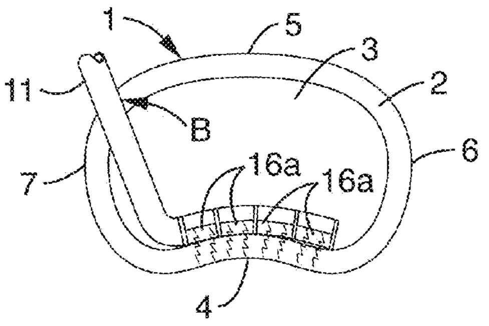
FIG. 10 shows an alternative mode of operating an ultrasound treatment device according to the invention using an anterior approach to treat a posterior wall region of the annulus fibrosus of a disc from within the nucleus of the disc.

For the purpose of further illustration, FIG. 10 shows a device 11 according to the invention used to treat a posterior wall 4 of disc 1, but according to an anterior approach through a region of anterior wall 5 adjacent to left lateral wall 7. Again, this may for example be a similar device as that shown and described with respect to FIGS. 7A-9.

Figure 11:
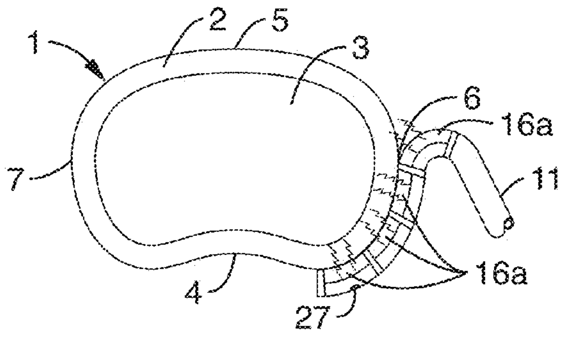

The devices and methods of the invention are also adapted for use in treating spinal disorders from outside of the annulus 2, though preferably still from an invasive location within the patient's body in order to provide the necessary and desired amounts of energy at only the highly localized, target locations. For example, FIG. 11 shows a right posterior-lateral approach to treat a region of annulus 2 from outside of disc 1. Because of surrounding tissues, it is highly desired (though not always required), to deliver only highly selective, directed US energy into only the region of annulus 2 being treated. In particular, truncal nerves often extend along such areas, as well as the spinal cord being located not to far away from such region. Therefore, a controllable, selective array of transducers as shown at transducers 16*a* radiates only toward the disc annulus 2, whereas the opposite side of device 11 is non-emissive. In fact, this opposite side may be selectively cooled to prevent from thermal heating of the area, and may include sensors to monitor such temperature around that area opposite the active US treatment zone, such as for example at thermocouples 27 shown in FIG. 11.

Figure 12:
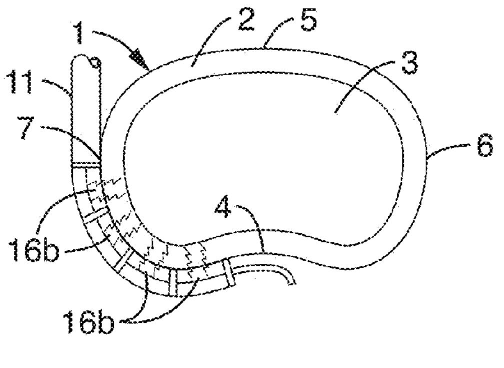
Figure 13:
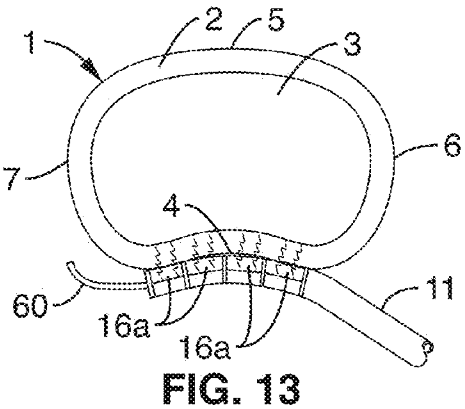

For the purpose of further illustration, FIG. 12 also shows US treatment from outside of a disc 1 according to the invention, but according to an anterior approach. FIG. 13 shows still another exterior treatment modality, however this particular location along the posterior wall 4 is particularly sensitive as the spinal cord is located immediately adjacent device 11 opposite transducers 16*a* and must not be harmed. Therefore, not only the radial emission of energy (either US or thermal heat) from device 11 must be insulated from that radial region corresponding to the spinal cord.

Though guidewire tracking mechanisms provide the illustrative embodiments for positioning in FIGS. 7A-13, other embodiments are contemplated. Moreover, positioning of a device 11 may include simultaneous or sequential positioning of thermometry probes for monitoring of sensitive tissue areas, etc.

A pre-shaped or otherwise directional introduction/delivery device may assist to point a device 11 to a localized area for treatment, such as shown for example in shadow in FIG. 3A for shaped tip 51 for delivery device 50. Such directionality from the delivery device 50 may be provided in addition to, or in the alternative to, providing guidewire tracking of device 11 or other additional positioning modes herein discussed. In addition, other positioning control mechanisms may be incorporated into device 11 itself as follows.

Figure 14A:
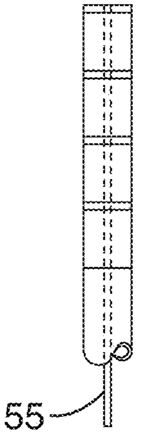
Figure 14B:
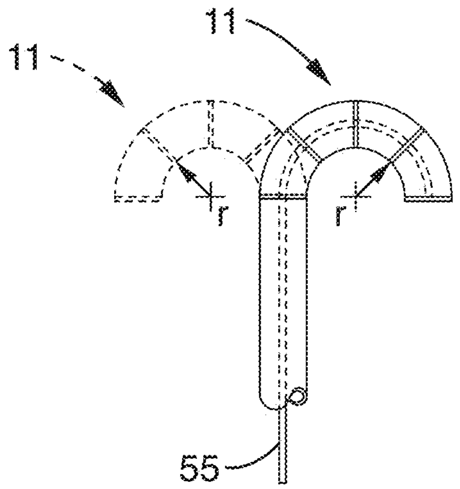
Figure 14C:
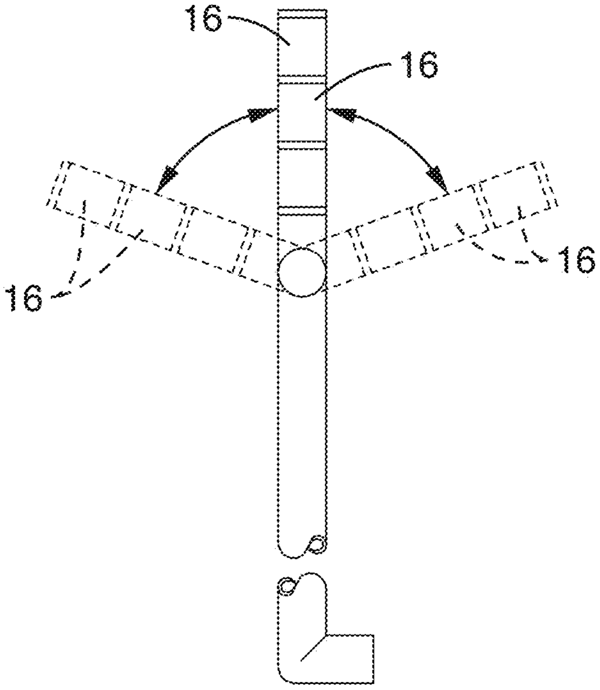
FIG. 14C shows a top perspective view of another ultrasound treatment device of the invention with a distal ultrasound treatment section that is adapted to be rotated about a hinge point for minimally invasive treatment of intervertebral discs and other spine or joint disorders.

One particular deflectable tip design is shown for device 11 in FIG. 14A-B. According to this embodiment, the region of device 11 that includes the array of transducers 16 is deflectable to take a variety of shapes, such as shown in right and left deflection modes around a radius r in FIG. 14B. Such deflection may be achieved using conventional deflection mechanisms, such as for example using an arrangement of one or more pull-wires 55 integrated into the tip region so that tension causes catheter deflection. In addition, such deflection may be achieved instead of along a length of an arc, around a pivot point, as shown in FIG. 14C. Such may be achieved in order to achieve different angles for surgical approaches into the desired treatment areas, such as in or around intervertebral discs. The transducer elements may be along a deflectable segment that is either round, or may be more planar as desired.

Figure 15A:
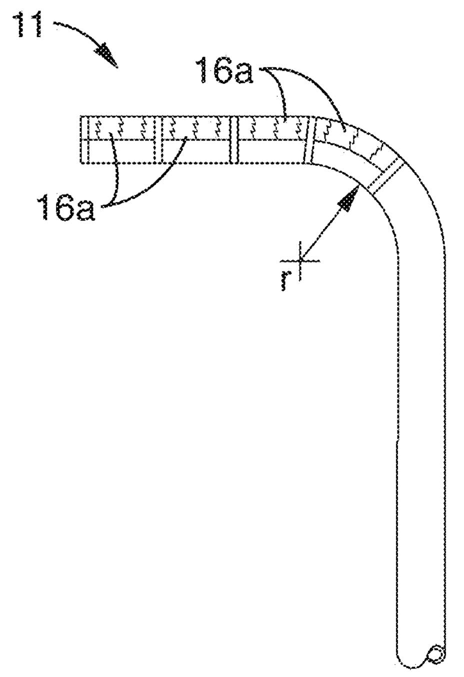
FIG. 15A shows a plan perspective view of the distal end portion of another ultrasound treatment device of the invention having a predetermined shape and operative region for ultrasound delivery that corresponds to particular desired approaches and ultrasound therapy to certain specified regions of tissue associated with an intervertebral disc.
Figure 15B:
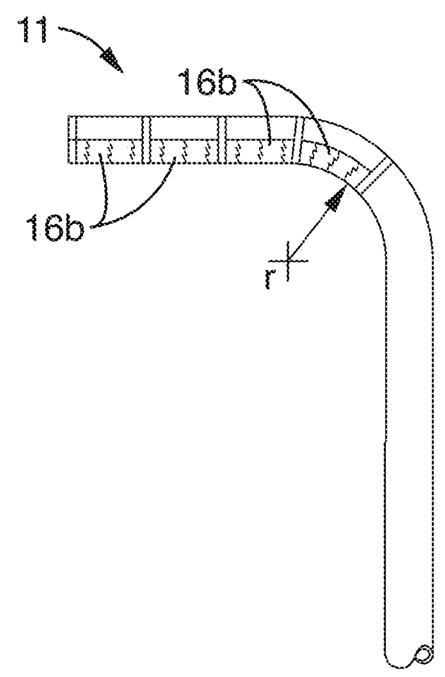
FIG. 15B shows a perspective view of another ultrasound treatment device having a similar shape to that shown in FIG. 15A, but having a different operative region for ultrasound delivery corresponding to delivering invasive therapy to a different desired region of a respective intervertebral disc.

Pre-shaped distal regions for device 11 may also provide for desired treatment of highly unique anatomies. A kit of devices, each having a particular shape is contemplated. Such shapes may be integrated in procedures with or without conjunctively using guidewire tracking. For example, FIG. 15A shows a pre-shaped distal end for device 11 having a simple distal curve around radius r. The transducers 16 are around the outer radius of such shaped end, and therefore this shape and orientation is suitable for example for treating an anterior wall 5 from within a disc 1 via a posterior-lateral approach, such as for example according to FIG. 8. A similar shaped end is shown in FIG. 15B, but the transducers 16 are instead on the inside radius r. This is more suitable for posterior-lateral approach with posterior wall treatment, such as for example in FIGS. 7A-F.

Figure 16:
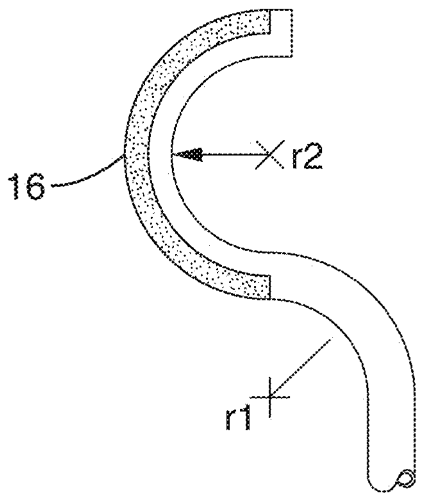
FIG. 16 shows a perspective view of another ultrasound treatment device having a different unique shape and operative region for ultrasound delivery corresponding to delivering invasive therapy to a different desired region of a respective intervertebral disc.

A further beneficial shape and orientation is shown in FIG. 16. Here, an acute bend shown around radius r2 is adapted to correspond to the more drastically rounded lateral wall regions 6,7 of a disc annulus 2 with an energy emission region on the outside of that bend. An additional bend region may be highly beneficial, though not always required, shown proximally of the distal bend around radius r2 and having a less drastic bend, in the opposite direction of r2, shown around radius r2. This configuration is highly beneficial for treating lateral wall regions 6,7 from a posterior-lateral approach (e.g. FIG. 9), though may be used in the same configuration or slightly modified for anterior approach.

Though ultrasound transducers and their many benefits for invasive energy delivery into tissues has been extensively herein described, various of the embodiments further contemplate use with other energy sources or treatment modalities, either instead of or in conjunction with ultrasound. Thus, treatment region 16 in FIG. 16 does not specifically show individual ultrasound segments as in the other figures, for the purpose of illustrating other energy sources or treatment modalities that my be incorporated thereon and still gain the benefit of the unique shape provided for inner disc ablation according to that figure. Other sources such as electrical (e.g. RF), light (e.g. laser), microwave, or plasma ion may be used. In addition, cryotherapy or chemical delivery may be achieved along the regions variously designated as "transducer 16", which may be accompanied by other modifications corresponding therewith, without departing from the scope contemplated by the embodiments.

According to the various deflectable or pre-shaped modes, or modes where energy delivery is limited to only one side of the device, the device 11 is preferably torqueable, such as by integrating into the shaft design a composite of braided fibers or other stiff members. This allows for more precise control of the distal tip regions as it deflects or takes its shape along a plane within the desired area of the body to treat.

The various embodiments for device 11 above may be adapted to incorporate active cooling, such as circulating cooling fluids within or around active energy emitting elements such as transducers 16 variously shown or described. Such cooling may be integrated into the particular device 11, or may be achieved by interfacing the particular device 11 inside of or otherwise with another device.

Figure 17A:
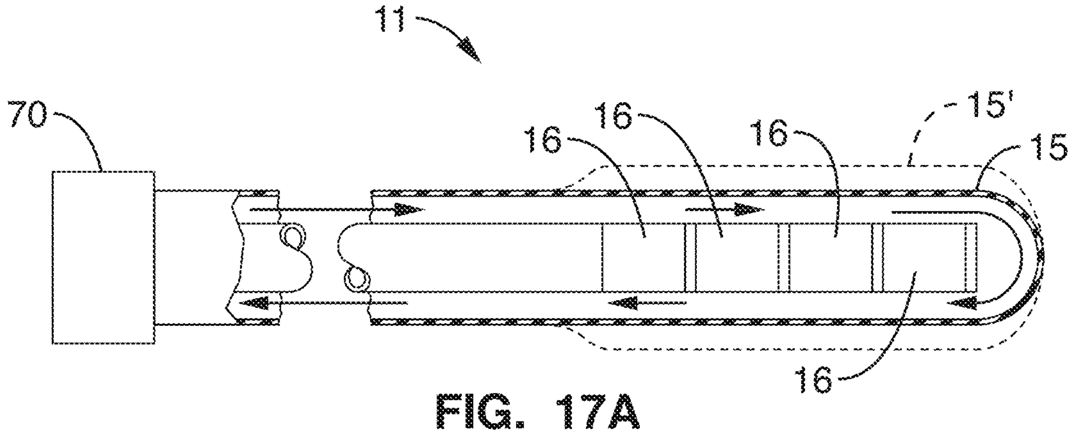
FIG. 17A shows a top view of an ultrasound treatment device assembly with transducers inside of an outer cooling jacket that is interfaced with a fluid circulation pump to actively cool the transducers.

FIG. 17A shows for example device 11 within an outer jacket 15 that may or may not be distendable, as shown in shadow at 15'. Outer jacket 15 is adapted to circulate fluids around transducers 16 and therefore is interfaced with a circulation pump 70 in an overall system. In an alternative embodiment sharing many common features as FIG. 17A, the device 11 shown in FIG. 17A provides for the cooling fluid to be delivered through an interior passageway of the interior ultrasound device, out the distal tip thereof within the outer jacket 15, and back over the outer surface of the interior device including the transducers 16.

Figure 17B:
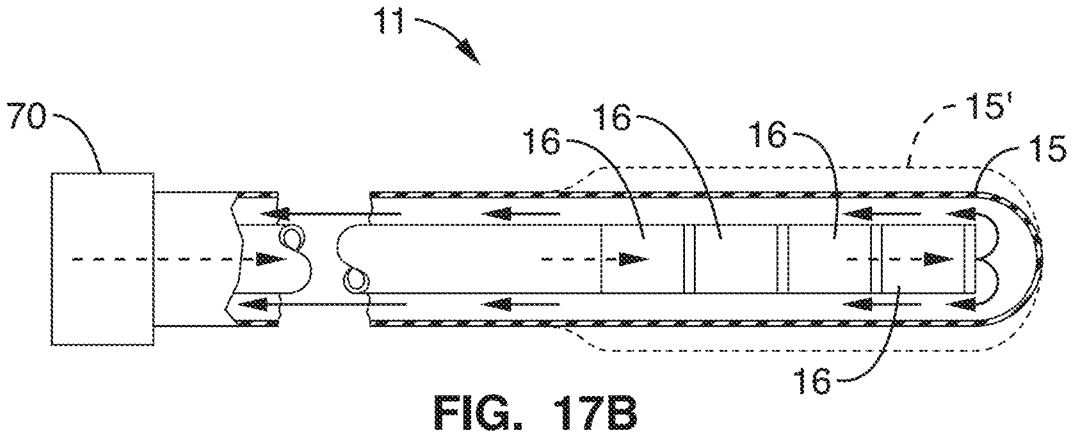
FIG. 17B shows a top view of another partially cross-sectioned ultrasound treatment device assembly similar to that shown in FIG. 17A, except showing the cooling fluid to circulate from within the ultrasound transducer device and into the surrounding sheath.

In either the FIG. 17A or 17B embodiments, device 11 may be fixed within outer jacket 15, or may be moveable relative to outer jacket 15, or visa versa. Fluids provided in an outer jacket surrounding transducers 16 according to the invention may also be used beneficially for ultrasound coupling to intended tissues to be treated. This may be in addition to or instead of being used for cooling. In particular, such coupling fluids may be provided in a jacket 15 that is conformable, such that irregular surfaces to be treated receive uniform energy coupling from the assembly. Or, pre-shaped, and symmetric or asymmetric shapes, may be provided as appropriate to provide such coupling. Ultrasound coupling may be further achieved by providing a non-liquid coupling member as a stand-off over a transducer in order to couple that transducer to the tissue—such as for example a sonolucent coupling gel pad, etc.

In addition to the various designs for device 11 described above for achieving positioning, e.g. guidewire tracking, pre-shaped, or deflectable, other mechanisms may also be incorporated for accurate positioning. For example, stiff or flexible distendable member(s) may be incorporated on device 11, e.g. a balloon or expandable cage, that distends to a predetermined-shaped (or just generally distends). This may help positioning, such as for example where the nucleus 3 is void of pulposus in order to position the transducers 16 within a balloon at a desired location within the annulus 2. In addition to positioning, such a member may also be used to aid coupling, tissue deforming, and tissue repositioning during a treatment procedure.

As previously discussed, the intervertebral disc applications of ultrasound herein contemplated require high selectivity for US or otherwise thermal therapy due to the presence of highly sensitive, non-targeted tissues in close proximity (e.g. spinal cord and other nerves). Therefore, though heat conduction may not be the intended mode of therapy with transducers 16, their concomitant heating during US sonic wave delivery may cause unwanted damage in either the targeted or non-targeted tissues. Accordingly, cooled lumens or balloons over the transducers may be employed to protect such tissues from such heat, or directivity of the ultrasound per the embodiments herein described my adequately protect sensitive non-targeted tissue. In the case of an active cooling mechanism, it is to be appreciated that such mechanism may be integrated directly onto device 11 that carries the transducers 16. Or, a separate co-operating device such as an outer sleeve carrying cooling fluids may be used. Such cooling chamber may be on the side of the transducer delivering the targeted US wave, in which case fluid in the chamber must be substantially sonolucent for efficient energy delivery. In the event the cooling is intended to protect a "back side" of the device only, other fluids may be used.

Applicators, such as the various embodiments shown for device 11 among the FIGS., and insertion tools, e.g. delivery device 50, may be adapted to be MR compatible for real time monitoring of a particular procedure. Also other imaging modalities may be used instead, or in conjunction with one another, in order to control and optimize the US treatment procedure, including for example for monitoring positioning, temperature, lesion assessment, coagulation, or otherwise changes in tissue structures related to the treatment (e.g. targeted tissue to be heated or adjacent tissues to monitor safety, such as regions of concern to preserve nerves associated with the spinal cord). In fact, US itself is an energy source that has been widely used for acoustic imaging in and around internal body structures. It is contemplated that imaging US devices may be incorporated into a device 11 directly, or indirectly incorporated as a separate cooperating device in system 10, and further that the US treatment transducers 16 herein shown and described may be operated in imaging modes before, during, or after thermal US therapy is performed with those same transducers 16.

In addition to the spine, the device systems and methods according to the embodiments may be used in other regions of the body, in particular other joints. Examples of such regions include knee, ankle, hip, shoulder, elbow, wrist, knuckles, spinal processes, etc. In such case, further modifications from the illustrative embodiments herein provided may be made in order to accommodate the unique anatomy and target tissue regions, without departing from the spirit and scope of the present invention.

While the device systems and methods have been herein described with respect to treating tissue via US exposure in order to provide hyperthermia effects, other non-thermal results may also be intended, either in conjunction with hyperthermia or in the alternative to. For example, drug activation and or enhanced drug delivery, such as for example via enhanced dispersion or cellular permeability or uptake, may be achieved by delivering certain specific therapeutic dosing of US energy, as has been well studied and characterized in the art. Such methods may for example aid in the treatment for example of arthritis in joints, etc.

The invention as described herein according to the particular embodiments is highly beneficial for treatment of the body, in particular joints, and in particular the spine. In general, these devices and methods are adapted for such treatment invasively from within the body. However, external applications are contemplated as well. In addition, treating living bodies according to the invention is believed to provide a highly therapeutic result for improved living. Nevertheless, use of the devices and methods as described herein are also contemplated for conducting scientific studies, in particular with respect to characterizing tissues in their relation to applied energy. Therefore, "therapeutic" applications may include those sufficient to induce a measurable change in tissue structure or function, whether living or post-mortem, prophylactic or ameliorative, research or clinical applications.

EXAMPLE

External Directional Ultrasound Thermal Therapy of Cadaver Spinal Discs

Figure 18A:
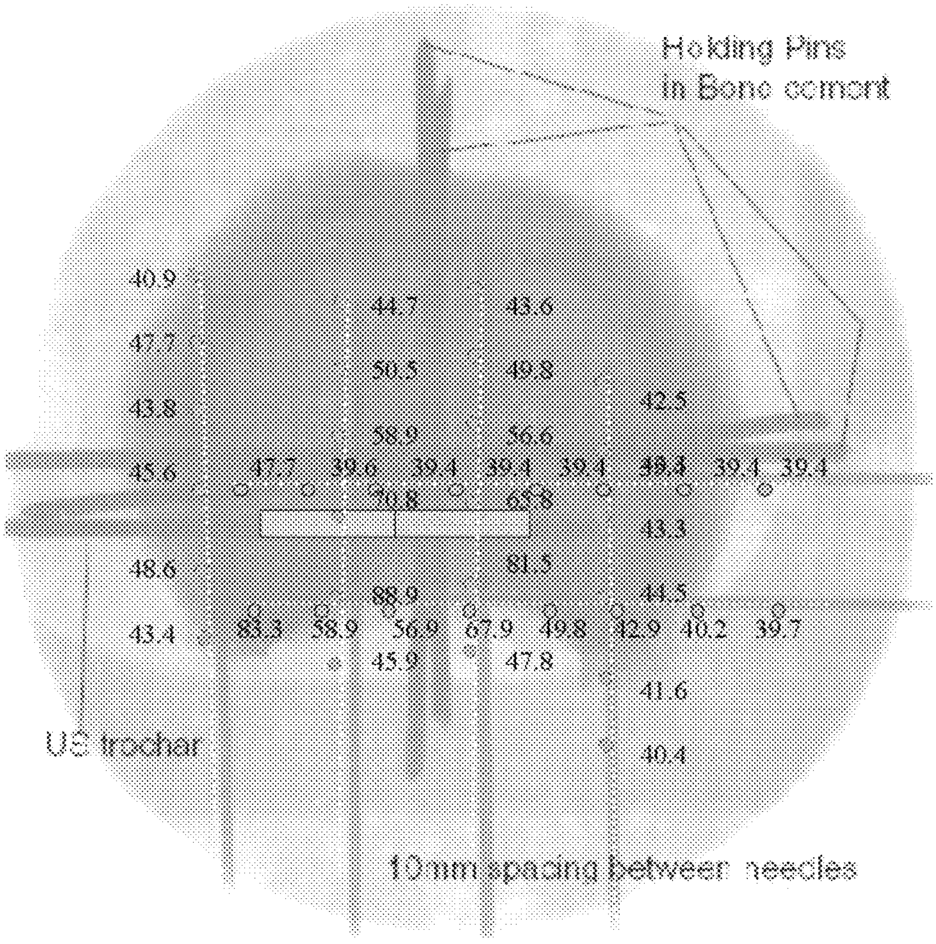
FIG. 18A shows an x-ray picture of an explanted disc being treated according to one aspect of the invention, and shows various data points along temperature monitoring probes inserted along certain desired locations for monitoring across the disc.

FIG. 18A shows an X-ray photograph of a cadaver intervertebral disc during invasive ultrasound treatment with a device and method according to the invention as follows. Temperature monitoring measurements are shown as overlay dotted lines and numbers over the X-ray.

An ultrasound probe was provided as follows. Two PZT ultrasound transducers were provided on a hypotube, each being 1.5 mm OD×10 mm long (0.012" wall thickness), and being spaced by about 1 mm. The ultrasound probe was inserted within a 13-g Brachytherapy Implant Catheter having a 2.4 mm O.D., which is commercially available from Best Industries. Water at room temperature was circulated through the outer catheter and over the transducers at about 40 ml/min during ultrasound transmission. The assembly of the outer catheter with inner transducers and probe was inserted laterally into a cadaver disc along the border of the nucleus pulposus and posterior wall of the annulus fibrosus. The approximate location of the transducers is shown in two rectangles in FIG. 18A. Thermocouple probes were inserted into the disc as shown in the X-ray, and with measurement locations reflected by the sample measurements in the overlay. The above test sample and instrumentation was placed within a 37 deg C. water bath during testing. Each transducer was run at approximately 10 W power, wherein temperature numbers shown in FIG. 18A generally represent temperatures at substantially steady state after actuating the transducers. Heat generated by the ultrasound probe was sufficient to cause therapeutic effects in surrounding tissues of the annulus and nucleus.

Another similar study was performed using ultrasound to heat a post-mortem intervertebral cadaver disc using a curvilinear ultrasound applicator directly coupled to tissue at 5.4 MHz and 10 W power. A temperature vs. time graph of the results at varied depths from the transducer surface are shown in FIG. 18B, which shows among other information that temperatures reached 70-85 degrees within 7 mm from the disc treatment surface and within 5 minutes of treatment.

Figure 18B:
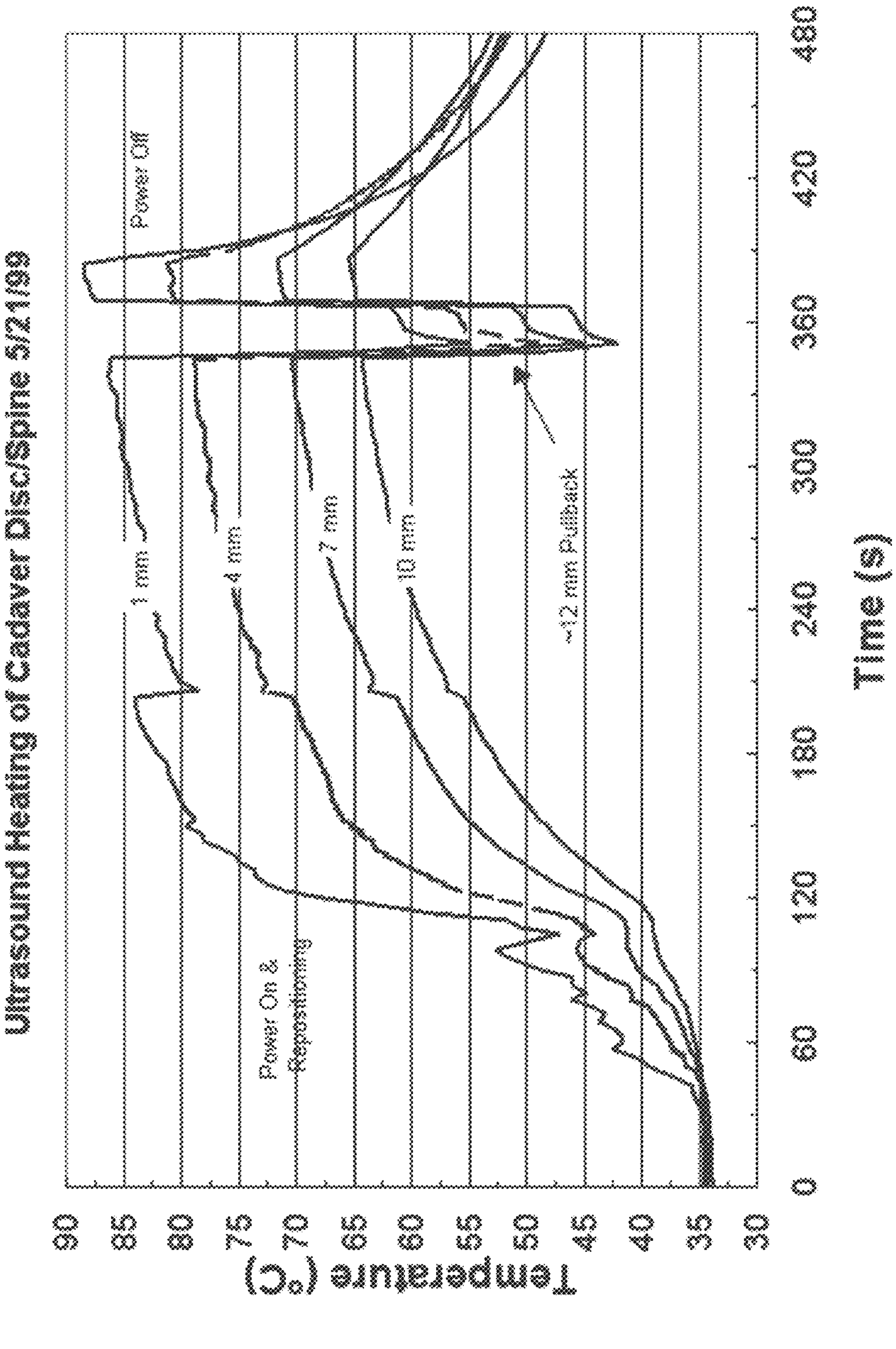
FIG. 18B shows a graph of temperature vs. time for an ultrasound heating study in an explanted cadaver spine disc, and shows curves for tissue depths of 1 mm, 4 mm, 7 mm, and 10 mm away from the directional heating transducer.

As shown in the graph of FIG. 18B, the elevated temperature achieved at 1 mm from the ultrasound transducer reached: over 45 degrees C. within 90 seconds (1½ minutes); over 70 degrees C. within 120 seconds (2 minutes); over 75 degrees C. in nearly 120 seconds; over 80 degrees C. within 180 seconds (3 minutes); and over 85 degrees C. by about 300 seconds (5 minutes).

Temperatures at 4 mm depth from the transducer reached: 45 degrees C. in less than 120 seconds (2 minutes); 55 degrees in close to about 120 seconds; 65 degrees C. within 150 seconds (2½ minutes); over 70 degrees C. within less than 210 seconds (3½ minutes); and over 75 degrees C. and still rising by about 240 seconds (4 minutes).

Temperatures at 7 mm depth from the transducer reached: 45 degrees C. by about 120 seconds (2 minutes); 55 degrees C. by about 150 seconds (2½ minutes); 60 degrees C. in nearly 180 seconds (3 minutes); 65 degrees C. within 240 seconds (4 minutes); and 70 degrees C. within 300 seconds (5 minutes).

Temperatures at 10 mm depth from the transducer reached: 45 degrees C. in less than 150 seconds (2½ minutes); 55 degrees C. in less than about 210 seconds (3½ minutes); over 60 degrees C. in less than 270 seconds (4½ minutes); and slightly less than about 65 degrees C. by 300 seconds (5 minutes).

In another regard, the graph in FIG. 18B also shows that temperatures above 45 degrees C. were reached within 90 seconds at 1 mm, 120 seconds at 4 mm and 7 mm, and 150 seconds at 10 mm depths from the transducer. Similarly, temperatures of at least 55 degrees C. were reached within about 120 seconds at 1 mm and 4 mm, 150 seconds at 7 mm, and 210 seconds at 10 mm depths. Temperatures of at least 65 degrees C. were reached within less than 120 seconds at 1 mm, 150 seconds at 4 mm, 240 seconds at 7 mm depths. Still further, temperatures above 70 degrees C. were reached within 120 seconds at 1 mm, 210 seconds at 4 mm, and 300 seconds at 7 mm depths. Even further heating to above 75 degrees C. were reached within close to 120 seconds at 1 mm, and 240 seconds at 4 mm depths.

Further observation of FIG. 18B in the time domain, in less than 150 seconds temperatures at up to 7 mm depth from the transducer reached at least 55 degrees C. Within about 210 seconds temperatures in tissue as deep as 4 mm deep reached over 70 degrees C., up to 7 mm deep reached at least 60 degrees C., and up to 10 mm deep reached over 55 degrees C. Within 270 seconds, temperatures 4 mm deep reached over 75 degrees C., up to 7 mm deep reached over 65 degrees C., and up to 10 mm deep reached over 60 degrees C. In still a further regard, by 300 seconds temperatures up to 7 mm deep reached at least 70 degrees C., and up to 10 mm deep reached almost 65 degrees C.

Upon further comparison of temperatures vs. depth according to the FIG. 18B graph: temperatures over 60 degrees C. (and for the most part up to 65 degrees or more) were achievable up to 10 mm deep; temperatures up to at least 70 degrees C. were achieved up to 7 mm deep; temperatures over 75 degrees were achieved up to at least 4 mm deep; and at 1 mm depth temperatures of over 80 degrees and even 85 degrees were observed.

As will be further developed below and elsewhere herein, such elevated heating, including at tissues as deep as 4 mm, 7 mm, and in some regards even 10 mm, is a highly beneficial aspect of the present invention. For example, other more conventional intervertebral disc heating devices, in particular the "IDTT" device elsewhere herein described, have been observed to be limited as to the extent and depth of heating possible.

For example, according to at least one study observing the heating effects of the "IDTT" radiofrequency electrical heating device (elsewhere herein described) also on cadaveric lumbar spine disc samples, the following observations were made. During intended modes of use for internal disc heating, and over treatment times of 17 minutes (1020 seconds), the IDTT devices tested were able to heat only the closest 1-2 mm of intervertebral disc tissue to temperatures just barely exceeding 60 degrees, with no tissue of 1 mm depth or greater exceeding 65 degrees C. despite reaching 90 degrees C. on the probe itself. Moreover, only tissues within a 7 mm radius of the heating probe exceeded 48 degrees C. during the 17 minute treatment time. Still further thermal dosing was limited such that the maximum predicted depth for damaging nociceptive fibers infiltrating the discs was believed to be only within a 6-7 mm radius.

Accordingly, substantial benefit is gained by using the ultrasound treatment device of the present invention to the extent depth of heating and heating to substantial temperatures and within reasonable times is desired.

EXAMPLE

Thermal Therapy of Pre-Stressed Spinal Joints

This Example provides an abstract summary, introduction, methods, results, and conclusions with respect to a certain group of studies performed to evaluate heat-induced changes observed in intervertebral discs, related structures such as in particular annulus fibrosus, and the related biomechanics, in particular with respect to "intact" discs, as follows.

1. Abstract.

The intervertebral disc is considered a principal pain generator for a substantial number of patients with low back pain. Thermal therapy has been disclosed to have a healing effect on other collagenous tissues, and has been incorporated into various minimally invasive treatments intended to treat back pain. Since the therapeutic mechanisms of thermal therapy have generally been previously unknown, proper dosage and patient selection has been difficult. Thermal therapy in one regard has been disclosed to acutely kill cells and denature and de-innervate tissue, leading to a healing response.

The purpose of this study was to quantify the acute biomechanical changes to the intact annulus fibrosus after treatment at a range of thermal exposures and to correlate these results with the denaturation of annular tissue. Intact annulus fibrosus from porcine lumbar spines was tested ex vivo. Changes in biomechanical properties, microstructure, denaturation temperature, and enthalpy of denaturation before and after hydrothermal heat treatment (at 37, 50, 60, 65, 70, 75, 80, and 85° C.) were determined. Shrinkage of excised annular tissue was also measured after treatment at 85° C. Significant biomechanical changes in the intact annulus were observed after treatment at 70° C. and above, but the effects were much smaller in magnitude than those observed in excised tissues. Histological and mDSC data indicated that denaturation had occurred in intact annular tissue treated to 85° C. for 15 minutes, though such effect was observed to be slight. It is believed based on observations made that constraints imposed on the tissue by the joint structure retard changes in properties. These findings have implications for dosing regimens when thermally treating disc tissue.

2. Introduction.

The goals of this study were to: 1) quantify acute biomechanical changes to the intact annulus fibrosus induced by a broad range of ex vivo thermal exposures; and 2) to correlate these results with denaturation of annular tissue using modulated differential scanning calorimetry (mDSC) and histological data.

3. Methods.

a. Mechanical Testing.

Forty-one spinal motion segments (18 $L_{12}$, 19 $L_{34}$, 19 $L_{56}$) consisting of the intervertebral disc (IVD) and each adjacent vertebral body were cut from 22 fresh frozen porcine lumbar spines (domestic farm pig weight range: 115-135 lbs). Muscular and ligamentous structures, facet joints, transverse processes, and posterior elements were dissected from the vertebral bodies to isolate the disc. Saline-soaked gauze was wrapped around the discs during preparation to minimize dehydration. Next, the nucleus was depressurized by drilling holes first through the vertebral bodies to the center of the nucleus in the superior-inferior direction, and then from the anterior faces of the vertebral bodies to the central hole. Plastic tubing was inserted into the anterior openings and affixed with cyanoacrylate. The vertebral bodies, anchored with 2.5 mm threaded rod, were embedded into fixation cups using polymethylmethacrylate (PMMA). An alignment bar mated with grooves in the fixation cups to ensure that the plane of the disc remained normal to the vertical loading axis. X-rays (Faxitron Cabinet X-Ray System, Hewlett-Packard, McMinnville, Oreg.) were taken of the specimens in the dorsal-ventral plane after equilibration in a 37° C. saline bath. Disc heights were determined by averaging three caliper readings from the dorsal-ventral x-rays.

Specimens were secured in fixation cups, mounted into a hydraulic materials testing machine (MTS Bionix 858, Eden Prairie, Minn.), and placed into a temperature controlled 0.15M saline bath at 37° C. to equilibrate. Saline at bath temperature was also circulated through the center of the discs via the tubing attached to the vertebral bodies; this allowed for a more rapid and uniform heat distribution within the annulus.

Temperatures were measured using two stainless steel thermocouple needle probes, one placed in the bath, and one inserted approximately halfway into the anterior annular wall. These fine-needle temperature probes were fabricated in-house using 25 micron constantan-manganin thermocouple junctions embedded within a 30 gauge (0.30 mm OD) needle. Superior-inferior x-rays were used to verify proper placement of the annular temperature probe.

The testing protocol consisted of a 20-minute thermal equilibration at 37° C., a 15-minute heat treatment, and another 20-minute equilibration at 37° C. Fast temperature changes were facilitated by exchanging the saline in the bath with that in a reservoir heated to the desired temperature and then maintained with temperature-controlled circulation. The target temperature (to within 7%) was reached within 5 minutes of exchanging the saline. During the equilibrations, the disc stress was maintained at 0 kPa.

Mechanical testing was performed at 37° C. just prior to heat treatment and again subsequent to heat treatment and re-equilibration at 37° C. Testing consisted of nine preconditioning cycles in axial tension-compression (−25 to +150N at 0.25 Hz), followed by one testing cycle to the same limits. The applied load was measured using a precision force transducer (Load Cell 662, MTS, Eden Prairie, Minn.), and the deformation of the disc was assumed to be the change in distance between fixtures, measured using the test system LVDT. Data was collected every 0.01 seconds during mechanical testing and every 15 seconds during heat treatment and equilibration. Heat treatment was to one of the following temperatures: 37 (Controls), 50, 60, 65, 70, 75, 80, or 85° C. Five specimens were tested at each treatment temperature except for the 60° C. group that had six specimens.

After testing, specimens were removed and the discs were cut in the transverse plane and scanned at a resolution of 600 dpi (CanoScan N656U, Canon, Inc., Costa Mesa, Calif.). Annulus areas were measured using imaging software (Scion Image, v. 4.0.2B, Frederick, Md.).

Two additional experiments were conducted to allow us to explore the limits of annular thermal response. In the first study, a specimen was prepared as described above and treated at 85° C. until the thermal contraction stabilized (within 0.01 mm). For the second study, sections of anterolateral annulus were excised from five lumbar discs (2 $L_{23}$, 3 $L_{45}$) from four different spines and treated at 85° C. using the same heating protocol as above. X-rays were taken before and after treatment, and changes in circumferential and radial dimensions after heat treatment were measured using digital calipers.

b. Microstructure

Tissue samples were excised from 37° C. and 85° C. mechanical test specimens, and from an excised specimen treated at 85° C. Samples were embedded in paraffin, sectioned in the circumferential plane at 6 microns, and stained with HBQ (Hall, 1986). The sections were imaged on a Nikon Eclipse E800 microscope (Nikon, Melville, N.Y.) under bright field to examine tissue structure, and under polarized light to assess collagen birefringence.

c. Modulated Differential Scanning Calorimetry

Traditional DSC measures the combined effects of reversible and nonreversible heat flow, but the two components can be measured separately if the modulated DSC (mDSC) technique is used. mDSC was performed on samples of anterolateral annulus fibrosus removed from fifteen previously treated specimens (Cambridge Polymer Group, Somerville, Mass.). Punches (approximately 10 mg) were removed from the control (37° C.) mechanical test specimens (n=5), mechanical test specimens treated at 85° C. (n=5), and from the excised annular specimens treated at 85° C. (n=5). Each sample was placed in 0.1% NaCl solution for 20 minutes, blotted, weighed, and crimped into an aluminum anodized hermetic DSC pan. Samples were placed into a Q1000 differential scanning calorimeter (TA Instruments, New Castle, Del.), equilibrated at 55° C., and then ramped from 55° C. to 95° C. at 0.5° C./min. Using an empty pan as a reference, total enthalpy of denaturation (EH) and the temperature corresponding to the nonreversible endothermic peak ($T_m$) were recorded. Following the mDSC procedure, samples were vacuum dehydrated, and the fractional dry mass (ratio of dry weight to wet weight) was recorded.

4. Data Analysis

The force and displacement data from the mechanical tests were converted to stress and strain. The stress and strain data for each mechanical test were then fit to a high-order polynomial, and an equation for the specimen tangent modulus was calculated as the derivative of this polynomial. A plot of modulus vs. applied stress was constructed. The stress at the inflection point—the transition between tension and compression—was the stress at which the second derivative of the polynomial was zero. The reference configuration was defined as the stress and strain at the pretreatment inflection point. Three biomechanical parameters were calculated from the modulus vs. applied stress curves to quantify heat-induced changes in the mechanical response (FIG. 19): the change in modulus at the inflection point (MI), the change in modulus at 150 kPa (M150), and the change in residual stress at inflection point (RSI). The percent change in hysteresis (HYST %) was calculated from the pre- and post-treatment load-displacement curves. The change in the modulus at the inflection point is a measure of the increase or decrease in the stability of the joint, while the change in the modulus at 150 kPa is an indication of how well the joint will withstand physiologic loading. The percent change in strain at 0 stress (E0%) was used to quantify axial shrinkage of the tissue.

Differences in each parameter with treatment temperature were compared using a one-way analysis of variance (ANOVA). Post-hoc multiple pairwise comparison tests (Fisher's Least Significant Difference) were performed to determine differences between treatment groups with a significance of $p<0.05$.

5. Results.

a. Mechanical Testing

Figure 21:
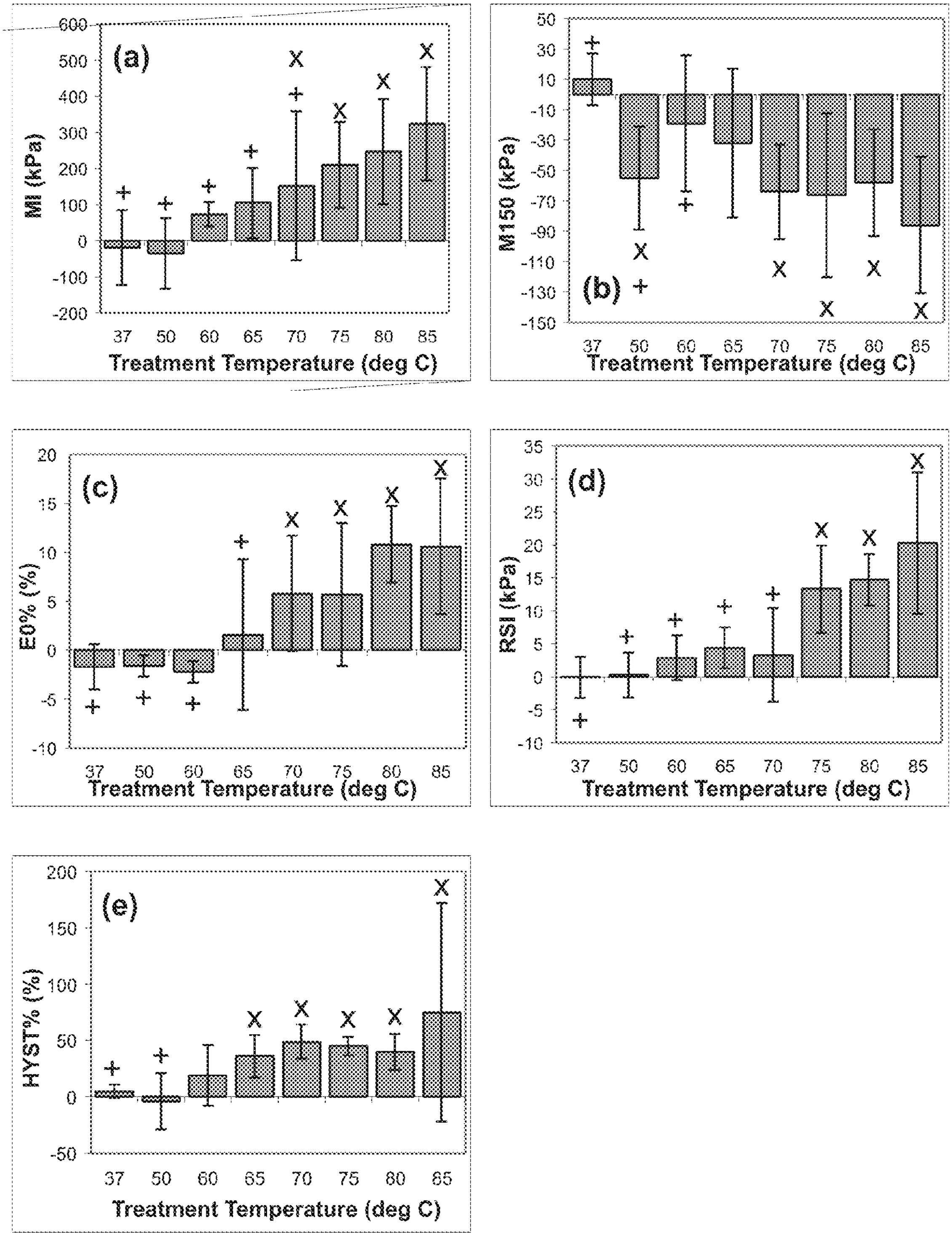
FIG. 21 shows graphs (a)-(e) that variously represent respective changes in certain tissue parameters that were observed after varied heat treatments.

FIG. 21 includes various graphs representing observed biomechanical parameters after varied heat treatments according to the present study as follows: graph (a) represents change in modulus at the inflection point (MI); graph (b) represents change in modulus at 150 kPa (M150), graph (c) represents percent change in strain at 0 stress (E0%), graph (d) represents change in residual stress at the inflection point (RSI), and graph (e) shows percent change in hysteresis (HYST %). Further to the graphs in FIG. 21, the reference letter "X" is used to designate where data is significantly different from 37° C. group, $p<0.05$; whereas the symbol "+" is used to designate where data is observed to be significantly different from the 85° C. group, $p<0.05$.

Figure 19:
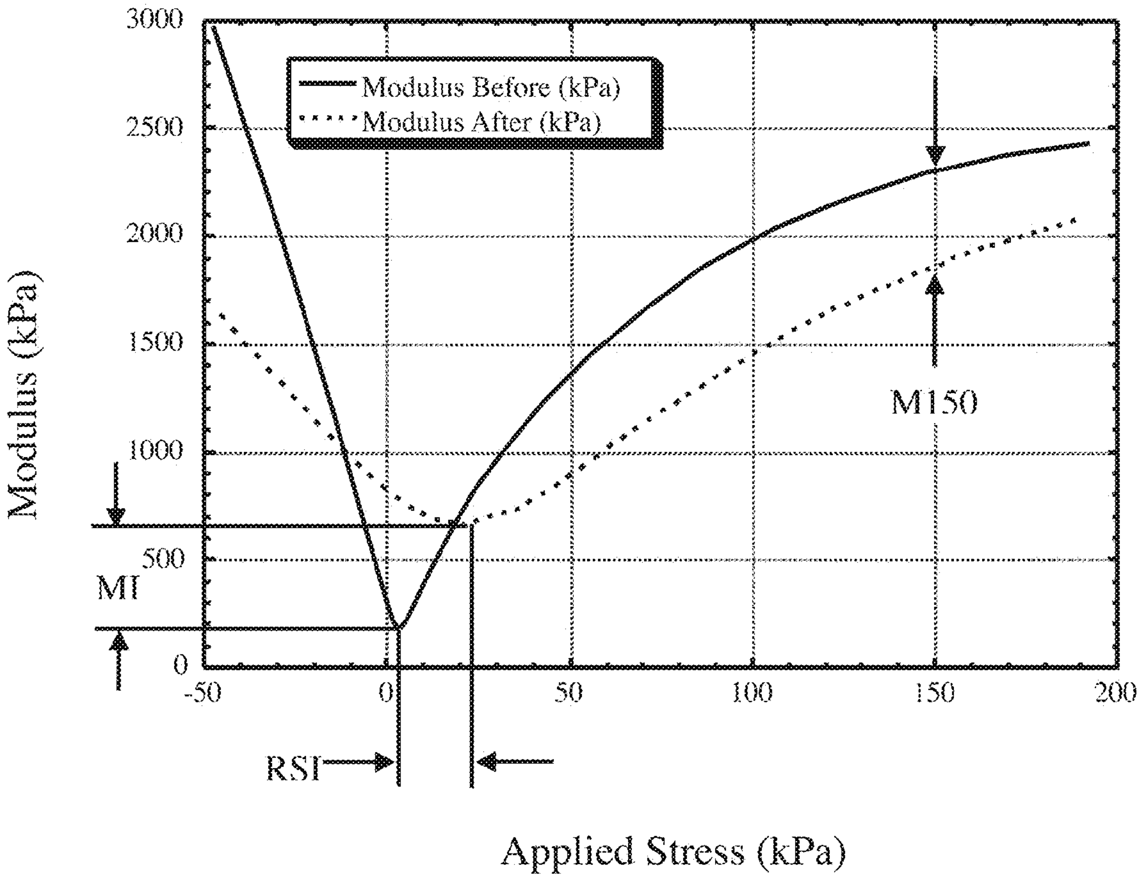
FIG. 19 shows a typical modulus versus applied stress plot according to a study performed in Example 2, and shows results before (solid line) and after (dashed line) heat treatment at 85° C., and indicates the following biomechanical parameters: change in modulus at the inflection point (MI), change in modulus at 150 kPa (M150), and change in residual stress at the inflection point (RSI).
Figure 20:
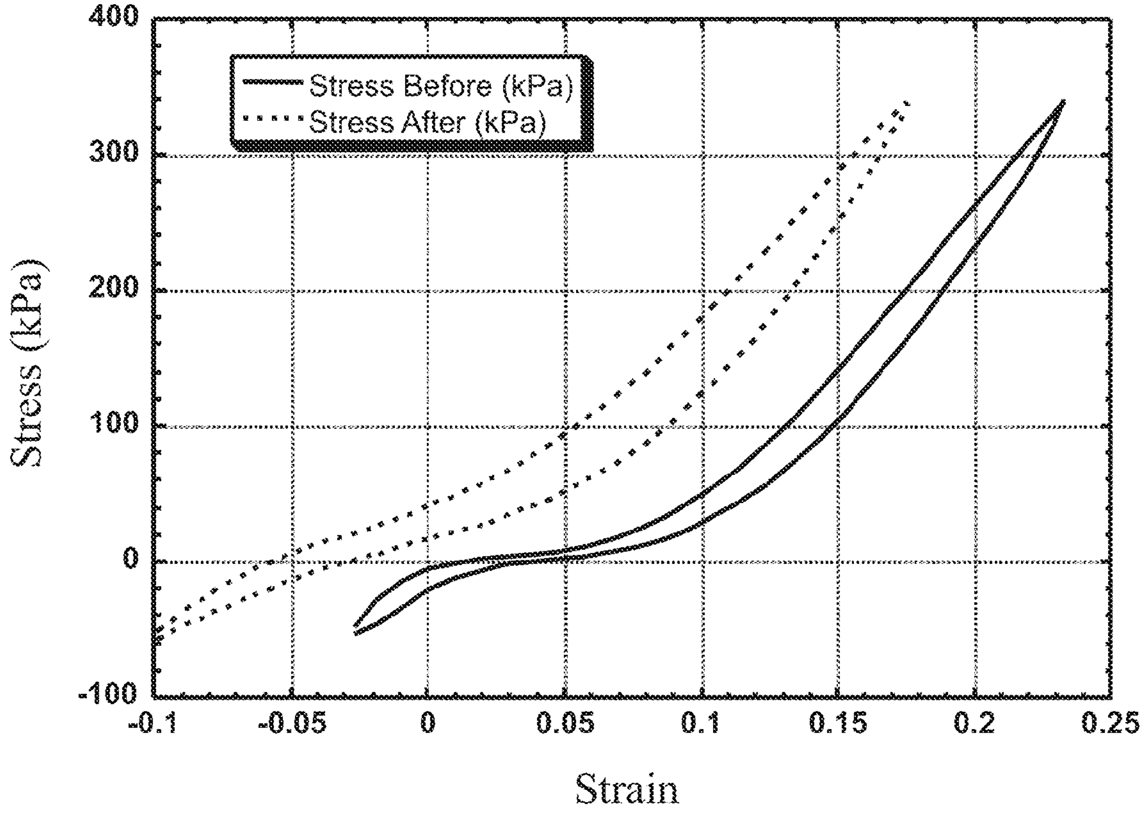
FIG. 20 shows a typical stress-strain plot before (solid line) and after (dashed line) treatment at 85° C., and shows for each cycle an upper line indicating the loading phase, and a lower curve indicating the unloading phase.

Significant differences between the control group and the heat-treated specimens were observed at temperatures of 70° C. and above (FIGS. 19, 20, 21). The variation increased with increasing treatment temperature. No significant changes were observed between the control group and the 50 and 60° C. groups, and the 65° C. treatment group showed a change only in the hysteresis parameter. The modulus at the inflection point (MI) increased by 152 kPa after treatment at 70° C. ($p<0.05$), and continued to increase with increasing heat treatment: the 85° C. group, with an average increase of 343 kPa after treatment as shown in FIG. 19), and was significantly different from both the control group ($p<0.001$) and the 70° C. group ($p<0.05$) according to the graph in FIG. 21*a*. The modulus at 150 kPa (M150) significantly decreased for groups treated at 70° C. and up, but did not continue to decrease with increasing treatment temperature; the decrease was 17% at 70° C. and 18% at 85° C. as shown in the graphs of FIGS. 19, 21*b*.

Relative to the control group, significant axial shrinkage (E0%) was first observed at the 70° C. treatment temperature. There was no significant difference observed in this particular experiment between the axial shrinkage after treatment at 70 and 85° C., although there was a trend towards continued increase ($p<0.10$) according to the graphical results in FIG. 21*c*. The change in the residual stress at the inflection point (RSI) after heat treatment was significantly larger for groups treated at temperatures of 75° C. and up with a trend towards increasing stress with increasing treatment temperature (75 vs. 85° C., $p=0.084$), as shown in the graph of FIG. 21*d*. A 36% percent increase in hysteresis (HYST %) was observed for the 65° C. group;

this was significantly larger than that of the control group ($p<0.05$) per the FIG. 21*e* graph.

The disc heights of the specimen exposed to long heat treatment time at 85° C. stabilized after approximately 2.5 hours. As a result of treatment, M150decreased 47%, MI increased 625 kPa, RSI was 47.3 kPa, and hysteresis increased 98%. The percent change in strain at 0 stress (E0%) was 22.5%.

Heat treatment of the excised annulus at 85° C. resulted in shrinkage of 45.1%±5.5% in the circumferential direction and expansion of 56.9%±25.4% in the radial direction. The shrinkage was accompanied by a color change from white to translucent, a finding that which was not present in our whole-disc samples.

b. Microstructure

Figure 22:
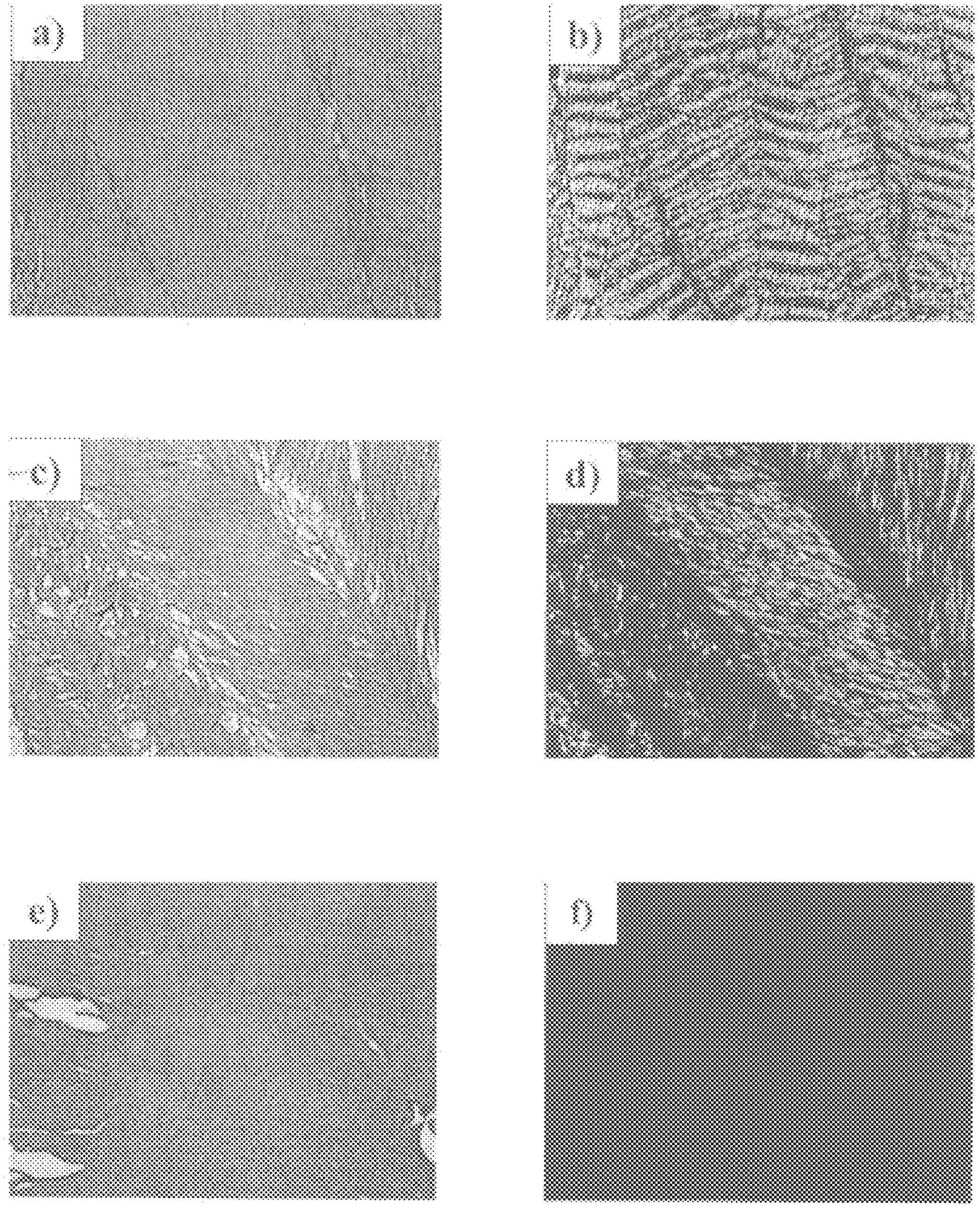
FIG. 22 shows various light microscopy photographs of various tissue samples, and includes bright light (left panel) and polarized light (right panel) microscopy of specimens treated, and shows pictures (a, b) for samples intact at 37° C.; pictures (c, d) for intact samples at 85° C.; and pictures (d, e) representing excised at 85° C.

The structure of the annular collagen, as indicated by its birefringence under polarized light microscopy, varied with heat treatment (FIGS. 22*a-f*). The structure of the excised sample treated at 85° C. changed dramatically relative to that of the control specimen: the 37° C. specimen was strongly birefringent under polarized light as shown in FIG. 22*b*, while the 85° C. excised specimen showed no birefringence as shown in FIG. 22*f*. The 85° C. mechanical test specimen appeared less birefringent than the control, as shown in FIG. 22*d*. Bright light microscopy revealed a structure consistent with that observed under polarized light. The heated excised specimen exhibited a homogenous morphology, as shown in FIG. 22*e*, with a complete loss of the original structure relative to the control shown in FIG. 22*a*. Tissue organization decreased, but was not absent, in the 85° C. mechanical test specimen shown in FIG. 22*c*.

c. Modulated Differential Scanning Calorimetry

The excised specimens did not exhibit an endothermic peak, and thus, values for $T_m$ and ΔH were not calculable. Both intact groups exhibited a full and clear endothermic denaturation event. There were no significant differences in $T_m$ and ΔH between the intact (37° C. & 85° C.) specimens. $T_m$ for the control group and the 85° C. intact group were 65.4±1.5° C. and 65.3±0.9° C. respectively, while ΔH was 11.5±2.4 W/g and 12.2±4.6 W/g. The fractional dry mass of the 85° C. intact group (0.33±0.03) and the 85° C. excised group (0.37±0.043) were both significantly higher than the control group (0.26±0.04; $p<0.05$ and $p<0.01$, respectively).

6. Discussion

In this study we examined the acute biomechanical effects of thermal treatment on the annulus fibrosus. The data demonstrate that treatment for 15 minutes at 70° C. or above is required to produce statistically significant biomechanical modification of the intact motion segment ex vivo. Heat treatments of 70° C. and higher resulted in stiffening of the annulus at low loads (i.e. in the 'toe' region, parameter MI) and a decrease in stiffness at higher applied loads (M150).

These results suggest that thermal therapy at temperatures 70° C. and greater leads to a more stable transition from flexion to extension. The depressurization we performed during specimen preparation created a neutral zone at the transition between tension and compression, within which small changes in force resulted in relatively large changes in displacement. After treatment at higher temperatures, this neutral zone was reduced or eliminated, as reflected in the graph shown in FIG. 20. It is further believed that the experimental model was illustrative of, and that this response would similarly affect, the neutral zone of intact discs. By contrast, our observation that heat treatment at temperatures greater than 70° C. softens the annulus at higher forces suggests that the acutely treated intact disc may be at increased risk of injury when brought to its range-of-motion limits. This confirms, in the unique setting of vertebral discs, similar behavior that has been noted in the shoulder capsule, where heat has been observed to both acutely shrink and decrease the linear-region stiffness of the joint. As a result of such prior observations in that setting, clinical practitioners have recommended joint protection for six to twelve weeks after treatment.

While the trends in our data are comparable to those reported for other tissues such as the shoulder capsule, the magnitude of the annular treatment effect in intact tissue is smaller. For instance, while shoulder capsule contraction has been reported in at least one study to be 60% after 80° C. treatment, we observed annular contraction of only 7.8% (E0%) after heating the intact disc to 85° C. Similarly, shoulder capsule stiffness reductions at high loads were much greater than those observed in the intact vertebral discs: we observed stiffness decreases of 20% (M150), while shoulder capsule stiffness decreases were on the order of 50%. It is believed that these differences are likely due to either the unique joint structure or the fiber orientation of the intact annulus, or both. The shoulder data was derived from experiments in which the capsule, a linearly oriented collagenous tissue, was cut into strips along the collagen fiber direction before testing. In contrast, intact annular collagen is oriented in two directions at ±65° to the spinal axis, and it is highly constrained both axially, by the adjacent vertebrae, and circumferentially, by its annular structure. When the in situ constraints on the annulus were removed by excising the tissue before heat treatment, we observed a 45% circumferential shrinkage, which is similar in magnitude to that reported for linear collagenous tissues. It is believed, therefore, based upon our observations, that in situ tissue constraint, rather than fiber orientation, may be the dominant mechanism responsible for the observed differences.

Our conclusion that in situ tissue constraint reduces the effects of thermal therapy on the annulus fibrosus, though not previously known or confirmed prior to this study, is further supported by results observed in several other previously reported studies. In one previous report, for example, only 6.6% shrinkage was observed in the patellar tendon, a linearly oriented collagenous tissue, after in situ treatment with laser energy. This difference was attributed to constraints imposed by the intact joint. Similarly, a number of other studies have been reported examining heat-induced changes in the mechanics of chordae tendineae. Tissue stress was observed to have a retarding effect: when tissue was stressed during heating, increases in the temperature, the heating time, or both, were required to achieve effects noted for unstressed tissue in these studies.

The mechanism by which tissue stress retards thermal denaturation has a thermodynamic basis. Tensile stress straightens tissue collagen and decreases configurational entropy, which in turn, increases the activation energy required for thermal denaturation. This retarding effect was clearly evident in intact annulus, where we observed that several hours of thermal treatment at 85° C. were required to achieve maximum contraction. In contrast, at least two groups of prior researchers examining excised collagenous tissues achieved maximum contraction within 5 minutes. Also, while M150 for an intact specimen treated at 85° C. for 15 minutes was only 18%, the decrease in stiffness (47%) after several hours of treatment at 85° C. was comparable to that elsewhere reported for excised shoulder capsule tissue.

Our polarized light microscopy data provides further evidence that tissue constraint effects both the temperature and time required to achieve a given amount of thermal damage. Collagen birefringence disappeared completely after heat treatment for 15 minutes at 85° C. in the unconstrained specimen, but it remained in the intact treated annulus. Clearly 15 minutes of treatment was not sufficient to fully denature the intact annular tissue. While it was not possible to quantify the degree of birefringence in the intact tissue after treatment at 85° C. relative to that at 37° C. with only one specimen, it appears that that the treated specimen was less birefringent than the control. These observations are consistent with the results of our mechanical tests.

Differences in the mechanical behavior of the intact annulus after treatment at temperatures greater than 70° C. indicate that the tissue underwent a thermally mediated change. However the results of the mDSC experiments indicate that tissue constraint prevented significant collagen denaturation: the main denaturation peak and enthalpy of denaturation of the intact annulus were unaffected by 15 minutes of treatment at 85° C. Although the increase in hysteresis after treatment implies an energetic change, the mechanisms by which the tissue was thermally modified are unclear. One possible explanation is provided by studies examining both the structure of collagenous tissue using scanning electron microscopy (SEM), and endothermic events, using DSC. Using these techniques, several investigators identified discrete stages of the denaturation process. They attributed the earliest denaturation (<56° C.) to the destruction of heat-labile cross-links (which are more pronounced in young animals), and showed that the structure of the fibrils remain intact during this process.

A second contributing factor for the biomechanical changes is suggested by the observed increase in fractional dry mass in both our constrained and unconstrained treated tissue relative to the control tissue. The increase in fractional dry mass indicates that the tissues heated at 85° C. swell less when equilibrated in saline. Since annular tissue hydration has been disclosed to be related to proteoglycan content, our finding indicates that the proteoglycans of the annulus have been affected by the heat treatment. Similar to collagen, proteoglycans are susceptible to denaturation through destruction of heat-labile hydrogen bonds. Alteration of annular proteoglycan can affect tissue properties since they have been previously disclosed to play a role in stabilizing the collagen matrix, as had been observed according to at least one prior disclosure in articular cartilage where the modulus decreases significantly when the proteoglycans are removed. It is thus believed that a portion of the observed biomechanical changes is due to changes in proteoglycan, the thermal properties of which are not extensively understood according to prior publications. Confirmation of such belief as to the specific mechanism with respect to proteoglycans may be achieved according to further study and observation by one of ordinary skill based upon review of this disclosure.

The retarding effect of stress on annular denaturation has a number of clinically relevant implications. First, to achieve a significant degree of collagen denaturation in vivo, the annulus should be heated either for long times or at high temperatures, or both. Second, thermal treatment according to the devices and methods of the present invention may be applied in a selective fashion. Since unstressed annular fibers are more susceptible to thermal treatment than stressed fibers, areas of slack tissue (e.g. the inner annulus in degenerating discs) are preferentially heated, while preserving structurally competent areas that are carrying stress (e.g. the outer annulus that retains stress into later stages of degeneration). Further, patient pre-positioning is desired for certain circumstances, allowing the practitioner to selectively stress particular annular regions, thereby further controlling the zone of biomechanical alterations.

In another regard, the present invention provides a useful tool when applied to selectively shrink proliferative fibrocartilage responsible for annular protrusion and prolapse. This is accomplished for example by providing the thermal therapy to degrade proteoglycans and decrease swelling.

In still a further regard, and as further supported by the results of this study, the present invention is used to provide thermal therapy in a manner specifically adapted to ablate annular nociceptors and cytokine producing cells while sparing tissue material properties. Thermal therapy in the range of 48-60° C. is sufficiently low to avoid collagen denaturation and biomechanical changes, yet this temperature region is desired for modes of thermal spine treatment intended to induce nerve injury and cellular death without significant biomechanical change from the heating (or with biomechanical change if desired and brought about by other means).

It is to be further appreciated that the results of this study, as to specific ranges and/or numbers, are potentially limited by the use of non-degenerate porcine intervertebral discs. While porcine discs are similar to human discs in many ways, there may be differences in denaturation temperature, which is dependent on a number of factors such as collagen cross-link type and density. However, the consistent tissue quality and size afforded by the porcine model minimizes inter-specimen variability and therefore provides a good system by which to investigate mechanisms of thermal/biomechanical interactions. The disc height also differs between human and porcine lumbar discs. Since the lumbar human disc is generally taller (averaging approximately 11 mm) than the porcine disc (averaging 3 mm in this study), it may be less influenced by vertebral constraint and therefore more able to thermally contract. In this regard, as with many previously disclosed devices and treatment methods, the exact extent of effect may vary even between species according to varied anatomy.

Notwithstanding the foregoing, future studies may be performed on human discs according to one of ordinary skill based upon this disclosure to confirm effects of specific treatment regimens. Moreover, it is further believed that the relationship between varied temperatures (and/or ranges) and predictably varied results are well correlated across species, though specific temperatures, temperature-time dosing, or magnitudes of observed results may differ. Accordingly, it is believed that the studies disclosed herein and aspects of the invention related thereto provide beneficial treatment regimens, though such may clearly require further tuning in order to be particularly adapted for specified use in treating a particular patient, patient group, or even animal type.

Further to the experimental model of the present Example, nuclear depressurization allowed for the biomechanical response of the intact annulus to be isolated. However, for intact discs, nuclear pressure will increase annular stress and therefore is believed to further retard thermal effects beyond that observed here. Finally, the ex vivo study summarized herein does not characterize any subsequent biologic remodeling that would occur after heat treatment in vivo. Remodeling likely further modifies annular tissue properties, and the magnitude and temporal sequence of this response may be further characterized in a suitable in vivo model. However, the acute effects provided hereunder provide significant benefit notwithstanding such potential for remodeling.

Despite these limitations, the foregoing observations and related description demonstrates a number of mechanisms by which thermal therapy influences the biomechanical response of the annulus fibrosus. Unique features of the disc—specifically tissue structure and stress-strain constraints due to attachment to adjacent vertebrae—have significant impact on the thermal treatment effect size. Future in vivo animal studies and controlled human trials may be further performed by one of ordinary skill in the art based at least in part on this disclosure in order to further link biomechanical and biological consequences of tissue heating to the various beneficial patient outcomes.

External Directional Ultrasound Thermal Treatment (“ExDUSTT”) System and Method

The following description relates generally to FIGS. 23-53 and provide further illustrative embodiments of the invention according to modes previously described above for providing an external directional ultrasound thermal treatment (or “ExDUSTT”) device, and method for treating spinal disorders therewith.

Figure 23:
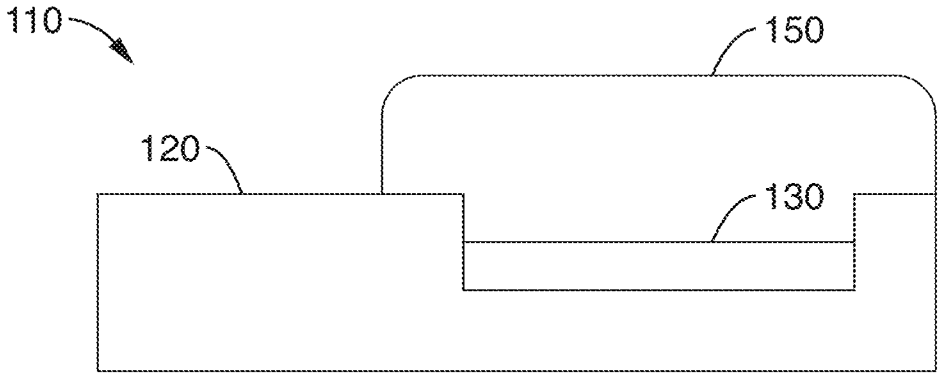
FIG. 23 shows a schematic side view of a distal end portion of an external directional ultrasound thermal treatment ("ExDUSTT™") device of the invention incorporating a directional, focused ultrasound emitter assembly that is adapted for external use adjacent to an intervertebral disc.

As illustrated in FIG. 23, the illustrative ExDUSTT applicator 110 of the present invention preferably has a support member 120 with an ultrasound transducer 130 mounted thereon within an outer covering 150 that is typically an inflatable coupling balloon such as is shown.

Figure 24:
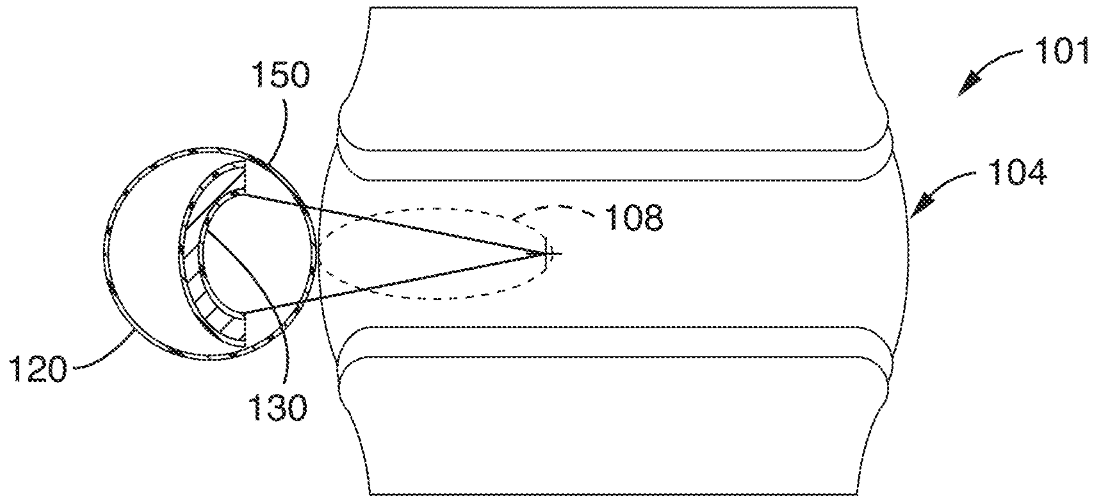
FIG. 24 shows an illustrated side view of a partially cross-sectioned ultrasound spinal treatment assembly similar to that shown in the ExDUSTT device shown in FIG. 23, and shows the assembly during one mode of use in treating a region of an intervertebral disc associated with a spinal joint.

According to the further view shown in FIG. 24 during one mode of use in treating a region 108 of an intervertebral disc 104 associated with a spinal joint 101, the transducer is generally chosen to be a curvilinear panel that is both directional and focusing (e.g. converging signals) to help highly localized deep heating, in particular useful for applications from outside the disc as shown. It is to be appreciated that “spinal joint” where used throughout this disclosure generally includes intervertebral discs, adjacent vertebral bodies, and associated structures such as posterior vertebral elements such as facet joints.

Figure 25:
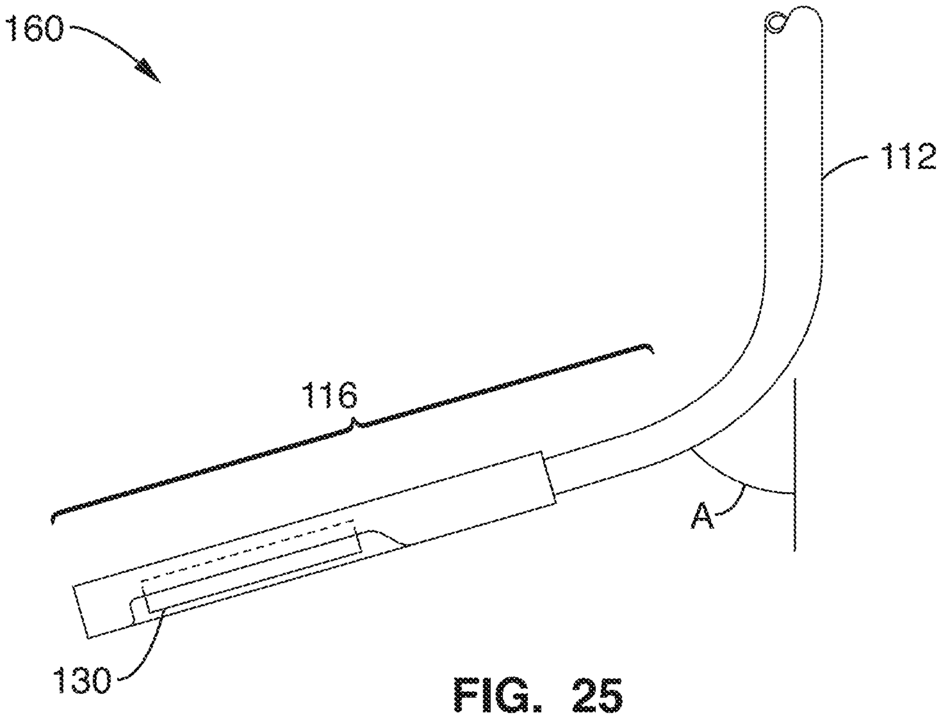
FIG. 25 shows a plan view of a distal end portion of a further ExDUSTT embodiment that incorporates a substantially rigid, pre-shaped probe device platform.
Figure 26:
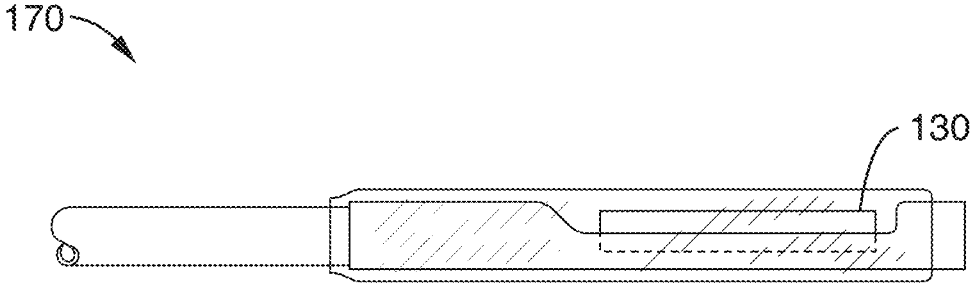
FIG. 26 shows a plan view of a distal end portion of another ExDUSTT device embodiment that incorporates a substantially flexible, catheter device platform according to another embodiment of the invention.

As shown in FIGS. 25 and 26, respectively, ExDUSTT devices of the present invention can be on many different delivery platforms, such as a rigid pre-shaped platform shown in FIG. 25 with the transducer 130 on the distal bend section 116 and canted at an angle A for angular directional ultrasound relative to the proximal shaft 112 axis, or on a catheter-based platform shown in FIG. 26. Both chassis are beneficial for respective purposes, and each for common purposes. However, the pre-shaped probe is in particular useful for angular directional heating at hard to reach places in the body, such as certain spinal locations, and the rigidity helps position control.

Figure 27A:
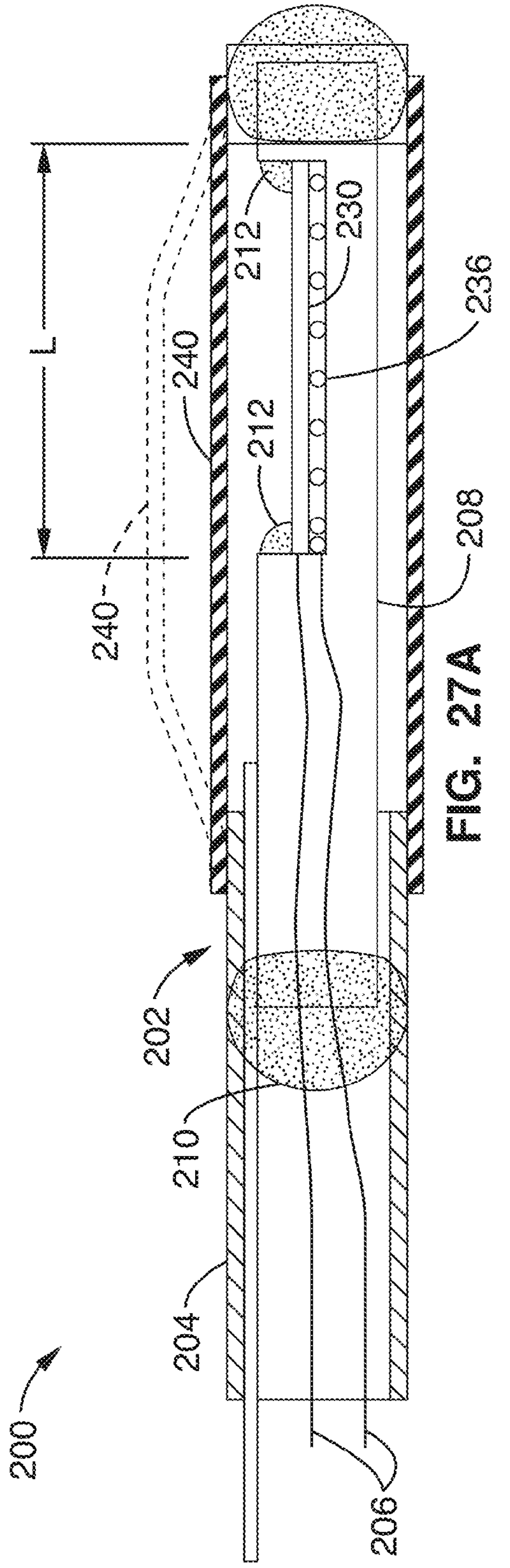
FIG. 27A shows a longitudinally cross-sectioned view of a distal end portion of an ExDUSTT device on a rigid probe platform similar to that shown in FIG. 25, and shows a substantially compliant elastomeric balloon over a curvilinear ultrasound transducer.
Figure 27B:
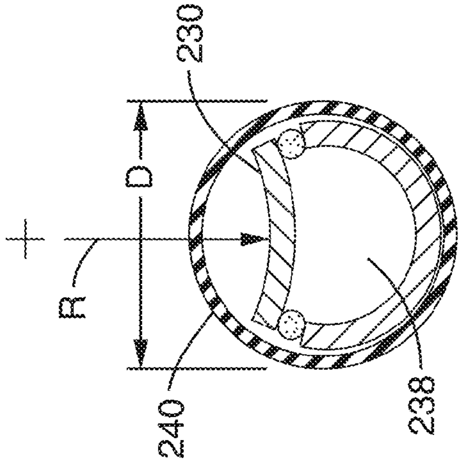
FIG. 27B shows a transverse cross-sectioned view through an ultrasound transducer mounting region of the ExDUSTT device shown in FIG. 27A.
Figure 28A:
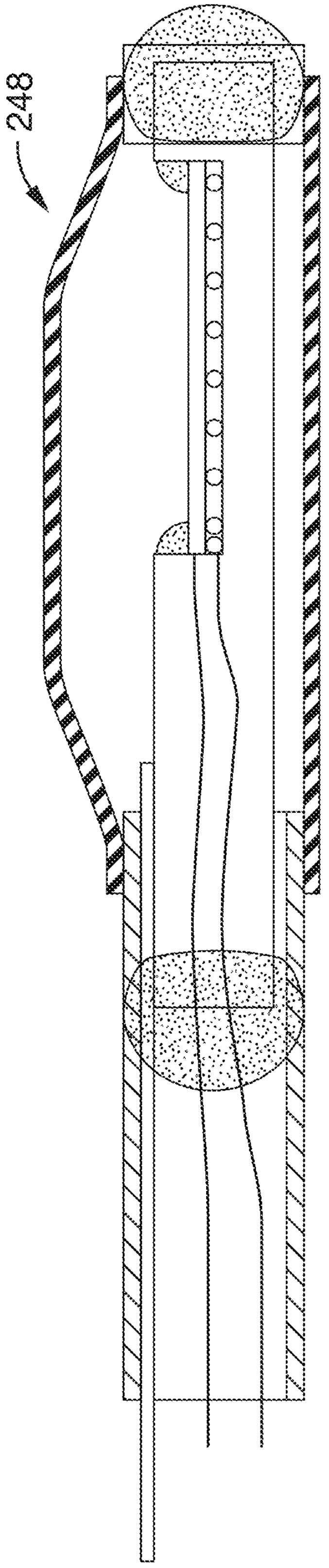
FIG. 28A shows a longitudinally cross-sectioned view of a distal end portion of another ExDUSTT device on a rigid probe platform that is also similar to that shown in FIG. 25, except with a substantially non-compliant pre-formed balloon over the curvilinear ultrasound transducer.
Figure 28B:
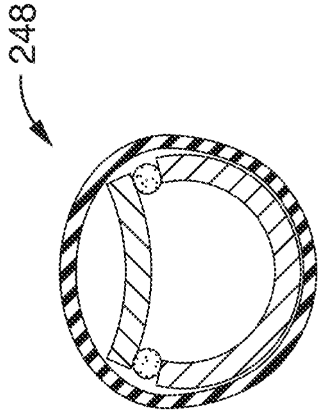
FIG. 28B shows a transverse cross-sectioned view through an ultrasound transducer mounting region of the ExDUSTT device shown in FIG. 28A.

FIG. 27A shows an illustrative rigid probe device 200 in finer detail for further understanding. Distal shaft 202 includes a 4 mm outer diameter brass tube 204 with 0.008" silver lead wires 206 and water flow lines (e.g. 0.0226" polyimide tubing) contained therein and coupled at the proximal end portion (not shown) to a proximal adapter. A distal 0.1135" stainless steel tubing 208 is shown secured with epoxy 210 within the brass tube 204, and has a window 212 cut out leaving support ridges upon which the transducer 230 is mounted with Nusil 1137 Silicone, as shown in finer detail in FIG. 27B. Further included beneath the transducer 230 are rubber threads 236 strung across the window 212 to help provide a good non-dampening support system. An outer inflation balloon is shown at 240 and in shadow in the expanded condition for tissue coupling. As can be appreciated from the figure, an air backing is thus provided at 238 to provide highly directional ultrasound delivery away from the central shaft of the device and out through the eccentric inflation balloon 240 having a diameter D and into tissue there. Moreover, as illustrated in FIG. 27B, the transducer 230 is curvilinear having a radius R around an axis that is aligned with the long axis of the support shaft and thus is focused into tissue along the transducer and balloon length as such. For the purpose of a complete description, one exemplary transducer that has been observed to be useful in this and other ExDUSTT designs herein shown and described has for example the following specifications: 0.394" long×0.98" wide×0.013" thick PZT4, 0.59" radius of curvature.

Various modifications may be made to the device just shown and described. For example, the balloon according to that Figure was elastomeric type, such as 0.005" wall silicone balloon. However, better repeatability of size and shape may be required than what such elastomers can offer, and thus a less compliant balloon of the preformed type may be used. This is shown for example at balloon 248 in FIGS. 28A-B that is for example a pre-shaped PET balloon having a wall thickness for example of 0.001". Further considerations for materials may be considered, such as for example thermal properties, ultrasound transmissivity, profile, etc.

Figure 29A:
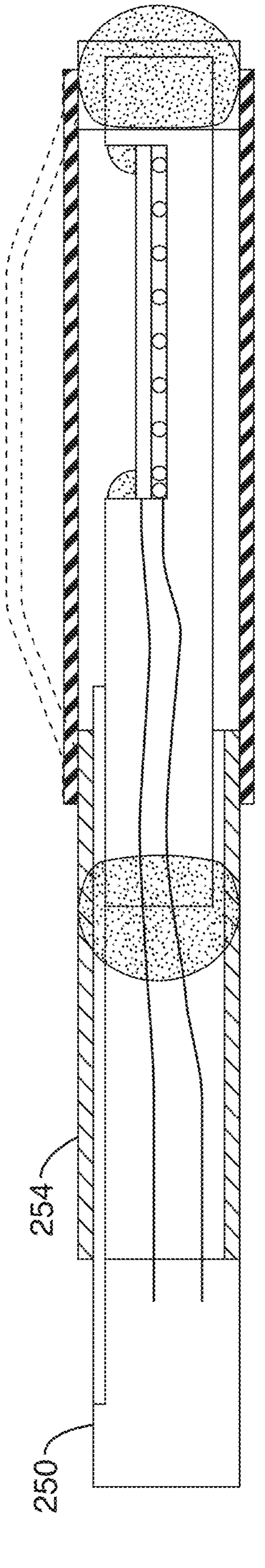
FIG. 29A shows a transverse cross-sectioned view of a distal end portion of another ExDUSTT device on a polymeric catheter delivery chassis similar to that shown in FIG. 26, and shows a substantially compliant elastomeric balloon over a transversely aligned, curvilinear ultrasound transducer.
Figure 29B:
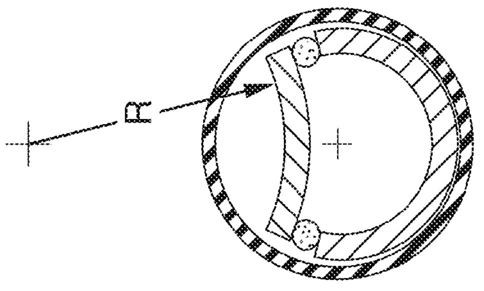
FIG. 29B shows a transverse cross-sectioned view through an ultrasound transducer mounting region of the ExDUSTT device shown in FIG. 29A.

Moreover, similar features as just described for the ExDUSTT device may be incorporated onto a different catheter chassis without much required modification, as referenced in FIGS. 29A-B. Here a proximal catheter shaft 250 is shown coupled to a distal 4 mm OD brass tube 254. Everything else may be the same as described above for the rigid probe designs. The catheter shaft 250 may be multi lumen, or may be a bundle of lumens, etc.

Figure 30A:
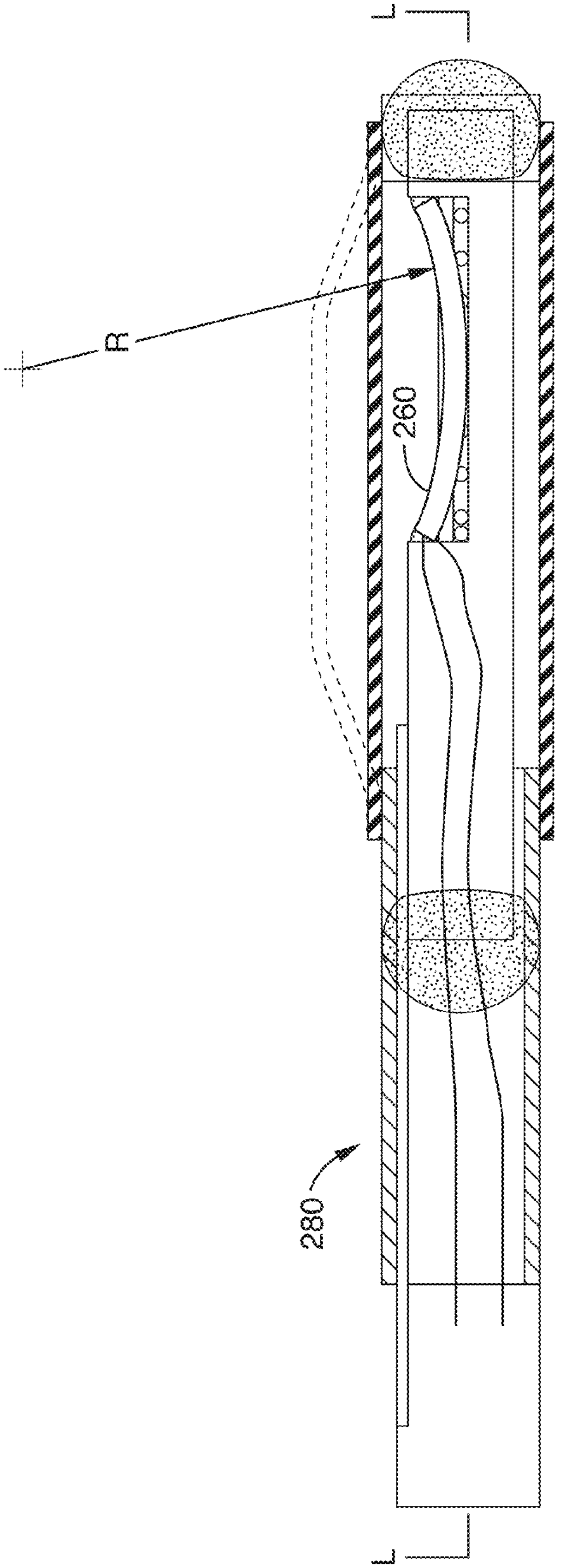
FIG. 30A shows a transverse cross-sectioned view of a distal end portion of another ExDUSTT device on a catheter delivery platform similar to that shown in FIG. 29A, except with an axially aligned, curvilinear ultrasound transducer within a substantially compliant elastomeric balloon.
Figure 30B:
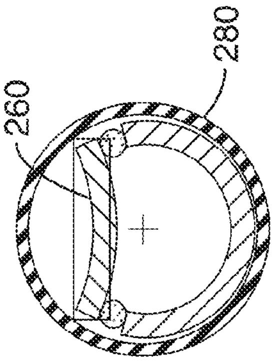
FIG. 30B shows a transverse cross-sectioned view through an ultrasound transducer mounting region of the ExDUSTT device shown in FIG. 30A.
Figure 31A:
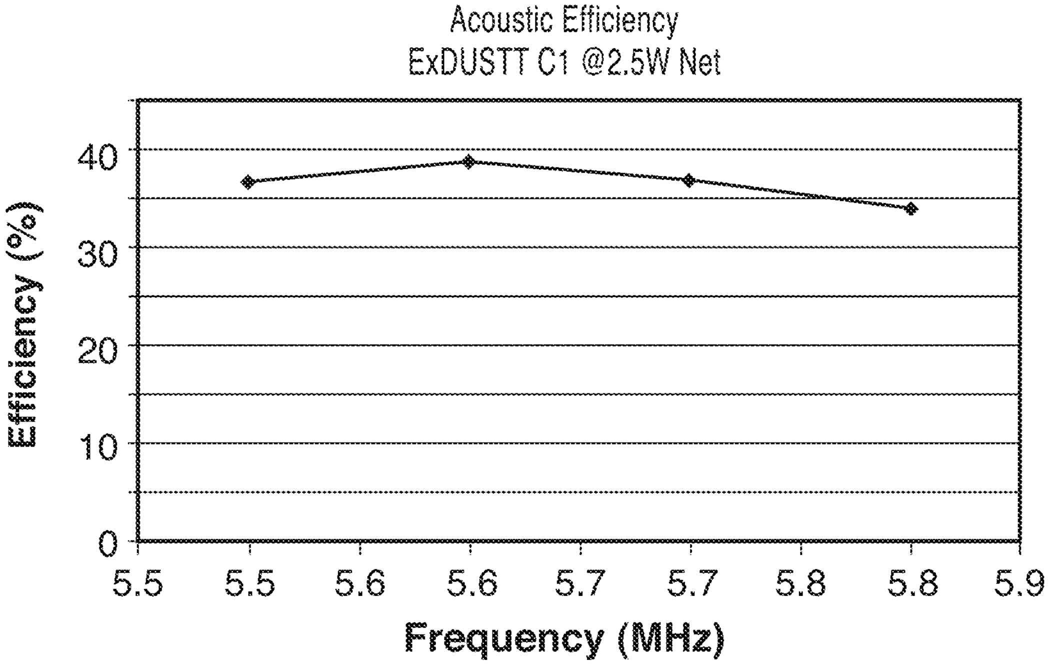
FIGS. 31A-B show two respective graphs for acoustic efficiency and acoustic output power, respectively, for one exemplary working embodiment of a rigid probe ExDUSTT device similar to that shown in FIG. 25.
Figure 31B:
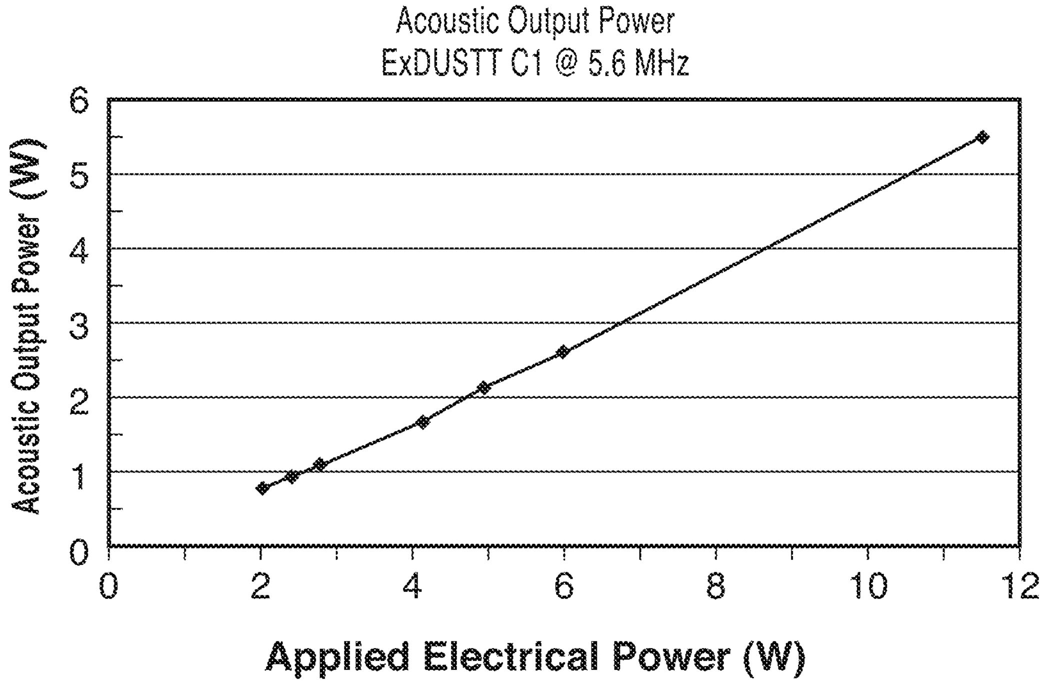
Figure 32A:
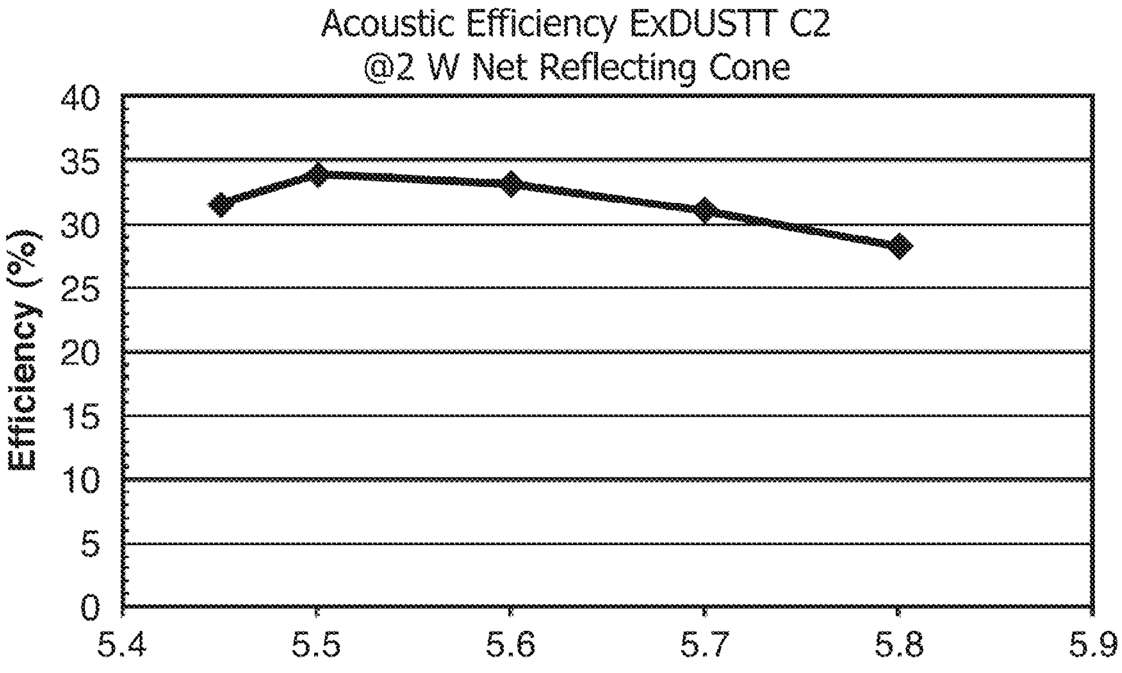
FIGS. 32A-B show two respective graphs for acoustic efficiency and acoustic output power, respectively, for one exemplary working embodiment of a catheter-based ExDUSTT device similar to that shown in FIG. 26.
Figure 32B:
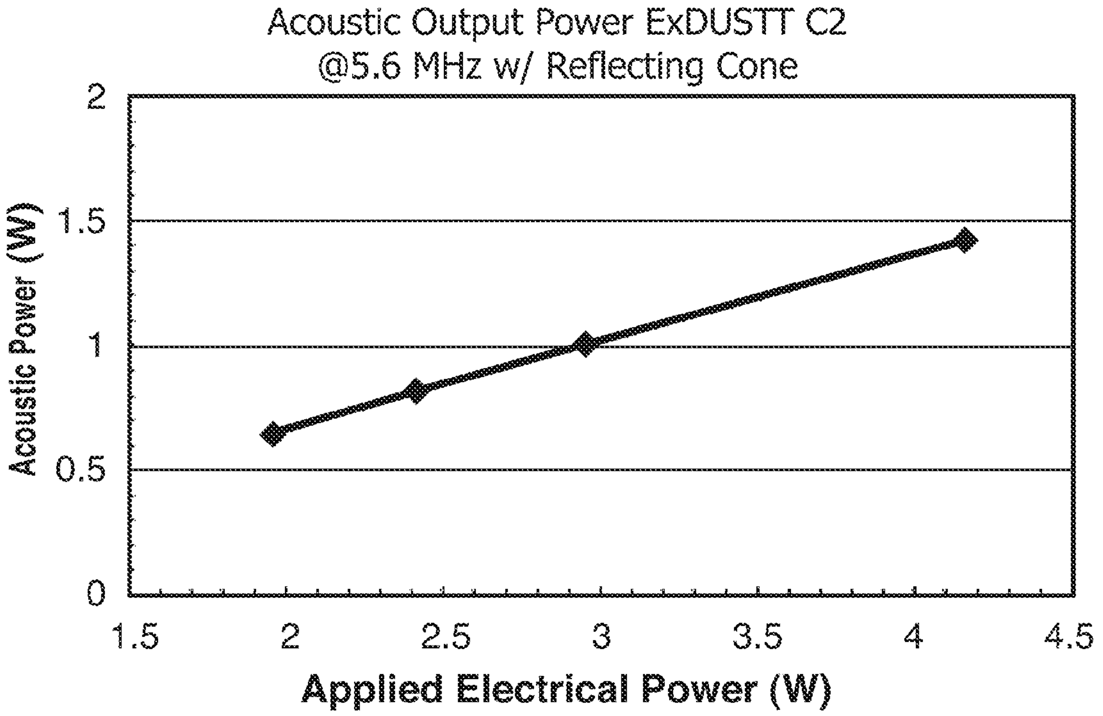

The transducers shown in the previous FIGS. are not the only configurations contemplated, either. For example, FIGS. 30A-B show a curvilinear transducer 260 with its radius of curvature R around an axis that is transverse (e.g. orthogonal) to the long axis L of the support shaft 280.

Further understanding of various modes of operating devices of the rigid probe type just shown and described are provided in FIGS. 31A-32B, which reflect operation at 5.6 MHz optimal frequency, with peak efficiency at 40%, and linear output and efficiency out to 12 W applied with 5.5 W emitted from the transducer.

Figure 33:
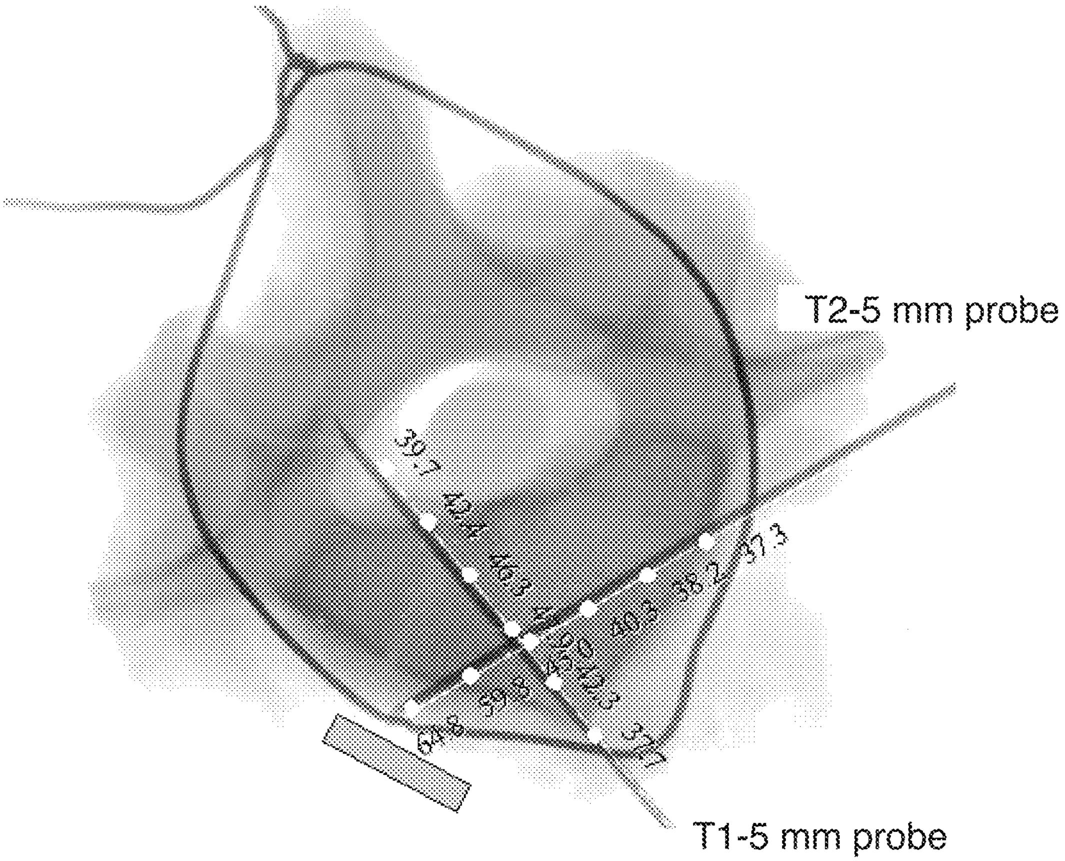
FIG. 33 shows a schematic drawing of an ultrasound heating assembly portion of a catheter-based ExDUSTT device similar to that shown in FIG. 26 superimposed over an X-ray picture of the intervertebral disc to illustrate one experimental set-up to evaluate the device, and also shows superimposed reference numbers designating certain monitored temperatures at various locations within the disc during one mode of treatment.

FIG. 33 shows a test set-up for ex-vivo pig spine treatment using a catheter-based ExDUSTT device over 5 minute heating period, and shows certain measured temperatures during a relatively low temperature mode of operation. T1 is a temperature probe 5 mm deep into tissue from the transducer coupling interface, whereas T2 temperature probe shows the temperature profile over varied depths from the transducer.

Figure 34A:
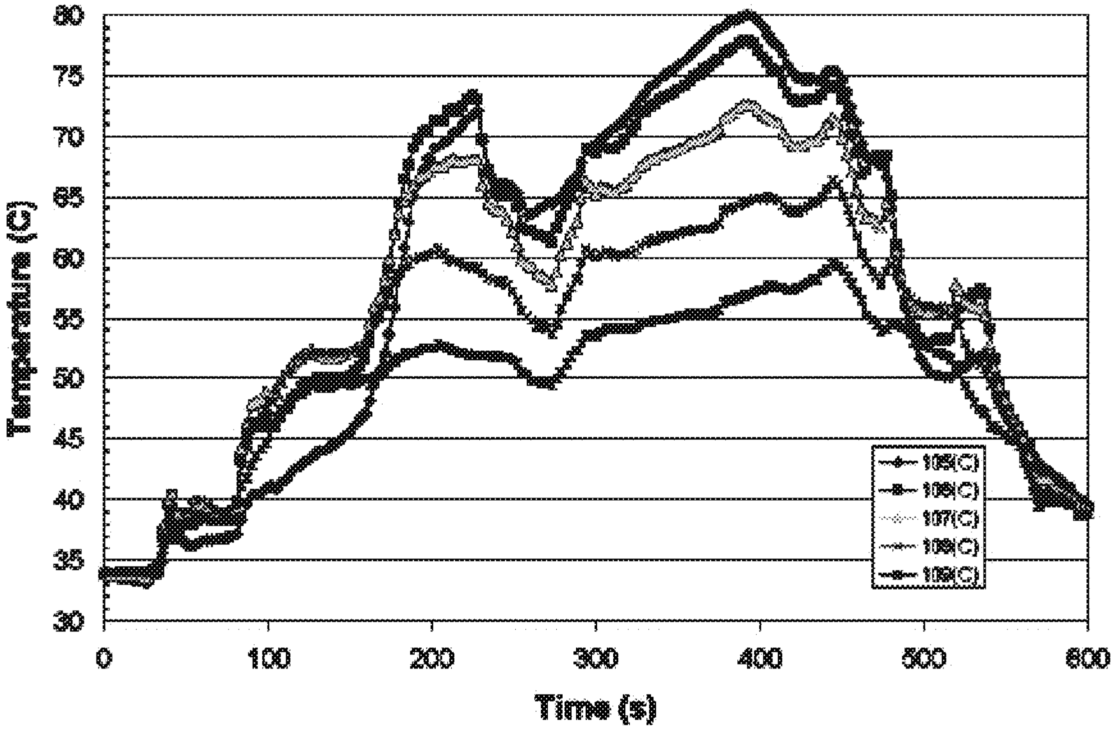
FIG. 34A-B show two respective graphs of temperature monitored over time at various thermocouples locations 105(C)-109(C) during two respective in-vivo thermal therapy treatments in an intervertebral pig disc using a catheter-based ExDUSTT device similar to that shown in FIG. 26 and according to an experimental set-up similar to that shown in FIG. 33.
Figure 34B:
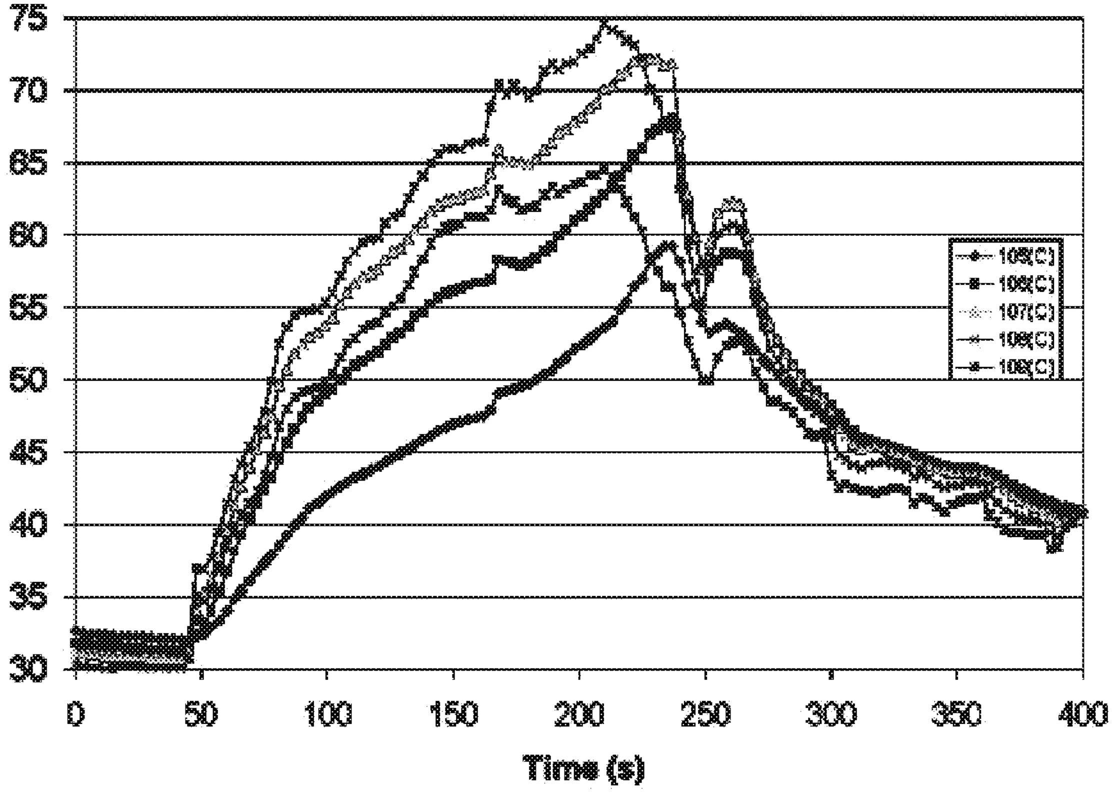

In contrast to the ex-vivo data shown in FIG. 33, FIGS. 34A-B show results for in-vivo treatments in pig discs, and show temperatures all exceeding 55 degrees, though temperatures close to the transducer exceeded well over 65 degrees and even up to 80 degrees.

Figure 35:
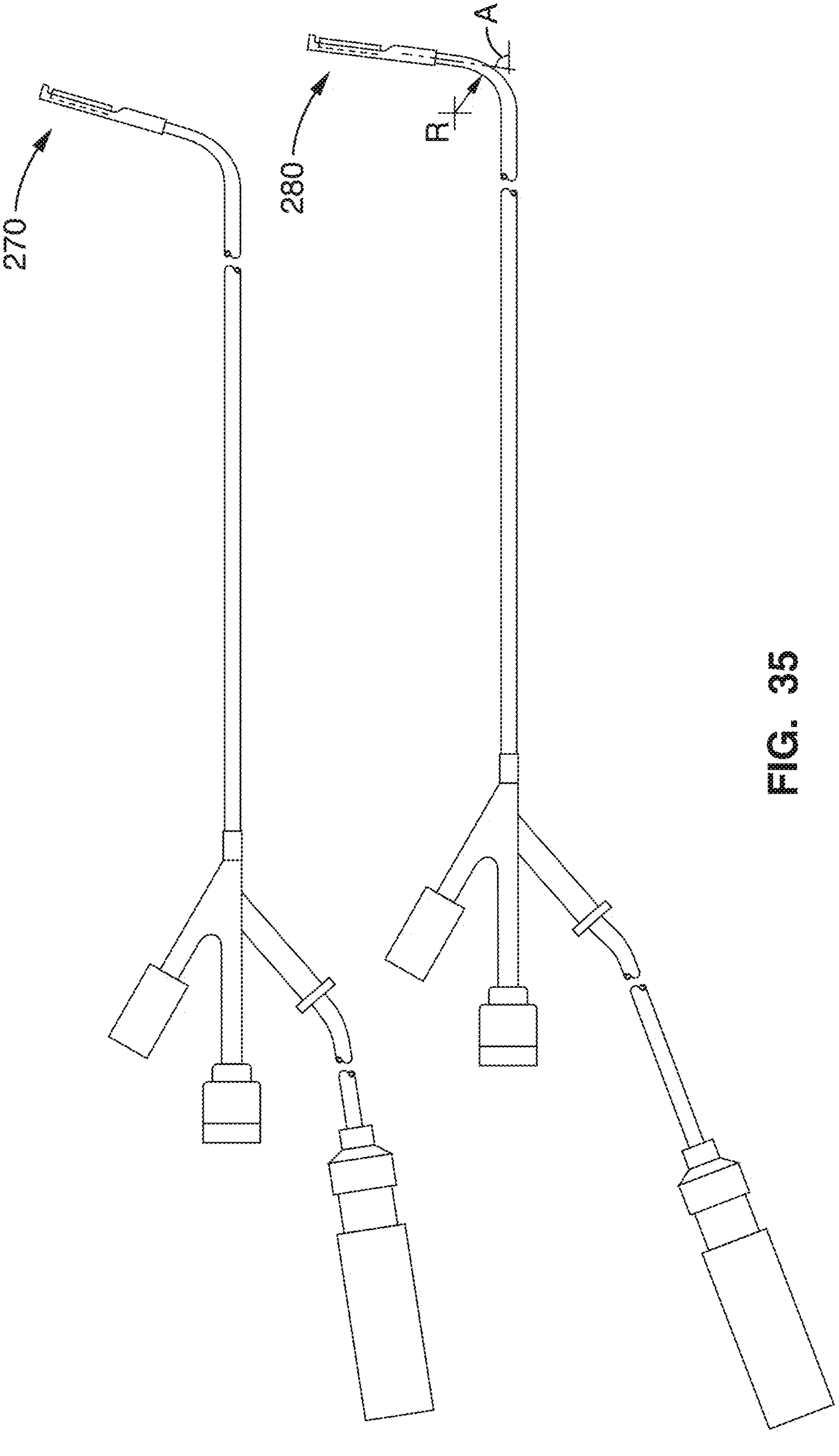
FIG. 35 shows two, respective ExDUSTT devices of pre-shaped, rigid probe construction similar to that shown in FIG. 25, except the devices shown are constructed according to different size embodiments incorporating ultrasound transducers having varied respective widths of 2.5 mm and 3.5 mm, respectively.
Figure 36A:
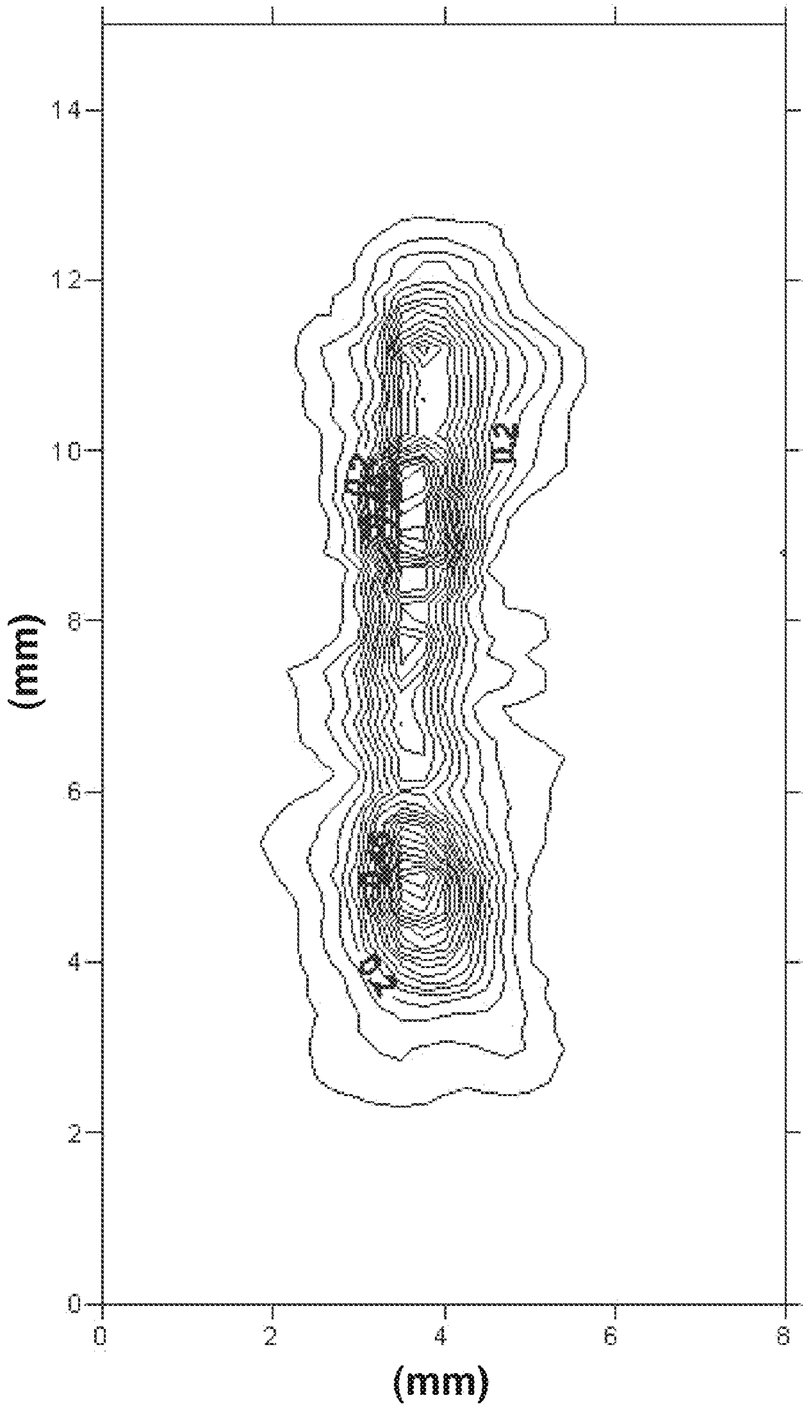
FIGS. 36A-B show top and angular perspective views, respectively, of certain power output profile across the face of the 2.5 mm wide transducer shown in FIG. 35A.
Figure 36B:
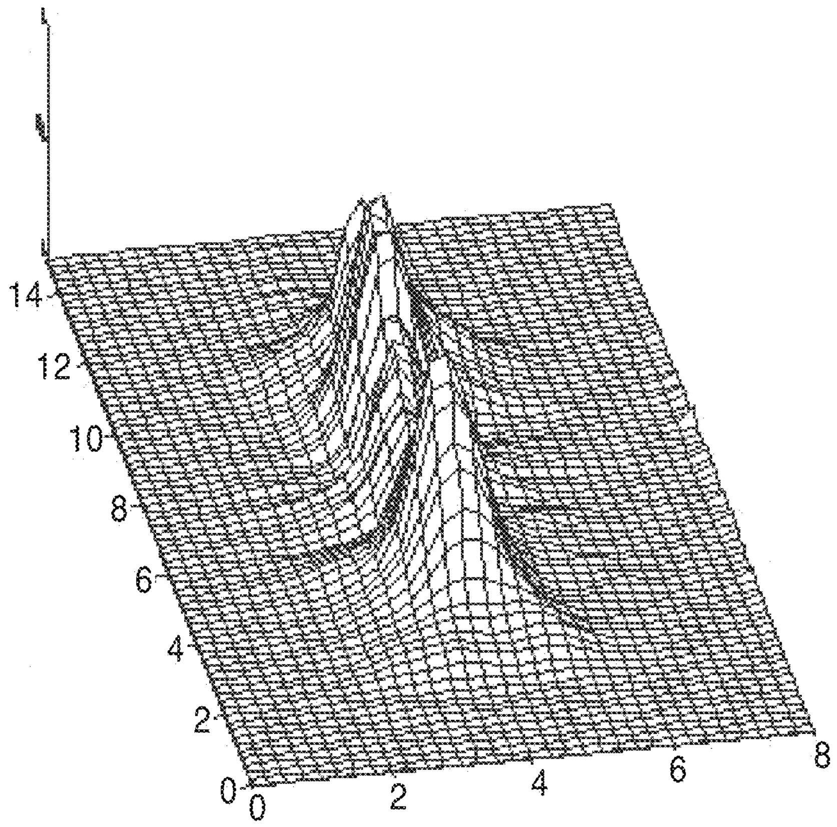
Figure 37A:
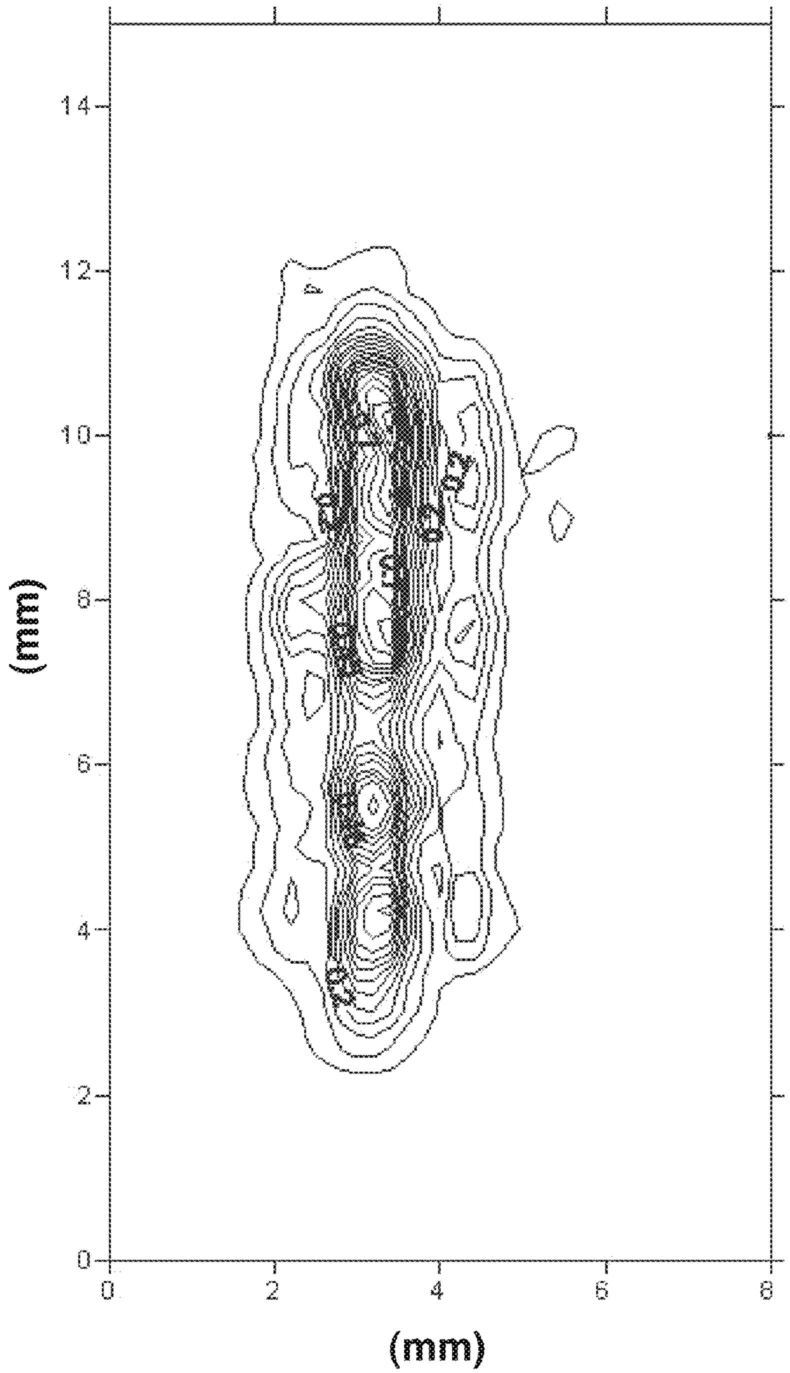
FIGS. 37A-B show top and angular perspective views, respectively, of certain power output profiles across the face of the 3.5 mm wide transducer shown in FIG. 31B.
Figure 37B:
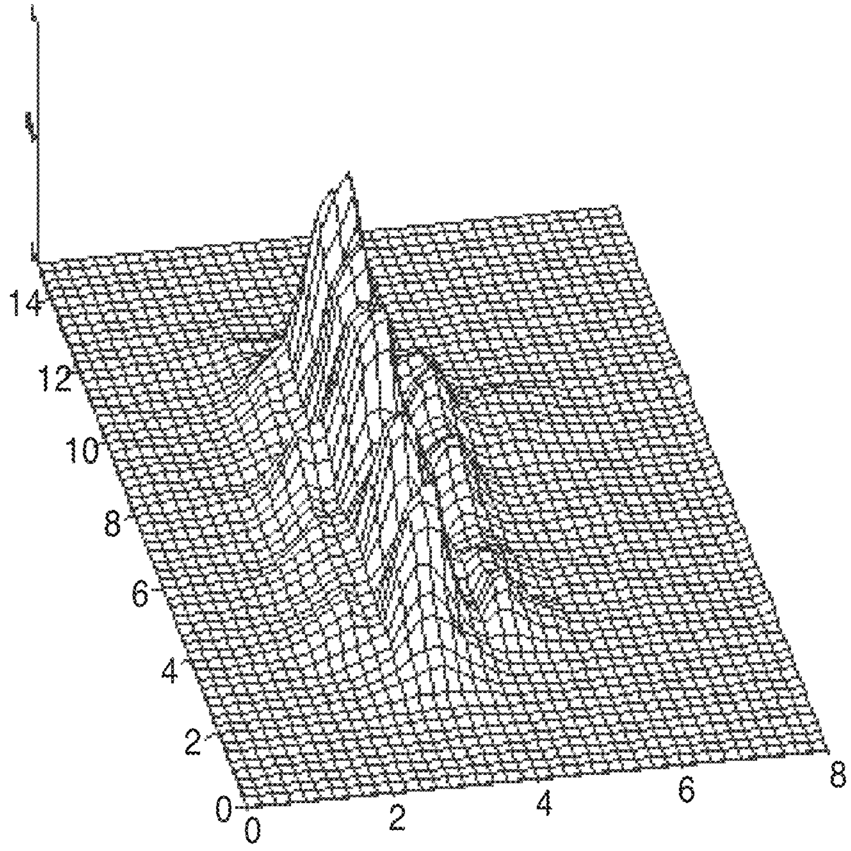

As illustrated in FIG. 35, various different sizes may be used depending upon the particular need, and a kit of different sizes, lengths, angles A, radii R, etc. may be provided. The devices 270, 280 shown in FIG. 35 generally differ in that the larger device supports a 3.5 mm wide ultrasound transducer, whereas the smaller device supports a 2.5 mm wide transducer. In general, other features may be similar unless desired to change them, whereas for the embodiment kit shown, each device has other components scaled to meet the 2.5:3.5 comparison for the transducer widths. Other variations may be made, however.

For the purpose of further characterization, and understanding of directivity and focus of energy delivery as relates to the present invention, FIGS. 36A-B and 37A-B show certain output power profiles across the transducer faces for both 2.5 mm and 3.5 mm curvilinear transducers, respectively. The radius of curvature for these transducers is around an axis that is aligned with the long axis of these plots.

Figure 38:
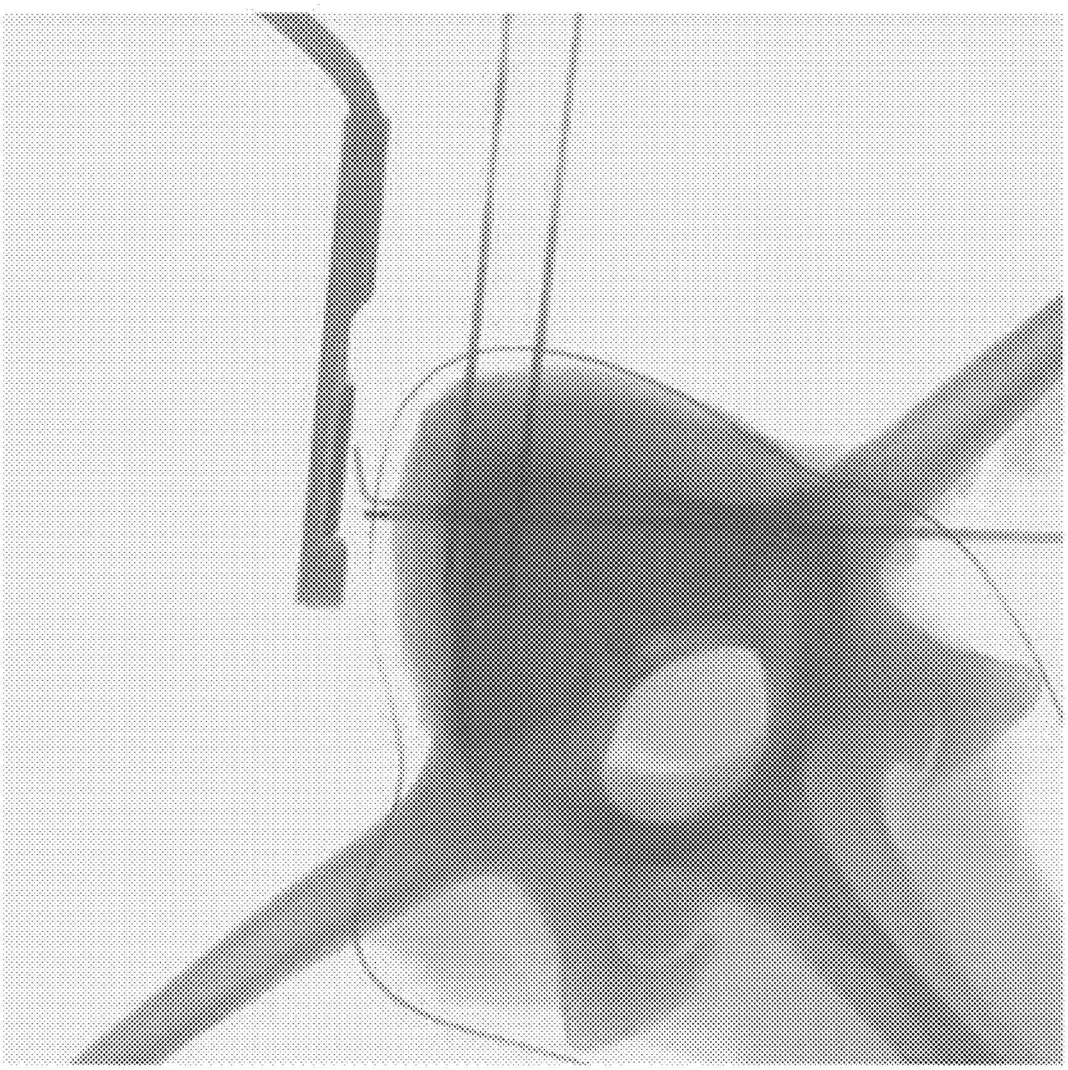
FIG. 38 shows an X-ray picture of a top view of an ex-vivo experimental arrangement similar to that shown schematically in FIG. 33, except showing a directional ultrasound heating assembly of a working embodiment for a probe-based ExDUSTT device such as shown in FIG. 25 positioned for desired heating of an intervertebral disc according to one modes of use, and shows various thermocouple probes within the disc to monitor experimental temperatures.
Figure 39:
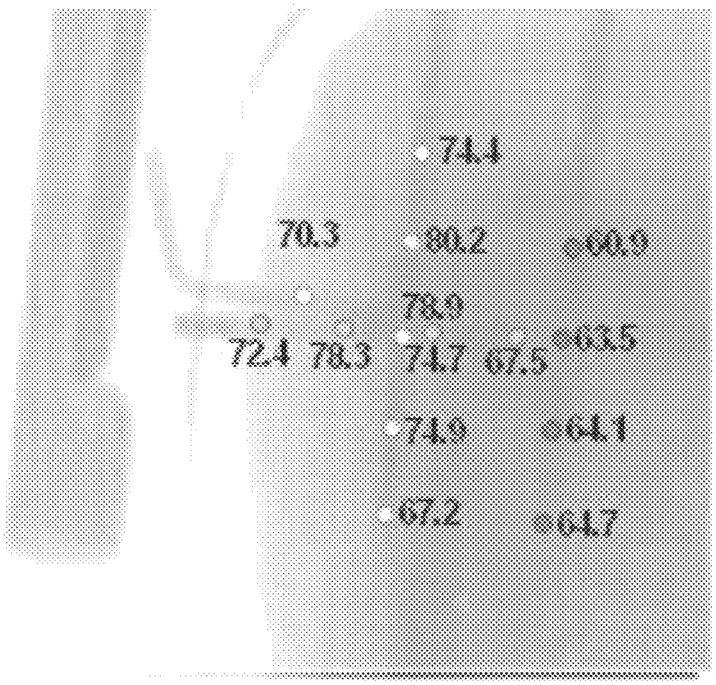
FIG. 39 shows an exploded view of the same Ex-DUSTT intervertebral disc treatment arrangement shown for the 3.5 mm probe-like ExDUSTT device in FIG. 38, and shows monitored temperature values at various respective locations along the axial and radial temperature probes during one relatively high temperature mode of use with active cooling at 0 degrees C.
Figure 40:
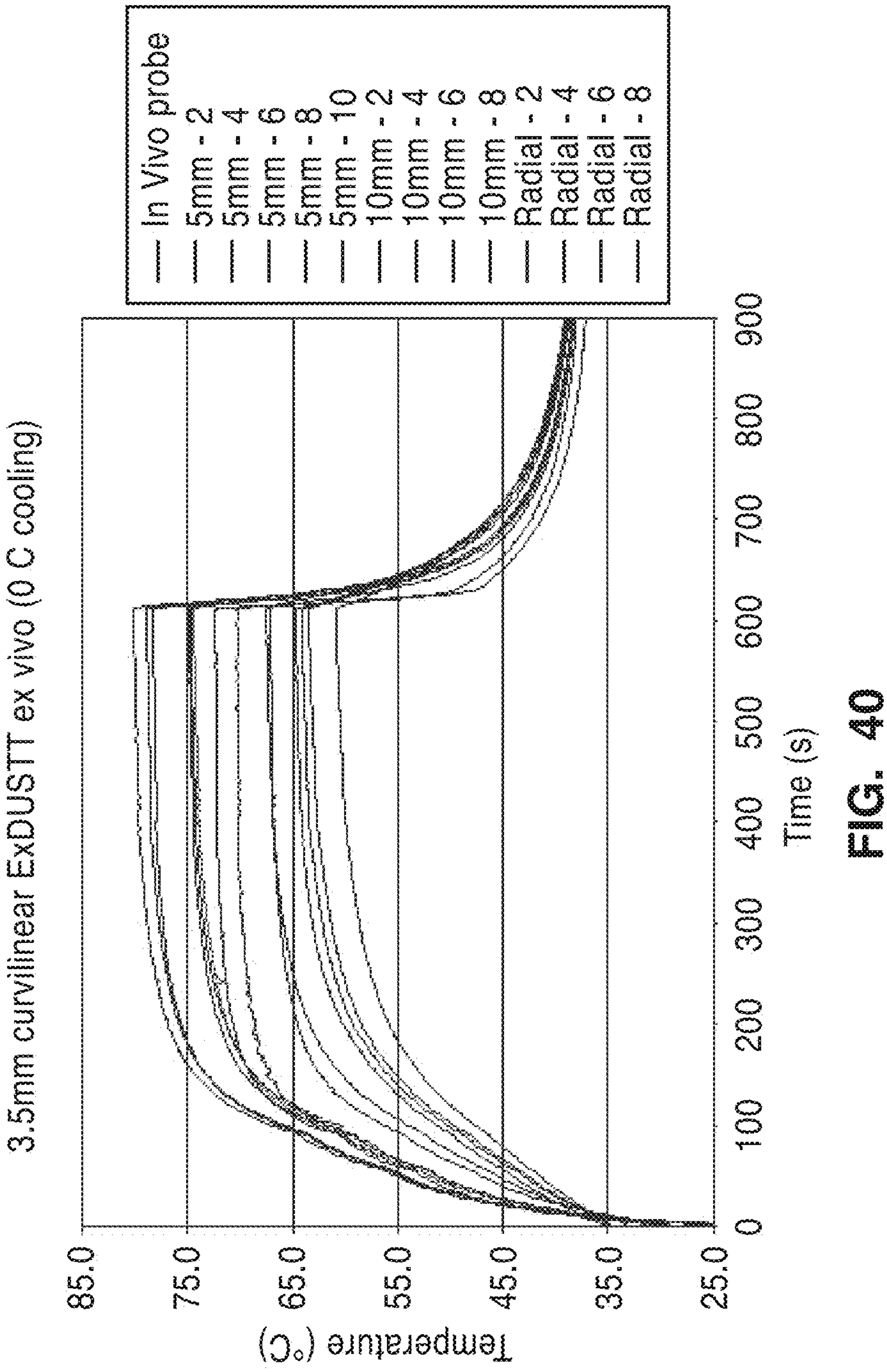
FIG. 40 shows a graph of temperature vs. time for the various temperature probes according to the thermal therapy arrangement shown in FIG. 39.

Various thermal treatment studies have been performed with working prototypes of the present invention and will be explained hereafter in part by reference to the test set-up for the rigid, pre-shaped bent ExDUSTT device shown in FIG. 38.

Figure 41:
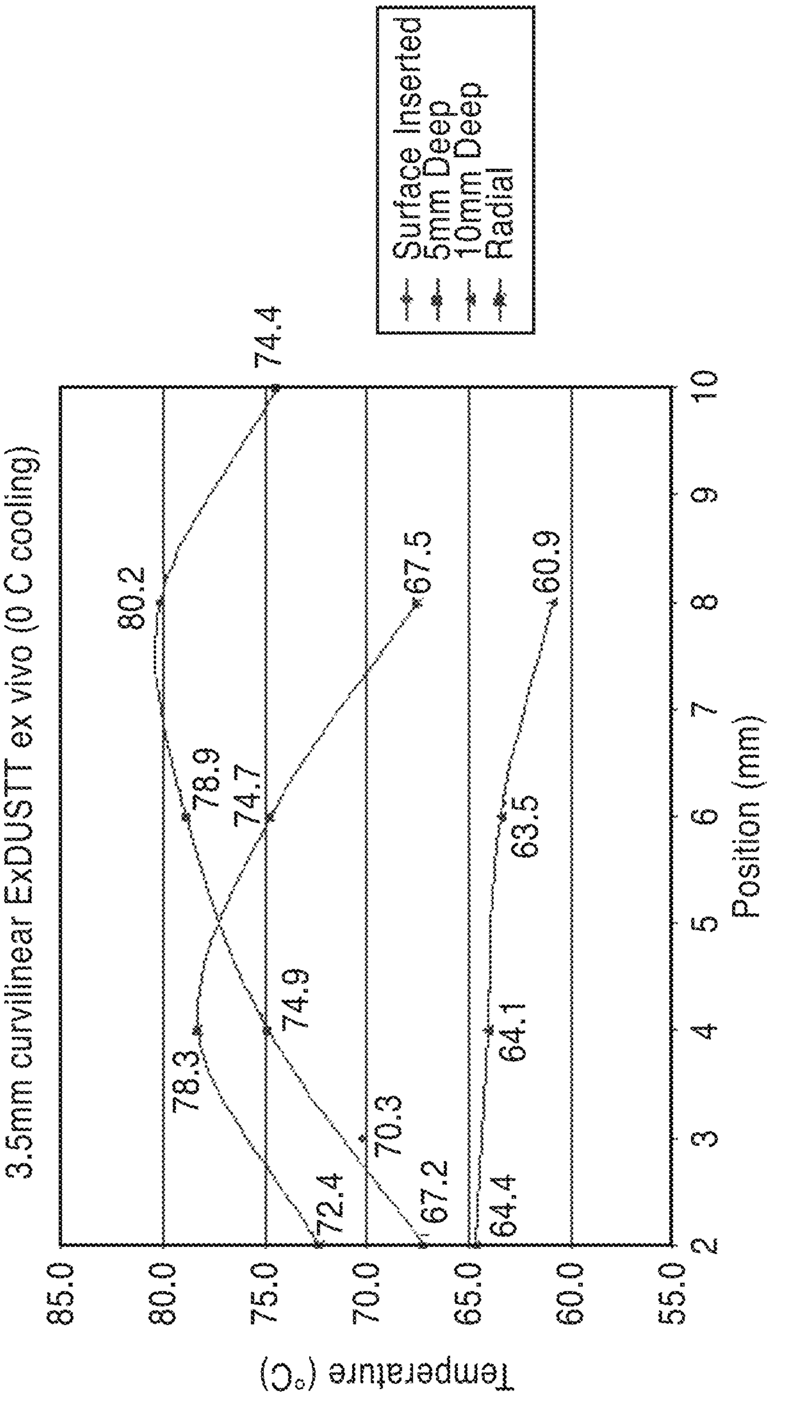
FIG. 41 shows a graph of temperature monitored along the 5 mm and 10 mm deep axial temperature sensor probes and the radial temperature sensor probes shown within the intervertebral disc and during treatment with the probe-based ExDUSTT with the 3.5 mm wide transducer shown in FIG. 38, and according to an ex-vivo study performed with active transducer cooling at 0 degrees C.
Figure 42:
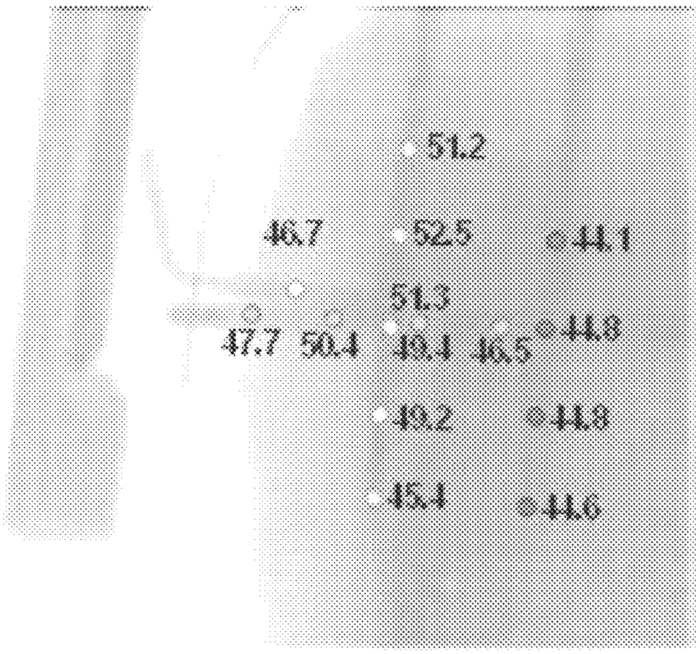
FIG. 42 shows the same exploded view of the experimental arrangement shown in FIG. 39, except shows thermocouple values corresponding to a relatively low temperature mode of operation with room temperature cooling.
Figure 43:
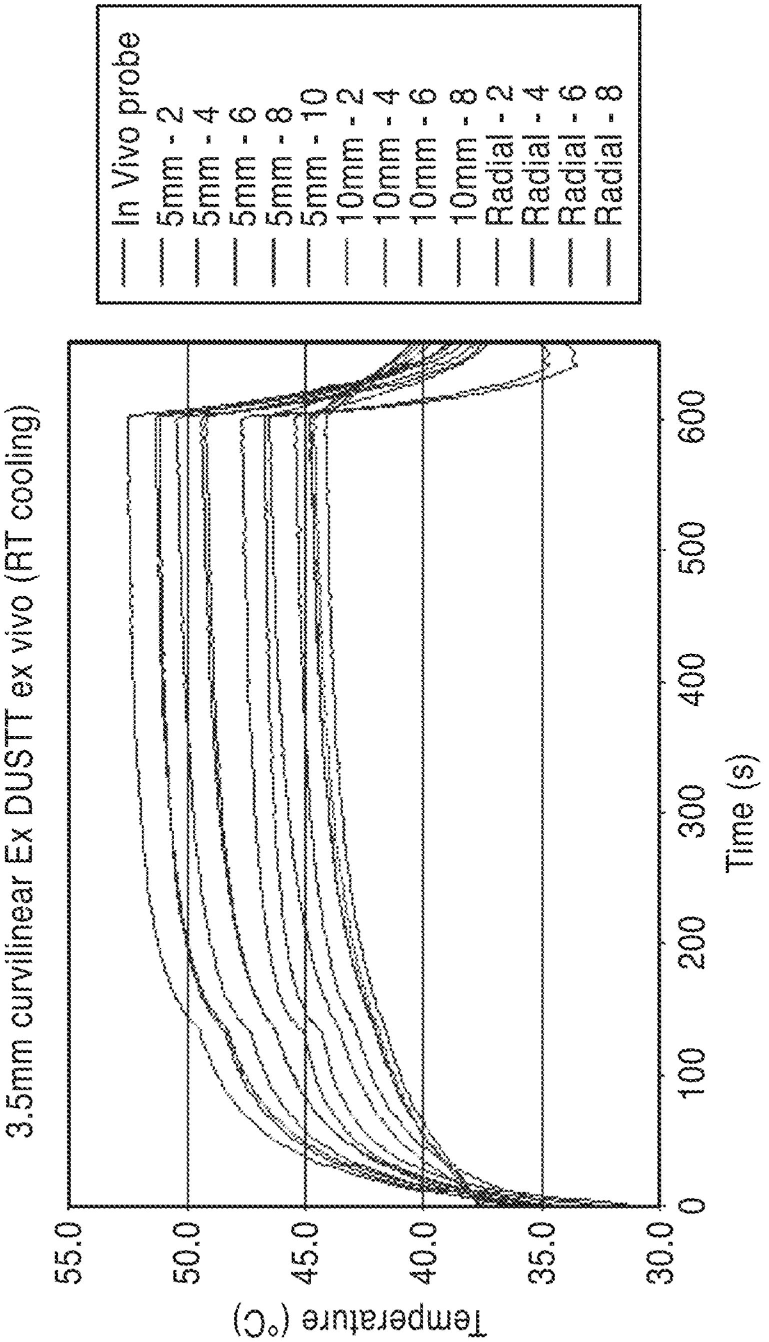
FIG. 43 shows a similar graph of temperature vs. time as that shown in FIG. 40, except with respect to data measured according to the arrangement illustrated for FIG. 42.
Figure 44:
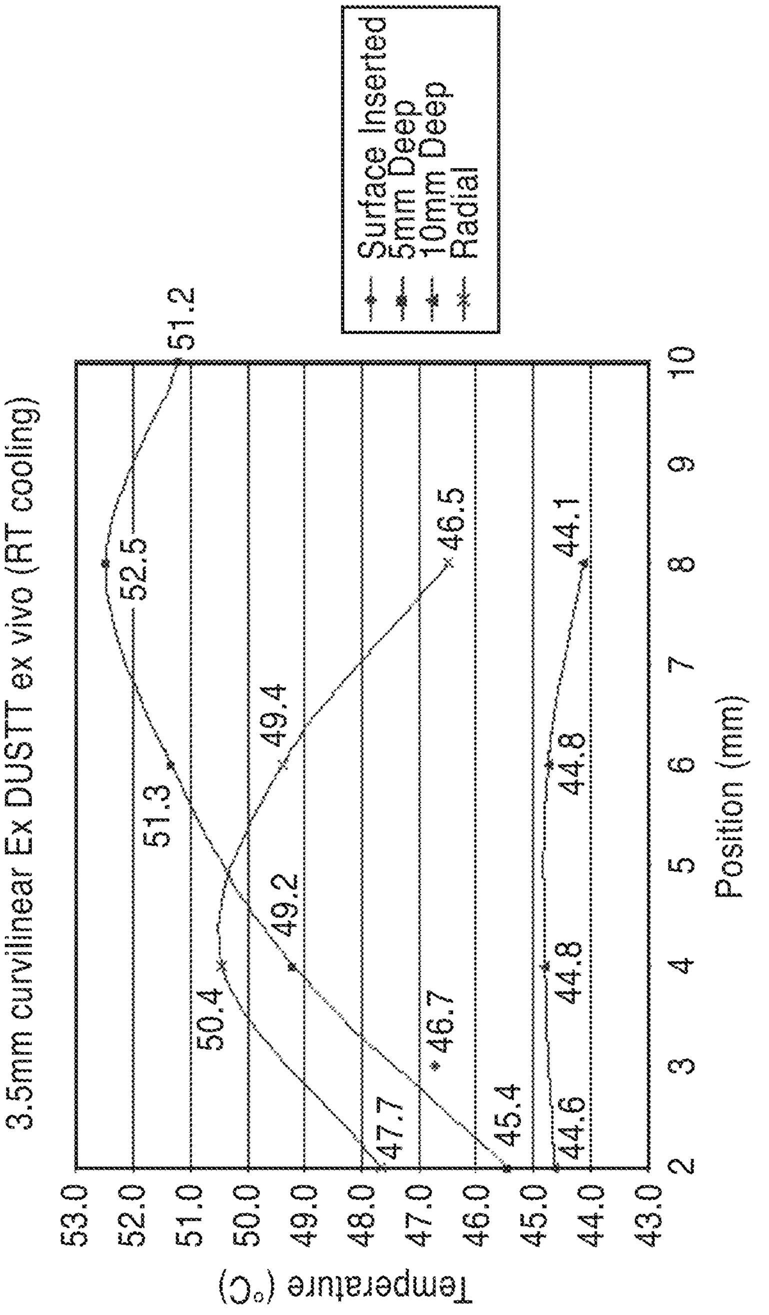
FIG. 44 shows another graph of certain temperature vs. transducer position results similar to the graph shown in FIG. 41, except showing results according to the mode of operation also variously illustrated in FIGS. 42-43.
Figure 45:
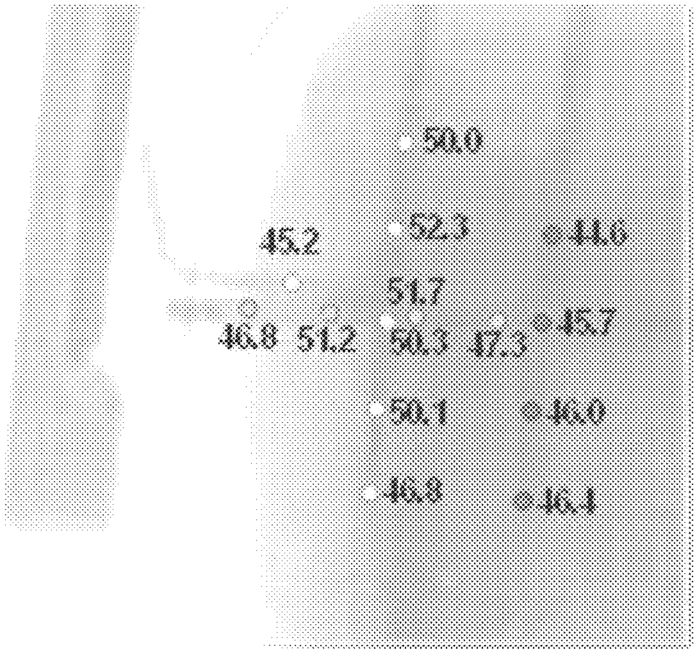
FIG. 45 shows a similar exploded X-ray picture to that shown in FIGS. 39 and 42, except showing thermocouple values according to a relatively low temperature mode of operation using a 3.5 mm wide transducer and cooling at 0 degrees C.
Figure 46:
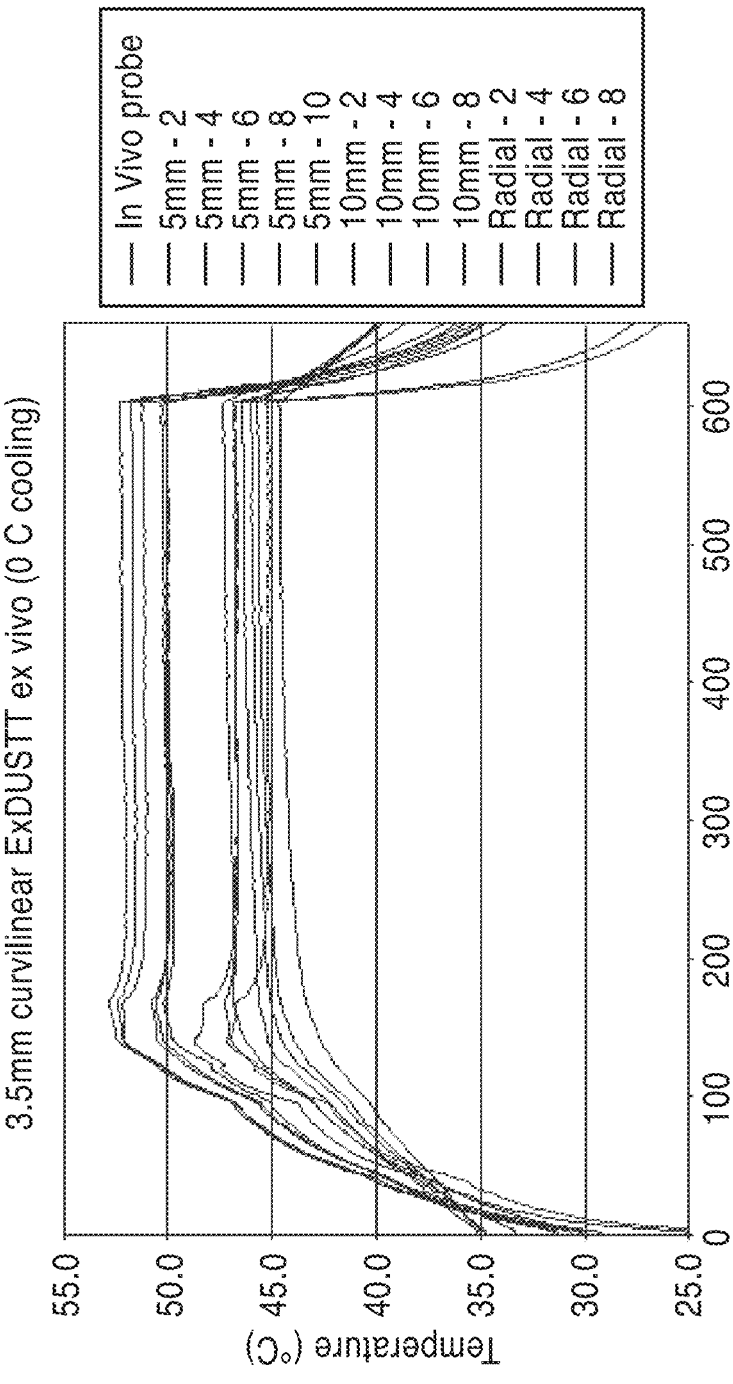
FIG. 46 shows another temperature vs. time graph, except with respect to the arrangement also illustrated in FIG. 45.
Figure 47:
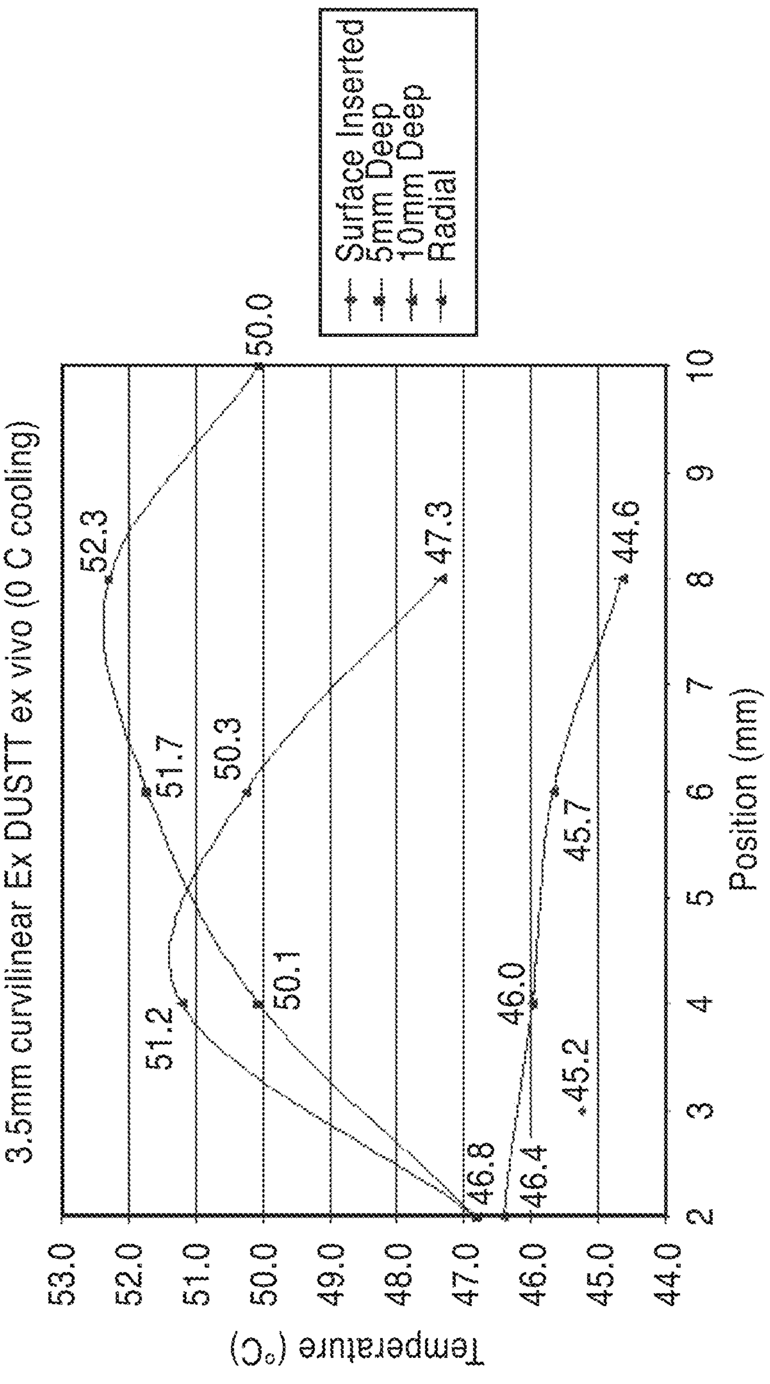
FIG. 47 shows a graph of temperature vs. thermocouple position results according to the thermal therapy arrangement illustrated in FIGS. 45 and 46.
Figure 48:
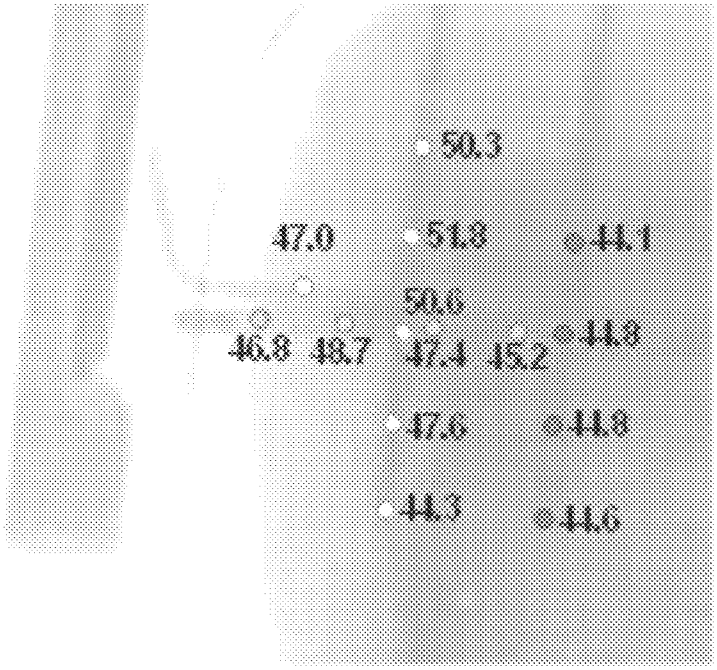
FIG. 48 shows another exploded X-ray picture of the same ExDUSTT arrangement, except according to use of a 2.5 mm wide transducer with relatively low temperature heating mode and cooling at 0 degrees C.
Figure 49:
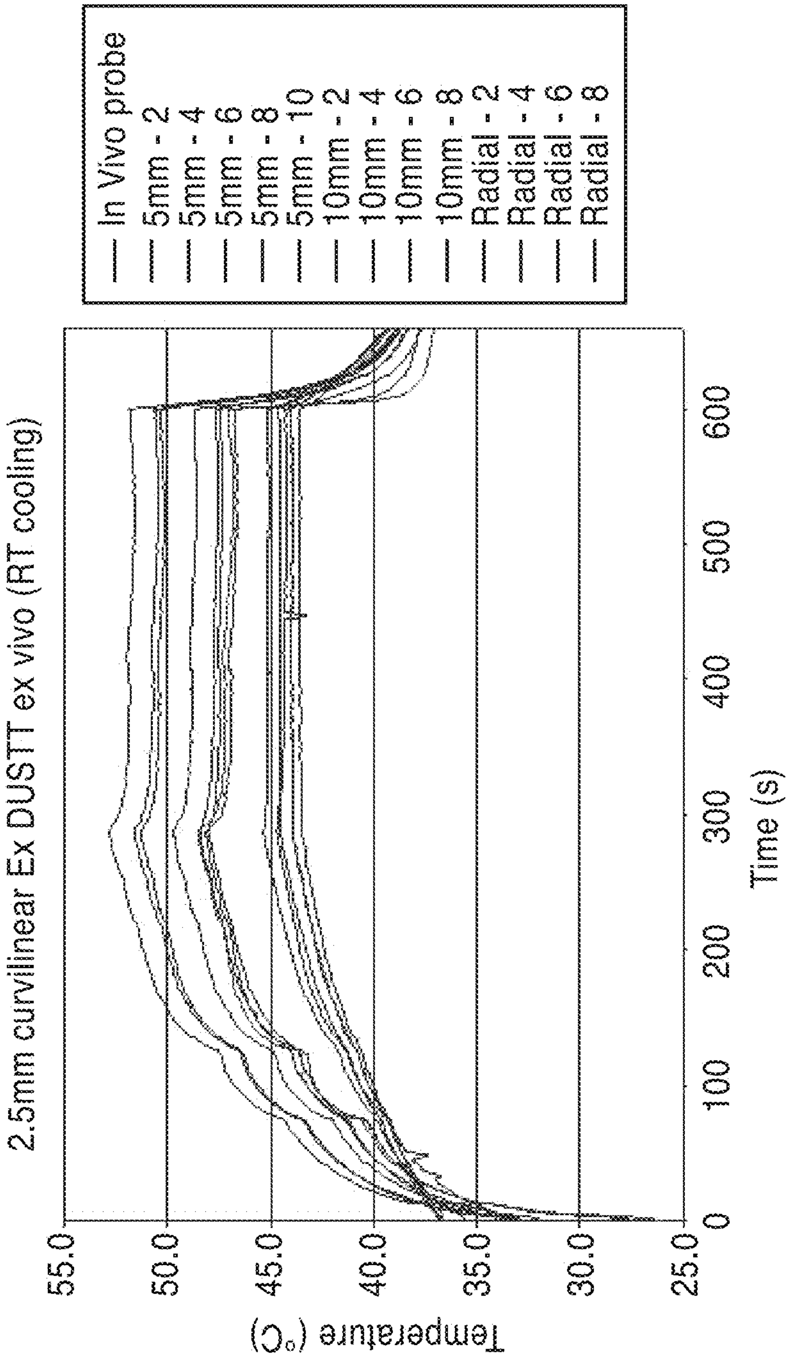
FIG. 49 shows another temperature vs. time graph for the ExDUSTT heating arrangement illustrated in FIG. 48.
Figure 50:
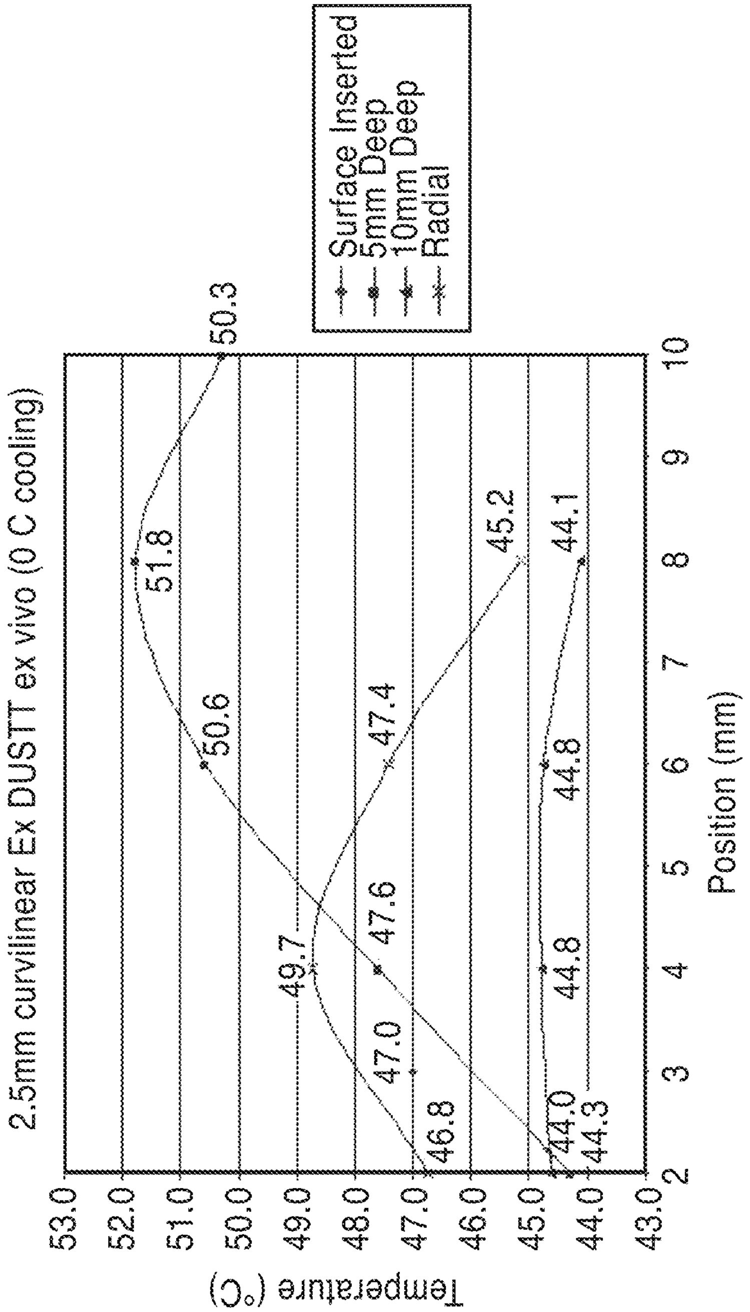
FIG. 50 shows another temperature vs. thermocouple position graph for a 2.5 mm curvilinear ExDUSTT ex-vivo disc treatment using 0 degree C. cooling and relatively low temperature mode of operation.
Figure 51:
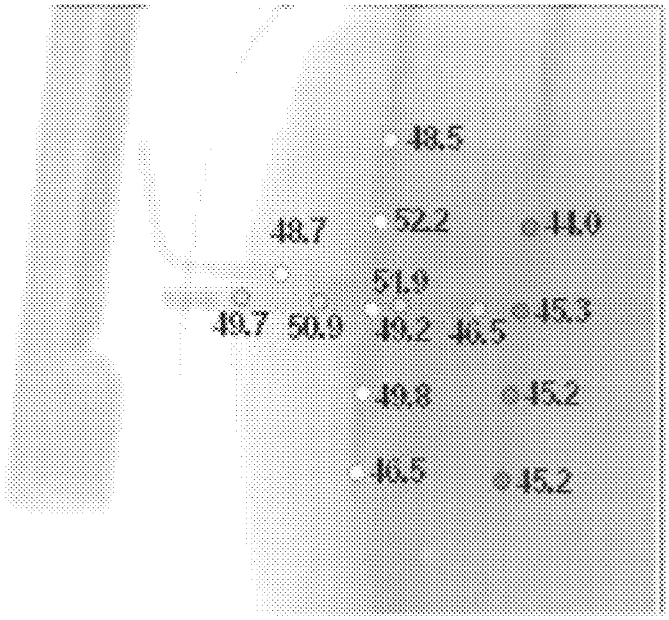
FIG. 51 shows another exploded X-ray picture, except with thermocouple values corresponding to use of a 2.5 mm transducer ExDUSTT device at a relatively low temperature mode of use with room temperature cooling.
Figure 52:
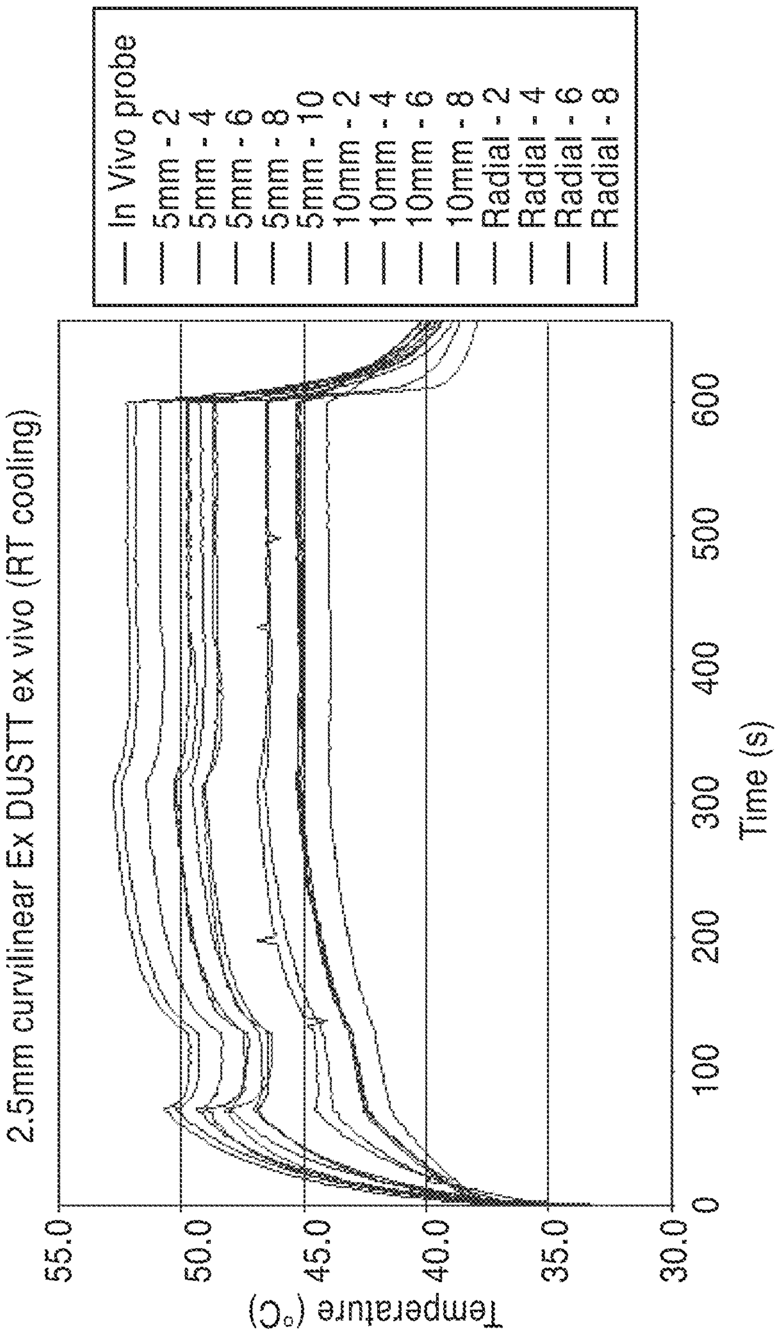
FIG. 52 shows a temperature vs. time graph according to the ExDUSTT mode of therapy also illustrated in FIG. 51.
Figure 53:
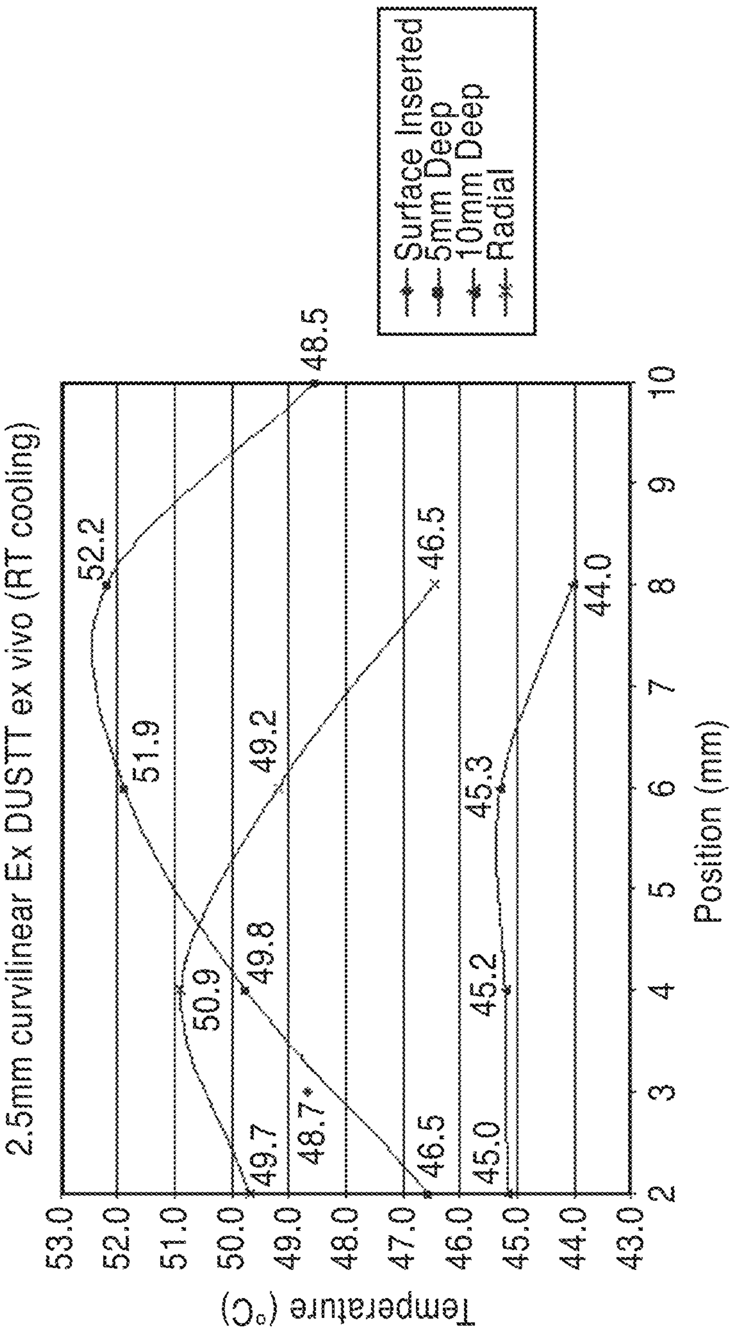
FIG. 53 shows a temperature vs. thermocouple position graph for the modes of ExDUSTT therapy illustrated in FIGS. 51 and 52.

For example, as shown in FIG. 41, all temperatures monitored using 0 degree C. cooling during relatively high temperature mode of operation were above 60 degrees C., even out to 10 mm deep, and in particular were above 70 degrees C. for most all data taken at 5 mm depth, whereas temperatures predicted at 7 mm deep were also in excess of 70 degrees. Other illustrative and informative results are reported up through FIG. 53 with respect to additional modes of ExDUSTT operation, which are best understood by further reference to the Brief Description of the Drawings above.

Various different modes and embodiments for curvilinear transducers may be suitable for use according to the various embodiments herein described, such as for example the various ExDUSTT device embodiments just described However, the following provides some further detail for particular modes and variations contemplated for the purpose of providing a more complete understanding In one regard, these transducer segments such as used in the ExDUSTT devices (and per for example the earlier embodiment in FIG. 6C) are sectors of larger diameter cylinders or plated tubes, with ultrasound energy emitted from the concave surface. Examples include 0.394" (+/−0.005")×0.098" (+/−0.002") linear wide×0.013 thick which form an 14.2 deg. Arc segment of 0.4 "inner radius tube. One can realize different diameters or arc segments, such as 9.5 deg. Arc segment of 0.591" inner radius tube. These can be purchased for example from vendors such as Boston Piezo-optics using materials such as PZT-4, 5, or 8.

The radius of curvature can be selected to sharpen or decrease the amount of energy concentration or apparent focusing (i.e., radius of curvature of 0.5, 0.75, 1.0, 1.5, 2.0 cm can be appreciated) with the higher radius of curvature and wider transducers giving more penetrating distributions. The width can vary to suit particular needs for operation or device compatibility, but may be for example between about 1.5 mm to about 6 mm; whereas the length can also vary to meet particular needs, such as for example from between about 2 mm to about 10 mm or greater. Transducers meeting these specifications are in particular useful for various of the embodiments herein described, provided however that such embodiments nor other aspects of the invention should not be considered to be so limited to only these dimensions.

These transducers can be mounted in transducer assemblies using a variety of suitable means. Flexible adhesives (e.g. silicone adhesive, Nusil), rigid epoxies or conformal coatings (Dow Corning) may be used. Rigid metal (brass or stainless steel) or plastic assemblies can be machined to hold the transducers and maintain air-backing. One more detailed example incorporated into many of the ExDUSTT devices shown and described includes a filed down, 15 mm long portion (or specified length) across a 180 degree plane transversely through a distal stainless-steel support hypotube. This forms a shelf for either side of the transducers to be mounted. Lead wires (such as for example either silver lead wire or miniature coaxial cable (Temflex, Inc)) are soldered to the transducer surfaces for power application and can be run within the central lumen of the SS.

A thin layer of silicone adhesive can be placed upon the edges of the tube structure, and the transducer segment placed. The transducer can then be sealed using silicone adhesive and/or conformal coating. The conformal coating can be accelerated using elevated heat for about 60 min. Alternatively, rubber thread can be used for a spacer with silicone adhesive, to keep transducers from contacting the metal surface. Other holding devices can be implemented, including pieces machined from brass bar or rod with gaps for the air space and offsets to support. In some implementations, it may be desired to circulate water or fluid behind the surface of the transducers.

These transducer assemblies can be either modular catheter form insertion into target tissue (intra-discal) or rigid external applicator. It is not necessary, but these transducers can be sealed using epoxy and polyester layers a previously described, or using mineral oil or other type of oil instead of Epotek, or the transducer can be left bare, though in many applications would be sealed on its edges and possibly top surface with conformal coating for watertight integrity and durability. Custom multilumen extrusions in materials such as pebax can form the flexible catheter member of which the transducer assembly is attached. The transducers are rigid, but if multiple segments are used, they may be coupled in a manner providing flexible hinges for better bendability in use.

Pre-shaped high-pressure balloons such as those herein shown for ultrasound tissue coupling can be provided in various shapes. Suitable sources include for example custom fabrication, such as for example by Advanced Polymers, or may be made in house by heat-stabilizing the PET heat-shrink in pre-determined shape using molds and Teflon-coated mandrels. These balloons can have a neck that is 3 mm OD and a one sided inflation with a 2 mm radius. Compliant balloons using silicone, c-flex, polyurethane, or other material can also be used for various applications indicating such compliance or elastomeric properties.

These devices can have temperature regulated flow, flow in general, or no flow at all. In addition, devices without encapsulating balloons can be realized with sterile saline or fluid flow used to cool and couple US to the interface.

Internal Directed Ultrasound Thermal Therapy ("InDUSTT™") System and Method

The following description relates to device and method embodiments in particular adapted for use internally within intervertebral discs or other joints, e.g. "InDUSTT" devices and methods.

Figure 54:
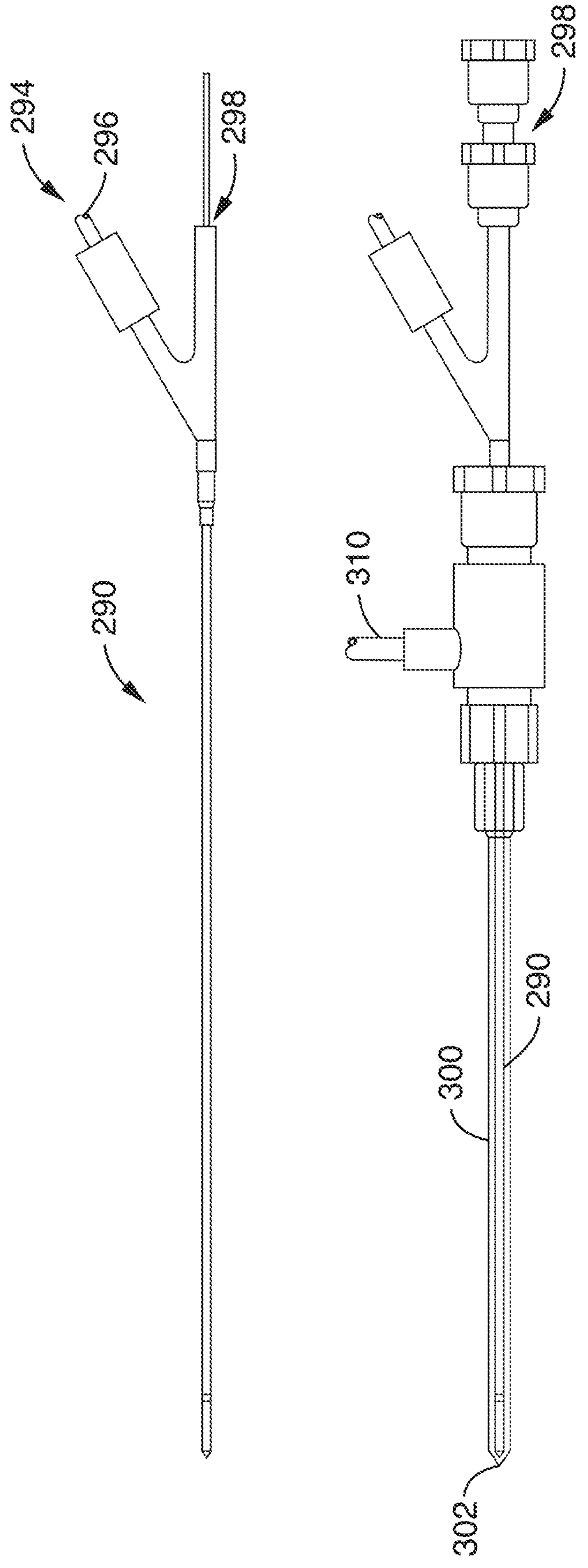
FIG. 54 shows a perspective view of an internal directional ultrasound thermal therapy system ("InDUSTT™") that includes a spinal disc delivery probe and an InDUSTT device that fits within the spinal disc delivery probe.

The following figures and accompanying description is to be read in conjunction with prior description herein made above, and in any event relate to InDUSTT devices such as that shown at catheter 290 in FIG. 54. More specifically, FIG. 54 illustrates arrangements for two alternative modes of InDUSTT assemblies and treatments as follows. Catheter 290 is shown at the top of the Figure in a "direct coupling mode" and is adapted to be delivered directly into a region of a spinal joint, e.g. within the disc or bony structure, with the transducer coupled directly to tissue. Thus, there is only shown a coupling 294 such as for electrical leads 296, and fluid cooling coupling 298. As shown in the assembly of FIG. 54 on the bottom, however, a catheter cooled or "cc" arrangement differs from the direction coupling or "cc" arrangement in that a catheter 290 is buried within a closed housing of an outer delivery device 300 that has a sharp pointed tip 302 for puncturing into an intervertebral disc. Water circulation ports 298,310 according to this arrangement cycle cooling fluids between a lumen within the internal catheter 290 and over the internal catheter 290 but within the outer sheath 300.

Figure 55A:
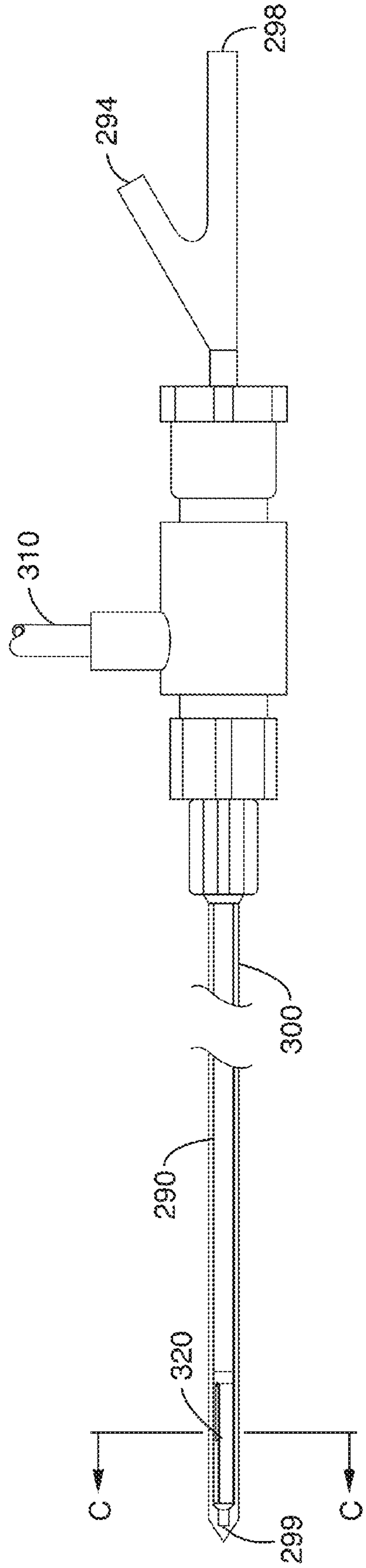
FIG. 55A shows a plan view of a schematic representation of an internal ultrasound thermal spine therapy device according to another embodiment of the invention.
Figure 55B:
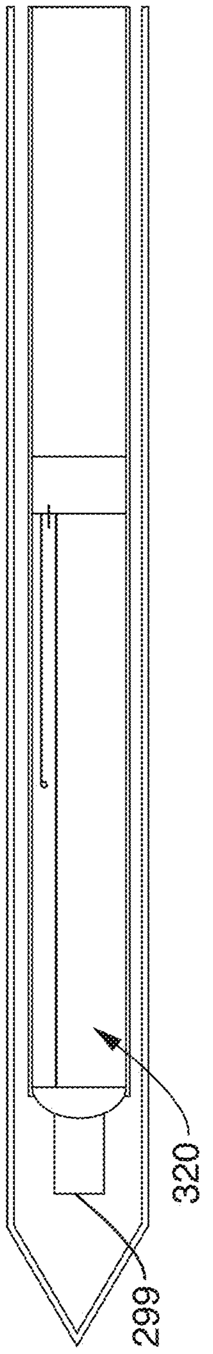
FIG. 55B shows an exploded view taken at region B shown in FIG. 55A, and shows enhanced detail of various aspects of the ultrasound heating assembly along the distal end portion of the InDUSTT system according to a further feature of that embodiment.
Figure 55C:
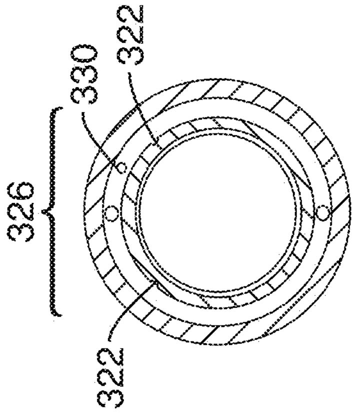
FIG. 55C shows a transverse cross-sectioned view taken along line C-C in FIG. 55A.

Further details of the cc arrangement are variously shown in FIGS. 55A-C, wherein a transducer 320 is of a cylindrical tubular type that has sectored grooves 322 (FIG. 55C) on either side of an electroded and active portion 326 for directional ultrasound delivery along about a 90 degree span of space radially outward from that section, and thus both directionality is achieved, as well as diverging US signal. Couplers shown include power lead coupler 294, water inflow coupler 298, water outflow coupler 310. As shown in FIG. 55B, the water cooling is aided by a distal port 299 in the internal catheter device 290. A thermocouple 330 is shown along the active sector, as well as others may be provided elsewhere (not shown) such as along the other dead sector as temperature monitoring may still be important there to protect certain tissues from conductive heating during US therapy on the opposite side of the catheter. The transducer shown may be for example 1.5 mm outer diameter, 0.9 mm inner diameter, by 10 mm long and mounted over a plastic support ring. The outer catheter 300 may be for example constructed from a simple polymeric tubing such as made from CELCON™ from Best Industries typically used conventionally for implanting radiation seeds in tumor therapy and of 13 gauge construction.

Figure 56A:
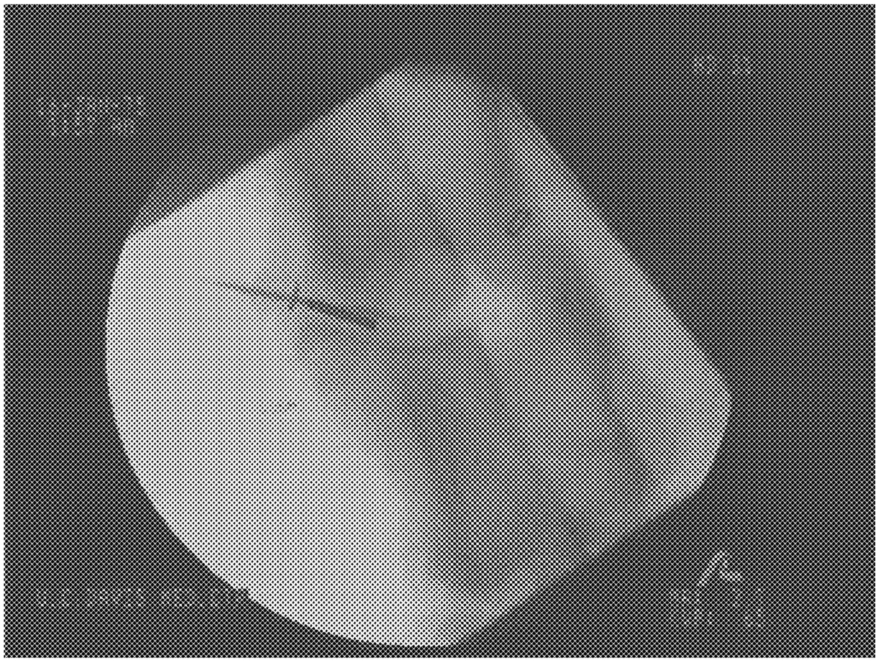
FIGS. 56A-B show respective X-ray pictures of the distal end portion of an InDUSTT system similar to that shown in FIGS. 54-55B positioned within an intervertebral disc during in-vivo thermal spinal treatments according to certain modes of the invention.
Figure 56B:
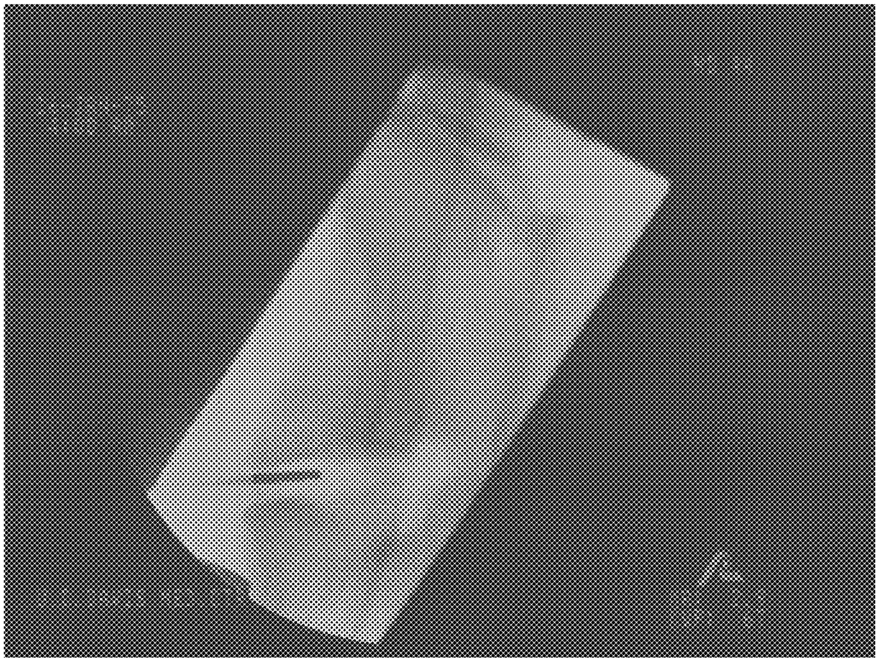
Figure 58:
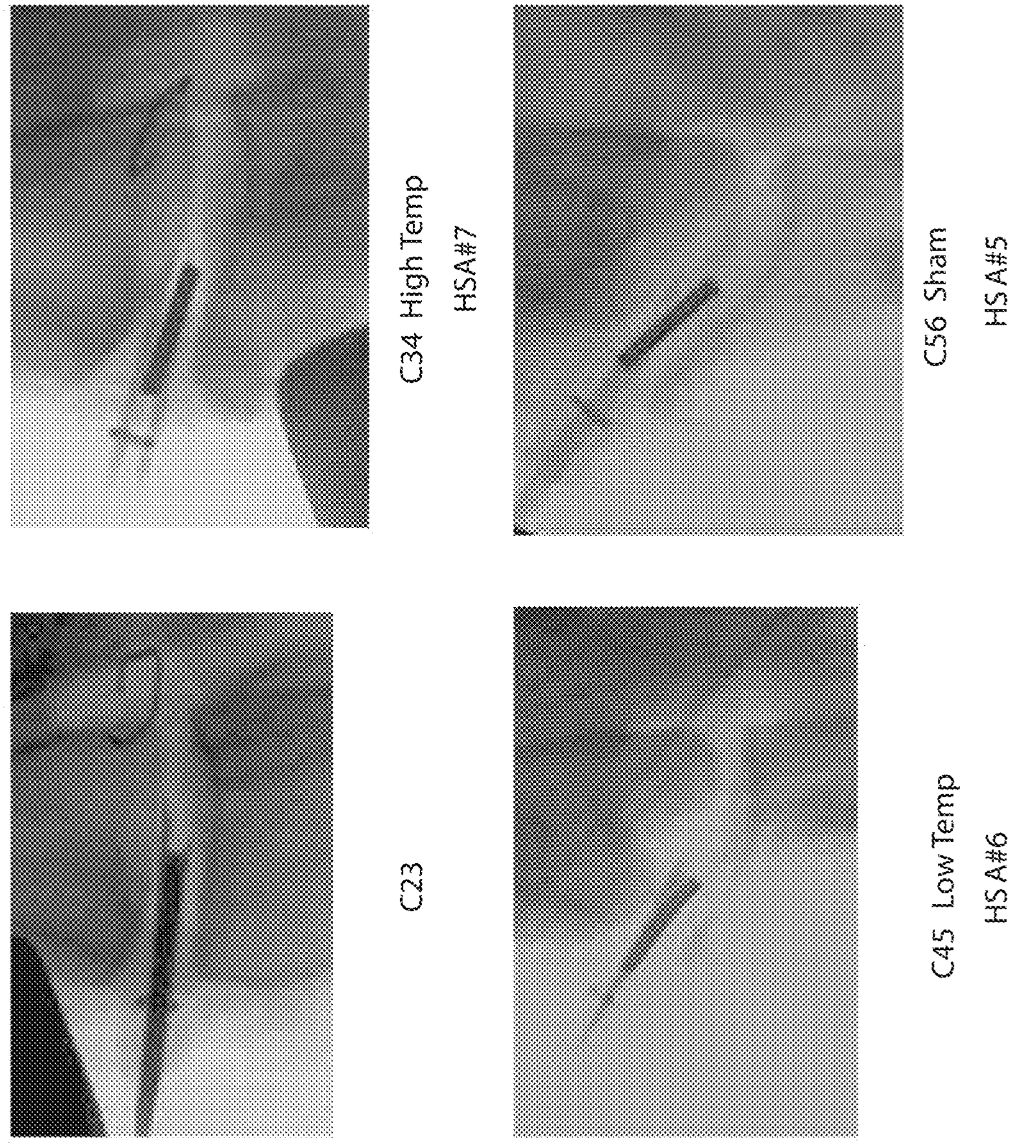
FIG. 58 shows various X-ray pictures of the placement of the InDUSTT transducer within the C2/3, C3/4, C4/5, and C5/6 intervertebral discs corresponding to the results provided in the table in FIG. 57.

For the purpose of providing a thorough understanding of the many different aspects and considerations of using the InDUSTT device just described, a significant amount of summary results from multiple studies of working embodiments is herein provided by reference to FIG. 56A and beyond. A thorough understanding of various aspects of these results and experimental arrangements shown is gleaned by review of the Brief Description of the Drawings above. In general, where discs are indicated by an arrangement such as "C3-4" or "C4/5" such designates the vertebrae in the animal between which the disc was treated. In addition, curve legends designating numbers for graphs (such as for example "Probe 1-1", "Probe 1-2", etc. in FIG. 65A) designate thermocouples along temperature monitoring probes in the disc tissue, typically spaced by 5 mm apart.

Accordingly, as is reflected in the graphs and other pictures and Figures, many different discs were treated. Still further, the test results shown also reflect an understanding of the effects of cooling at different temperatures, as well as direct coupling versus catheter cooled coupling, as well as relatively high versus relatively low temperature modes of use.

While the results shown in these latter FIGS are in non-human animal models, the results, and in particular the relationships between results between different treatment groups, correlate to the human condition and are confirmed by earlier human cadaver studies performed. Actual values may of course differ, however, but it is believed that the extreme ends of the results would apply across vertebrate animal species. Moreover, the date suggests that directivity is confirmed, as is the ability to achieve high temperatures over 70 degrees or even 75 degrees, as well as control heating to lower temperatures for other intended treatments.

Figure 59A:
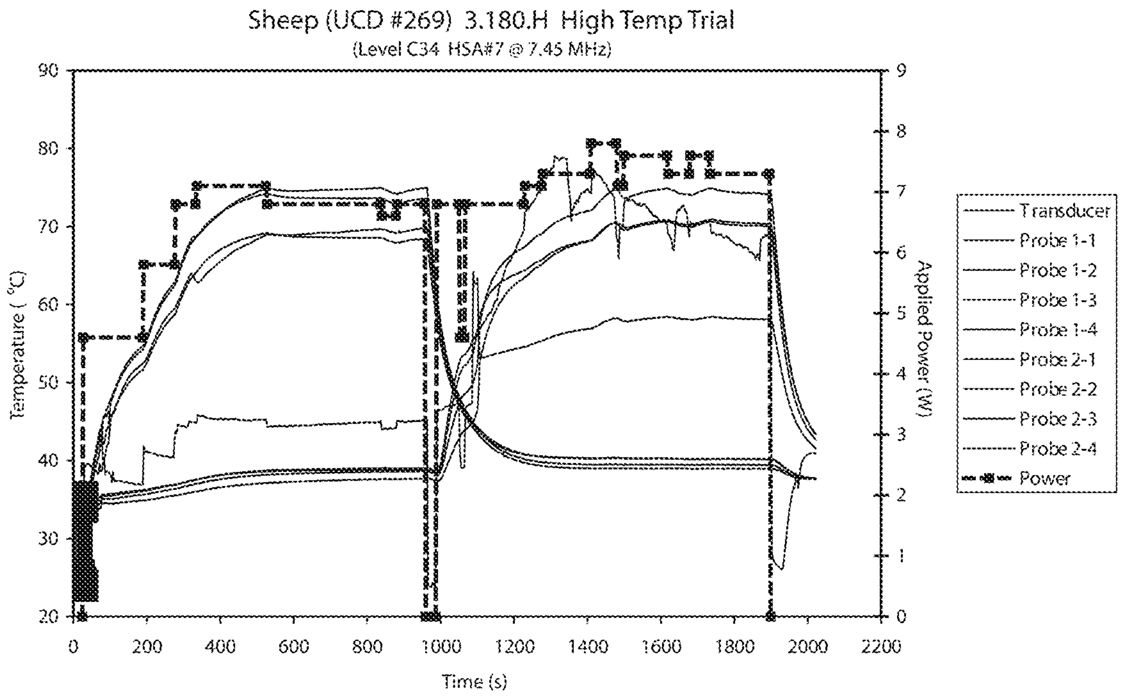
FIG. 59A shows a graph of temperature vs. time during InDUSTT heating of a C3/4 intervertebral disc according to a relatively high temperature mode of use, and shows curves for various respective thermocouple probe positions.
Figure 59B:
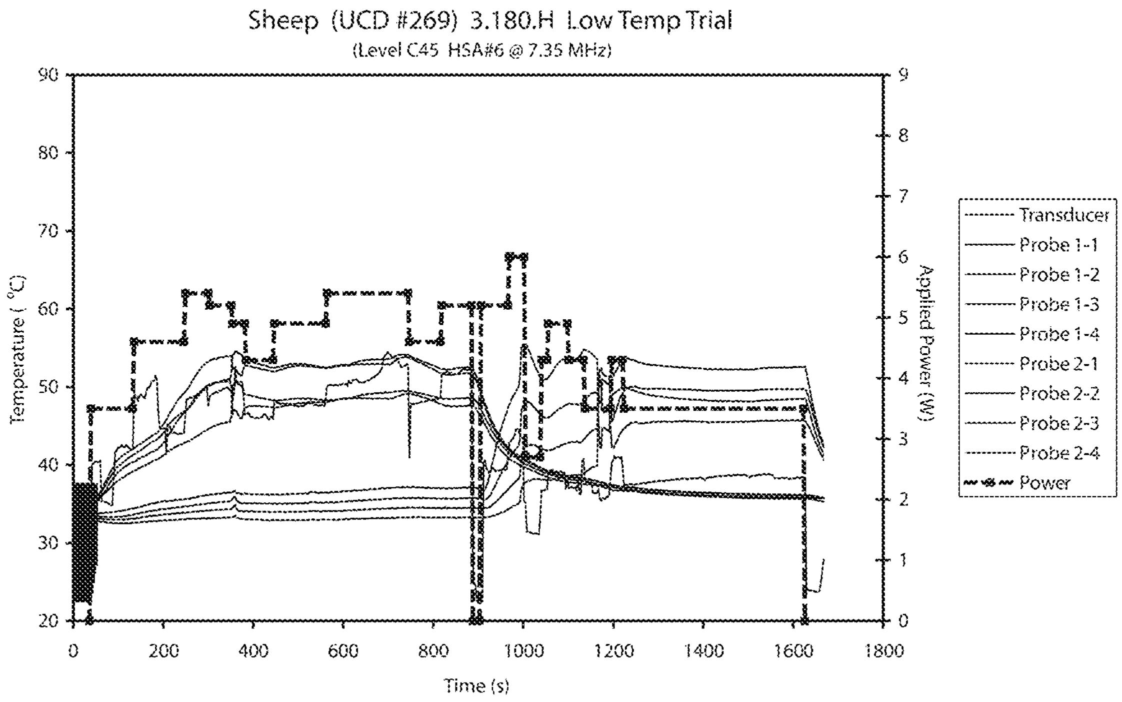
FIG. 59B shows a graph of temperature vs. time using the same InDUSTT device as that used for creating the data shown in FIG. 59A, except shows results according to a relatively low temperature mode of use in a C4/5 intervertebral disc location.
Figure 59C:
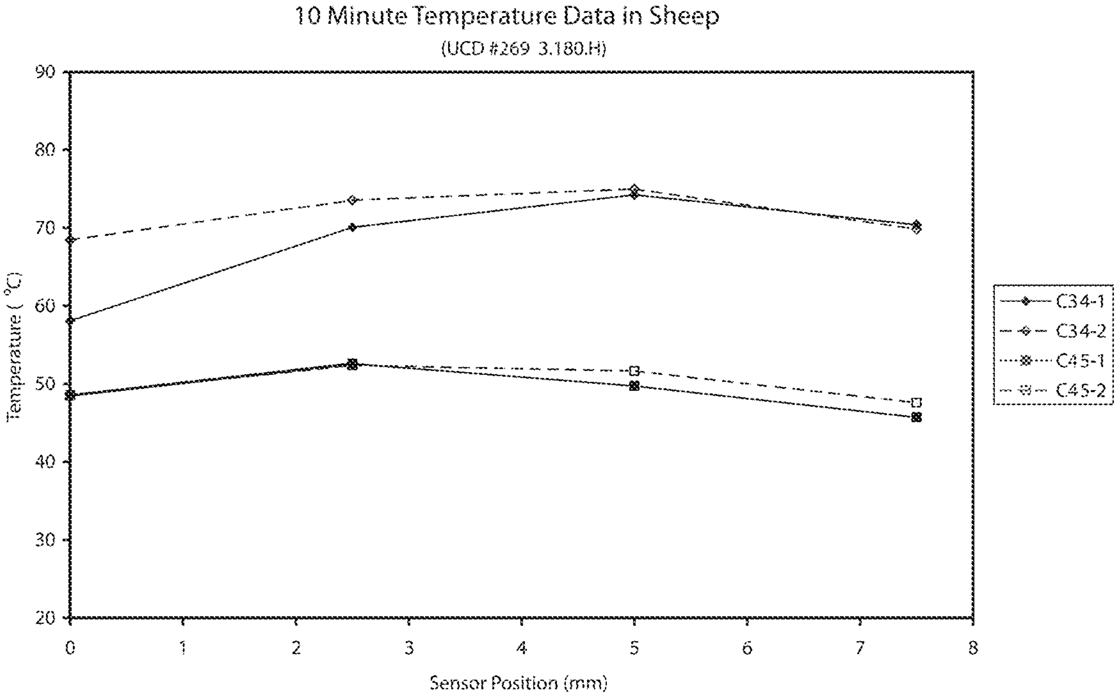
FIG. 59C shows a graph of temperature monitored at various temperature sensor positions during 10 minute InDUSTT heating, and shows curves for results in two separate intervertebral discs each heated with a different one of two separate InDUSTT systems of the invention.
Figure 62A:
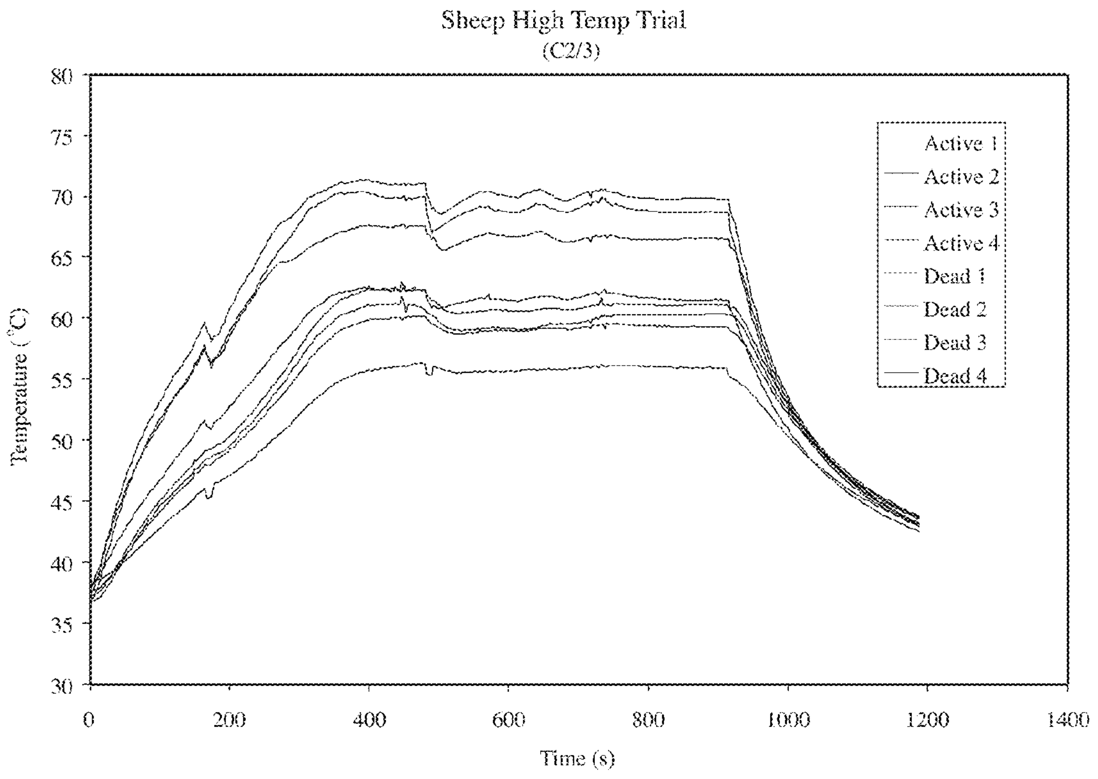
FIG. 62A shows a graph of temperature vs. time corresponding to the C2/3 disc treatment shown in FIG. 61 and according to a relatively high temperature mode of use.
Figure 62B:
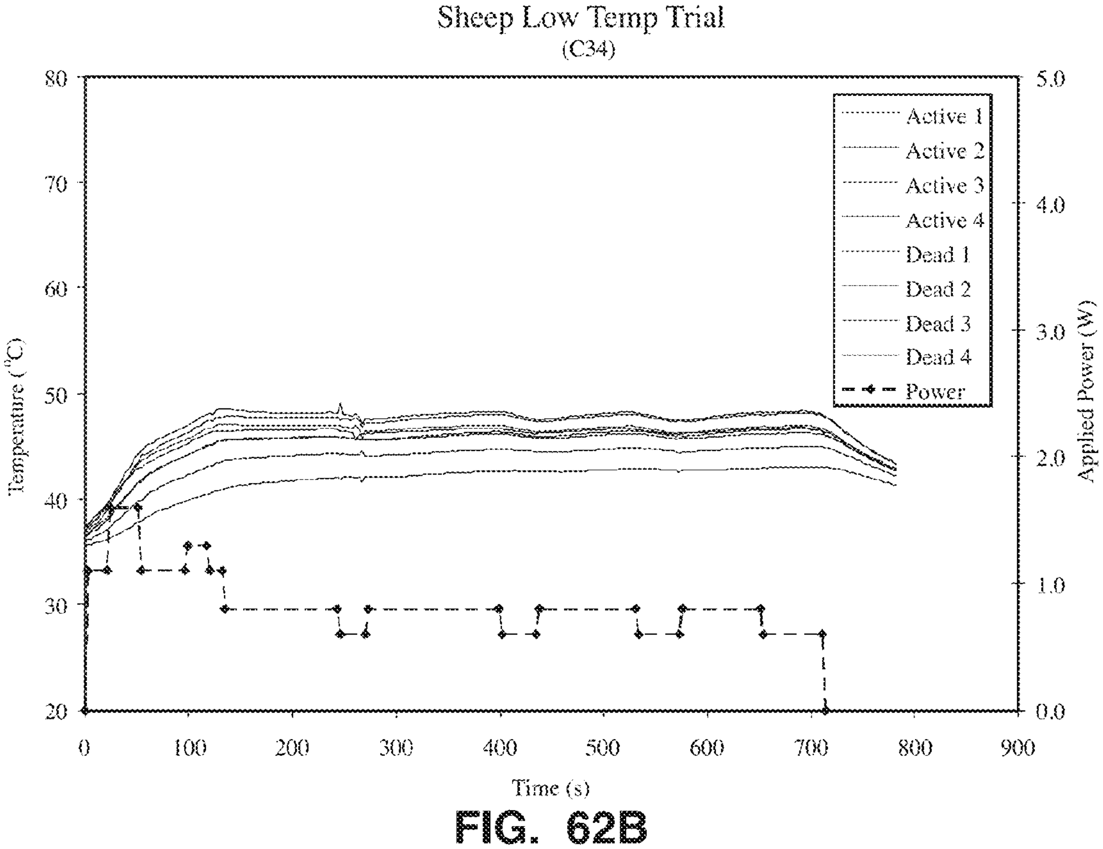
FIG. 62B shows a graph of temperature vs. time corresponding to the C3/4 disc treatment shown in FIG. 61, and according to a relatively low temperature mode of use.
Figure 62C:
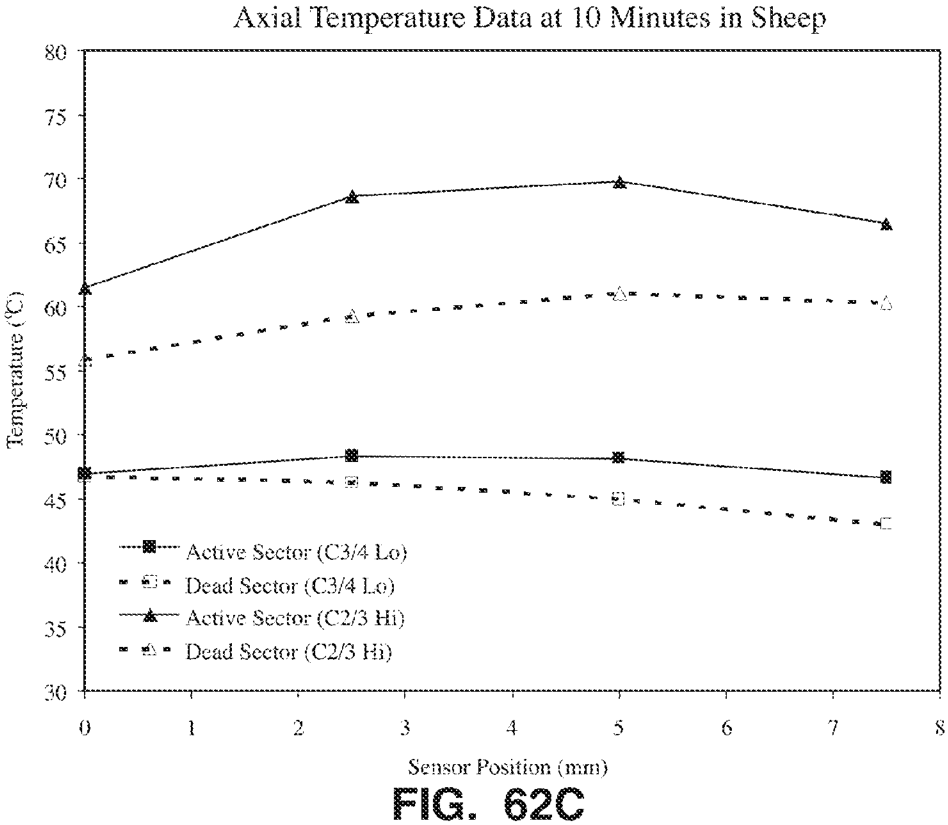
FIG. 62C shows a graph of temperature monitored at various temperature sensor positions during 10 minute directly coupled InDUSTT heating, and shows curves for thermal treatment results at both dead sectors and active sectors of the transducer in the C2/3 disc at relatively high temperature power level, and at similar locations in the C3/4 disc at the corresponding, relatively low temperature power level.
Figure 62D:
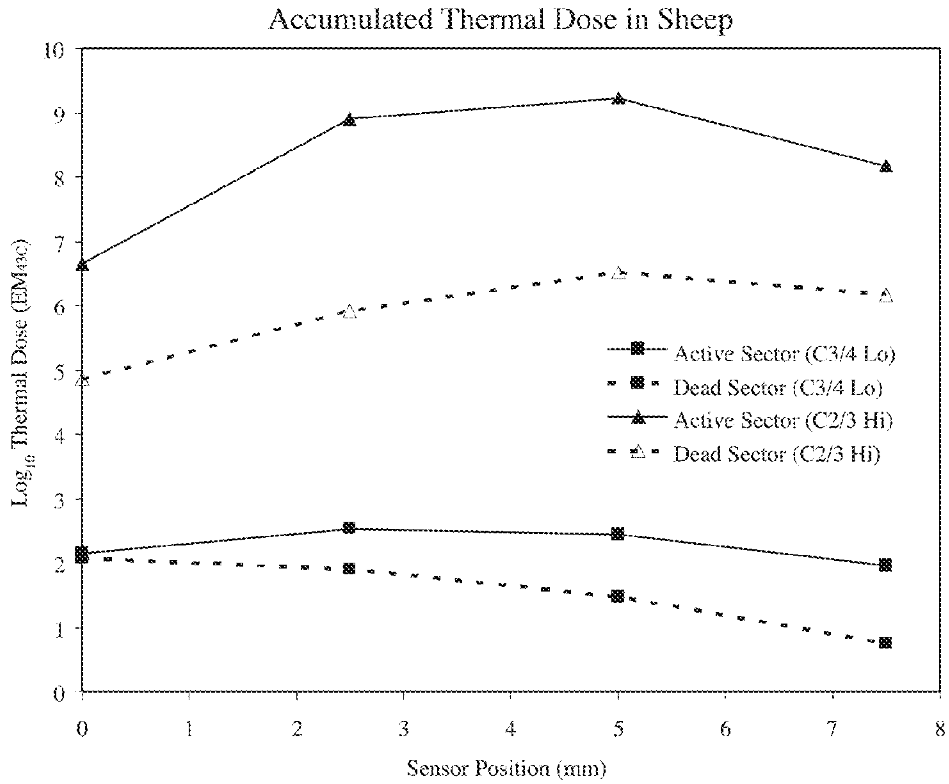
FIG. 62D shows a graph of accumulated thermal dose versus temperature sensor position for the 10 minute treatments at the C2/3 and C3/4 discs at the relatively high and low temperature power levels, respectively.

In one example, FIGS. 59A and B show two sets of lines that cross at time equal to about 900 seconds. This indicates a period of time when the InDUSTT device, with sectored, directional ultrasound emission, was rotated. Accordingly, the uniform change in temperature reflects the preferential heating that can be achieved with such device and not heretofore possible. For further illustration, FIG. 65A shows similar results according also to turning a directional device to realign the active sector to different transducers.

Various embodiments have been herein described, including ExDUSTT, InDUSTT, rigid-probe based, catheter based, directly coupled, actively cooled, sectored transducers, curvilinear transducers, axially aligned transducers, transversely aligned transducers, relatively large transducers, relatively small transducers, compliant elastomeric coupling balloons, relatively non-compliant pre-formed coupling balloons, relatively high temperature modes of operation, relatively low temperature modes of operation, low temperature cooling, room temperature cooling, preshaped, flexible, guidewire delivery, and deflectable/steerable delivery platforms. It is to be appreciated that the more detailed description for such embodiments provided herein is for the purpose of illustration, and other modes of achieving such may be suitable for inclusion according to the invention without departing from the present scope. Moreover, the combinations of such features herein shown are highly beneficial, but not intended to be limiting. Other combinations may be made without departing from the intended scope hereof. For example, the particular embodiments shown and described for "ExDUSTT" applications are described as such merely according to their highly beneficial ability to perform in that arrangement, but they may be used as InDUSTT devices as well, despite their particular external use benefits. The opposite is true, as well, with respect to InDUSTT devices which may also be used in other external locations such as for disc heating. The devices shown and described may be used within or around the bony structures of spinal joints, too. Moreover, where various of the features may be highly beneficial for particular applications, they may not be necessary for other applications. For example, directional energy delivery is a highly beneficial aspect of the various ultrasound embodiments herein shown and described, in particular where highly localized heating is desired while other surrounding tissues need to be protected such as nerves. However, in other applications, such as some complete disc remodeling applications for example, non-directional emission may be suitable to heat all the surrounding tissue equally.

It is to be appreciated that the various modes of devices and operation herein described, together with tissue characterization studies performed and herein presented, provide a significant understanding with respect to adapting and controlling thermal therapy, or other modes of ultrasound delivery for therapy, in special areas in the body such as joints, and in particular spinal joints and their discs and bony structures. Back pain and other issues in these joints are significant medical issues that may be addressed with the present invention according to its many different modes and aspects.

Long-Term Implantable Ultrasound Delivery Devices, Systems, and Methods

The foregoing embodiments, including the devices, systems, and methods described, have been generally described above with respect to their use as temporary implants, (e.g. per the percutaneous catheter or probe devices and respective treatment techniques described in the preceding Figures, such as for example with respect to the various ExDUSTT and InDUSTT devices shown and described). However, according to a highly beneficial aspect of the present invention, an ultrasound treatment system and method is provided for long-term implantation, either permanent or semi-permanent, as is described in more detail below by reference to various embodiments.

Figure 66:
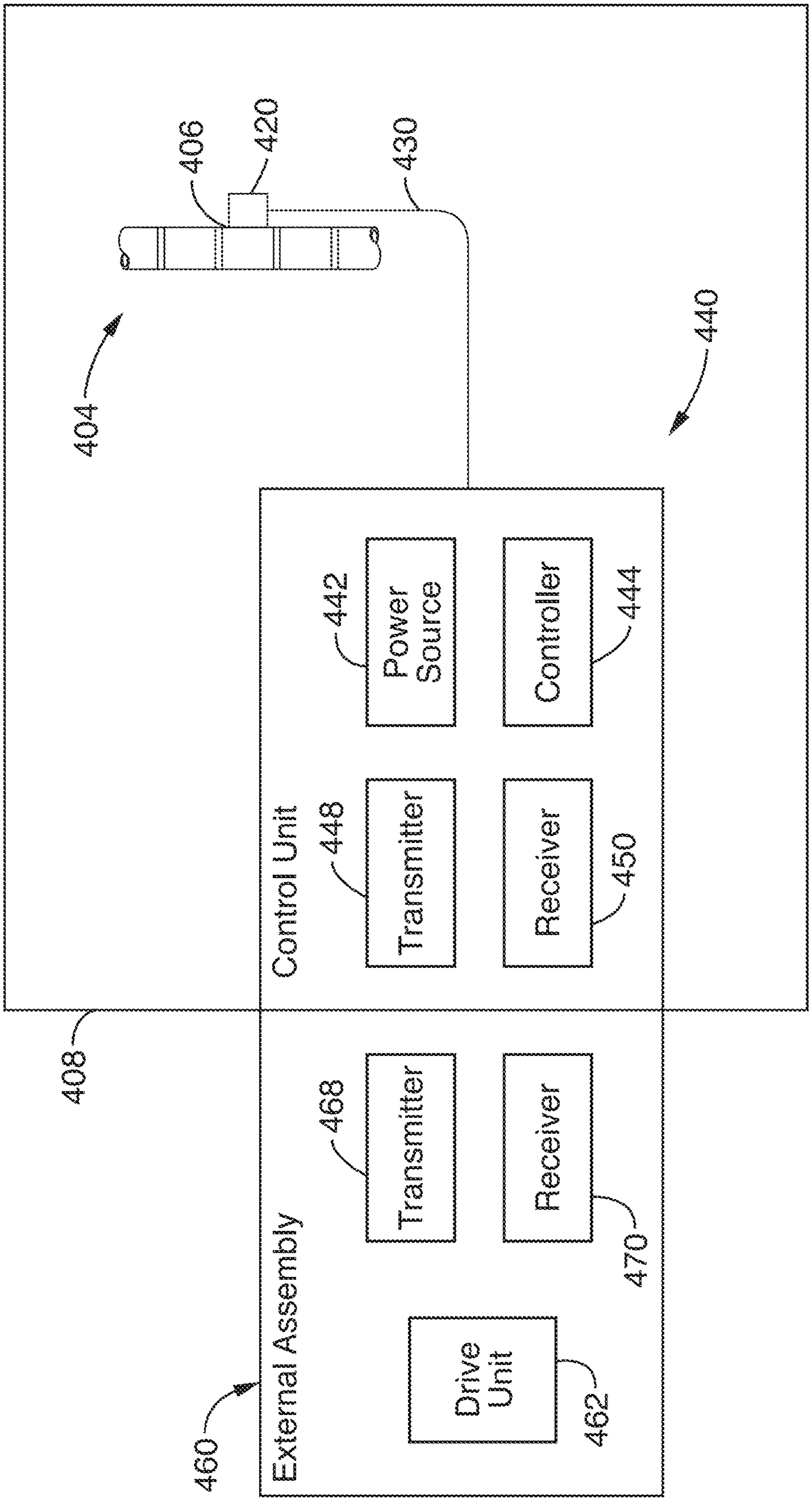
FIGS. 66-68 show respective schematic views of different embodiments for a long-term implantable ultrasound spinal therapy device system according to the present invention.
Figure 67:
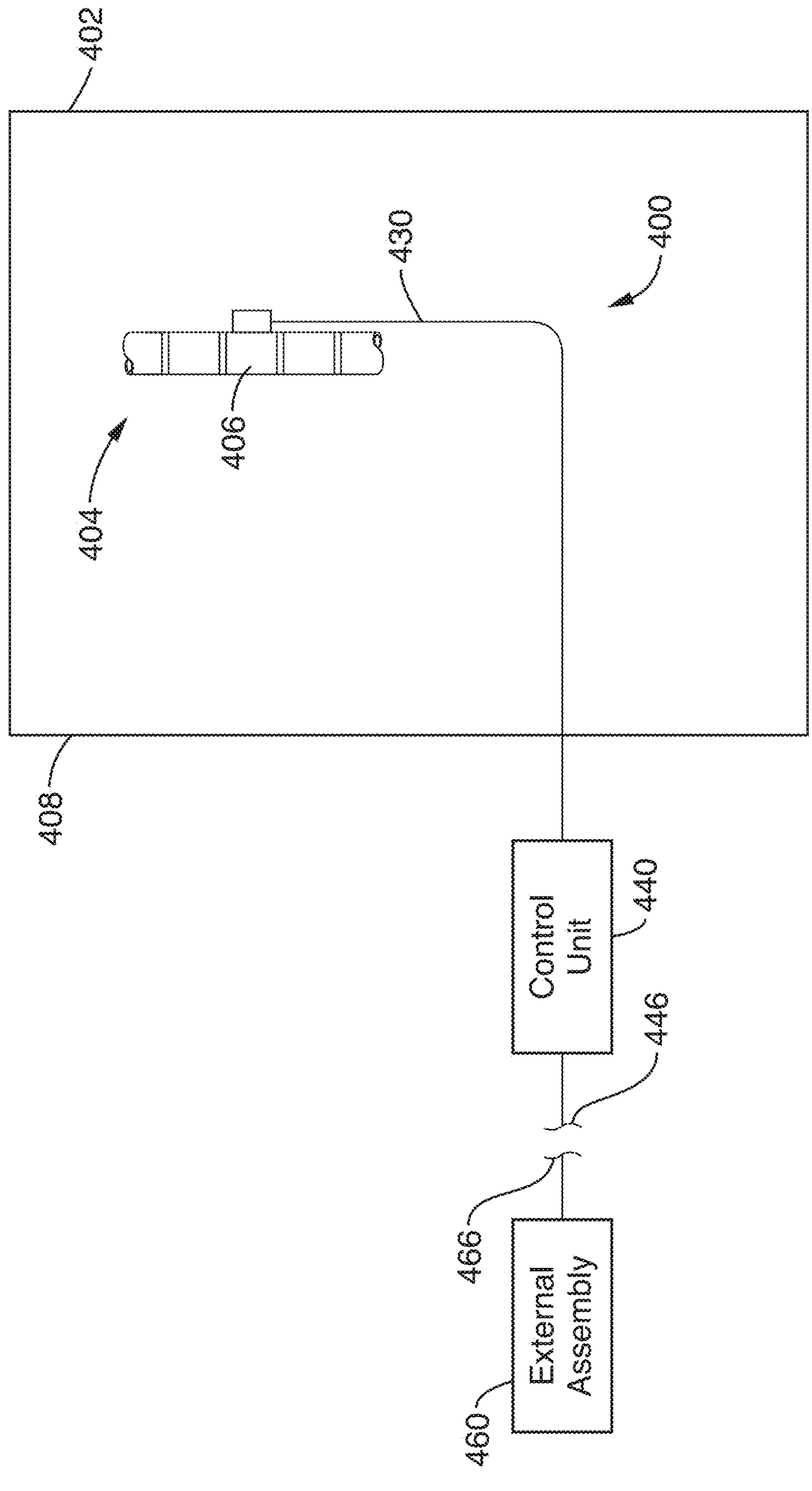
Figure 68:
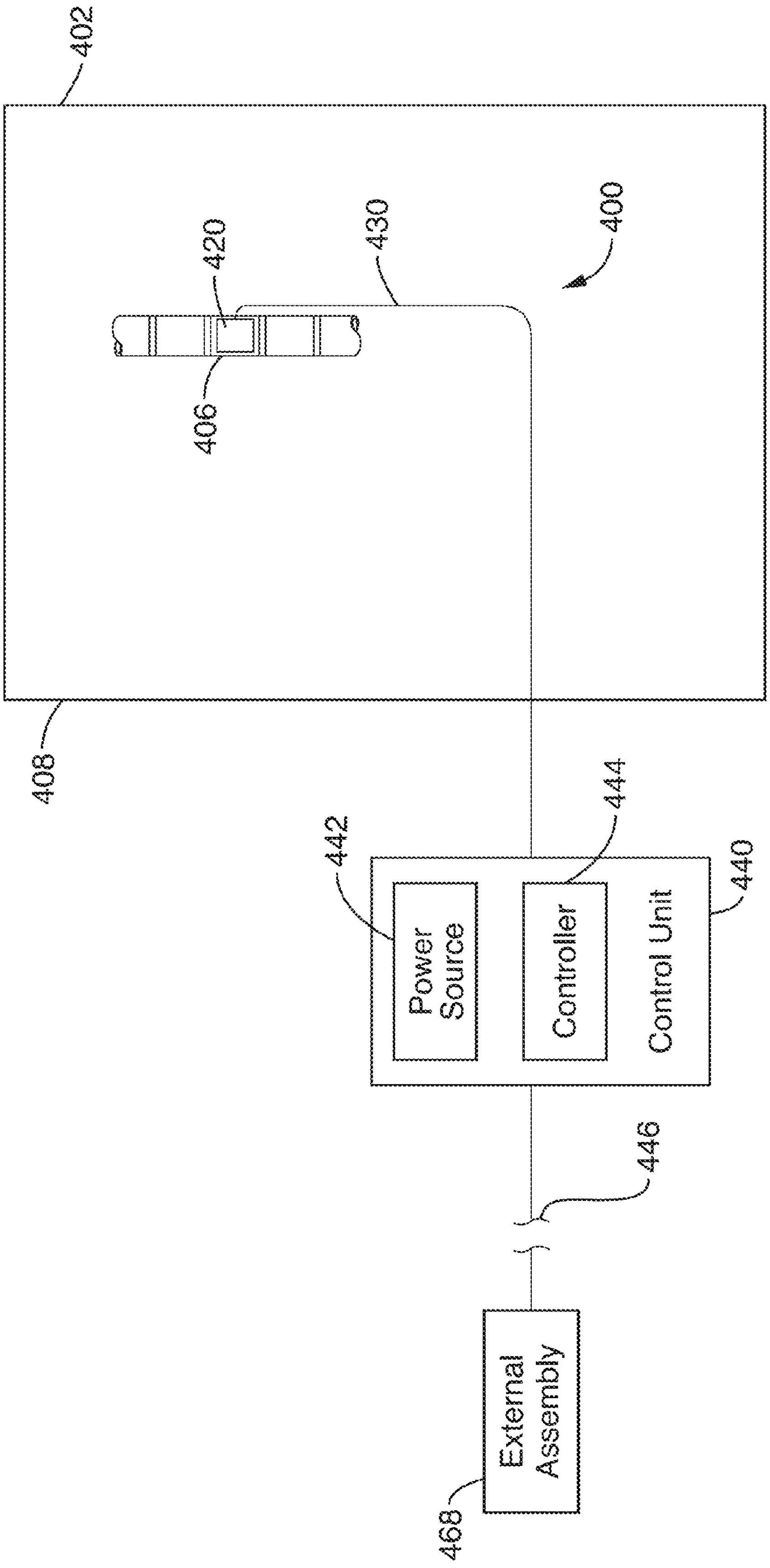

The long-term implantable ultrasound system of the invention is shown schematically according to various illustrative embodiments in FIGS. 66-68 by reference to a patient's body 402 that includes a spine 404 and outer skin barrier 408.

More specifically, FIG. 66 shows long-term implantable ultrasound therapy system 400 and includes a long-term implantable ultrasound treatment assembly 420 positioned at a location adjacent to a spinal joint 406. A coupling assembly 430 connects treatment assembly 420 with a control unit 440 that is shown in this embodiment to also be implanted as a long-term implant within the body 402 of the patient. Control unit 440 includes for example a power source 442 that cooperates with a controller 444. Further to the illustrative embodiment, control unit 440 is adapted to communicate with an external assembly 460 via a transmitter 448 and a receiver 450 of control unit 440 and reciprocal transmitter 468 and receiver 470 for external assembly 460. Such cooperation may be for example in order to provide telemetry to receive and process data monitored by control unit 440 regarding the treatment with ultrasound assembly 420, such as monitored parameters including for example temperature, thermal dose, number of treatments, duration of treatment, power levels. Or, such cooperation between internally implanted control unit 440 and external assembly 460 may be for the purpose of downloading new software such as operation protocols to the drive unit 462 tailored to advance therapy to account for new therapeutic information or to advance or otherwise modify an overall therapy protocol to a different stage. Or, to the extent power source 442 is a rechargeable battery, coupling between control unit 440 and external source 460 may be done for the purpose of recharging the battery, which may be done across the patient's skin barrier 408 according to previously disclosed methods, though which may be modified to meet the particular needs for a particular case. Examples of such remote, transdermal power recharging include use of induction by creating a magnetic field across the skin barrier 408 in a particular manner so as to recharge the batter of power source 442.

FIG. 67 shows another embodiment similar to that of FIG. 66, except however that control unit 440 is positioned externally of body 402 such that coupling assembly 430 bridges across the skin barrier 408. This provides the ability to recharge, monitor, control the control unit 440 and related treatment without requiring the remote transmission across the skin barrier 408 and other tissues as required in the FIG. 66 embodiment. According to this and the FIG. 68 embodiment, the externally located control unit 440 has a coupler 446 that is adapted to couple to external assembly 460 via its reciprocal coupler 466, which is shown schematically but may be for example for similar communication purposes provided above with respect to sending and receiving data and other information to monitor or control therapy.

In addition, such couplers 446,466 may provide for a recharging of the power source 442, such as a rechargeable battery. In still another regard, control unit 440 may be replaced by a simple coupler for the various leads connecting ultrasound assembly 420 with the outside world, and all control of therapy is done via a removable attachment to the external assembly 460. This may in particular be useful with respect to therapy protocols requiring relatively few, discrete applications of energy that will thus allow for selective attachment to the therapeutic control system.

FIG. 68 shows yet another embodiment similar to FIG. 67, except however illustrating that the ultrasound treatment assembly 420 is positioned within a structure of the spinal joint 420, which may be for example a bony structure such as vertebral body or posterior body, e.g. facet joint, or may be an intervertebral disc.

It is to be further appreciated that these embodiments, and in particular the embodiments of FIGS. 67 and 68 providing external access to control unit 440, may beneficially provide features not easily provided in the completely implanted embodiment of FIG. 66. For example, cooling assemblies may be incorporated into the externally accessible embodiments, such as circulating cooling fluids to a cannula port provided there. However, it is further contemplated that cooling may be accomplished with the fully implanted assembly, such as by circulating cooling Freon within a closed internal loop between control unit 440 and transducer assembly 420, or merely circulating water at body temperature therebetween, though such may be gradually elevated during the thermal therapy, but nevertheless provides a heat sink to circulate heat conduction away from the treatment area.

Accordingly, the various embodiments previously described above with respect to ExDUSTT and InDUSTT ultrasound delivery system arrangements may be appropriately adapted for use with the long-term implant arrangement of the present invention to provide long-term thermal therapy with various beneficial aspects of those prior devices. Such modifications may be made, for example, to materials of contruction, shapes, size, etc., to adapt them for particular intended long-term use. Moreover, various disclosures cited above with respect to long-term electrical implants may be further modified to accommodate the particular needs to delivery, drive, operate, and monitor ultrasound therapy according to the present invention. In addition, various features provided with respect to other ultrasound energy delivery systems disclosed among various published references may also be appropriately modified with respect to the long-term, implantable ultrasound therapy provided herein.

It is to be appreciated therefore that the present invention satisfies the foregoing needs left heretofore unmet by prior disclosures by implanting, in one regard, an ultrasound therapy source in the patient and providing for the heat source to be controlled automatically or manually. This allows for automatic, periodic treatment and/or manual control by a patient or health care professional.

By way of example, and not of limitation, in addition to the various embodiments provided herein above by reference to the various Figures, a heat source such as that described in U.S. Pat. No. 5,620,497 (but miniaturized if desired) would be implanted in a target site. The target site could be soft tissue, a joint, the spine, or any other location in the body where application of heat will yield a desired effect. Coupled to the heat source is a control apparatus, such as a microprocessor, that will activate the heat source at predetermined times to automatically provide for periodic treatment. Using conventional programming techniques, the microprocessor can administer a treatment continuously or at spaced apart intervals. Application of heat during a particular treatment interval can be with continuous wave heat or pulsed application of heat. Combinations of continuous wave and pulsed application of heat can be programmed as well. The treatment could be repeated after a predetermined time period, such as once every hour, once every day, or any other desired period of time. Another example of a treatment would be to heat a target region for a fixed duration once every week for two months. Such controls would be contained for example in the control module 440, or external assembly 460, or a combination of resources allocated between them, such as shown for example in any of FIGS. 66-68.

It is to be further appreciated by reference to the illustrative embodiments of FIGS. 66-68 that control of the applicator should be considered broadly, though particular benefits are gained by each of the particular embodiments between those figures such that the applicator (heat source) can be activated/controlled via telemetry, an isolated self-contained implantable control unit, or via percutaneous or extracorporeal connection (such as catheter(s)) to exterior control and monitoring device(s).

In one further mode, a manual control can be provided so that the patient can "force" a treatment in response to pain or another sensory stimulus. The software will "intercept" the manual control signal and compare the time between the manual control signal and the prior automatic treatment, or between two prior manually forced treatments, to determine if the interval between treatments is too short. If so, the manual control would be locked out until at least a predetermined interval has passed. Optionally, the passing of the interval can be signaled to the patient using visual and/or audible indicators such as lights and buzzers. Or, more control can be left to the patient without such preventative measures required.

The control apparatus portion of the invention can be external to the patient, such as worn in pouch on a belt or in any other convenient manner. Such applies for example to either or both of external assembly 460 (if included) and control unit 440 (e.g. per the FIG. 67-68 embodiments). Leads from the ultrasound transmission source would, in that case, extend through the patient as is known with other electrically operated implantable devices such as for example certain insulin pumps or temporary cardiac pacemakers or defibrillators. The patient then could wear the apparatus, and an associated battery power supply, on his or her body.

In another embodiment, the entire apparatus, including power supply, could be implanted, again using techniques and arrangements known for other systems and methods, such as in the cardiac pacemaker art, electrical spinal stimulator systems, and the like. Another example includes an implantable ultrasound heating apparatus adjacent to intervertebral disc for chronic treatment of lower back pain. The device could deliver a single treatment session on demand (pain) of the patient, or follow some protocol.

According to further embodiments, temperature sensors could be used for treatment control and verification-feedback. A heating or acoustic device can be inserted into a tumor for repeated heating and activation of chemotherapeutic agents on a semi-regular basis. A drug can be released from the applicator, such as via a reservoir or eluting coating, or another implant closely associated therewith.

It is further contemplated that the devices of the present invention beneficially use ultrasound delivery according to highly beneficial embodiments. Such delivery may be for heating, such as described in detail above by reference to the prior embodiments. Or, such ultrasound delivery may be for other purposes in addition to or alternative to heating, as will be explained further below. Moreover, other sources may be used in conjunction with or instead of ultrasound. Radiofrequency current, microwave, thermal conduction based sources, magnetic, and laser sources can each be utilized.

Additional examples of various modes of use include, but are not limited to: frequent ultrasound exposure to bony endplates to stimulate bone growth; intervertebral fusion; and ultrasound exposure of postero-lateral processes for fusion.

Accordingly, the invention provides a long-term, permanent or semi-permanent implant, and thus modifies the non-permanent devices heretofore used for ultrasound thermal therapy. The heat source would employ biocompatible, flexible technology that can be permanently or semi-permanently implanted to maintain the desired treatment (whether acoustic exposure or thermal) protocol. Moreover, it is also contemplated that, despite the benefits provided for such long-term adaptive use, the present embodiments may also be used as temporary implants, such as in certain more acute settings under the care of healthcare professionals.

The wire leads for thermometry sensing and power leads are connected through skin/body wall and sutured in place. Cooling tubes may be further provided if cooling is necessary or desired. For example, such cooling arrangements as described above for the previous embodiments may be further adapted for use in the long-term implant systems of the present embodiments, including with respect to particular temperatures, such as for example at: less than 37 degrees C. (such as 0 degrees C.); over 37 degrees C.; and in some cases 43 degrees C. or above. Moreover, the various modes for fluid flow in and around the transducer may be used, and cooling may be provided for tissue interface regions, or for non-targeted tissues.

Further contemplated for use within system 400 according to the varied embodiments among FIGS. 66-68 may be temperature regulation, such as by use of thermal sensors (e.g. thermocouples or thermisters) located in or around the transducer assembly. Such aspects may be according to the various embodiments incorporating temperature monitoring and control as elsewhere herein described for the various embodiments above.

Tissue coupling may also be achieved according the various embodiments elsewhere herein described for temporary implants, though may be again modified to suit the particular needs for long-term implantation, such as with respect to minimizing the intrusiveness by providing reduced dimensions (e.g. with respect to coupling pads or balloons), or modifying the types of materials used. For example, for highly compliant balloon materials, long term inflation may result in significant creep and expansion of the membrane that may produce undesired results, and thus for certain such long-term implants balloons of the less compliant construction may be desired with respect to that consideration. However, the balloon materials may also be chosen to minimize potential long-term wear and tissue erosion issues that might arise at the tissue interface. This may be particularly important for implants at locations where motion is experienced, such as at mobile portions of spinal joints. In such case, more compliant balloon materials may be less traumatic over prolonged periods of time with movement experienced at such interface.

It is contemplated that the overall cooperation between components in system 400 shown in FIGS. 66-68 may be accomplished according to a wide variety of arrangements, and thus the coupling assembly 430 is shown very schematically. Such assembly 430 may include for example a single cannula connecting transducer assembly 420 and control unit 440, which cannula may house transducer power delivery leads, fluid delivery lumens for coupling balloon inflation and/or cooling fluid circulation, temperature sensor leads, or the like. These may share lumens in various combinations, or a multi-lumen assembly may be provided. Or, separate members may be used to connect such coupling elements between control unit 440 and ultrasound transducer 420. In this arrangement, though more attaching members are strung within the body, they may be rendered smaller and more flexible, and their overall effect may be less intrusive to the body's internal environment than would result from a single or even multiple combination bundle(s), respectively.

The various modes of operation for the ultrasound implants generally require use of an RF Oscillator, such as for example operating between about 0.5 to about 12 MHz, and with pulse modulation for various of the modes described above, or without such modulation for continuous wave embodiments. Moreover, an RF power amplifier may be incorporated therewith. Such may be provided in the control unit 440 directly coupled to the ultrasound transducer 420 and worn as the internal or external implant in or on the patients body, respectively, per the embodiments shown in FIGS. 66-68. Or, coupling to a remote external source with these features may be used, such as at external assembly 460 in those Figures. This may be in particular the case for example when therapeutic ultrasound delivery is desired only at discrete periods of time and the patient may hook-up to the RF drive assembly that drives the transducer.

Accordingly, RF sources previously described with respect to ultrasound therapy systems, or those previously disclosed for use with respect to electrical energy delivery implants, may be modified appropriately to meet the unique needs for driving the long-term implantable ultrasound transducers of the invention and according to the therapeutic ranges desired, such as those illustrative modes of operation herein described above.

Various modes of ultrasound delivery are contemplated, either to provide thermal therapy, or non-thermal ultrasound therapy, and whether to provide for mechanical tissue remodeling, controlled cell death, or enhanced tissue permeability to drug delivery. In one regard, with respect to desired levels of thermal therapy using the ultrasound systems, such modes of therapy previously described above with respect to the other embodiments described by example for temporary implant use may be accomplished with the implantable systems of the present embodiments.

Various particular modes of operation and intended therapies are additionally provided as follows for further illustration.

According to one exemplary mode, ultrasound is delivered with a power between about 0.1 to about 1 W/cm2, operated at about 1.5 MHz, and at 1 kHz repetition with 100-200 micro-second burst (100-200 cycle burst) for example a total of between about 10 to 30 minutes daily. This is considered beneficial for example for stimulating bone growth.

According to another mode for more elevated heating, ultrasound is delivered with a transducer emission power between about 0.5 to about 2 W/cm2, at frequencies between about 5 to about 12 MHz, according to continuous wave delivery modes. Such may be continual all the time, though power limitations may require significant interface with external power sources, and tissue tolerance and/or degradation may result. Or, such may be limited in total time over a given period, such as for example between about 5 to about 60 minutes/day. This is useful for example to achieve moderate heating considered to be beneficial for example to provide enhanced drug delivery therapy.

Where long-term, continual drug delivery enhancement is desired, a protocol of timed bursts may also be used as follows. Power may be between about 1 to about 30 W/cm2, with bursts lasting between 50 to 200 microseconds, repetition between about 1 Hz to about 5 kHz, and with ultrasound frequencies between about 0.5 to about 15 MHz.

In still another mode, delivery of up to about 12 to about 15 MHz is considered beneficial for providing both heating in addition to acoustic stimulation.

Various time periods may be employed for ultrasound delivery, including for example periods of energy delivery of 5, 15, 30, 60, 120, or more minutes, which can be given multiple times per day, for extended time periods. These periods may represent continuous wave, pulsed burst wave, and may be in one treatment segment, or aggregated over various spaced treatment intervals.

The parameters provided above for various different heating modalities are illustrative only, and may be varied according to a particular combination of conditions and other related parameters for operation, as elsewhere herein described. For example, where power output is described by way of W/cm2, other parameters may be observed and/or controlled for desired results, such as for example power per length of transducer treatment segment, e.g. 0.1-10 W per 1 cm applicator length. In another example, where particular frequency ranges are desired, this may allow particular transducer constructions to be used for optimal overall results, such as adjusting the size to meet the frequency of operation. For example, lower frequency transmissions are generally accomplished by transducers of larger wall thickness than higher frequency transmissions.

Therefore, various ultrasound transducers are considered useful for the present long-term implant embodiments and may be similar to others previously described above, though in many cases will be modified to suit the different long-term implant needs, either by physical constraints, or according to different desired modes of operation. Examples of transducers considered suitable for many indications include, for example, providing the transducers according to constructions that are adapted to operate between about 0.5 and about 1.5 MHz., which would be useful for pulsing at low frequencies. Further details of a suitable transducer may include for example a PZT4 material (or 5 or 8) with wall thickness for example of about 0.058 "for 1.5 MHz variety and about 0.174" for 0.5 MHz varieties. Examples of appropriate lead wire assemblies include lead wires of about 0.002" thickness for use with low energy ultrasound applications.

Various materials for construction may be used to make the long term implantable parts of the overall implant system, such as lead assemblies, e.g. coupling assembly 430 in FIGS. 66-68, or with respect to housing the transducer(s). Examples of suitable materials may include silicone (Nusil™, e.g. Nusil™ 6640), Pebax™, and polyester (e.g. commercially available from Advanced Polymers) to the extent compatible with long term implantation. Moreover, coatings may be used on such materials to enhance biocompatibility, including bioactive agents such as anti-inflammatory, healing promoters, or other species of agents may be used to meet the particular needs. Moreover, such agent coatings may be adapted to elute from the implantable device surface to provide treatment to the tissue interfaced with or around the device, either within the zone of ultrasound treatment, or outside the targeted range (e.g. for protective therapy in view of the thermal conduction in the area, such as to enhance protection of nerves).

Suture tags or other mechanisms such as fixation loops may be placed along edges of applicators or transducer assembly for permanent attachment or semi-permanent fixation of device. Many such fixation devices have been previously disclosed, and may be modified for use according to the present invention by one of ordinary skill based upon review of this disclosure. In any event, the configuration and type of such fixation device may be particularly tailored for the intended environment where the transducer assembly is to be positioned for long-term implantation. Such may affix to bone, connective tissue, or muscle in the adjacent tissue. Moreover, fixation may also be implemented for the control module and/or power source if also implanted within the body, as well as the respective coupling assembly or assemblies between the ultrasound treatment assembly and the respective control unit.

Pulsed ultrasound delivery is one particular mode for operating the implantable ultrasound delivery device of the present invention. In one particular regard, such mode of operation is considered highly beneficial for regeneration of various tissues. For example, therapeutic angiogenesis is the controlled induction or stimulation of new blood vessel formation to reduce unfavorable tissue effects caused by local hypoxia and to enhance tissue repair. The effects of ultrasound on wound healing, chronic ulcers, fracture healing and osteoradionecrosis may be explained by the enhancement of angiogenesis. Optimum intensities of between about 0.1 and about 0.4 W/cm2 (e.g. special average temporal average or "SATA") with 1 MHz ultrasound stimulates the production of angiogenic factors such as IL-8, fibroblast growth factor (bFGF) and vascular endothelial growth factor (VEGF) in cells such as osteoblasts and fibroblasts. Such is in particular applicable to long-term implants such as according to the present invention, though it is contemplated that repeat treatments with temporary implants may accomplish such results, such as according to the prior embodiments above. However, such repeated temporary modes of therapy would also require increased morbidity associated with repeat invasions into the body.

The following are further illustrative examples of modes of operation intended to provide certain desired results.

In one regard, a pulsed ultrasound delivery modality (e.g. less than or equal to about 70 microseconds) at about 5 MHz frequency of oscillation is considered applicable for uses where nerve stimulation is desired.

Low-intensity US accelerates regeneration of peripheral nerves, repairing of pseudarthrosis and bone fractures, will enhance formation of new bone tissue, osteogenesis and in the repairing of fractures.

Ultrasonic treatments at 0.5 W/cm2, 1.5 MHz, for durations of 5, 15, and 25 min/day for four weeks, will accelerate bone formation at the fracture site for such durations. Ultrasound at 0.5 $W/cm^2$ are stimulatory to fracture repair, if given for example for about 15 min/day.

Ultrasound at an intensity equal to about 0.4 $W/cm^2$, and at frequency of about 1 MHz, will stimulate collagen synthesis in tendon fibroblasts in response to an injury of the connective tissue matrix, and also stimulate cell division during periods of rapid cell proliferation. Increasing the treatment time, such as for example doubling the treatment time to 40 minutes daily, will significantly increase the histologic quality of repair cartilage. Daily low-intensity pulsed ultrasound will have a positive effect on the healing of osteochondral defects, with 40 minutes daily significantly increasing the histologic quality of the repair cartilage.

Further more detailed information related to various modes of thermal therapy and/or ultrasound delivery and related effects on tissue, and which provide further understanding of the various operational modes just described above according to using long-term implantable devices according to the present invention, is generally disclosed among the following references: Cook, J. L., J. L. Tomlinson, et al. (1999). "Induction of meniscal regeneration in dogs using a novel biomaterial." *Am J Sports Med* 27(5): 658-65; Cook, S. D., S. L. Salkeld, et al. (2001). "Improved cartilage repair after treatment with low-intensity pulsed ultrasound." *Clin Orthop* (391 Suppl): S231-43; Ramirez, A., J. A. Schwane, et al. (1997). "The effect of ultrasound on collagen synthesis and fibroblast proliferation in vitro." *Med Sci Sports Exerc* 29(3): 326-32; Reher, P., N. Doan, et al. (1999). "Effect of ultrasound on the production of IL-8, basic FGF and VEGF." *Cytokine* 11(6): 416-23; Rubin, C., M. Bolander, et al. (2001). "The use of low-intensity ultrasound to accelerate the healing of fractures." *J Bone Joint Surg Am* 83-A(2): 259-70; and Tsai, C. L., W. H. Chang, et al. (1992). "Preliminary studies of duration and intensity of ultrasonic treatments on fracture repair." *Chin J Physiol* 35(1): 21-6; Foster K R, Widerhold M L, "Auditory responses in cats produced by pulsed ultrasound," J Acoust Soc Am. 1978 April, 63(4):1199-205. The disclosures of these references are herein incorporated in their entirety by reference thereto.

Additional information related to various aspects generally of implantation in and around the spine, various additional modes of operating implantable energy delivery devices, or various different types of conditions that may be also treated according to the present invention may be found in one or more of the following issued U.S. Pat. No. 6,233,488 to Hess; U.S. Pat. No. 6,493,592 to Leonard et al. Still further information is provided in one or more of the following U.S. Patent Application Publications: 2001/0049527 to Cragg, now U.S. Pat. No. 6,558,390; and 2002/0115945 to Herman et al., now U.S. Pat. No. 7,065,408. More information is also provided in the following PCT International Publication: WO 02/09808. Whereas the various disclosures of these references do not describe a long-term, implantable therapeutic ultrasound system such as according to the present invention, their disclosures may be considered helpful in gaining a complete understanding of certain aspects of the invention and various intended environments of use, and therefore are herein incorporated in their entirety by reference thereto.

Other modes of using the long-term implantable ultrasound therapy devices of the invention are also contemplated, including in combination with other therapies for cooperative effects. For example, the ultrasound therapy may be used for or during local anesthesia. Examples of disclosures intended to provide prolonged local anesthesia, such as with respect to joints and other body spaces, are variously provided in the following issued U.S. Pat. No. 6,046,187 to Berde et al.; U.S. Pat. No. 6,248,345 to Goldenheim et al.; and U.S. Pat. No. 6,426,339 to Berde et al. The disclosures of these references are herein incorporated in their entirety by reference thereto.

Again, many different modes of operation, and intended therapeutic effects, have been provided to give a thorough understanding of applications by which the long-term implantable ultrasound therapy systems of the invention provide clinical benefit. However, other modes, specific designs and constructions, may be specially adapted for particular applications and according to particular constraints, such as for example patient anatomy, time of treatment, extent and area of tissue to treat, frequency of pain, etc. Such modifications are considered within the intended scope of the present invention, which should be considered broadly.

Moreover, ultrasound has been featured as the highly beneficial therapeutic energy source of choice for the various embodiments herein shown and described. However, other energy sources should be considered within the intended scope of various aspects of the invention to the extent capable of achieving such desired, novel results. Examples of such aspects include: active cooling (including at the transducer, interfacing tissue, or non-targeted tissue); directional energy coupling; focused energy delivery (e.g. converging energy signals); use of coupling members to achieve uniform energy delivery into tissue interface; thermal treatments according to specified thermal dosing or temperature ranges to achieve certain desired tissue responses; and coupling of energy into tissues with desired temperature elevations at various depths of tissues (and within desired ranges of time).

Although the description above contains many specificities, these should not be construed as limiting the scope of the invention but as merely providing illustrations of some of the presently preferred embodiments of this invention. Thus the scope of this invention should be determined by the appended claims and their legal equivalents. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

What is claimed is:

1. A method for delivering ultrasonic energy within a vertebral body of a vertebra to treat skeletal joint pain of a subject, the vertebral body comprising a bony structure located above a lower vertebral endplate and below an upper vertebral endplate of the vertebra, the method comprising:

penetrating a vertebral body by inserting a distal end of a cannula through an outer wall of the vertebral body and within the bony structure of the vertebral body;

wherein the cannula comprises a sharp distal tip and a central bore;

inserting an ultrasound energy delivery device through the central bore of the cannula and into the vertebral body;

wherein the ultrasound energy delivery device comprises at least one ultrasound transducer; and activating the ultrasound energy delivery device to deliver ultrasound energy to at least a portion of the vertebral body sufficient to denervate a target region of the vertebral body;

wherein the ultrasound energy delivery device is positioned within the vertebral body when the ultrasound device is activated.

2. The method of claim 1, wherein inserting the ultrasound energy delivery device through the central bore of the cannula and into the vertebral body comprises advancing the ultrasound energy delivery device out of the distal tip of the cannula.

3. The method of claim 2, wherein the ultrasound energy delivery device is configured to deliver ultrasound energy in a first direction, and wherein the ultrasound energy delivery device is configured not to deliver a substantial level of ultrasound energy in a second direction.

4. The method of claim 1, further comprising deflecting a deflectable portion of the ultrasound energy delivery device.

5. The method of claim 4, wherein the ultrasound energy is delivered from the deflectable portion of the ultrasound energy delivery device.

6. The method of claim 1, further comprising steering the ultrasound energy delivery device to the target region.

7. The method of claim 6, wherein the ultrasound energy delivery device is steered by manipulating a proximal end of the ultrasound device.

8. The method of claim 1, further comprising passing coolant through a portion of the ultrasound energy delivery device to cool at least one of the portion of the vertebral body and the at least one ultrasound transducer.

9. The method of claim 1, further comprising:

removing the ultrasound energy delivery device from the body of the subject; and removing the cannula from the body of the subject.

10. The method of claim 1, wherein the ultrasound energy delivery device is delivered as a long-term implant.

11. The method of claim 10, wherein the long-term implant comprises a control unit, a receiver, and a transmitter configured to facilitate communication with an external source outside of the body of the subject.

12. The method of claim 1, wherein the ultrasound transducer delivers a converging field of ultrasound energy to the region of tissue.

13. The method of claim 1, wherein the ultrasound transducer delivers a diverging field of ultrasound energy to the region of tissue.

14. The method of claim 1, wherein the ultrasound transducer delivers a substantially collimated field of ultrasound energy to the region of tissue.

15. A method for delivering ultrasonic energy within a vertebral body of a vertebra to treat skeletal joint pain of a subject, the vertebral body comprising a bony structure located above a lower vertebral endplate and below an upper vertebral endplate of the vertebra, the method comprising:

inserting a distal end of a spinal needle through an outer wall of a vertebral body and within the bony structure of the vertebral body;

wherein the spinal needle comprises a sharp distal tip configured to penetrate the outer wall of the vertebral body and a needle bore;

inserting an ultrasound energy delivery device through the needle bore of the spinal needle and within the vertebral body;

wherein the ultrasound energy delivery device comprises at least one ultrasound transducer; and causing the at least one ultrasound transducer to deliver acoustic energy to at least a portion of the vertebral body sufficient to denervate a target region of the vertebral body comprising a nociceptive nerve.

16. The method of claim 15, further comprising deflecting a deflectable portion of the ultrasound energy delivery device upon insertion.

17. The method of claim 16, wherein the ultrasound energy is delivered from the deflectable portion of the ultrasound energy delivery device.

18. The method of claim 15, further comprising passing coolant through a portion of the ultrasound energy delivery device to cool at least one of the portion of the vertebral body and the ultrasound transducer.

19. The method of claim 15, further comprising:

removing the ultrasound energy delivery device from the body of the subject; and removing the spinal needle from the body of the subject.

20. The method of claim 15, wherein the ultrasound energy delivery device is delivered as a long-term implant.

* * * * *